US 9,978,954 B2

(12) United States Patent
Tokito et al.

(10) Patent No.: US 9,978,954 B2
(45) Date of Patent: May 22, 2018

(54) BENZOBIS (THIADIAZOLE) DERIVATIVE, INK COMPRISING SAME, AND ORGANIC ELECTRONIC DEVICE COMPRISING SAME

(71) Applicant: UBE INDUSTRIES, LTD., Ube-shi (JP)

(72) Inventors: Shizuo Tokito, Yonezawa (JP); Daisuke Kumaki, Yonezawa (JP); Masashi Mamada, Yonezawa (JP); Kenjiro Fukuda, Yonezawa (JP); Yasuhiro Tanaka, Ichihara (JP); Hidetaka Shima, Ube (JP); Yasuhiro Yoneda, Ube (JP); Harunori Fujita, Ichihara (JP); Kazuaki Kakita, Ichihara (JP); Youji Omata, Ube (JP); Natsuko Yamada, Ichihara (JP); Takashi Honma, Ichihara (JP); Toshikazu Machida, Ichihara (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 97 days.

(21) Appl. No.: 15/022,906

(22) PCT Filed: Aug. 29, 2014

(86) PCT No.: PCT/JP2014/072839
§ 371 (c)(1),
(2) Date: Mar. 17, 2016

(87) PCT Pub. No.: WO2015/041026
PCT Pub. Date: Mar. 26, 2015

(65) Prior Publication Data
US 2016/0276598 A1  Sep. 22, 2016

(30) Foreign Application Priority Data

Sep. 20, 2013 (JP) .................................. 2013-196221
Feb. 14, 2014 (JP) .................................. 2014-026969

(51) Int. Cl.
*H01L 51/00* (2006.01)
*C07D 513/04* (2006.01)
(Continued)

(52) U.S. Cl.
CPC ........ *H01L 51/0071* (2013.01); *C07D 513/02* (2013.01); *C07D 513/04* (2013.01);
(Continued)

(58) Field of Classification Search
CPC .................................................... C07D 513/04
See application file for complete search history.

(56) References Cited

U.S. PATENT DOCUMENTS 8,294,144 B2* 10/2012 Fujiyama ............. C07D 333/50
257/40
9,290,516 B2* 3/2016 Tokito .................. C07D 513/04
(Continued)

FOREIGN PATENT DOCUMENTS

JP   A-2004-134694   4/2004
JP   A-2006-502981   1/2006
(Continued)

OTHER PUBLICATIONS

Fujisaki et al., Air-Stable n-type organix thin-film transistor array and high gain complementary inverter on flexible substrate, Applied Physics Letters, vol. 97, 133303-1 to 133303-3 (2010).
(Continued)

*Primary Examiner* — Vu A Nguyen
(74) *Attorney, Agent, or Firm* — Knobbe Martens Olson & Bear LLP

(57) ABSTRACT

A benzobis(thiadiazole) derivative represented by the following general formula (1):

(Continued)

in which R¹ represents a linear or branched alkyl group, or any one of the groups of the following formula (2):

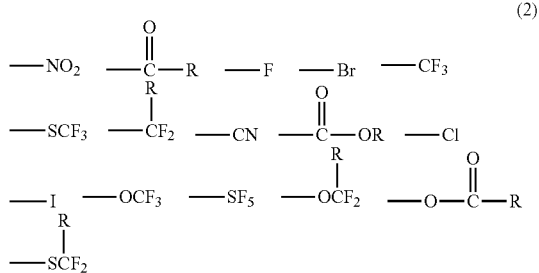

(2)

in which R represents a linear or branched alkyl group;
R² represents a hydrogen atom; and
R³ represents a hydrogen atom, a linear or branched alkyl group, or any one of the groups of the formula (2);
with the proviso that
at least one of R¹ and R³ represents any one of the groups of the formula (2); and
two R¹ groups, two R² groups, and two R³ groups may be the same as, or different from each other.

19 Claims, 9 Drawing Sheets

(51) Int. Cl.
*C09D 11/52* (2014.01)
*H01L 27/32* (2006.01)
*C07D 513/02* (2006.01)
*H01L 51/05* (2006.01)
*H01L 51/42* (2006.01)
*H01L 51/50* (2006.01)

(52) U.S. Cl.
CPC .......... *C09D 11/52* (2013.01); *H01L 51/0068* (2013.01); *H01L 27/3274* (2013.01); *H01L 51/0097* (2013.01); *H01L 51/0558* (2013.01); *H01L 51/0566* (2013.01); *H01L 51/4253* (2013.01); *H01L 51/5056* (2013.01); *H01L 51/5072* (2013.01); *Y02E 10/549* (2013.01)

(56) References Cited

U.S. PATENT DOCUMENTS

2006/0052612 A1    3/2006    Stossel et al.
2015/0059853 A1    3/2015    Tokito et al.

FOREIGN PATENT DOCUMENTS

| JP | A-2006-206503 | 8/2006 |
| JP | A-2009-541307 | 11/2009 |
| JP | A-2009-280515 | 12/2009 |
| JP | A-2013-124231 | 6/2013 |
| JP | B-6216712 | 9/2017 |
| WO | WO 2007/148914 A1 | 12/2007 |
| WO | WO 2013/141182 A1 | 9/2013 |

OTHER PUBLICATIONS

Kono et al., Dithienylbenzobis(thiadiazole) based organic semiconductors with low LUMO levels and narrow energy gaps, Chemical Communications, The Royal Society of Chemistry, vol. 46, pp. 3265-3267, Apr. 13, 2010.
International Preliminary Report on Patentability in International Patent Application No. PCT/JP2014/072839, dated Mar. 31, 2016.
Office Action in Japanese Patent Application No. 2015-537625, dated Feb. 6, 2018.

\* cited by examiner (1-1)

(1-2)

(1-3)

BENZOBIS (THIADIAZOLE) DERIVATIVE, INK COMPRISING SAME, AND ORGANIC ELECTRONIC DEVICE COMPRISING SAME

The present invention was made pursuant to a joint research agreement between Ube Industries., Ltd. and National University Corporation Yamagata University.

TECHNICAL FIELD

The present invention relates to a benzobis(thiadiazole) derivative, and an ink comprising the same, and organic electronic devices comprising the same, including an organic thin film transistor, an organic electroluminescence device, a display device, a display, and a photovoltaic cell (solar cell).

BACKGROUND ART

Conventionally, benzobisthiazole compounds attract attention as a compound used for an organic thin film transistor (organic TFT), an organic electroluminescence device (organic EL device), or an organic thin film photovoltaic cell, and various derivatives in which the main skeleton is benzobis(thiadiazole) are studied and developed vigorously.

A benzobis(thiadiazole) compound into which a strong electron-withdrawing group is introduced in order to improve the mobility of hole and electron, or the stability in the atmosphere, in particular, is proposed. For example, Non Patent Literature 1 and Non Patent Literature 2 disclose a compound in which trifluoromethylphenyl group is bound to benzobis(thiadiazole) via thienylene group (hereinafter, also referred to as "FPTBBT"). The compound has a mobility improved by the introduction of trifluoromethylphenyl group which is a strong electron-withdrawing group.

Patent Literature 1 also discloses a benzobisthiadiazole compound as an n-type organic semiconductor material, and the compound synthesized herein is 4,8-bis[3,5-bis(trifluoromethyl)phenyl]benzo[1,2-c;4,5-c']bis[1,2,5]thiadiazole only. Additionally, although the result of the measurement of cyclic voltammetry (CV) of 4,8-bis[3,5-bis(trifluoromethyl)phenyl]benzo[1,2-c;4,5-c']bis[1,2,5]thiadiazole is described herein, a device such as a thin film transistor (TFT) was not produced with the compound and was not evaluated for the properties, and therefore it is unclear whether the compound has adequate properties as an organic semiconductor material. In addition, no mention is made of the solubility in Patent Literature 1.

Meanwhile, it is generally known that a compound having a strong electron-withdrawing group introduced into thiophene ring has an improved stability or mobility of electron, although the compound is not a compound in which the main skeleton is benzobis(thiadiazole). (See, for example, Patent Literature 2.)

Moreover, Patent Literature 3, which was published on Sep. 26, 2013, discloses a benzobis(thiadiazole) derivative which is soluble in an organic solvent, and also discloses organic electronic devices comprising the benzobis(thiadiazole) derivative, including an organic thin film transistor.

CITATION LIST

Patent Literature

Patent Literature 1: JP-A-2013-124231
Patent Literature 2: JP-A-2009-280515
Patent Literature 3: WO2013/141182A1

Non Patent Literature

Non Patent Literature 1: Chem. Commun., 46, 3265 (2010)
Non Patent Literature 2: Applied Physics Lett., 97, 133303 (2010)

SUMMARY OF INVENTION

Technical Problem

However, various derivatives in which the main skeleton is benzobis(thiadiazole) generally have very low solubility in organic solvents, and therefore it is very difficult to form a thin film from any of the derivatives by a coating method, which is industrially advantageous. In addition, any of the derivatives still has an inadequate mobility of hole and electron from a practical viewpoint.

In the development of organic electronic devices, it is important to achieve both solvent solubility and high mobility. However, it is generally difficult to achieve both of them, which is not unique to benzobis(thiadiazole) derivatives.

An object of the present invention is to provide a benzobis(thiadiazole) derivative, which is soluble in an organic solvent and allows the formation of a thin film by a coating method, and has an excellent mobility of hole and/or electron (field-effect mobility) and also has an excellent stability in the atmosphere. Another object of the present invention is to provide organic electronic devices comprising the benzobis(thiadiazole) derivative, including an organic thin film transistor, an organic electroluminescence device, a display device, a display, a photovoltaic cell, a RFID tag, and a sensor.

Solution to Problem

The present invention relates to the following items.

[1] A benzobis(thiadiazole) derivative represented by the following general formula (1):

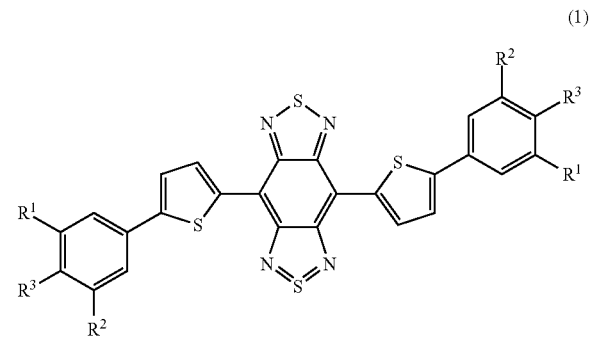

wherein
$R^1$ represents a linear or branched alkyl group, or any one of the groups of the following formula (2):

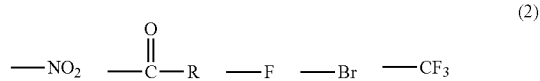

-continued

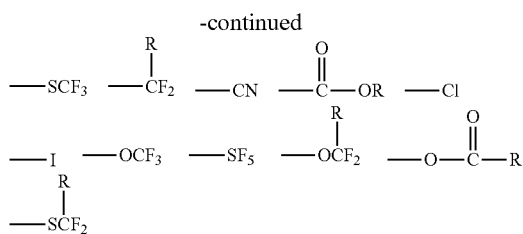

wherein R represents a linear or branched alkyl group;
R² represents a hydrogen atom; and
R³ represents a hydrogen atom, a linear or branched alkyl group, or any one of the groups of the formula (2);
with the proviso that
at least one of R¹ and R³ represents any one of the groups of the formula (2); and
two R¹ groups, two R² groups, and two R³ groups may be the same as, or different from each other.

[2] The benzobis(thiadiazole) derivative as described in [1], wherein
R¹ is any one of the groups of the formula (2);
R² is a hydrogen atom; and
R³ is a hydrogen atom, or a linear or branched alkyl group.

[3] The benzobis(thiadiazole) derivative as described in [1], wherein
R¹ is a linear or branched alkyl group;
R² is a hydrogen atom; and
R³ is any one of the groups of the formula (2).

[4] The benzobis(thiadiazole) derivative as described in any one of [1] to [3], wherein the group of the formula (2) is any one of the groups of the following formula (3):

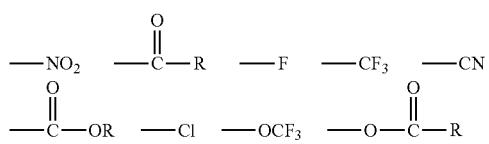 (3)

wherein R represents a linear or branched alkyl group.

[5] The benzobis(thiadiazole) derivative as described in any one of [1] to [4], wherein
R¹ is a linear or branched alkyl group;
R² is a hydrogen atom; and
R³ is any one of trifluoromethyl group, trifluoromethoxy group, or cyano group.

[6] The benzobis(thiadiazole) derivative as described in any one of [1] to [5], wherein the benzobis(thiadiazole) derivative is soluble in an organic solvent.

[7] An organic semiconductor ink comprising the benzobis(thiadiazole) derivative as described in any one of [1] to [6].

[8] An organic semiconductor ink comprising two or more of organic semiconductors, wherein one or more of the organic semiconductors is the benzobis(thiadiazole) derivative as described in any one of [1] to [6].

[9] An organic electronic device comprising an organic layer, which comprises the benzobis(thiadiazole) derivative as described in any one of [1] to [6].

[10] An organic thin film transistor, comprising a gate electrode, a gate insulating layer, an organic semiconductor layer, a source electrode, and a drain electrode on a substrate, wherein
the organic semiconductor layer comprises the benzobis(thiadiazole) derivative as described in any one of [1] to [6].

[11] An organic electroluminescence device, comprising an anode, a luminescent layer, a hole transport layer and/or an electron transport layer, and a cathode on a substrate, wherein
the hole transport layer and/or the electron transport layer comprise the benzobis(thiadiazole) derivative as described in any one of [1] to [6].

[12] A display device, in which an organic electroluminescence device is driven/lighted by the use of an organic thin film transistor, wherein
the organic thin film transistor is the organic thin film transistor as described in [10].

[13] An active-matrix display device, wherein
pixels are arranged in a matrix form, the pixel comprising the organic thin film transistor as described in [10] and an organic electroluminescence device.

[14] The display device as described in [12] or [13], wherein
the organic electroluminescence device is the organic electroluminescence device as described in [11].

[15] A display device, in which an organic electroluminescence device is driven/lighted by the use of an organic thin film transistor, wherein
the organic electroluminescence device is the organic electroluminescence device as described in [11].

[16] An organic thin film photovoltaic cell, comprising an anode, a charge separation layer comprising a hole transport material and an electron transport material, and a cathode on a substrate, wherein
the charge separation layer comprises the benzobis(thiadiazole) derivative as described in any one of [1] to [6].

[17] An organic thin film photovoltaic cell, comprising an anode, a charge separation layer comprising a hole transport material and an electron transport material, a hole transport layer and/or an electron transport layer, and a cathode on a substrate, wherein
the hole transport layer and/or the electron transport layer comprise the benzobis(thiadiazole) derivative as described in any one of [1] to [6].

[18] A RFID tag, which is activated by the use of an organic thin film transistor, wherein
the organic thin film transistor is the organic thin film transistor as described in [10].

[19] A sensor, which is activated by the use of an organic thin film transistor, wherein
the organic thin film transistor is the organic thin film transistor as described in [10].

[20] The organic electronic device as described in [9], the organic thin film transistor as described in [10], the organic electroluminescence device as described in [11], the display device as described in any one of [12] to [15], the organic thin film photovoltaic cell as described in [16] or [17], the RFID tag as described in [18], or the sensor as described in [19], wherein
the substrate is a flexible substrate.

Advantageous Effects of Invention

According to the present invention, there may be provided a benzobis(thiadiazole) derivative (hereinafter, also referred to as "benzobis(thiadiazole) compound"), which is soluble in an organic solvent and allows the formation of a thin film by a coating method, and has an excellent mobility of hole and/or electron (field-effect mobility) and also has an excellent stability in the atmosphere. It is industrially advantageous that a thin film (layer) can be formed by a coating method (or printing), because high-temperature process and high-vacuum process are not required, and the handling is easy, and therefore a device with a large screen can be produced at a low cost. The benzobis(thiadiazole) derivative of the present invention has an excellent mobility of hole and electron (field-effect mobility) and an excellent stability in the atmosphere, and therefore may be suitably used for, for example, organic electronic devices including an organic thin film transistor, an organic electroluminescence device, a display device, a display, a photovoltaic cell, a RFID tag, and a sensor. The compound may be also suitably used for many other devices.

BRIEF DESCRIPTION OF DRAWINGS

FIG. 1-1 is a diagram illustrating one example of the complementary inverter (logic inverting) circuit.

DESCRIPTION OF EMBODIMENTS

<Benzobis(thiadiazole) Compound>

Figure 1:
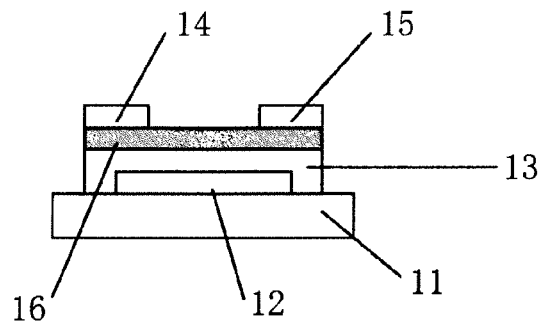
FIG. 1 is a longitudinal sectional view illustrating the layer configuration of one example of the organic thin film transistor (organic TFT) of the present invention.
Figure 1:
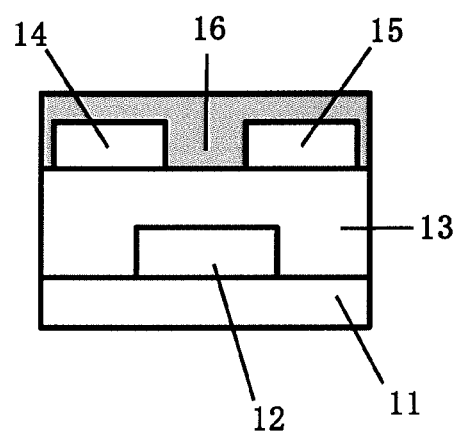
Figure 1:
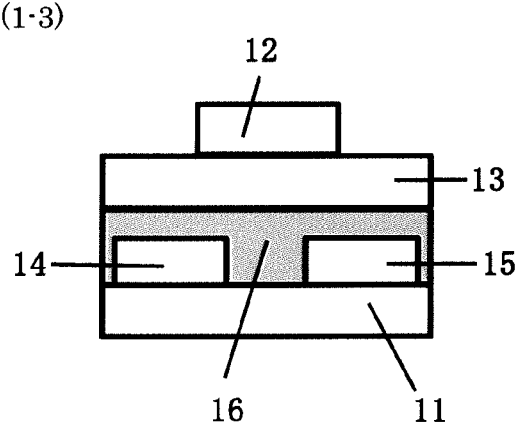
Figure 1:
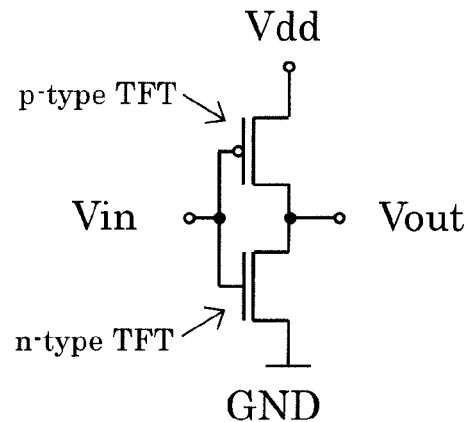

The benzobis(thiadiazole) compound (benzobis(thiadiazole) derivative) of the present invention is represented by the general formula (1) as described below. The benzobis(thiadiazole) compound of the present invention has an excellent solubility in a solvent, due to the substitution of a substituent for the meta position ($R^1$) with respect to the thienylene group on the benzene ring. However, another meta position ($R^2$) is preferably a hydrogen atom, from the viewpoint of the improvement in field-effect mobility.

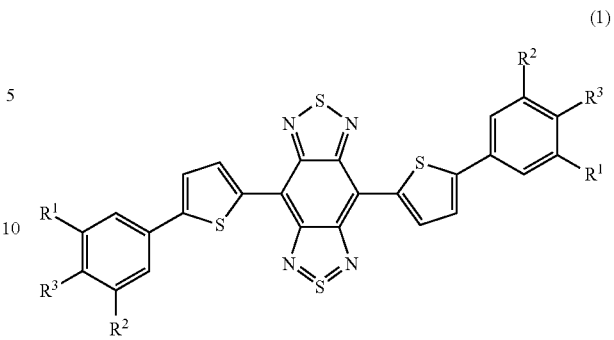

wherein
$R^1$ represents a linear or branched alkyl group, or any one of the groups of the following formula (2):

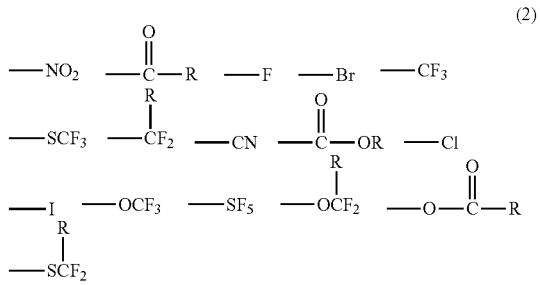

wherein R represents a linear or branched alkyl group;
$R^2$ represents a hydrogen atom; and
$R^3$ represents a hydrogen atom, a linear or branched alkyl group, or any one of the groups of the formula (2);
with the proviso that
at least one of $R^1$ and $R^3$ represents any one of the groups of the formula (2); and
two $R^1$ groups, two $R^2$ groups, and two $R^3$ groups may be the same as, or different from each other.

It is preferred that $R^1$ is any one of the groups of the formula (2), $R^2$ is a hydrogen atom, and $R^3$ is a hydrogen atom, or a linear or branched alkyl group in the general formula (1). It is also preferred that $R^1$ is a linear or branched alkyl group, $R^2$ is a hydrogen atom, and $R^3$ is any one of the groups of the formula (2).

It is generally preferred that two $R^1$ groups, two $R^2$ groups, and two $R^3$ groups each are the same as each other, although two $R^1$ groups, two $R^2$ groups, and two $R^3$ groups may be the same as, or different from each other.

The linear or branched alkyl group preferably contains 1 to 30 carbon atoms, more preferably 3 to 25 carbon atoms, and particularly preferably 5 to 20 carbon atoms, from the viewpoint of the mobility and the solubility.

Specific examples of the linear or branched alkyl group include methyl group, ethyl group, propyl group, isopropyl group, butyl group, t-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, 1-methylpropyl group, 1-methylbutyl group, 2-methylhexyl group, 2-ethylhexyl group, 3-methylhexyl group, 3-ethylhexyl group, 2-methyloctyl group, 2-ethyloctyl group, 3-methyloctyl group, 2-hexyldecyl group, 2-octyldodecyl group, 2-decyltetradecyl group, and 3-ethyloctyl group.

Examples of the linear alkyl group include the structures as described below.
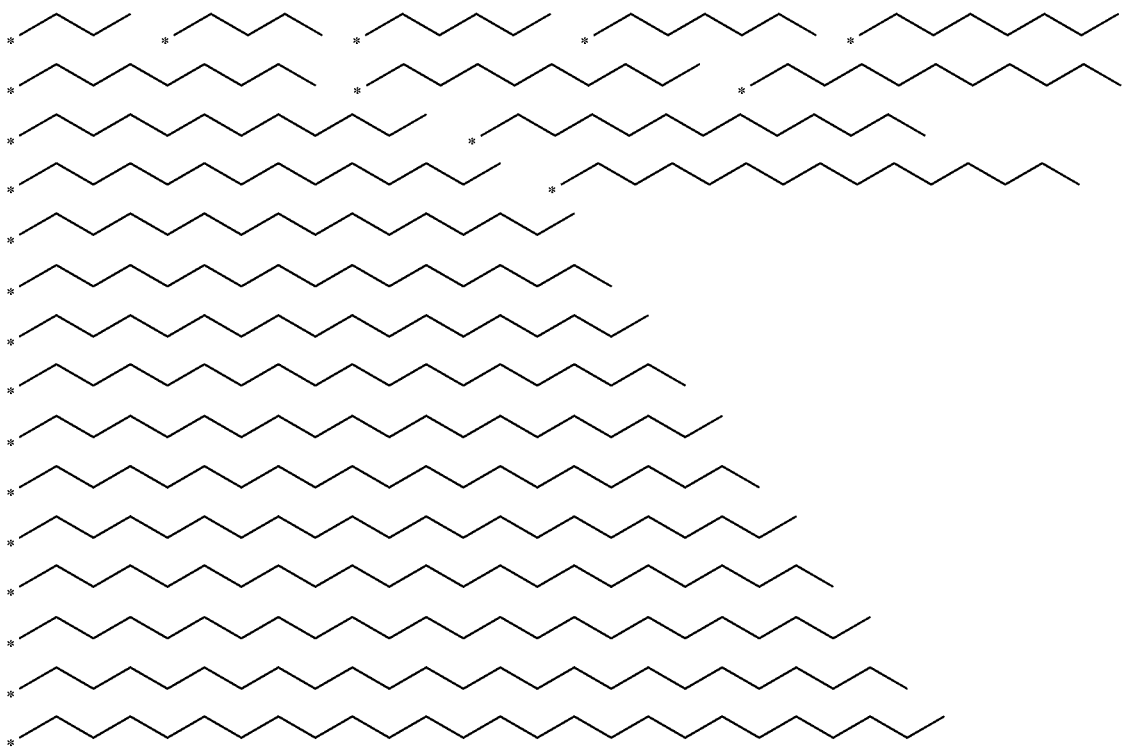
Examples of the branched alkyl group include the structures as described below.
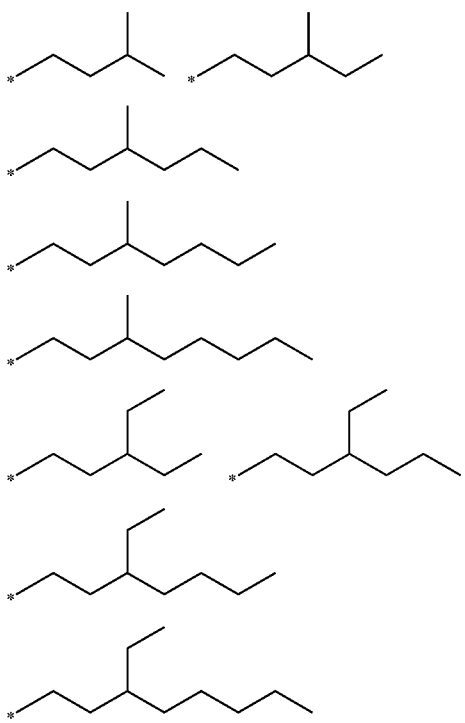
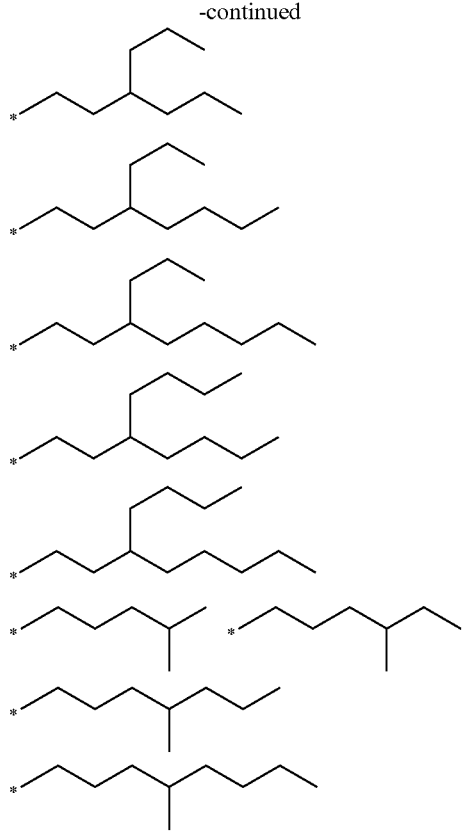

-continued

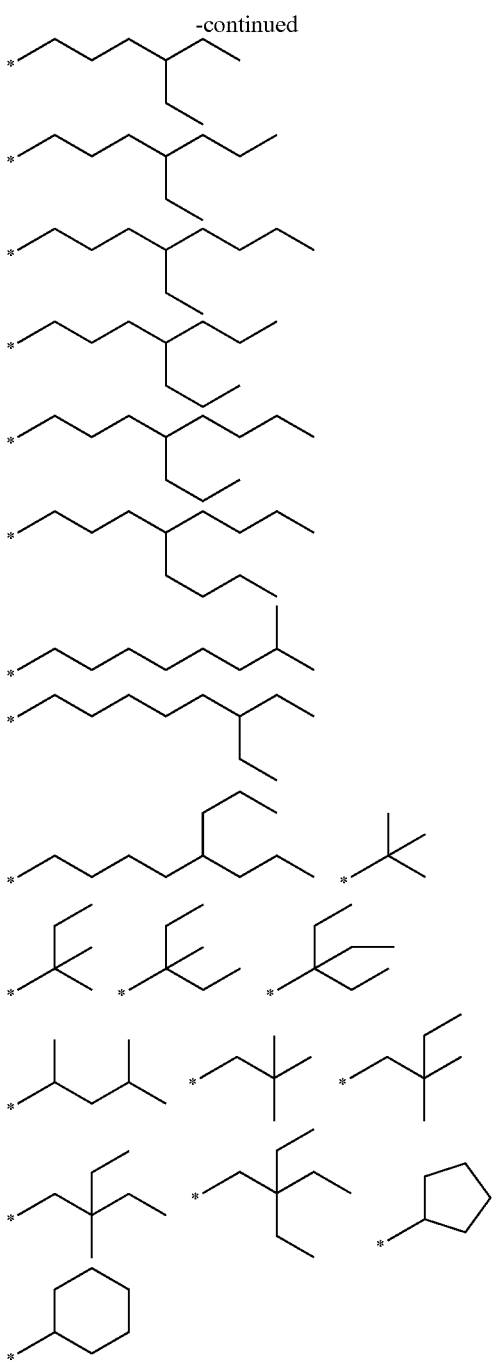

In the structures as described above, an asterisk (*) denotes a bond. The same shall apply hereinafter.

Among the groups of the formula (2), any one of the groups of the following formula (3) is preferred.

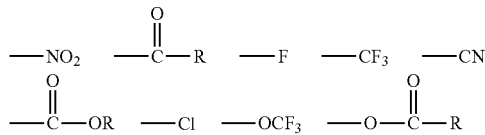

wherein R represents a linear or branched alkyl group.

The R group is preferably a linear or branched alkyl group containing 1 to 30 carbon atoms, more preferably a linear or branched alkyl group containing 1 to 20 carbon atoms, and more preferably a linear or branched alkyl group containing 1 to 15 carbon atoms.

Specific examples of the R group include methyl group, ethyl group, propyl group, isopropyl group, butyl group, t-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, 2-ethylhexyl group, 2-hexyldecyl group, 2-octyldodecyl group, and 2-decyltetradecyl group.

The group of the formula (2) is particularly preferably fluorine (—F), chlorine (—Cl), trifluoromethyl group (—CF$_3$), trifluoromethoxy group (—OCF$_3$), cyano group (—CN), or nitro group (—NO$_2$), and more preferably trifluoromethyl group (—CF$_3$), trifluoromethoxy group (—OCF$_3$), or cyano group (—CN).

Examples of the benzobis(thiadiazole) compound of the present invention include the compounds represented by the formulae (1) to (17) and (63) to (135) as described below. In the formulae, R represents a linear or branched alkyl group. In addition, —COR, —CO$_2$R, and —OCOR represent the following structures, respectively.

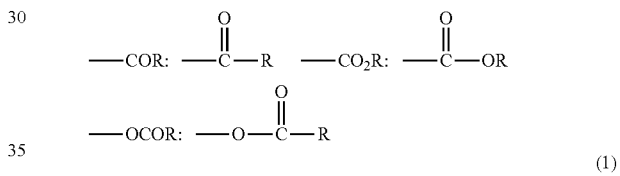

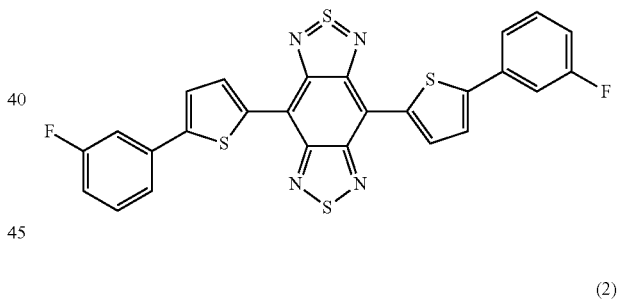

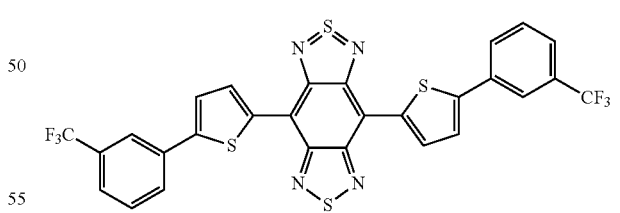

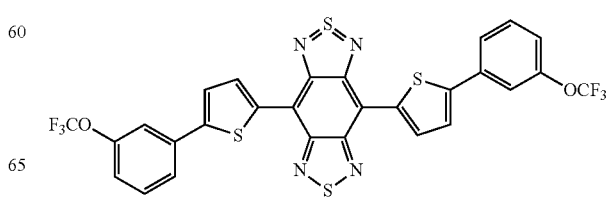

-continued
(4)
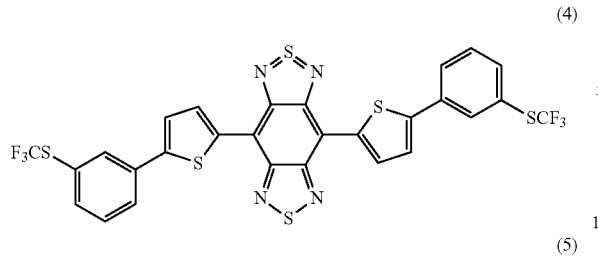
(5)
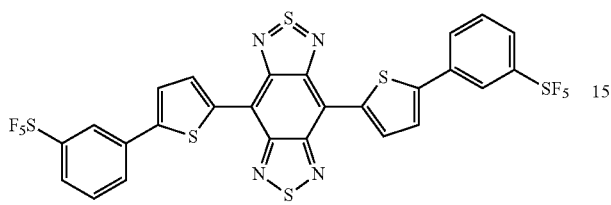
(6)
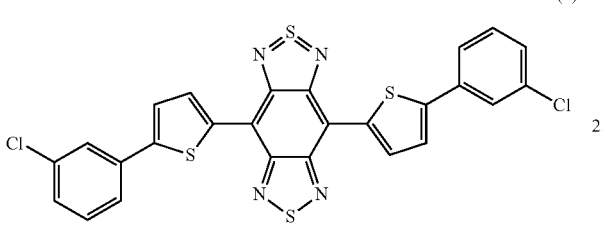
(7)
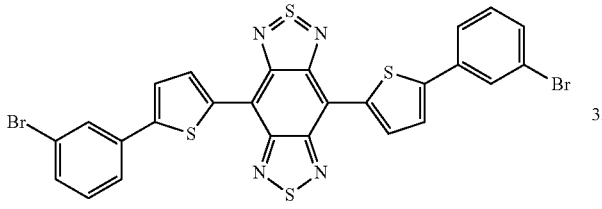
(8)
(9)
(10)
-continued
(11)
(12)
(13)
(14)
(15)
(16)
(17)

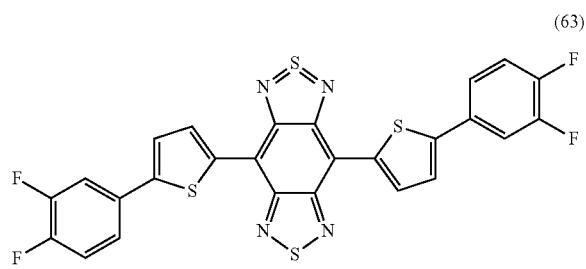
(63)
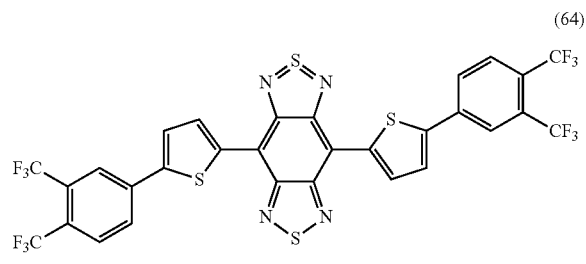
(64)
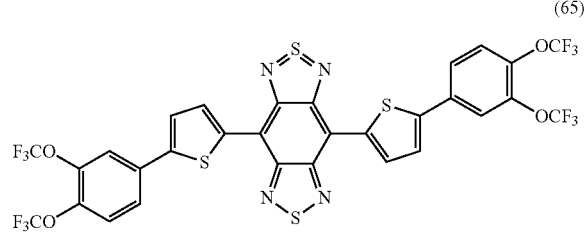
(65)
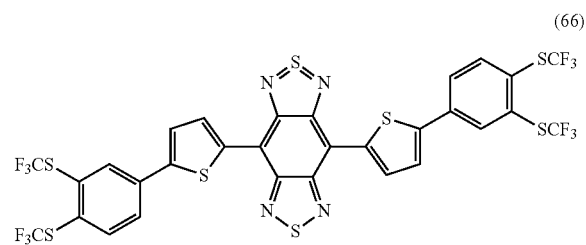
(66)
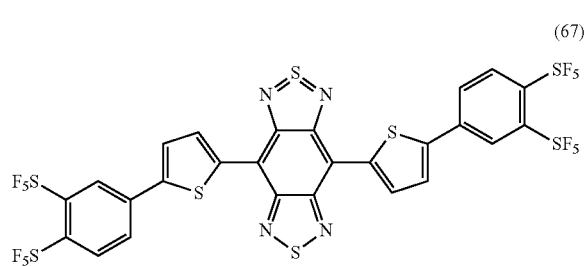
(67)
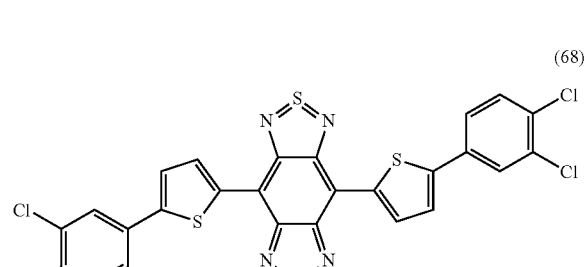
(68)
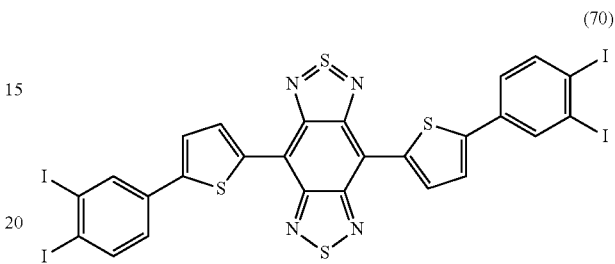
(69)
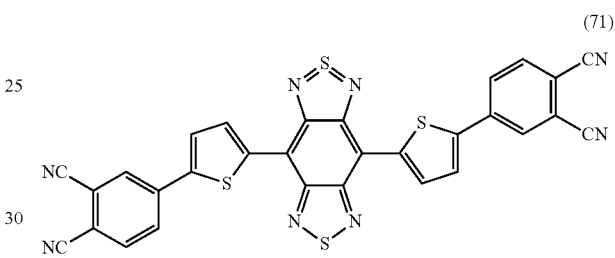
(70)
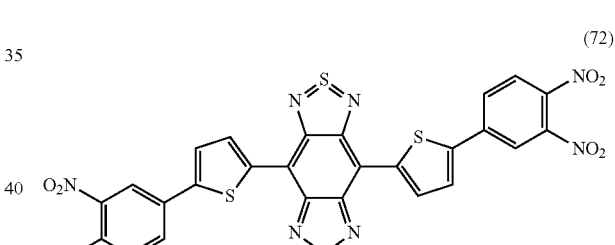
(71)
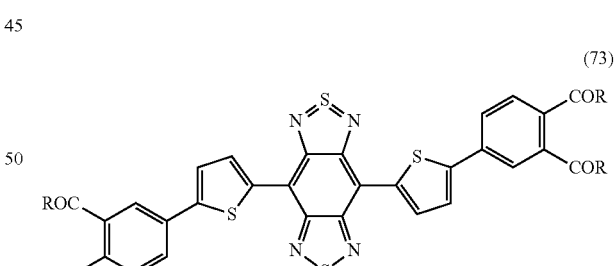
(72)
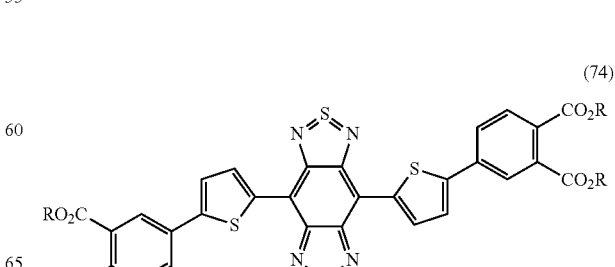
(73)
(74)

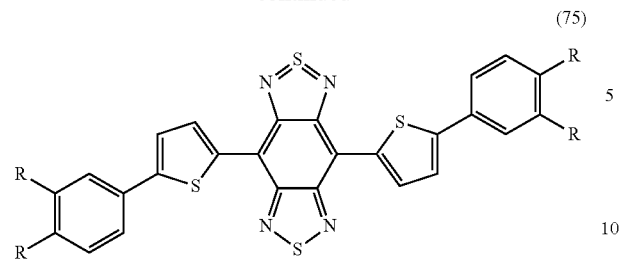
(75)
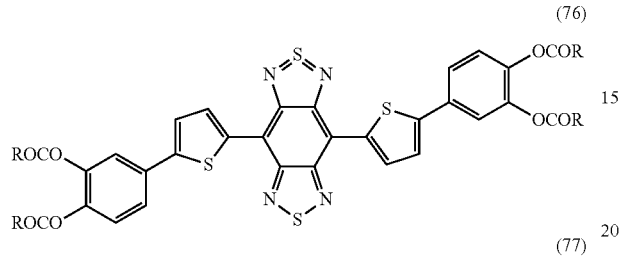
(76)
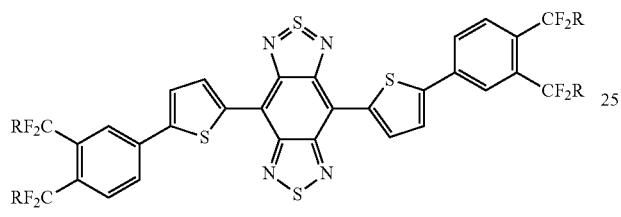
(77)
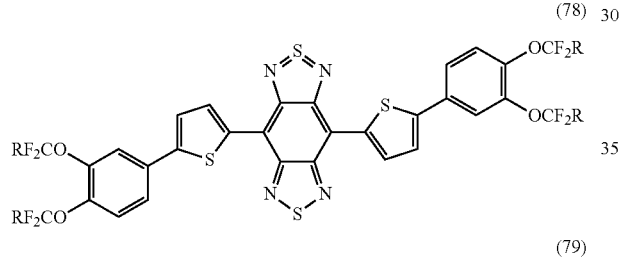
(78)
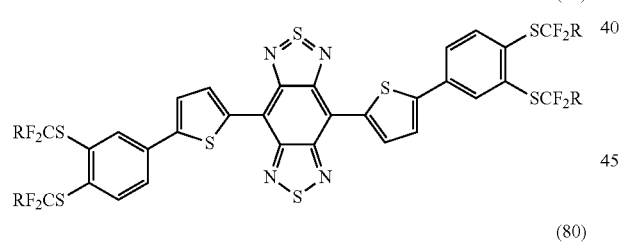
(79)
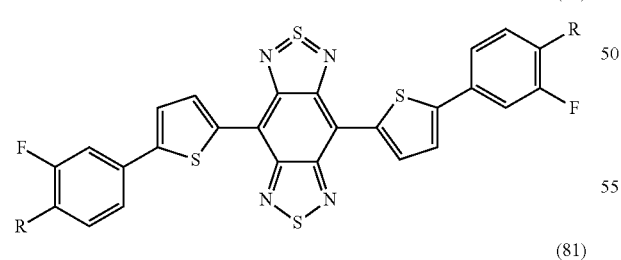
(80)
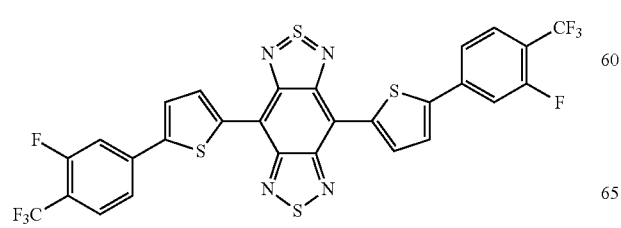
(81)
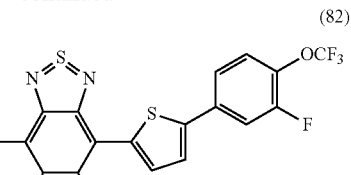
(82)
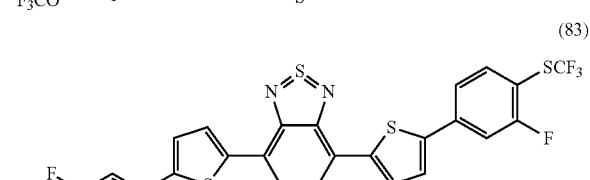
(83)
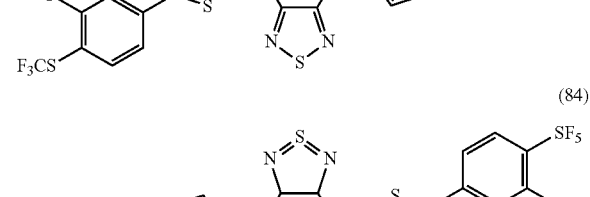
(84)
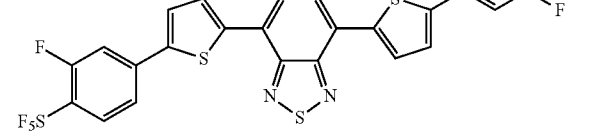
(85)
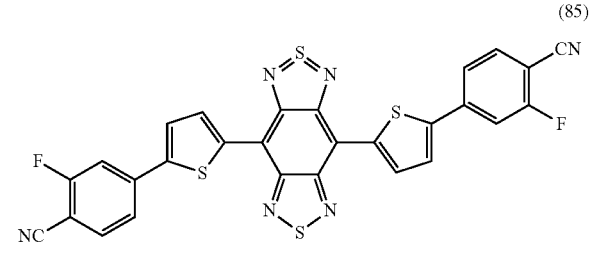
(86)
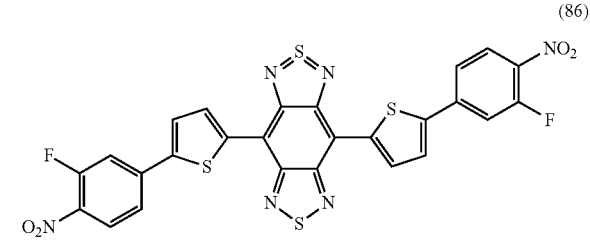
(87)
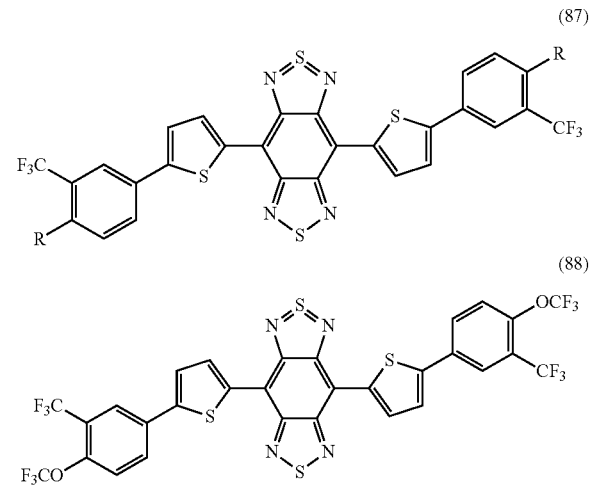
(88)

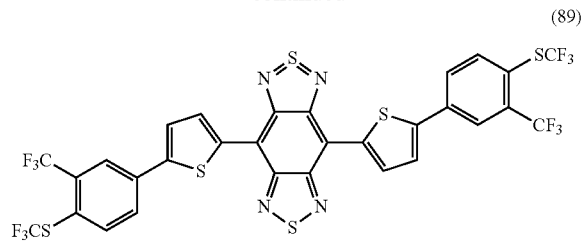 (89)
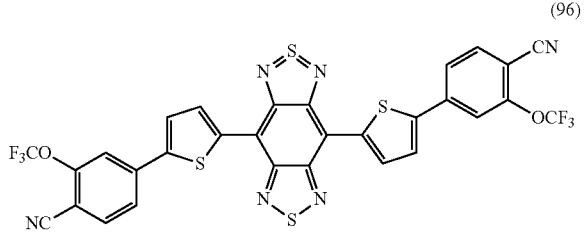 (96)
 (90)
 (97)
 (91)
 (98)
 (92)
 (99)
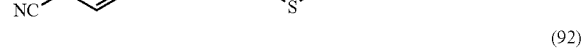 (93)
 (100)
 (94)
 (101)
 (95)
 (102)

(103)
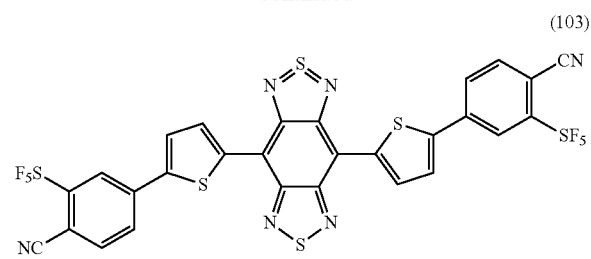
(104)
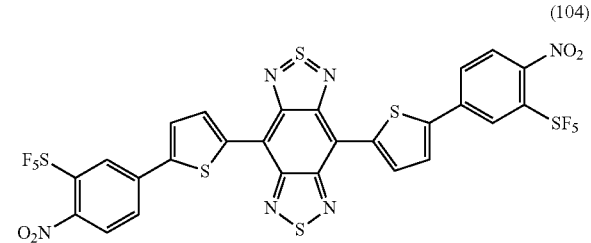
(105)
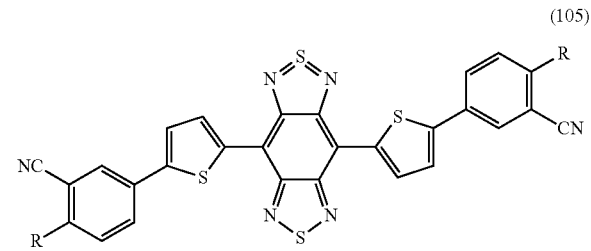
(106)
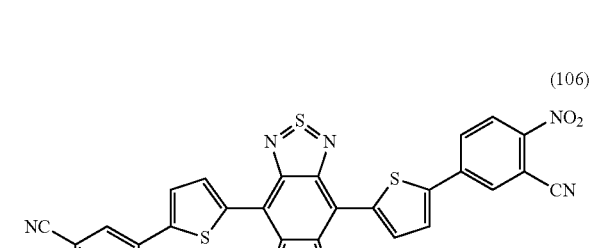
(107)
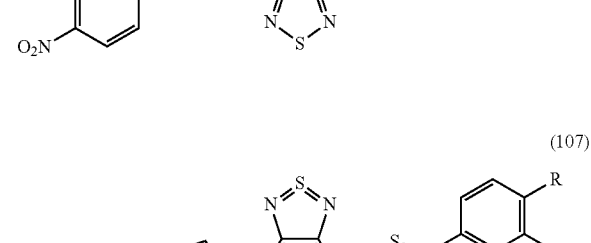
(108)
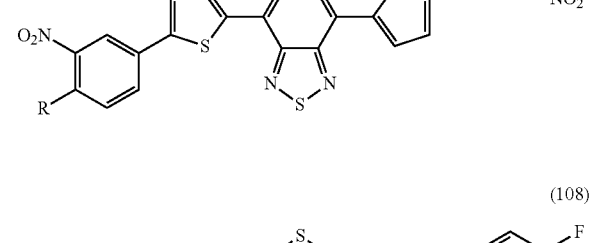
(109)
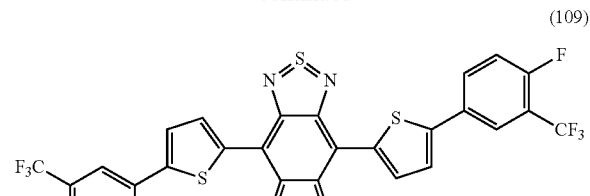
(110)
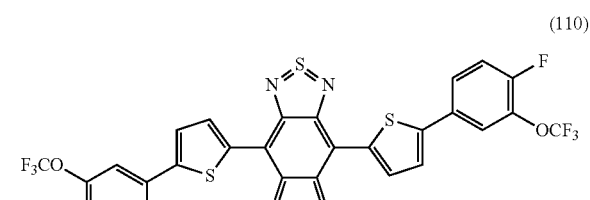
(111)
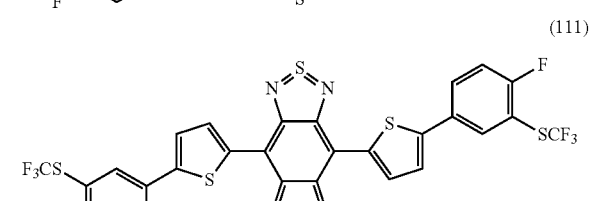
(112)
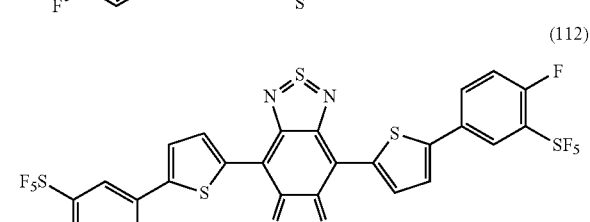
(113)
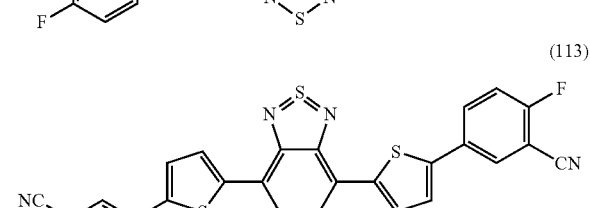
(114)
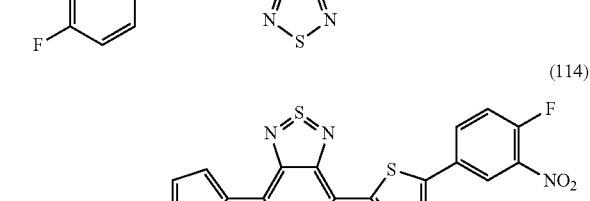
(115)
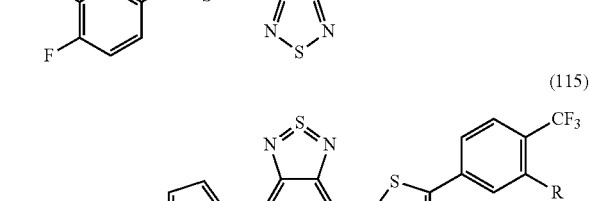

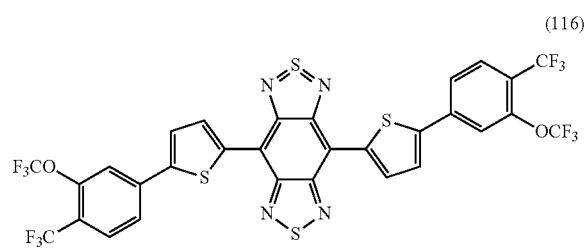
(116)
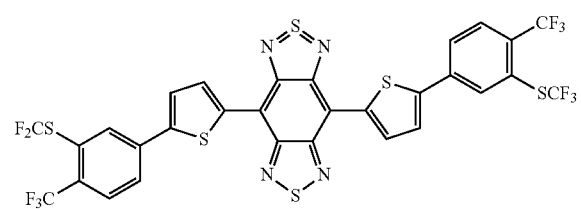
(117)
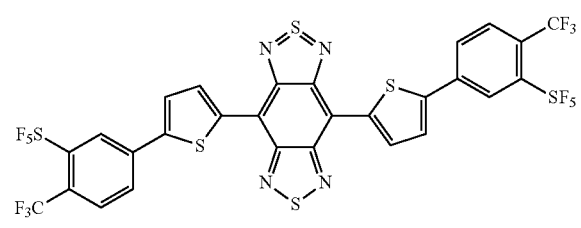
(118)
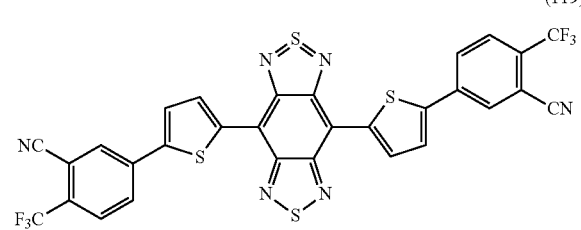
(119)
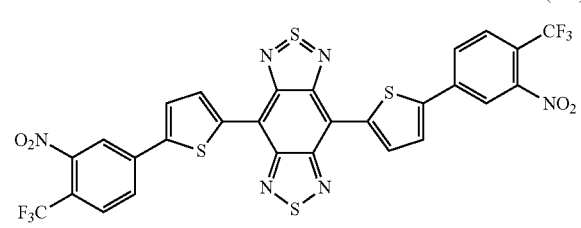
(120)
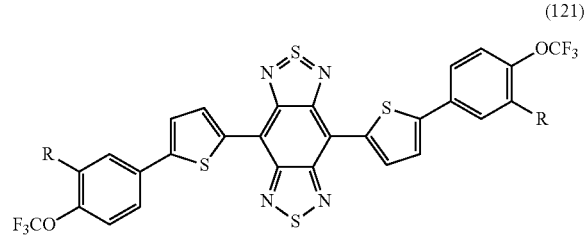
(121)
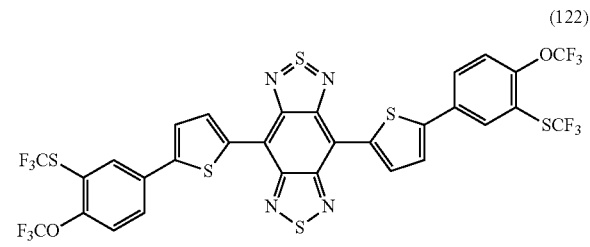
(122)
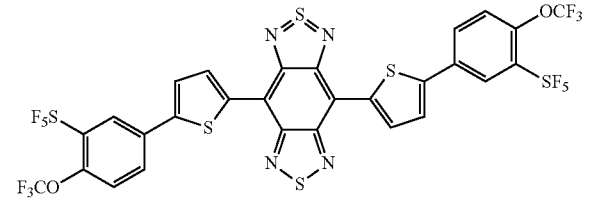
(123)
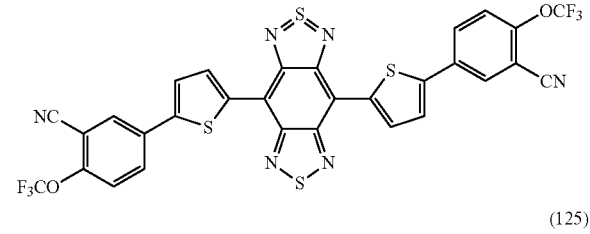
(124)
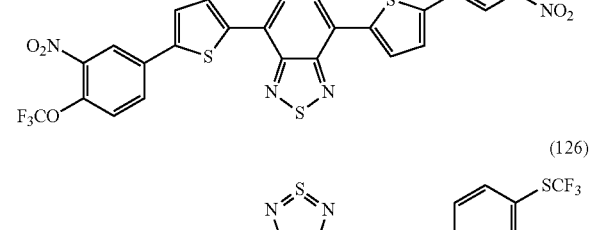
(125)
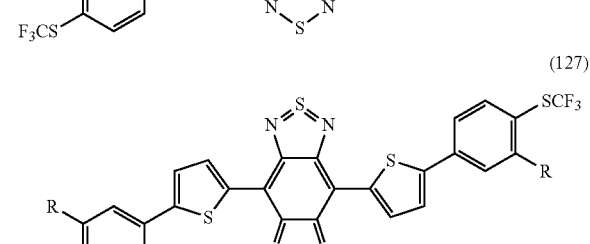
(126)
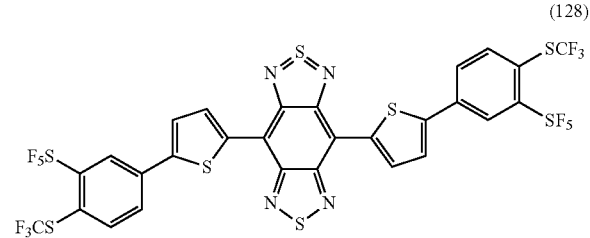
(127)
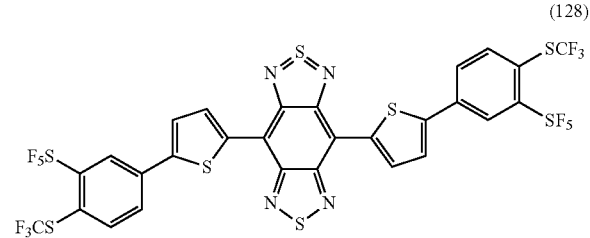
(128)

-continued
(129)
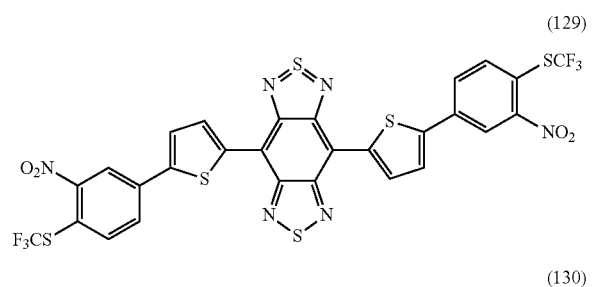
(130)
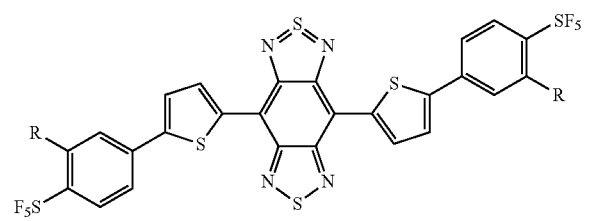
(131)
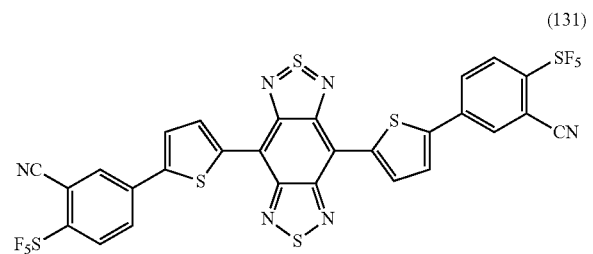
(132)
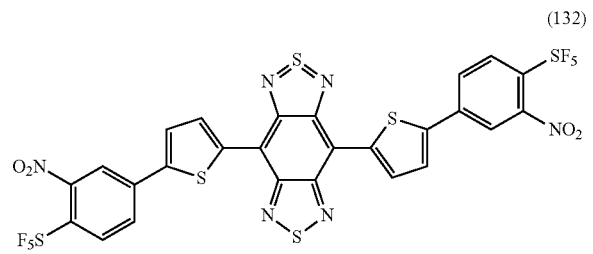
(133)
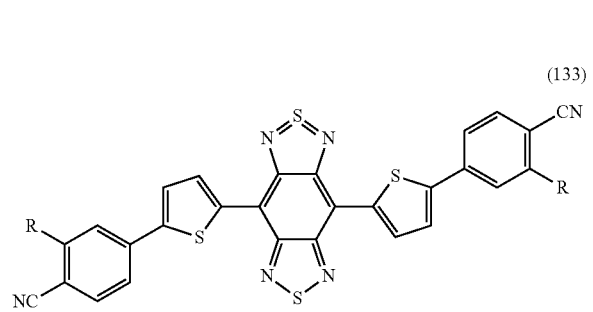
(134)
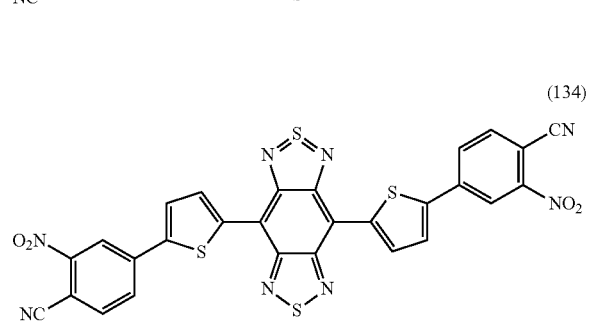
-continued
(135)
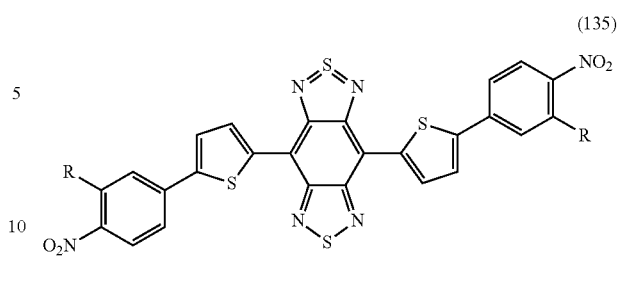
The benzobis(thiadiazole) compound of the present invention may be synthesized in accordance with the reaction scheme as described below (three steps of coupling step, stannylation step, and BBT step), for example, by reference to (1) Tetrahedron, 53, 10169 (1997), or (2) Organic Lett., 12, 3340 (2010), or the like.
(Coupling Step)
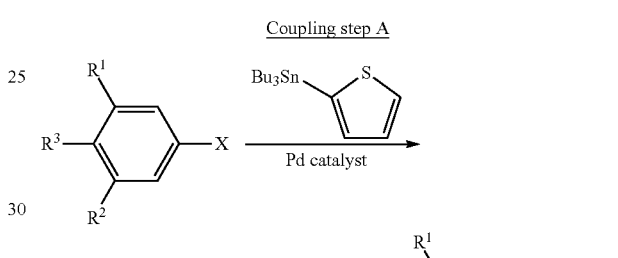
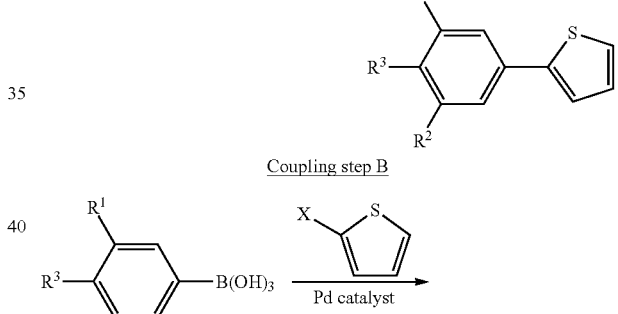
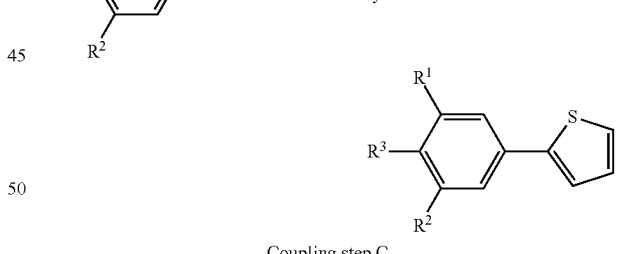
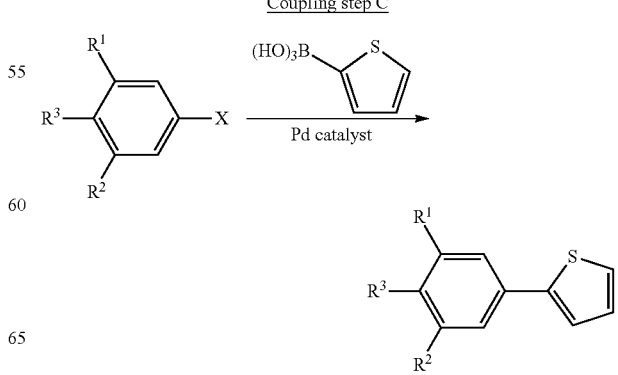

-continued
Coupling step D

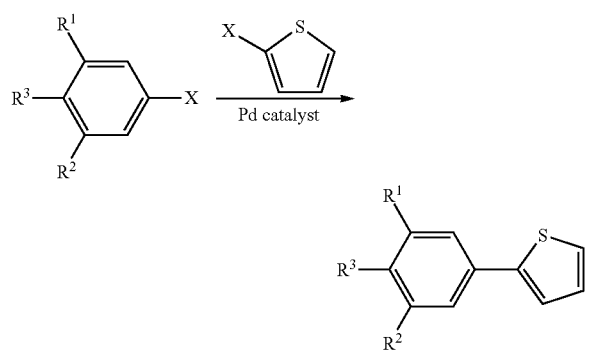

In the formulae, $R^1$, $R^2$ and $R^3$ are defined as above, and X represents a halogen atom, and is preferably a bromine atom or iodine atom. Meanwhile, as for the palladium catalyst (Pd catalyst), one, or two or more of palladium complexes such as tetrakis(triphenylphosphine)palladium (Pd(PPh$_3$)$_4$), dichlorobis(triphenylphosphine)palladium (PdCl$_2$(PPh$_3$)$_2$), bis(tri-tert-butylphosphine)palladium (Pd(PtBu$_3$)$_2$), palladium acetate (Pd(OAc)$_2$) and palladium chloride (PdCl$_2$) are preferred, and PdCl$_2$(PPh$_3$)$_2$ and Pd(Ph$_3$)$_4$ are more preferred.

(Stannylation Step)

Stannylation step A

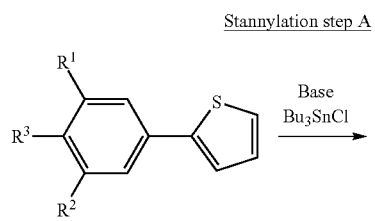

-continued

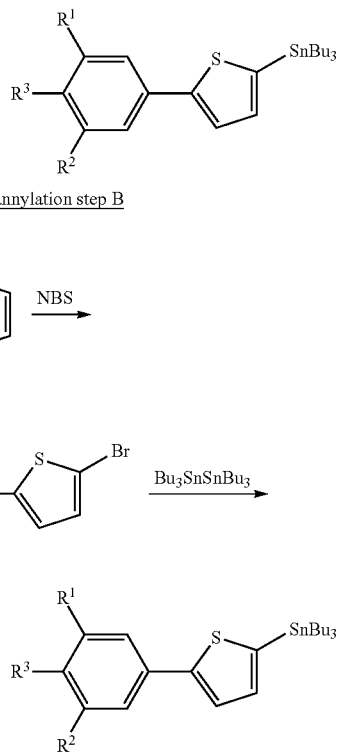

In the formulae, $R^1$, $R^2$ and $R^3$ are defined as above, and NBS represents N-bromosuccinimide, and Bu represents butyl group. Meanwhile, as for the base, n-BuLi (wherein Bu represents butyl group) or LDA (lithium diisopropylamide) is preferred.

(BBT Step)

BBT step A

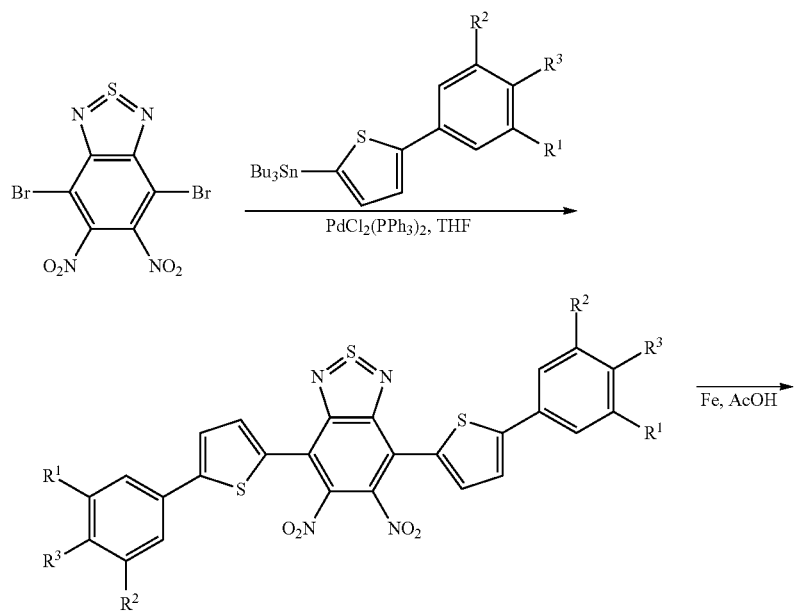

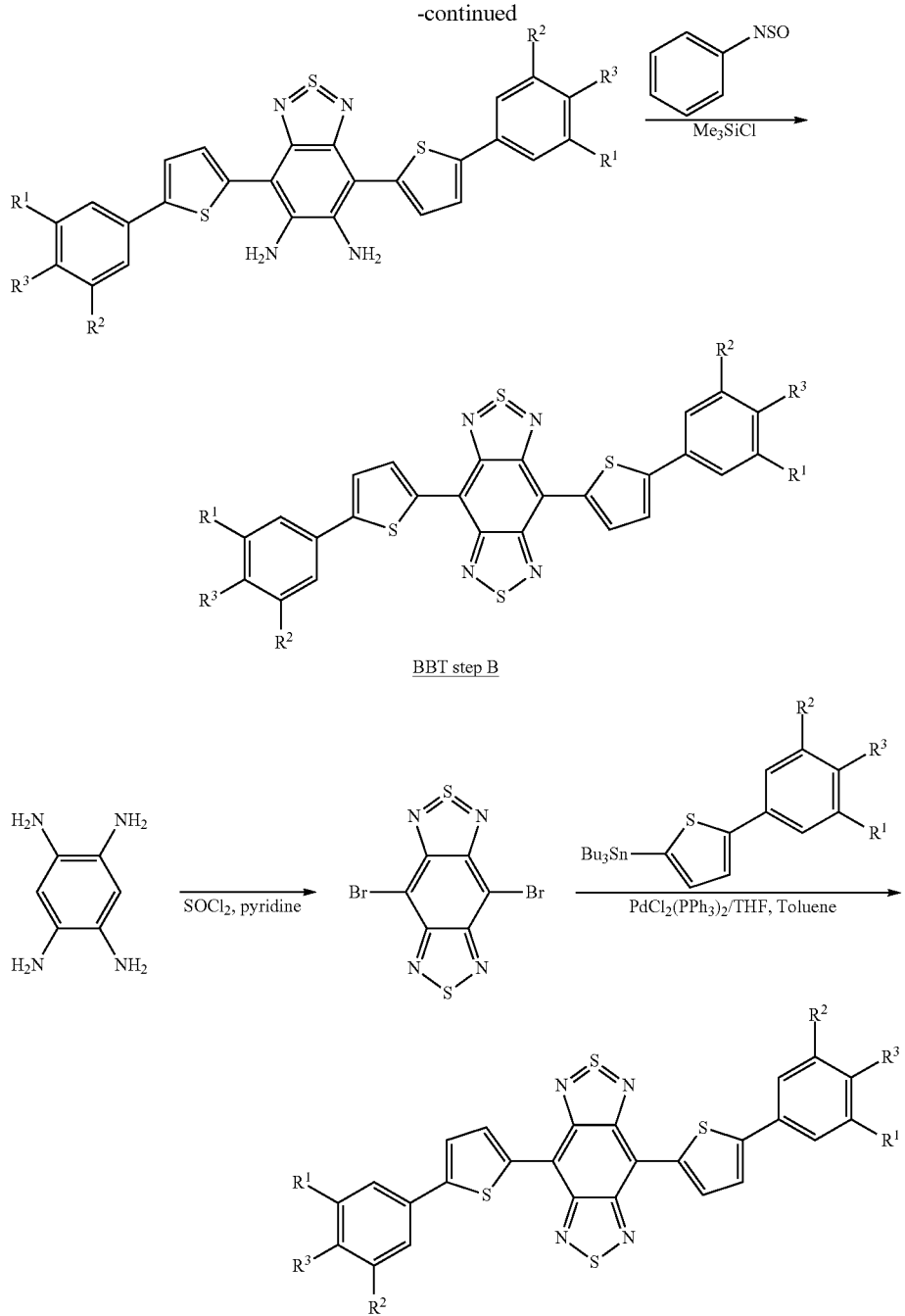

In the formulae, $R^1$, $R^2$ and $R^3$ are defined as above, and Bu represents butyl group, Ph represents phenyl group, AcOH represents acetic acid, and Me represents methyl group.

The process for producing the benzobis(thiadiazole) compound of the present invention comprises three steps of coupling step, stannylation step, and BBT step, and any one of the coupling steps A to D, any one of the stannylation steps A to B, and any one of the BBT steps A to B as described above may be appropriately selected and combined without limitation.

After the completion of the reaction, the benzobis(thiadiazole) compound of the present invention may be isolated and purified from the obtained reaction solution by performing common operations such as filtration, concentration, extraction, distillation, sublimation, recrystallization, and column chromatography, for example. It is preferred that Soxhlet extraction with an organic solvent is incorporated into the purification step, as it is simple, in order to remove different impurities having different solubility from the compound, and thereby improve the purity of the compound.

The benzobis(thiadiazole) compound of the present invention is generally soluble in water, or at least one of various organic solvents, for example, various organic solvents including alcohols such as methanol, ethanol, propanol, ethylene glycol, isobutanol, 2-butanol, 2-ethyl-1-butanol, n-octanol, benzyl alcohol, and terpineol; ketones such as acetone, methyl ethyl ketone, methyl isobutyl ketone, cyclopentanone, cyclohexanone, acetophenone, and isophorone; esters such as methyl acetate, ethyl acetate, butyl acetate, methyl benzoate, butyl benzoate, methyl salicylate, ethyl malonate, 2-ethoxyethane acetate, and 2-methoxy-1-methylethyl acetate; amides such as N,N-dimethylformamide, N,N-dimethylacetamide, N,N-diethylformamide, N-methyl pyrrolidone, N-ethylpyrrolidone, and hexamethylphosphoric triamide; ureas such as 1,3-dimethyl-2-imidazolidinone, and 1,3-dimethylimidazolidine-2,4-dione; sulfoxides such as dimethyl sulfoxide, and diethyl sulfoxide; sulfones such as sulfolane; nitriles such as acetonitrile, propionitrile, butyronitrile, and benzonitrile; lactones such as γ-butyrolactone; ethers such as diethyl ether, diisopropyl ether, tetrahydrofuran, 2-methyltetrahydrofuran, dioxane, tert-butyl methyl ether, anisole, phenetole, 1,2-dimethoxybenzene, 1,3-dimethoxybenzene, 1,4-dimethoxybenzene, 1,2-methyl anisole, 1,3-methyl anisole, 1,4-methyl anisole, 1,2-methylene dioxybenzene, 2,3-dihydrobenzofuran, phthalan, octyloxybenzene, diphenyl ether, and ethyl cellosolve; carbonates such as dimethyl carbonate, and 1,2-butylene glycol carbonate; thioethers such as thioanisole, and ethyl phenyl sulfide; aromatic hydrocarbons such as benzene, toluene, xylene, mesitylene, pseudocumene, hemimellitene, durene, isodurene, prehnitene, ethylbenzene, cumene, tert-butyl benzene, cyclohexyl benzene, triisopropyl benzene, phenyl acetylene, indane, methyl indane, indene, tetralin, naphthalene, 1-methyl naphthalene, 2-methyl naphthalene, phenyl octane, and diphenyl methane; phenols such as phenol, 1,2-cresol, 1,3-cresol, 1,4-cresol, 1,2-methoxyphenol, 1,3-methoxyphenol, and 1,4-methoxyphenol; halogenated aromatic hydrocarbons such as chlorobenzene, 1,2-dichlorobenzene, 1,3-dichlorobenzene, 1,2,4-trichlorobenzene, bromobenzene, 1,2-dibromobenzene, 1,3-dibromobenzene, 1,4-dichlorotoluene, 1-chloronaphthalene, 2,4-dichlorotoluene, 2-chloro-1,3-dimethylbenzene, 2-chlorotoluene, 2-chloro-1,4-dimethylbenzene, 4-chloro-1,2-dimethylbenzene, 2,5-dichlorotoluene, m-chlorotoluene, 1-chloro-2,3-dimethylbenzene, 4-(trifluoromethoxy) anisole, and trifluoromethoxy benzene; aliphatic hydrocarbons such as hexane, heptane, octane, cyclohexane, and limonene; halogenated aliphatic hydrocarbons such as dichloromethane, chloroform, carbon tetrachloride, 1,2-dichloroethane, 1,3-dichloropropane, and 1,2-dibromoethane; pyridines such as 2,6-dimethyl pyridine, and 2,6-di-tert-butyl pyridine; and the like. Among them, halogenated aromatic hydrocarbons, aromatic hydrocarbons, and halogenated aliphatic hydrocarbons may be preferably used as the solvent. These solvents may be used singly, or may be used in combination of two or more.

The term "soluble" as used herein means that the compound has a solubility of preferably 0.03 wt % or more, more preferably 0.05 wt % or more, more preferably 0.1 wt % or more, for water or an organic solvent at normal pressure and a temperature of the boiling point or lower, preferably 80° C. or lower, more preferably 60° C. or lower, more preferably from 20° C. to 30° C. It is not required that the benzobis (thiadiazole) derivative of the present invention be soluble in water and all organic solvents, and the derivative may be soluble in water or at least one of organic solvents as described above, for example. The benzobis(thiadiazole) derivative which is soluble in at least one organic solvent is referred to as being "soluble in an organic solvent".

The benzobis(thiadiazole) compound of the present invention is generally soluble in one or more organic solvents, and may preferably have a solubility in an organic solvent of 0.1 wt % or more, more preferably 0.3 wt % or more, for example.

Accordingly, the benzobis(thiadiazole) compound of the present invention may be dissolved in such an organic solvent, and the obtained solution may be used as an organic semiconductor ink. When an organic semiconductor ink can be prepared, it is easy to handle and it can be stored. Additionally, although vapor deposition and coating are generally exemplified as a method of forming an organic semiconductor layer, the cost of vapor deposition is very high as compared with coating because a high-temperature heat source and a high vacuum are required for vapor deposition. When the organic semiconductor ink of the present invention is used, an organic semiconductor layer can be formed by coating and the cost can be significantly reduced.

Additionally, the benzobis(thiadiazole) derivative of the present invention is stable in the atmosphere, and therefore the coating thereof may be performed in the atmosphere and there is no need to create an atmosphere of an inert gas such as argon gas. In view of this, cost reduction may be achieved.

The organic semiconductor ink of the present invention comprises one or more of the benzobis(thiadiazole) compounds of the present invention, and may comprise one or more of other organic semiconductors. As for the solvent constituting the ink, one solvent may be used alone, or two or more solvents may be mixed and used. In addition, the organic semiconductor ink of the present invention may comprise additives to control the properties of the ink such as an additive to adjust the viscosity of the ink, and an additive to control the hydrophilicity or the water-repellency of the ink, an anti-oxidizing agent, a light stabilizing agent, a surface conditioning agent (leveling agent), a surfactant, a storage stabilizing agent, a lubricating agent, a wettability improving agent, and a coupling agent. The effects of the addition thereof include the improvement in the electric charge mobility, in addition to the optimization of the viscosity of the ink, the improvement in the film-forming properties of the ink, and the like. Moreover, it is particularly preferred, in view of the circuit production process, that any one of the additive components as described above is added to the organic semiconductor ink when a plurality of different types of organic semiconductors are used in a circuit, or when the same organic semiconductor is used but a plurality of properties are adjusted. Separate formations of organic semiconductors with the required properties in the required portions in a circuit may be achieved by a change of the organic semiconductor ink, which is a simple operation, and therefore the degree of freedom of the circuit production may be improved.

The content of the benzobis(thiadiazole) compound of the present invention in the ink is not particularly limited, and may be appropriately selected. For example, the content may be from about 0.001 wt % to about 10 wt %, and may be preferably from about 0.01 wt % to about 1 wt % from the viewpoint of the film-forming properties. Additionally, in the cases where the organic semiconductor ink of the present invention comprises other organic semiconductors, the total content of the other organic semiconductors and the benzobis(thiadiazole) derivative of the present invention may be from 0.001 wt % to 10 wt %, for example. Meanwhile, the amount of the various additives as described above to be added is not particularly limited, and may be appropriately selected.

Examples of the other organic semiconductor include polymer semiconductor compounds. The polymer semiconductor compound as used herein is a polymer compound characterized by exhibiting semiconductor properties, and specific examples thereof include polyacetylene polymer, polydiacetylene polymer, polyparaphenylene polymer, polyaniline polymer, polytriphenylamine polymer, polythiophene polymer, polypyrrole polymer, polyparaphenylenevinylene polymer, polyethylenedioxythiophene polymer, copolymers comprising naphthalenediimide as one component, copolymers comprising perylenediimide as one component, and copolymers comprising diketopyrrolopyrrole as one component. Among these polymer semiconductor compounds, polyaniline polymer, polythiophene polymer, polypyrrole polymer, polyparaphenylenevinylene polymer, copolymers comprising naphthalenediimide as one component, copolymers comprising perylenediimide as one component, copolymers comprising diketopyrrolopyrrole as one component, and the like are preferred.

Additional examples of the other organic semiconductor include low-molecular-weight semiconductor compounds other than the benzobis(thiadiazole) compound of the present invention. The low-molecular-weight semiconductor compound as used herein is a low-molecular-weight compound characterized by exhibiting semiconductor properties, and specific examples thereof include acene derivatives, phenylenevinylene derivatives, triphenylamine derivatives, fluorene derivatives, azaacene derivatives, thienoacene derivatives, thiophene derivatives, benzothiophene derivatives, thienothiophene derivatives, thiazole derivatives, thiazolothiazole derivatives, tetrathiafulvalene derivatives, phthalocyanine derivatives, porphyrin derivatives, naphthalenediimide derivatives, perylenediimide derivatives, benzothiadiazole derivatives, naphthobisthiadiazole derivatives, diketopyrrolopyrrole derivatives, and fullerene derivatives. Among these low-molecular-weight semiconductor compounds, acene derivatives, thienoacene derivatives, thiophene derivatives, thienothiophene derivatives, tetrathiafulvalene derivatives, naphthalenediimide derivatives, perylenediimide derivatives, diketopyrrolopyrrole derivatives, fullerene derivatives, and the like are preferred.

In addition, examples of the other organic semiconductor include organic semiconductors described in Chem. Rev., 2012, Vol. 112, pp. 2208-2267.

The organic semiconductor ink of the present invention may also comprise an insulating polymer compound as an additive component, as necessary. The insulating polymer compound as used herein is synthetic resin, plastic, synthetic rubber, or the like, and specific examples thereof include polyethylene, polypropylene, polyvinyl chloride, polystyrene, polyester, phenol resin, acrylic resin, amide resin, nylon, vinylon, polyisoprene, polybutadiene, acrylic rubber, acrylonitrile rubber, and urethane rubber. The effects of the addition thereof include the optimization of the viscosity of the ink, and the improvement in the film-forming properties of the ink.

In addition, the organic semiconductor ink of the present invention may comprise a conductive polymer compound as an additive component, as necessary. The conductive polymer compound as used herein is a polymer compound characterized by exhibiting electrical conductivity, and specific examples thereof include polyacetylene polymer, polydiacetylene polymer, polyparaphenylene polymer, polyaniline polymer, polytriphenylamine polymer, polythiophene polymer, polypyrrole polymer, polyparaphenylenevinylene polymer, polyethylenedioxythiophene polymer, and a mixture of polyethylenedioxythiophene and polystyrene sulfonic acid (generic name: PEDOT-PSS). Among these conductive polymer compounds, polyacetylene polymer, polyparaphenylene polymer, polyaniline polymer, polytriphenylamine polymer, polythiophene polymer, polypyrrole polymer, polyparaphenylenevinylene polymer, and the like are preferred. The effects of the addition thereof include the improvement in the electric charge mobility, in addition to the optimization of the viscosity of the ink, the improvement in the film-forming properties of the ink, and the like.

The organic semiconductor ink of the present invention may also comprise low-molecular-weight compounds such as the compounds as described below, as necessary, as an additive to control the properties of the ink. Specific examples thereof include aliphatic hydrocarbons such as decane, undecane, dodecane, tridecane, tetradecane, pentadecane, hexadecane, heptadecane, octadecane, nonadecane, and icosane; aliphatic alcohols such as hexanol, heptanol, octanol, nonanol, decanol, undecanol, dodecanol, tridecanol, tetradecanol, pentadecanol, hexadecanol, heptadecanol, octadecanol, nonadecanol, and eicosanol; aliphatic amines such as hexylamine, heptylamine, octylamine, nonylamine, decylamine, undecylamine, dodecylamine, tridecylamine, tetradecylamine, pentadecylamine, hexadecylamine, heptadecylamine, octadecylamine, nonadecylamine, and eicosylamine; aliphatic thiols such as hexanethiol, heptanethiol, octanethiol, nonanethiol, decanethiol, undecanethiol, dodecanethiol, tridecanethiol, tetradecanethiol, pentadecanethiol, hexadecanethiol, heptadecanethiol, octadecanethiol, nonadecanethiol, eicosanethiol, phenylmethanethiol, (2-methylphenyl)methanethiol, (3-methylphenyl)methanethiol, (4-methylphenyl)methanethiol, (2-fluorophenyl)methanethiol, (3-fluorophenyl)methanethiol, (4-fluorophenyl) methanethiol, and 2-phenylethanethiol; and aromatic thiols such as benzenethiol, 2-methylbenzenethiol, 3-methylbenzenethiol, 4-methylbenzenethiol, 2-ethylbenzenethiol, 3-ethylbenzenethiol, 4-ethylbenzenethiol, 2-aminobenzenethiol, 3-aminobenzenethiol, 4-aminobenzenethiol, 2-isopropylbenzenethiol, 3-isopropylbenzenethiol, 4-isopropylbenzenethiol, 2-(dimethylamino)benzenethiol, 3-(dimethylamino)benzenethiol, and 4-(dimethylamino)benzenethiol. The effects of the addition thereof include the improvement in the electric charge mobility, in addition to the optimization of the viscosity of the ink, the improvement in the film-forming properties of the ink, and the like. Among these low-molecular-weight compounds, aliphatic thiols and aromatic thiols are preferred for the purpose of improving the wettability of the ink, and thereby improving the mobility.

A layer, or a thin film of the benzobis(thiadiazole) compound of the present invention may be formed by coating of an organic semiconductor ink comprising the benzobis(thiadiazole) compound. The coating of the organic semiconductor ink comprising the benzobis(thiadiazole) compound of the present invention may be performed by any known methods, for example, spin-coating method, drop-casting method, casting method, Langmuir-Blodgett method, or the like. In addition, any known method commonly known as printing technique may be applied as the coating method, and the printing may be performed by, for example, ink-jet method, screen method, offset method, gravure method, flexographic method, microcontact method, or the like.

A layer, or a thin film comprising the benzobis(thiadiazole) compound of the present invention is formed when the solvent component is removed from the organic semiconductor ink of the present invention after a substrate is coated or printed with the ink. The conditions of the removal of the solvent component may be appropriately selected.

It is preferred that the solvent component be naturally-dried, or air-dried at room temperature, for example. Meanwhile, in the cases where the solvent has a high boiling point, and therefore is hard to remove, the solvent may be removed at around room temperature under a reduced pressure, or alternatively, the solvent may be removed by heating at about 50° C. to about 200° C., or alternatively, the solvent may be removed by the combination of both of them and by heating under a reduced pressure.

In addition, for the purpose of improving the semiconductor properties of the layer or the thin film comprising the benzobis(thiadiazole) compound of the present invention, the layer or the thin film comprising the benzobis(thiadiazole) compound may be subjected to heat treatment. In this case, the conditions of the heat treatment may be appropriately selected, and examples thereof include a process in which the layer or the thin film is heated at a temperature of from about 50° C. to about 250° C. for 0.1 hour to 24 hours. The step may double as the solvent removal step.

In addition, for the purpose of improving the semiconductor properties of the layer or the thin film comprising the benzobis(thiadiazole) compound of the present invention, the layer or the thin film comprising the benzobis(thiadiazole) compound may be subjected to treatment by exposure to a vapor of a solvent.

Examples of the solvent used in this step include water, and various organic solvents, including alcohols such as methanol, ethanol, propanol, ethylene glycol, isobutanol, 2-butanol, 2-ethyl-1-butanol, n-octanol, benzyl alcohol, and terpineol; ketones such as acetone, methyl ethyl ketone, methyl isobutyl ketone, cyclopentanone, cyclohexanone, acetophenone, and isophorone; esters such as methyl acetate, ethyl acetate, butyl acetate, methyl benzoate, butyl benzoate, methyl salicylate, ethyl malonate, 2-ethoxyethane acetate, and 2-methoxy-1-methylethyl acetate; amides such as N,N-dimethylformamide, N,N-dimethylacetamide, N,N-diethylformamide, N-methylpyrrolidone, N-ethylpyrrolidone, and hexamethylphosphoric triamide; ureas such as 1,3-dimethyl-2-imidazolidinone, and 1,3-dimethylimidazolidine-2,4-dione; sulfoxides such as dimethyl sulfoxide, and diethyl sulfoxide; sulfones such as sulfolane; nitriles such as acetonitrile, propionitrile, butyronitrile, and benzonitrile; lactones such as γ-butyrolactone; ethers such as diethyl ether, diisopropyl ether, tetrahydrofuran, 2-methyltetrahydrofuran, dioxane, tert-butyl methyl ether, anisole, phenetole, 1,2-dimethoxybenzene, 1,3-dimethoxybenzene, 1,4-dimethoxybenzene, 1,2-methyl anisole, 1,3-methyl anisole, 1,4-methyl anisole, 1,2-methylene dioxybenzene, 2,3-dihydrobenzofuran, phthalan, octyloxybenzene, diphenyl ether, and ethyl cellosolve; carbonates such as dimethyl carbonate, and 1,2-butylene glycol carbonate; thioethers such as thioanisole, and ethyl phenyl sulfide; aromatic hydrocarbons such as benzene, toluene, xylene, mesitylene, pseudocumene, hemimellitene, durene, isodurene, prehnitene, ethylbenzene, cumene, tert-butyl benzene, cyclohexyl benzene, triisopropyl benzene, phenyl acetylene, indane, methyl indane, indene, tetralin, naphthalene, 1-methyl naphthalene, 2-methyl naphthalene, phenyl octane, and diphenyl methane; phenols such as phenol, 1,2-cresol, 1,3-cresol, 1,4-cresol, 1,2-methoxyphenol, 1,3-methoxyphenol, and 1,4-methoxyphenol; halogenated aromatic hydrocarbons such as chlorobenzene, 1,2-dichlorobenzene, 1,3-dichlorobenzene, 1,2,4-trichlorobenzene, bromobenzene, 1,2-dibromobenzene, 1,3-dibromobenzene, 1,4-dichlorotoluene, 1-chloronaphthalene, 2,4-dichlorotoluene, 2-chloro-1,3-dimethylbenzene, 2-chlorotoluene, 2-chloro-1,4-dimethylbenzene, 4-chloro-1,2-dimethylbenzene, 2,5-dichlorotoluene, m-chlorotoluene, 1-chloro-2,3-dimethylbenzene, 4-(trifluoromethoxy) anisole, and trifluoromethoxy benzene; aliphatic hydrocarbons such as hexane, heptane, octane, cyclohexane, and limonene; halogenated aliphatic hydrocarbons such as dichloromethane, chloroform, carbon tetrachloride, 1,2-dichloroethane, 1,3-dichloropropane, and 1,2-dibromoethane; pyridines such as 2,6-dimethyl pyridine, and 2,6-di-tert-butyl pyridine; and the like. Among them, halogenated aromatic hydrocarbons, aromatic hydrocarbons, and halogenated aliphatic hydrocarbons may be preferably used. These solvents may be used singly, or may be used in combination of two or more.

The solvent vapor exposure treatment step is performed, for example, by leaving the layer or the thin film comprising the benzobis(thiadiazole) compound and a solvent, without the direct contact of the layer or the thin film comprising the benzobis(thiadiazole) compound with the solvent, in an enclosed space. In order to increase the amount of the solvent vapor, the solvent may be heated at a temperature of from about 40° C. to about 150° C. Subsequent to the solvent vapor exposure treatment step, the solvent removal step and subsequent steps may be appropriately selected.

The benzobis(thiadiazole) compound of the present invention has excellent mobility of hole and electron (field-effect mobility), and therefore may be suitably used for organic electronic devices such as an organic thin film transistor, an organic electroluminescence device, a display device, a display, a photovoltaic cell, a RFID tag, and a sensor, for example. In addition, the benzobis(thiadiazole) compound of the present invention may find extensive application in fields such as backlight, optical communication, electrophotography, illuminating light source, recording light source, exposing light source, reading light source, sign, signboard, and interior goods, as well as distribution management, stock management, commodity management, individual identification, and temperature measurement, pressure measurement, load measurement, brightness/darkness measurement, and biological information measurement.

<Organic Thin Film Transistor>

The organic thin film transistor (hereinafter, referred to as "organic TFT") of the present invention will be described below. The organic thin film transistor of the present invention is the one in which an organic semiconductor layer comprises the benzobis(thiadiazole) derivative of the present invention. It is effective to use the benzobis(thiadiazole) derivative of the present invention for a semiconductor layer of an organic TFT, because the orientation direction of the molecule may be readily aligned and high field-effect mobility may be achieved.

Any known structure and any known material may be used for the organic thin film transistor of the present invention, except that the semiconductor layer comprises the benzobis(thiadiazole) derivative of the present invention.

It is preferred that the thickness of the semiconductor layer be thin, as long as the layer does not lose its necessary function. The thickness of the semiconductor layer to perform its necessary function is generally 1 nm to 10 μm, preferably 5 nm to 5 μm, and more preferably 10 nm to 1 μm.

FIG. 1 shows the layer configuration of one example of the organic TFT of the present invention. The organic TFT shown in FIG. 1 (1-1) has a bottom gate-top contact structure, and is formed by laminating a gate electrode 12, a gate insulating layer 13, an organic semiconductor layer 16, and a drain electrode 14 and a source electrode 15, in this order, on a substrate 11.

The organic TFT shown in FIG. 1 (1-2) and the organic TFT shown in FIG. 1 (1-3) have a bottom gate-bottom contact structure and a top gate-bottom contact structure, respectively. From the viewpoint of miniaturization and integration of the transistor device, a bottom gate-bottom contact structure or a top gate-bottom contact structure is generally suitable. Each symbol in FIGS. 1 (1-2) and (1-3) represents the same as in FIG. 1 (1-1).

As the substrate 11, materials such as glass, quartz, silicon and ceramic, and plastic materials may be used, for example.

As described above, the benzobis(thiadiazole) derivative of the present invention is generally soluble in water or an organic solvent, and an organic semiconductor layer may be formed by dissolving the benzobis(thiadiazole) derivative in a solvent to provide an organic semiconductor ink, and applying the ink. An organic semiconductor layer may be formed at a relatively low temperature by a coating method, and therefore a material having a low heat resistance may be used as the substrate 11 if other elements such as an electrode can be formed in an environment wherein the temperature is not high.

Thus, the present invention has allowed the use of various plastic materials having relatively low heat resistance as the substrate 11, and therefore has allowed the use of a material having flexibility. In this case, the substrate 11 may be a flexible substrate, thereby allowing the arrangement of the organic TFT on a curved surface, or the like, as well as on a plane surface, and enhancing the degree of freedom of the design of an organic electronic device comprising an organic TFT in its entirety.

As the gate electrode 12, metals such as gold, platinum, chromium, tungsten, tantalum, nickel, copper, aluminum, silver, magnesium and calcium, and alloys thereof, and materials such as polysilicon, amorphous silicon, graphite, tin-doped indium oxide (ITO), zinc oxide and conductive polymer may be used, for example. The gate electrode 12 may be formed by well-known film-formation methods such as vacuum deposition, electron-beam evaporation deposition, RF sputtering, and printing.

As the gate insulating layer 13, materials such as $SiO_2$, $Si_3N_4$, SiON, $Al_2O_3$, $Ta_2O_5$, amorphous silicon, polyimide resin, polyvinyl phenol resin, polyparaxylylene resin, polystyrene resin, polymethyl methacrylate resin, polyfluorocarbon resin, and divinyltetramethylsiloxane benzocyclobutene resin may be used, for example. The gate insulating layer 13 may be formed by well-known film-formation methods as listed for the gate electrode 12.

In the organic thin film transistor of the present invention, the organic semiconductor layer 16 comprises one or more of the benzobis(thiadiazole) derivatives of the present invention, and may be formed by well-known film-formation methods such as vacuum deposition, and spin-coating, for example. The organic semiconductor layer 16 may be formed by a coating (printing) method, because the benzobis(thiadiazole) compound of the present invention is soluble in an organic solvent. In addition, the organic semiconductor layer 16 may comprise one or more of other organic compounds.

As the drain electrode 14 and the source electrode 15, metals such as gold, platinum, chromium, tungsten, tantalum, nickel, copper, aluminum, silver, magnesium and calcium, and alloys thereof, and materials such as polysilicon, amorphous silicon, graphite, tin-doped indium oxide (ITO), zinc oxide and conductive polymer may be used, for example. The drain electrode 14 and the source electrode 15 may be formed by well-known film-formation methods as listed for the gate electrode 12.

The organic TFT of the present invention generally has good n-type properties, and therefore may be combined with a p-type organic TFT to form the complementary inverter (logic inverting) circuit shown in FIG. 1-1. (The circuit is also referred to as "NOT circuit" sometimes.) In the figure, Vin represents an input signal line, Vout represents an output signal line, Vdd represents a power supply line, and GND represents an earth connection. Additionally, in the figure, the upper transistor is a p-type TFT, and the lower transistor is an n-type TFT.

In order to activate the circuit, an electric potential difference capable of driving the transistors is applied to Vdd relative to GND. When Vin is at the same electrical potential as GND, the p-type TFT is in ON-state and the n-type TFT is in OFF-state, and therefore almost the same electrical potential as Vdd is output to Vout. On the other hand, when Vin is at the same electrical potential as Vdd, the p-type TFT is in OFF-state and the n-type TFT is in ON-state, and the electrical potential of Vout is almost the same as the electrical potential of GND. Thus the electrical potential opposite to Vin is output to Vout, and therefore the circuit is referred to as "inverting circuit". The circuit is a basic circuit which constitutes a digital logic circuit. The circuit is preferably used in view of the construction of a logic circuit with a low electric power consumption, because only a small electric current flows only at the moment of logic inversion.

The organic TFT of the present invention, which has good n-type properties, may also be combined with a p-type organic TFT to form a NAND circuit, a NOR circuit, a flip-flop circuit, or the like. These circuits may be combined and integrated based on a design according to the purpose to form an integrated logic circuit, which may be applied to a display circuit, a RFID circuit, a sensor circuit, and the like.

<Organic Electroluminescence Device>

The organic electroluminescence device (hereinafter, referred to as "organic EL device") of the present invention will be described below. The organic EL device of the present invention is the one in which a hole transport layer and/or an electron transport layer comprise the benzobis(thiadiazole) derivative of the present invention. It is effective to use the benzobis(thiadiazole) derivative of the present invention for a hole transport layer and/or an electron transport layer of an organic EL device, because the benzobis(thiadiazole) derivative has excellent hole and electron transport properties.

Any known structure and any known material may be used for the organic EL device of the present invention, except that the hole transport layer and/or the electron transport layer comprises the benzobis(thiadiazole) derivative of the present invention.

The organic EL device is a device in which at least one or more organic compound layers, including a luminescent layer, are formed between an anode and a cathode. The organic EL device is typically configured to have a device structure of (anode/hole transport layer/luminescent layer/cathode), (anode/luminescent layer/electron transport layer/cathode), (anode/hole transport layer/luminescent layer/electron transport layer/cathode), or the like.

Figure 2:
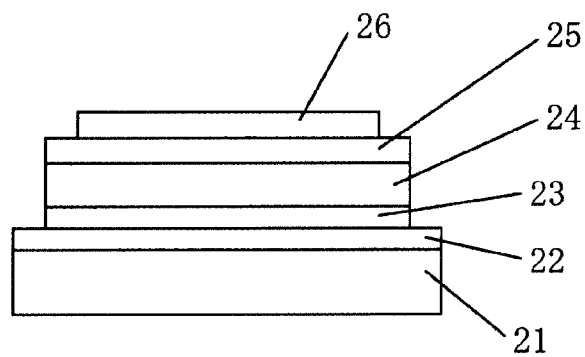
FIG. 2 is a longitudinal sectional view illustrating the layer configuration of one example of the organic EL device of the present invention.

FIG. 2 shows the layer configuration of one example of the organic EL device of the present invention. The organic EL device shown in FIG. 2 is formed by laminating an anode 22, a hole transport layer 23, a luminescent layer 24, an electron transport layer 25, and a cathode 26, in this order, on a substrate 21.

When a predetermined direct voltage is applied between the anode 22 and the cathode 26 of the organic EL device configured as described above, light with high intensity is emitted from the luminescent layer 24. The mechanism of the light emission is considered as follows.

Specifically, when a predetermined direct voltage is applied between the two layers as described above, holes which flow from the anode 22 to the hole transport layer 23 are transported to the luminescent layer 24. Meanwhile, electrons which are injected from the cathode 26 to the electron transport layer 25 are transported to the luminescent layer 24. In the luminescent layer 24, electrons diffuse and migrate, and recombine with holes to achieve a state of electrically neutralization. When the recombination occurs, a certain energy is released, and the organic luminescent material in the luminescent layer 24 is excited to the excitation state by the energy. When the material returns to the ground state from the excited state, light is emitted.

When the benzobis(thiadiazole) derivative of the present invention, which has high field-effect mobility, is used for the hole transport layer 23 and/or the electron transport layer 25 of the organic EL device, holes and electrons may be efficiently injected into the luminescent layer, and therefore the luminous efficiency may be enhanced.

As the substrate 21, transparent materials such as glass and plastics may be used, for example.

As the anode 22, a light-transmission material is generally used. Specifically, tin-doped indium oxide (ITO), indium oxide, tin oxide, and indium oxide-zinc oxide alloy may be preferably used. A thin film of metal such as gold, platinum, silver, and magnesium alloy may also be used. In addition, organic materials such as polyaniline, polythiophene, polypyrrole, and derivatives thereof may also be used. The anode 22 may be formed by well-known film-formation methods such as vacuum deposition, electron-beam evaporation deposition, RF sputtering, and coating (printing).

As the cathode 26, alkali metals such as Li, K and Na, and alkali-earth metals such as Mg and Ca, which have small work function, may be preferably used, from the viewpoint of the electron injection properties. In addition, Al which is stable, and the like may also be preferably used. In order to achieve both stability and electron injection properties, the cathode may be a layer comprising two or more materials, and the materials are described in detail, for example, in JP-A-H02-15595, JP-A-H05-121172, etc. The cathode 26 may be formed by well-known film-formation methods such as vacuum deposition, electron-beam evaporation deposition, and RF sputtering.

As the luminescent layer 24, a host material such as quinolinol complex and aromatic amine which is doped with (doping) a coloring material such as coumarin derivatives, DCM, quinacridone and rubrene may be preferably used. The luminescent layer 24 may also be formed from a host material only. In addition, a high-efficiency organic EL device may be produced by forming the luminescent layer 24 doped with iridium metal complex. The luminescent layer 24 may be formed by well-known film-formation methods such as vacuum deposition, sputtering, and coating (printing).

The benzobis(thiadiazole) derivative of the present invention is used for the hole transport layer 23 and/or the electron transport layer 25. The benzobis(thiadiazole) derivative may be used singly, or may be used in combination of two or more. In addition, the hole transport layer 23 and the electron transport layer 25 may comprise one or more of other compounds.

In the cases where the benzobis(thiadiazole) derivative of the present invention is not used for the hole transport layer 23, materials such as N,N'-bis(3-methylphenyl)-N,N'-bis(phenyl)-benzidine (TPD), N,N'-bis(naphthalene-1-yl)-N,N'-bis(phenyl)-2,2'-dimethyl benzidine (α-NPD), and 2,2-bis(3-(N,N-di-p-tolylamino)phenyl)biphenyl (3DTAPBP), for example, may be used as the hole transport layer 23. In the cases where the benzobis(thiadiazole) derivative of the present invention is not used for the electron transport layer 25, materials such as 2-(4-biphenyl)-5-(4-tert-butylphenyl)-1,3,4-oxazole (PBD), 1,3-bis[2-(4-tert-butylphenyl)-1,3,4-oxadiazo-5-yl]benzene (OXD-7), and 2,2',2"-(1,3,5-benzinetriyl)-tris(1-phenyl-1-H-benzimidazole) (TPBi), for example, may be used as the electron transport layer 25.

As the method of film-formation of the hole transport layer 23 and the electron transport layer 25, the methods as listed for the method of film-formation of the luminescent layer 24 may be used. In addition, the hole transport layer 23 and the electron transport layer 25 may be formed by a coating (printing) method, because the benzobis(thiadiazole) compound of the present invention is soluble in an organic solvent. The thicknesses of the hole transport layer 23 and the electron transport layer 25 may be appropriately selected, and may be generally 1 nm to 1 μm, preferably 1 nm to 100 nm.

The organic luminescence device of the present invention may be configured to comprise an electron injection layer, a hole injection layer, an electron blocking layer, a hole blocking layer, a protective layer, and the like, in addition to the layers as described above. These layers may be formed by the methods as listed for the method of film-formation of the luminescent layer 24.

<Display Device>

The display device of the present invention will be described below. The display device of the present invention is the one in which the driving and lighting of the organic EL device is controlled by the organic TFT, and the organic TFT is the organic TFT of the present invention as described above, or the organic EL device is the organic EL device of the present invention as described above. As for the display device of the present invention, it is preferred that the organic TFT is the organic TFT of the present invention, and the organic EL device is the organic EL device of the present invention.

Figure 3:
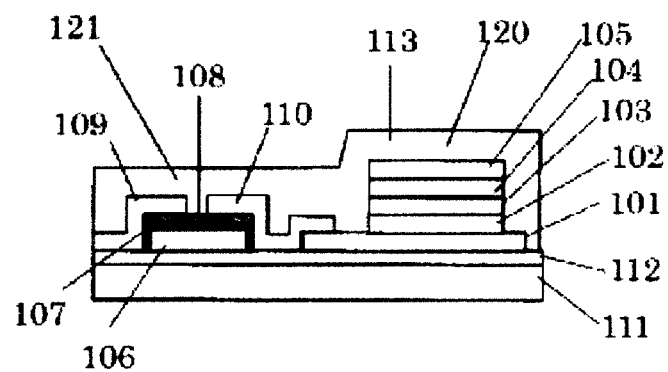
FIG. 3 is a longitudinal sectional view illustrating the layer configuration of one example of the display device of the present invention.

FIG. 3 shows one example of the display device of the present invention. The display device shown in FIG. 3 comprises an organic EL device 120 comprising a cathode 101, an electron transport layer 102, a luminescent layer 103, a hole transport layer 104 and an anode 105, and an organic TFT 121 comprising a gate electrode 106, a gate insulating layer 107, an organic semiconductor layer 108, a source electrode 109 and a drain electrode 110 on a substrate 111 with a barrier layer 112 therebetween. Additionally, the upper part of the layer structure is coated with a protective film 113.

The display device has a structure in which the cathode 101 of the organic EL device 120 (electrode closer to the substrate 111) is electrically connected to the drain electrode 110 of the organic TFT 121. When a voltage is applied to the gate electrode 106, an electric current flows between the source electrode and the drain electrode, and the organic EL device 120 emits light. In addition, the display device may have a structure in which the anode is electrically connected to the drain electrode of the organic TFT.

In the present invention, it is preferred that the organic TFT, and the organic EL device which is driven/lighted by the organic TFT are the organic TFT of the present invention, and the organic EL device of the present invention, both of which comprise the benzobis(thiadiazole) derivative of the present invention, as described above. However, one of them may comprise no benzobis(thiadiazole) derivative of the present invention, and may be formed from a known material and have a known structure.

In addition, an active-matrix organic EL display may be formed by arranging devices (pixels) as shown in FIG. 3, in which the organic TFT for switching and the organic EL device are combined, in a matrix form. The active-matrix organic EL display has the advantages of having a low possibility of the application of unnecessary voltage to a non-selected point even in the case of a great number of pixels; having a low possibility of the efficiency reduction and deterioration even in high-duty operation; and having excellent response properties.

Any known structure and any known material may be used for the display device (display) of the present invention, except that the organic TFT of the present invention and/or the organic EL device of the present invention are employed. The display device may be produced by any known method.

<Photovoltaic Cell>

The photovoltaic cell (hereinafter, referred to as "organic PV device") of the present invention will be described below. The organic PV device of the present invention is the one in which one or more of a charge separation layer comprising a hole transport material and an electron transport material, a hole transport layer, and an electron transport layer comprise the benzobis(thiadiazole) derivative of the present invention. It is effective to use the benzobis(thiadiazole) derivative of the present invention for a charge separation layer and/or a hole transport layer and/or an electron transport layer of an organic PV device, because the benzobis(thiadiazole) derivative has excellent hole and electron transport properties.

Any known structure and any known material may be used for the organic PV device of the present invention, except that one or more of the charge separation layer, the hole transport layer and the electron transport layer comprises the benzobis(thiadiazole) derivative of the present invention.

The organic PV device is a device in which at least one or more organic compound layers, including a charge separation layer, are formed between an anode and a cathode. The organic PV device is typically configured to have a device structure of (anode/charge separation layer/cathode), (anode/charge separation layer/electron transport layer/cathode), (anode/hole transport layer/charge separation layer/electron transport layer/cathode), or the like.

Figure 4:
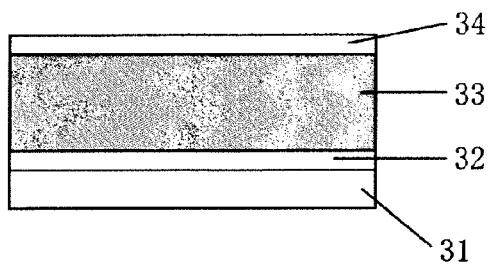
FIG. 4 is a longitudinal sectional view illustrating the layer configuration of one example of the photovoltaic cell of the present invention.

FIG. 4 shows the layer configuration of one example of the organic PV device of the present invention. The organic PV device shown in FIG. 4 is formed by laminating an anode 32, a charge separation layer 33, and a cathode 34, in this order, on a substrate 31.

When the organic PV device configured as described above is irradiated with light, holes and electrons are generated in the charge separation layer 33, and an electric current is taken out if the anode 32 is connected to the cathode 34. The mechanism of the generation of electricity is considered as follows.

Specifically, when the charge separation layer 33 is irradiated with light, the light is absorbed, and the organic molecule is excited by the energy to provide charge separation, and generate holes and electrons. The holes are transported to the anode 32 by the hole transport material in the charge separation layer 33, and the electrons are transported to the cathode 34 by the electron transport material in the charge separation layer 33 and taken out to the external circuit.

When the benzobis(thiadiazole) derivative of the present invention, which has high field-effect mobility, is used for the charge separation layer 33 of the organic PV device, holes and electrons may be efficiently taken out from the charge separation layer 33, and therefore the electricity generation efficiency may be enhanced. In addition, when the benzobis(thiadiazole) derivative of the present invention is used for the hole transport layer and for the electron transport layer, holes may be efficiently transported to the anode and electrons may be efficiently transported to the cathode, respectively, and therefore the electricity generation efficiency may be enhanced.

As the substrate 31, transparent materials such as glass and plastics may be used, for example.

As the anode 32, a light-transmission material is generally used. Specifically, tin-doped indium oxide (ITO), indium oxide, tin oxide, and indium oxide-zinc oxide alloy may be preferably used. A thin film of metal such as gold, platinum, silver, and magnesium alloy may also be used. In addition, organic materials such as polyaniline, polythiophene, polypyrrole, and derivatives thereof may also be used. The anode 32 may be formed by well-known film-formation methods such as vacuum deposition, electron-beam evaporation deposition, RF sputtering, and coating (printing).

As the cathode 34, alkali metals such as Li, K and Na, and alkali-earth metals such as Mg and Ca, which have small work function, may be preferably used, from the viewpoint of the electron taking-out properties. In addition, Al which is stable, and the like may also be preferably used. In order to achieve both stability and electron taking-out properties, the cathode may be a layer comprising two or more materials. The cathode 34 may be formed by well-known film-formation methods such as vacuum deposition, electron-beam evaporation deposition, and RF sputtering.

The benzobis(thiadiazole) derivative of the present invention is used for the charge separation layer 33. The benzobis(thiadiazole) derivative may be used singly, or may be used in combination of two or more. In addition, the charge separation layer 33 may comprise one or more of other compounds.

Examples of the materials constituting the charge separation layer, together with the benzobis(thiadiazole) derivative, include poly(3-hexylthiophene-2,5-diyl) (P3HT) and poly[2-methoxy-5-(2-ethylhexyloxy)-1,4-phenylenevinylene] (MEH-PPV), as the hole transport material, and fullerene C60, (6,6)-phenyl-C61-butyric acid methyl ester (C61-PCBM), fullerene C70 and (6,6)-phenyl-C71-butyric acid methyl ester (C71-PCBM), as the electron transport material.

The charge separation layer 33 may be formed by well-known film-formation methods such as vacuum deposition, sputtering, and coating (printing). In addition, the charge separation layer 33 may be formed by a coating (printing) method, because the benzobis(thiadiazole) compound of the present invention is soluble in an organic solvent. The thickness of the charge separation layer 33 may be appropriately selected, and may be generally 5 nm to 1 μm, preferably 10 nm to 500 nm.

The organic PV device of the present invention may further comprise a hole transport layer and/or an electron transport layer. The benzobis(thiadiazole) derivative of the present invention may also be preferably used for these layers. The benzobis(thiadiazole) derivative may be used singly, or may be used in combination of two or more. In addition, the hole transport layer and the electron transport layer may comprise one or more of other compounds.

In the cases where the benzobis(thiadiazole) derivative of the present invention is not used for the hole transport layer or the electron transport layer, materials such as poly(3,4-ethylenedioxythiophene)-poly(styrenesulfonate) (PEDOT-PSS), for example, may be used as the hole transport layer, and materials such as 2,9-dimethyl-4,7-diphenyl-1,10-phenanthroline (BCP), for example, may be used as the electron transport layer. As the method of film-formation of the hole transport layer and the electron transport layer, the methods as listed for the method of film-formation of the charge separation layer 33 may be used. The thicknesses of the hole transport layer and the electron transport layer may be appropriately selected, and may be generally 1 nm to 1 μm, preferably 1 nm to 100 nm.

<RFID Tag>

The RFID tag (Radio Frequency Identification tag) of the present invention will be described below. The RFID tag of the present invention is activated by the use of an organic TFT, and the organic TFT is the organic TFT of the present invention as described above (an organic TFT which comprises an organic semiconductor layer comprising the benzobis(thiadiazole) derivative of the present invention).

The RFID tag is an electronic device comprising an integrated circuit section (hereinafter, referred to as "IC section") and an antenna section, wherein the ID, i.e. personal identification information, or the like, stored in the IC section can be wirelessly communicated with a reader-writer device via the antenna section, and the information stored in the IC section can be read out and conversely information can be written to the IC section by the reader-writer device in a non-contact manner. Article information management, distribution management, individual authentication, and the like can be performed when an RFID tag is stuck on an article or printed on an article, and an RFID tag is applied to various fields. The responsiveness of an RFID tag may be enhanced when the benzobis(thiadiazole) derivative of the present invention is used for the semiconductor layer of the organic TFT constituting the IC section of the RFID tag, because the high field-effect mobility may be achieved.

Any known structure and any known material, which is described in Solid-State Electronics 84 (2013) 167-178, for example, may be used for the RFID tag of the present invention, except that the organic TFT of the present invention is employed. The RFID tag may be produced by any known method.

The IC section of the RFID tag generally comprises a plurality of organic TFTs. In that case, among a plurality of organic TFTs, all of the organic TFTs may be the organic TFTs of the present invention, or alternatively, a part of the organic TFTs may be the organic TFTs of the present invention and a part of the organic TFTs may be organic TFTs which do not comprise the benzobis(thiadiazole) derivative of the present invention.

<Sensor>

The sensor of the present invention will be described below. The sensor of the present invention is activated by the use of an organic TFT, and the organic TFT is the organic TFT of the present invention as described above (an organic TFT which comprises an organic semiconductor layer comprising the benzobis(thiadiazole) derivative of the present invention).

The sensor may be applied to a system wherein the physical state of the organic semiconductor constituting the organic TFT is changed by an external stimulus applied to the organic TFT, and thereby the electric current and/or the electric voltage derived from the organic TFT are changed. Examples thereof include a temperature sensor and a light sensor, which detect the temperature or the light by the change of the physical state of the organic semiconductor constituting the organic TFT when the organic semiconductor is subjected to heat or light. Examples thereof also include a bending-stress sensor and a pressure sensor, which detect the stress or the pressure by the change of the physical state of the organic semiconductor constituting the organic TFT when the organic semiconductor is subjected to stress. Examples thereof also include a chemical sensor, which detects a certain chemical substance, for example, water molecule, oxygen molecule, or the like, by the change of the physical state of the organic semiconductor constituting the organic TFT when the organic semiconductor is influenced by the chemical substance. Additionally, the present invention may also be applied to a chemical sensor, which detects a certain chemical substance by the change of the electric current and/or the electric voltage derived from the organic TFT which occurs when the metal electrode constituting the organic TFT is influenced by the chemical substance. The responsiveness or the dynamic range may be enhanced when the benzobis(thiadiazole) derivative of the present invention is used for the semiconductor layer of the organic TFT constituting the sensor, because the high field-effect mobility may be achieved.

Any known structure and any known material may be used for the sensor of the present invention, except that the organic TFT of the present invention is employed. The sensor may be produced by any known method.

The sensor may comprise a single organic TFT, or may comprise a plurality of organic TFTs, which depends on the intended use. In the case where the sensor comprises a plurality of organic TFTs, among the organic TFTs, all of the organic TFTs may be the organic TFTs of the present invention, or alternatively, a part of the organic TFTs may be the organic TFTs of the present invention and a part of the organic TFTs may be organic TFTs which do not comprise the benzobis(thiadiazole) derivative of the present invention.

In the various organic electronic devices of the present invention (the organic electronic devices, or organic thin film devices, which comprise the benzobis(thiadiazole) derivative of the present invention) as described above, a plastic substrate may be used as the substrate. The plastic to be used as the substrate may preferably have excellent heat resistance, dimensional stability, solvent resistance, electrical insulation property, processability, low air permeability, and low hygroscopicity. Examples of the plastic include polyethylene terephthalate, polyethylene naphthalate, polystyrene, polycarbonate, polyacrylate, and polyimide.

In the case of plastic substrate, it is preferred that a moisture-permeation blocking layer (gas barrier layer) be formed on the electrode side of the substrate, or the side opposite to the electrode, or on both sides. As the material constituting the moisture-permeation blocking layer, inorganic materials such as silicon nitride and silicon oxide may be preferably used. The moisture-permeation blocking layer may be formed by well-known film-formation methods such as RF sputtering. In addition, a hard-coating layer or an undercoating layer may be formed as necessary.

In addition, for the purpose of hydrophobizing the surface of the substrate, the substrate in the organic electronic device of the present invention may be subjected to a substrate surface modification treatment, for example, the substrate may be treated with hexamethyldisilazane, coated with a resin such as polystyrene, subjected to a UV ozone treatment, or the like.

EXAMPLES

The present invention will be more specifically described below with reference to the Examples. However, the scope of the present invention should not be limited to these Examples.

[Evaluation of Solubility]

The evaluation of the solubility of the synthesized compound was conducted by the following method.

About 2-3 mg of the compound was precisely weighed, and each solvent was added to the compound such that a predetermined concentration of the solute (0.5 wt %, 0.3 wt %, 0.2 wt %, 0.1 wt %, 0.05 wt %, or 0.03 wt %) was reached. The resultant mixture was stirred for 30 minutes at a predetermined temperature, and then it was evaluated by visual appearance observation whether or not the solute (synthesized compound) was completely dissolved in the solvent, which was the result of the evaluation of the solubility. As the solvent, chloroform (boiling point 61° C.), toluene (boiling point 111° C.), xylene (boiling point 144° C.), mesitylene (boiling point 165° C.), chlorobenzene (boiling point 130° C.), para-chlorotoluene (boiling point 162° C.), and ortho-dichlorobenzene (boiling point 181° C.) were used.

[Production/Evaluation of Organic TFT]

In the Examples as described below, a bottom gate-top contact device was produced on a silicon substrate in accordance with "Procedure for Producing organic TFT" as described below and the evaluation of the device was conducted, unless otherwise described in each section.

(Procedure for Producing Organic TFT)

In the case where the production of the organic semiconductor layer by spin-coating method was carried out therein, an organic TFT was produced in accordance with the following procedure:

(Production of TFT substrate)-(Production of organic semiconductor layer by spin-coating method)-(Production of source electrode and drain electrode) or (Production of TFT substrate)-(Surface modification of TFT substrate)-(Production of organic semiconductor layer by spin-coating method)-(Production of source electrode and drain electrode).

In the case where the production of the organic semiconductor layer by drop-casting method was carried out therein, an organic TFT was produced in accordance with the following procedure:

(Production of TFT substrate)-(Production of organic semiconductor layer by drop-casting method)-(Production of source electrode and drain electrode) or (Production of TFT substrate)-(Surface modification of TFT substrate)-(Production of organic semiconductor layer by drop-casting method)-(Production of source electrode and drain electrode).

In the case where the production of the organic semiconductor layer by vacuum deposition method was carried out therein, an organic TFT was produced in accordance with the following procedure:

(Production of TFT substrate)-(Production of organic semiconductor layer by vacuum deposition method)-(Production of source electrode and drain electrode) or (Production of TFT substrate)-(Surface modification of TFT substrate)-(Production of organic semiconductor layer by vacuum deposition method)-(Production of source electrode and drain electrode).

Meanwhile, in the Examples as described below, when a bottom gate-bottom contact device was produced, in the case where the production of the organic semiconductor layer by drop-casting method was carried out therein, a bottom gate-bottom contact type organic TFT was produced in accordance with the following procedure:

(Production of TFT substrate)-(Production of source electrode and drain electrode)-(Production of organic semiconductor layer by drop-casting method) or (Production of TFT substrate)-(Surface modification of TFT substrate)-(Production of source electrode and drain electrode)-(Production of organic semiconductor layer by drop-casting method).

(Production of TFT Substrate)

A commercially available silicon wafer having a thermally grown silicon oxide with a film thickness of 200 nm formed on the surface was used as the substrate for the organic TFT. The silicon wafer had low resistance, and also functioned as the gate electrode of the organic TFT. In addition, the silicon oxide film was used as the gate insulating film. The silicon wafer was washed with a mixture solution of hydrogen peroxide water and sulfuric acid, and the surface was cleaned by UV ozone treatment immediately before the silicon wafer was used in the subsequent step. The substrate thus treated is referred to as "bare substrate" hereinafter.

(Surface Modification of TFT Substrate)

The "bare substrate" was immersed and left still in hexamethyldisilazane, which was commercially available, for 12 hours or more, so that the surface of the substrate was modified. The substrate thus treated is referred to as "HMDS-modified substrate" hereinafter.

A solution prepared by dissolving 0.5 wt % polystyrene, which was commercially available, in xylene was applied onto the "bare substrate" by spin-coating, and then heated at 150° C. for 1 hour, so that a polystyrene thin film with a thickness of about 20 nm was formed on the surface of the substrate. The substrate thus treated is referred to as "PS substrate" hereinafter.

A mixture solution of polyvinylphenol and melamine in propylene glycol monomethyl ether acetate as the solvent, which was prepared from polyvinylphenol and melamine, which were commercially available, was applied onto the "bare substrate" by spin-coating, and then heated at 180° C. for 1 hour, so that a polyvinylphenol-melamine thin film with a thickness of about 20 nm was formed on the surface of the substrate. The substrate thus treated is referred to as "PVP substrate" hereinafter.

A CYCLOTENE™ solution, which was commercially available from Dow Electronic Materials, was applied onto the "bare substrate" by spin-coating, and then heated sequentially under the conditions of 150° C. for 6 minutes, 210° C. for 40 minutes, and 300° C. for 1 hour, so that a divinyltetramethylsiloxane benzocyclobutene resin thin film with a thickness of about 20 nm was formed on the surface of the substrate. The substrate thus treated is referred to as "CYC substrate" hereinafter.

(Production of Organic Semiconductor Layer by Spin-coating Method)

With the use of the synthesized compound (organic semiconductor compound), a solution (organic semiconductor ink) with the solvent and the solute concentration described in each section was prepared, and with the use of the semiconductor ink, an organic semiconductor layer with a thickness of about 20-50 nm was formed on the substrate described in each section by spin-coating. And then, the organic semiconductor layer was subjected to thermal annealing under the conditions described in each section, as necessary. The spin-coating and the thermal annealing were performed in nitrogen atmosphere, unless otherwise described in each section.

(Production of Organic Semiconductor Layer by Drop-casting Method)

With the use of a solution prepared by dissolving 1 wt % Teflon® AF1600X in Fluorinert™ FC-43, which was commercially available, a partition wall pattern to receive a semiconductor ink in the next step was formed on the "PVP substrate", and then heated at 100° C. for 30 minutes, so that a partition wall was formed.

With the use of the synthesized compound (organic semiconductor compound), a solution (organic semiconductor ink) with the solvent and the solute concentration described in each section was prepared, and the semiconductor ink was dropped into the partition wall which was formed in the step as described above, and then dried at 60° C., so that an organic semiconductor layer was formed. The partition wall and the organic semiconductor layer were formed in the atmosphere, unless otherwise described in each section. And then, the organic semiconductor layer was subjected to thermal annealing in nitrogen atmosphere under the conditions described in each section, as necessary.

(Production of Organic Semiconductor Layer by Vacuum Deposition Method)

With the use of the synthesized compound (organic semiconductor compound), an organic semiconductor layer with a thickness of about 50 nm was formed on the substrate described in each section by vacuum deposition. During the formation of the organic semiconductor layer, the pressure in the chamber of the vapor deposition apparatus was $2\times10^{-5}$-$6\times10^{-4}$ Pa, and the organic semiconductor compound was contained in a crucible and heated by a filament wound around the crucible, to perform vapor deposition. The deposition rate was 0.2±0.1 Å/sec.

(Production of Source Electrode and Drain Electrode)

A gold film was formed on the organic semiconductor layer by vacuum deposition, using a metal mask, to form a source electrode and a drain electrode. The channel width and the channel length of the organic TFT were 1000 μm and 70 μm, respectively. The thickness of the electrode layer was about 50 nm.

(Evaluation of Field-effect Mobility)

The field-effect mobility (μ) was determined from the result of the measurement of the transfer characteristics of the produced organic TFT using a semiconductor characterization system, Model 4200-SCS from KEITHLEY Inc.

The field-effect mobility (μ) can be calculated using the following formula (Formula A), which represents the drain current $I_d$.

$$I_d = (W/2L)\mu C_i(V_g-V_t)^2 \qquad \text{(Formula A)}$$

wherein L and W represent the channel length and the channel width, respectively, and $C_i$ represents the capacity of the insulating layer per unit area, and $V_g$ represents the gate voltage and $V_t$ represents the threshold voltage. The measurement of the transfer characteristics reveals the threshold voltage and the drain current at a certain gate voltage, and therefore the field-effect mobility can be determined therefrom.

Example 1

Synthesis of Compound (C1) (Compound of the Formula (3); 4,8-bis[5-(3-(trifluoromethoxy)phenyl)thiophene-2-yl]benzo[1,2-c:4,5-c']bis[1,2,5]thiadiazole)

(Step 1-1: Synthesis of Compound (C1a))

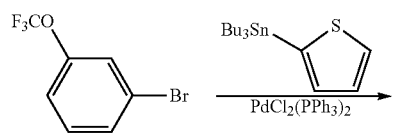

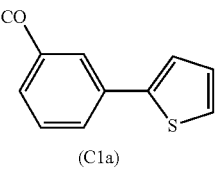

Into a 300-mL glass reaction vessel equipped with a stirring apparatus were placed 14.0 g (58 mmol) of 1-bromo-3-(trifluoromethoxy)benzene, 4.1 g (5.8 mmol) of dichlorobis(triphenylphosphine) palladium (II), 28.2 g (76 mmol) of 2-(tributyltin)thiophene, and 140 mL of anhydrous toluene. The mixture was reacted at an internal temperature of about 100° C. for 4 hours. After the completion of the reaction, the solvent was concentrated, and then 400 mL of hexane was added to the concentrate, and the mixture was filtered through [silica gel:potassium carbonate=90:10 (wt %)]. The filtrate was concentrated, and the concentrate was subjected to distillation under a reduced pressure, to provide 17.3 g of a colorless liquid. Subsequently, 8.0 g of the distillate was purified by silica gel column chromatography, to provide 5.0 g of Compound (C1a) in the form of a colorless liquid.

The properties of Compound (C1a) were as follows. Unless otherwise specified hereinafter, the measurement was carried out at room temperature (25° C.).

$^1$H-NMR (400MHz; CDCl$_3$; δ(ppm)); 7.07-7.11 (m, 1H), 7.10-7.16 (m, 1H), 7.29-7.35 (m, 2H), 7.35-7.42 (m, 1H), 7.42-7.47 (m, 1H), 7.50-7.55 (m, 1H)

(Step 1-2: Synthesis of Compound (C1b))

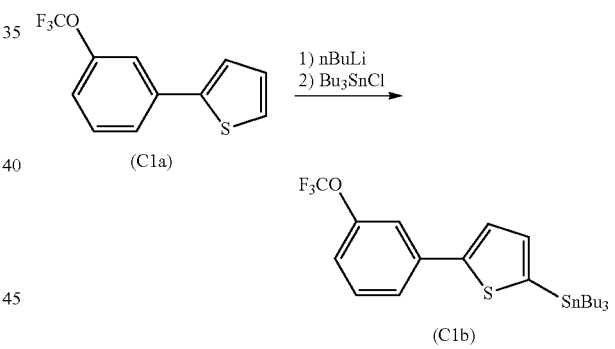

Into a 100-mL glass reaction vessel equipped with a stirring apparatus were placed 5.0 g (20.5 mmol) of Compound (C1a), and 50 mL of anhydrous tetrahydrofuran. While the internal temperature was kept at –60° C. or lower, 16.6 mL (27 mmol) of 1.6 mol/L solution of n-butyl lithium in hexane was added to the mixture. The mixture was stirred at the same temperature for 30 minutes, and then 9.0 g (27 mmol) of tributyl tin chloride was added to the mixture at the same temperature. The temperature of the mixture was increased to room temperature, and the mixture was stirred overnight. A THF-water mixture solution was added to the reaction solution to stop the reaction, and then the solvent was distilled off. Subsequently, hexane was added to the concentrate, and the mixture was filtered through [silica gel:potassium carbonate=90:10 (wt %)]. The filtrate was concentrated, and the concentrate was purified by reverse phase silica gel column chromatography, to provide 10.0 g of Compound (C1b) in the form of a pale yellow liquid.

The properties of Compound (C1b) were as follows.
$^1$H-NMR (400MHz; CDCl$_3$; δ(ppm)); 0.86-0.95 (m, 9H), 1.03-1.24 (m, 6H), 1.26-1.42 (m, 6H), 1.48-1.72 (m, 6H), 7.06-7.12 (m, 1H), 7.10-7.20 (m, 1H), 7.33-7.41 (m, 1H), 7.42-7.48 (m, 2H), 7.51-7.58 (m, 1H)

(Step 1-3: Synthesis of Compound (C1))

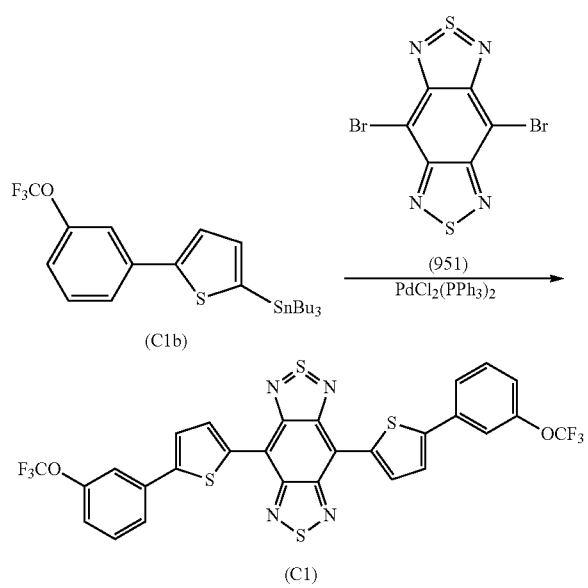

Into a 100-mL glass reaction vessel equipped with a stirring apparatus were placed 8.5 g (16 mmol) of Compound (C1b), 1.4 g (4.0 mmol) of dibromobenzobisthiadiazole (Compound (951)) which was synthesized by reference to the method described in Organic Lett., Vol. 12, No. 15, p.3340 (2010), 0.84 g (1.2 mmol) of dichlorobis(triphenylphosphine) palladium (II), and 50 mL of anhydrous toluene. The mixture was reacted at an internal temperature of about 100° C. for 6 hours. Subsequently, the reaction solution was filtered, to provide 2.1 g of a crude product. A portion of the crude product was purified by sublimation, to provide 0.25 g of Compound (C1) in the form of a green solid.

The properties of Compound (C1) were as follows.

$^1$H-NMR (400MHz; 1,2-dichlorobenzene-$d_4$: 140° C.; δ(ppm)); 7.01-7.12 (m, 2H), 7.22-7.34 (m, 2H), 7.41-7.49 (m, 2H), 7.55-7.66 (m, 4H), 8.97-9.06 (m, 2H) TOF-HRMS (ASAP−); 677.9750 (M−); Calcd. 677.9747

The solubility of Compound (C1) was evaluated, and 0.1 wt % of Compound (C1) was completely dissolved in toluene at 100° C. Also, 0.1 wt % of Compound (C1) was completely dissolved in mesitylene at 80° C. Also, 0.3 wt % of Compound (C1) was completely dissolved in mesitylene at 130° C.

Example 2

Synthesis of Compound (C2) (Compound of the Formula (2); 4,8-bis[5-(3-(trifluoromethyl)phenyl)thiophene-2-yl]benzo[1,2-c:4,5-c']bis[1,2,5]thiadiazole)

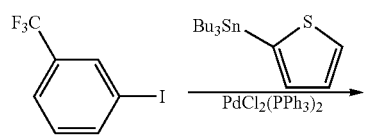

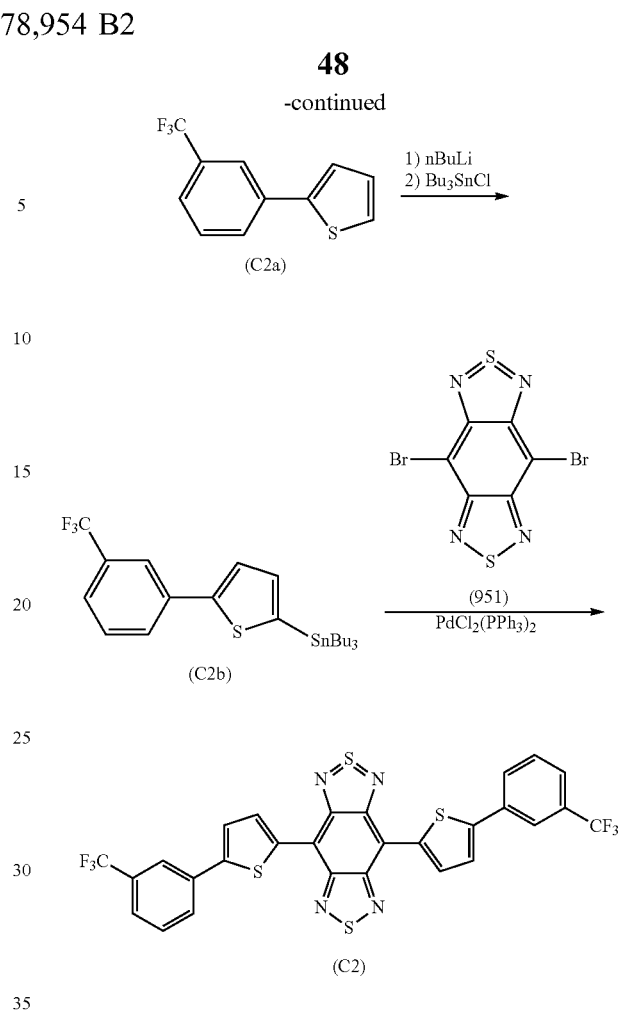

Compound (C2) was obtained in the same way as in Example 1, except that 1-iodo-3-(trifluoromethyl)benzene was used instead of 1-bromo-3-(trifluoromethoxy)benzene.

The properties of Compound (C2a) were as follows.

$^1$H-NMR (400MHz; CDCl$_3$; δ(ppm)); 7.10-7.12 (m, 1H), 7.33-7.38 (m, 2H), 7.47-7.54 (m, 2H), 7.76-7.78 (m, 1H), 7.84 (brs, 1H)

The properties of Compound (C2b) were as follows.

$^1$H-NMR (400MHz; CDCl$_3$; δ(ppm)); 0.86-0.95 (m, 9H), 1.03-1.24 (m, 6H), 1.26-1.42 (m, 6H), 1.48-1.72 (m, 6H), 7.15-7.16 (m, 1H), 7.46-7.48 (m, 3H), 7.77-7.79 (m, 1H), 7.85 (brs, 1H)

The properties of Compound (C2) were as follows.

$^1$H-NMR (400MHz; 1,2-dichlorobenzene-$d_4$: 100° C.; δ(ppm)); 7.57-7.61 (m, 2H), 7.66-7.68 (m, 2H), 7.71-7.72 (m, 2H), 8.05-8.07 (m, 2H), 8.25 (brs, 2H), 9.28-9.29 (m, 2H)

The solubility of Compound (C2) at 25° C. was evaluated, and 0.03 wt % of Compound (C2) was completely dissolved in toluene at 25° C. and also completely dissolved in mesitylene at 25° C. Also, 0.1 wt % of Compound (C2) was completely dissolved in toluene at 100° C. Also, 0.1 wt % of Compound (C2) was completely dissolved in all of mesitylene, chlorobenzene, and ortho-dichlorobenzene at 80° C. Also, 0.3 wt % of Compound (C2) was completely dissolved in chlorobenzene at 100° C. Also, 0.5 wt % of Compound (C2) was completely dissolved in ortho-dichlorobenzene at 100° C.

Comparative Example 1

Synthesis of Compound (RC1) (4,8-bis[5-(4-(trifluoromethoxy)phenyl) thiophene-2-yl]benzo[1,2-c:4,5-c']bis[1,2,5]thiadiazole)

(Step R1-1: Synthesis of Compound (RC1a))

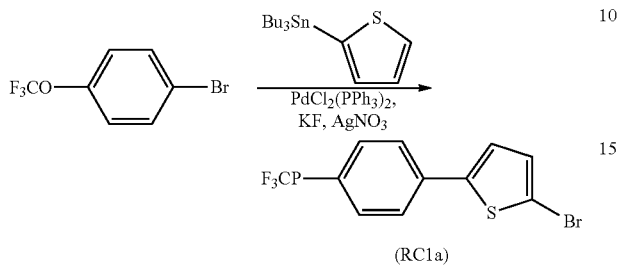

(RC1a)

Into a 1 L glass reaction vessel equipped with a thermometer and a stirring apparatus were placed 3.0 g (4.3 mmol) of palladium chloride triphenylphosphine, 10 g (174 mmol) of potassium fluoride, 25 g (86.8 mmol) of 4-(trifluoromethoxy)iodobenzene, 17 g (104.2 mmol) of 2-bromothiophene, 14.2 g (86.8 mmol) of silver nitrate, and 500 mL of anhydrous dimethyl sulfoxide. The mixture was subjected to freeze-degassing twice. The mixture was heated at 100° C. for 5 hours in argon atmosphere, and then cooled to room temperature. Inorganic substances were removed by filtration with Celite, and then the solvent was distilled off using a vacuum pump. The crude product obtained was purified by silica gel column chromatography, to provide 16.7 g of Compound (RC1a) in the form of a light yellow solid.

The properties of Compound (RC1a) were as follows.
$^1$H-NMR (300MHz; CDCl$_3$; δ(ppm)); 7.01-7.04 (m, 2H), 7.20-7.24 (m, 2H), 7.49-7.54 (m, 2H)
CI-MS; 324 (M+1)

(Step R1-2: Synthesis of Compound (RC1b))

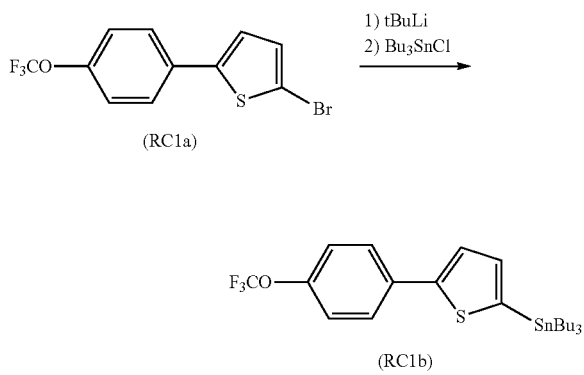

Into a 500-mL glass reaction vessel equipped with a thermometer and a stirring apparatus were placed 15 g (46.4 mmol) of Compound (RC1a), and 300 mL of anhydrous tetrahydrofuran. The mixture was cooled to −65° C. While the internal temperature was kept at −65° C., 33.6 mL (53.4 mmol) of solution of t-butyl lithium in tetrahydrofuran was added dropwise to the mixture, and then the mixture was stirred for 30 minutes. Subsequently, 15.7 mL (58 mmol) of tributyl tin chloride was added dropwise to the mixture. The mixture was stirred at the same temperature for 1 hour, and then reacted at room temperature for 1 hour, and the reaction solution was filtered with neutral alumina. The solvent was distilled off, and then the residue was purified by column chromatography (C8-modified silica gel), to provide 18.8 g of Compound (RC1b) in the form of a yellow liquid.

The properties of Compound (RC1b) were as follows.
$^1$H-NMR (300MHz; CDCl$_3$; δ(ppm)); 0.88-0.93 (m, 9H), 1.10-1.16 (m, 6H), 1.29-1.42 (m, 6H), 1.51-1.64 (m, 6H), 7.13-7.14 (m, 1H), 7.18-7.22 (m, 2H), 7.39-7.40 (m, 1H), 7.61-7.64 (m, 2H)
CI-MS; 535 (M+2)

(Step R1-3: Synthesis of Compound (RC1c))

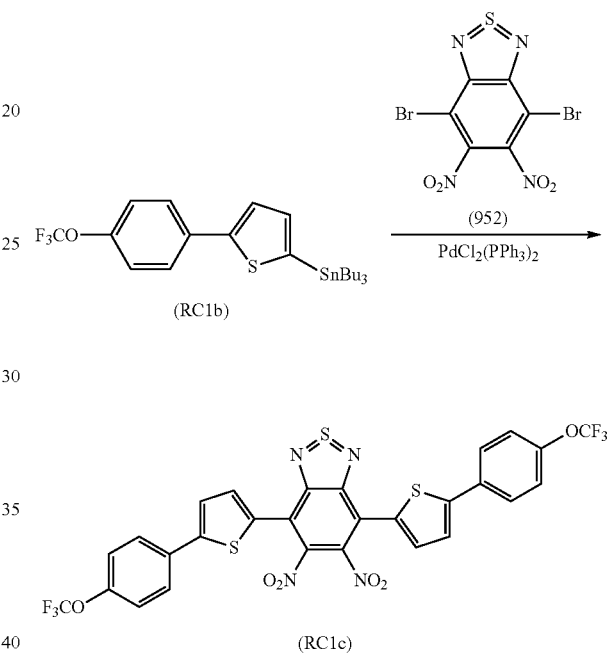

Into a 200-mL glass reaction vessel equipped with a thermometer and a stirring apparatus were placed 2.95 g (7.7 mmol) of Compound (952) which was synthesized by reference to the method described in Chem. Pharm. Bull., 28, 1909 (1980), 9.0 g (16.9 mmol) of Compound (RC1b), 1.08 g (1.54 mmol) of bistriphenylphosphine palladium dichloride, and 80 mL of anhydrous tetrahydrofuran. The mixture was subjected to freeze-degassing twice, and then refluxed for 5 hours. The reaction was carried out again in the same amounts by the same operations. Subsequently, the reaction solutions from the two sets of reactions were combined, and 100 mL of saturated aqueous solution of potassium fluoride was added to the combined reaction solution, and then the mixture was stirred for 30 minutes. Subsequently, the reaction solution was subjected to extraction with 700 mL of chloroform twice, and then the extract was dried over magnesium sulfate, and the solvent was distilled off. The residue was purified by silica gel column chromatography, to provide 13.5 g of Compound (RC1c) in the form of a red solid.

The properties of Compound (RC1c) were as follows.
EI-MS; 710 (M+)

(Step R1-4: Synthesis of Compound (RC1d))

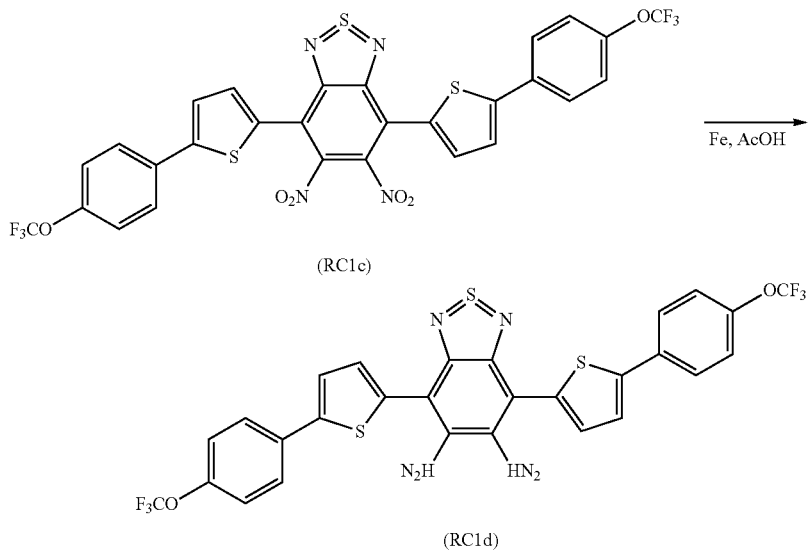

Into a 200-mL glass reaction vessel equipped with a thermometer and a stirring apparatus were placed 13 g (18.3 mmol) of Compound (RC1c), 12.3 g (220 mmol) of iron powder, and 130 mL of acetic acid. The temperature of the mixture was increased from room temperature to 100° C., and then the mixture was reacted at 100° C. for 1.5 hours. Subsequently, the reaction mixture was cooled to room temperature, and then inorganic substances were removed by filtration, and the solvent was distilled off. The obtained solid was purified by silica gel column chromatography, to provide 5.7 g of Compound (RC1d) in the form of a brown solid.

The properties of Compound (RC1d) were as follows.

$^1$H-NMR (300MHz; CDCl$_3$; δ(ppm)); 4.49 (brs, 2H), 7.23-7.27 (m, 2H), 7.36-7.38 (m, 2H), 7.42-7.43 (m, 2H), 7.65-7.71 (m, 2H)

EI-MS; 650 (M+)

(Step R1-5: Synthesis of Compound (RC1))

Into a 200-mL glass reaction vessel equipped with a thermometer and a stirring apparatus were placed 5 g (7.7 mmol) of Compound (RC1d), and 100 mL of anhydrous pyridine. The mixture was heated to 80° C. Subsequently, 1.85 mL (16.1 mmol) of N-thionylaniline was added dropwise to the mixture, and then 9.7 mL (76.8 mmol) of trimethylsilyl chloride was added dropwise thereto over 1 minute, and the mixture was reacted for 8 hours. Subsequently, the solvent was distilled off, and then 150 mL of methanol was added to the obtained solid, and the mixture was refluxed for purification for 15 minutes, and then the formed solid was obtained. The reflux for purification with 150 mL of methanol was repeated twice, to provide 2.93 g of a crude product of Compound (RC1) in the form of a dark green solid. The crude product was purified by heat-washing with chloroform, recrystallization from toluene, and then sublimation, to provide a purified product of Compound (RC1).

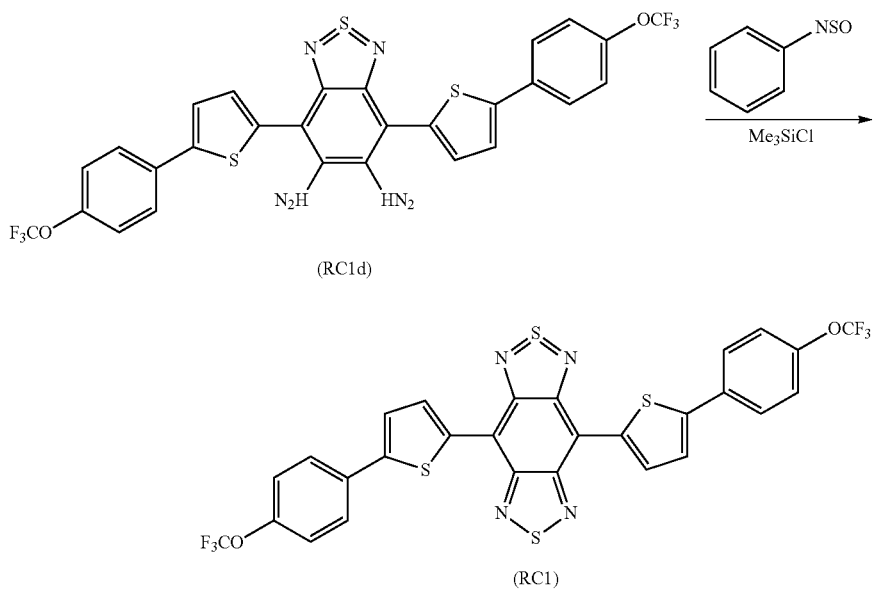

The properties of Compound (RC1) were as follows.

$^1$H-NMR (400MHz; DMSO-$d_6$, 180° C.); δ(ppm)) 7.60-7.62 (m, 4H), 7.91 (brs, 2H), 8.06-8.13 (m, 4H), 9.18 (brs, 2H)

CI-MS; 678 (M+)

The solubility of Compound (RC1) at 100° C. was evaluated, and 0.03 wt % of Compound (RC1) was not completely dissolved in any of toluene, mesitylene, chlorobenzene, and ortho-dichlorobenzene.

Comparative Example 2

Synthesis of Compound (RC2) (4,8-bis[5-(4-(trifluoromethyl)phenyl) thiophene-2-yl]benzo[1,2-c:4,5-c']bis[1,2,5]thiadiazole: FPTBBT)

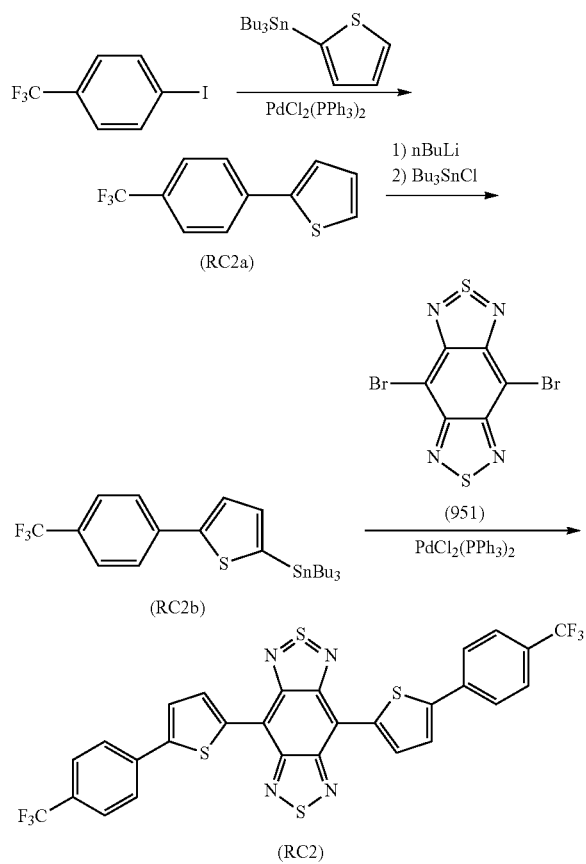

Compound (RC2) was obtained in the same way as in Example 1, except that 1-iodo-4-(trifluoromethyl)benzene was used instead of 1-bromo-3-(trifluoromethoxy)benzene.

The properties of Compound (RC2a) were as follows.

$^1$H-NMR (400MHz; CDCl$_3$; δ(ppm)); 7.10-7.12 (m, 1H), 7.35-7.36 (m, 1H), 7.38-7.40 (m, 1H), 7.61-7.64 (m, 2H), 7.69-7.72 (m, 2H)

The properties of Compound (RC2b) were as follows.

$^1$H-NMR (400MHz; CDCl$_3$; δ(ppm)); 0.86-0.95 (m, 9H), 1.03-1.24 (m, 6H), 1.26-1.42 (m, 6H), 1.48-1.72 (m, 6H), 7.16-7.17 (m, 1H), 7.49-7.51 (m, 1H), 7.59-7.63 (m, 2H), 7.70-7.72 (m, 2H)

The properties of Compound (RC2) were as follows.
FAB-MS(-); 646

The solubility of Compound (RC2) at 100° C. was evaluated, and 0.03 wt % of Compound (RC2) was not completely dissolved in any of toluene, mesitylene, chlorobenzene, and ortho-dichlorobenzene.

Reference Example 1

Synthesis of Compound (RR1) (4,8-bis[5-(2-(trifluoromethoxy)phenyl) thiophene-2-yl]benzo[1,2-c:4,5-c']bis[1,2,5]thiadiazole)

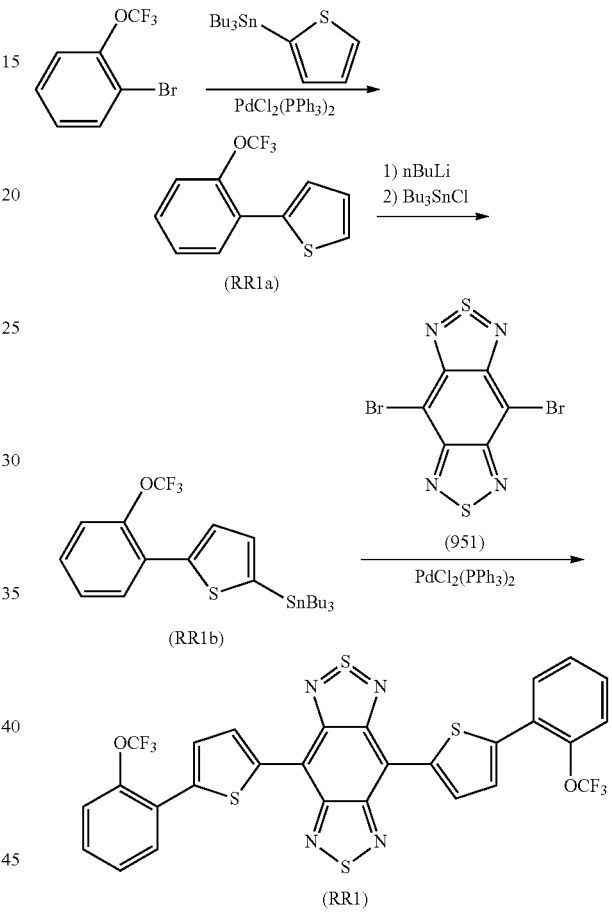

Compound (RR1) was obtained in the same way as in Example 1, except that 1-bromo-2-(trifluoromethoxy)benzene was used instead of 1-bromo-3-(trifluoromethoxy)benzene.

The properties of Compound (RR1a) were as follows.

$^1$H-NMR (400MHz; CDCl$_3$; δ(ppm)); 7.09-7.14 (m, 1H), 7.27-7.37 (m, 3H), 7.37-7.41 (m, 1H), 7.41-7.44 (m, 1H), 7.63-7.70 (m, 1H)

The properties of Compound (RR1b) were as follows.

$^1$H-NMR (400MHz; CDCl$_3$; δ(ppm)); 0.86-0.94 (m, 9H), 1.02-1.24 (m, 6H), 1.26-1.42 (m, 6H), 1.48-1.72 (m, 6H), 7.12-7.22 (m, 1H), 7.24-7.36 (m, 3H), 7.52-7.57 (m, 1H), 7.66-7.73 (m, 1H)

The properties of Compound (RR1) were as follows.

$^1$H-NMR (400MHz; 1,2-dichlorobenzene-$d_4$; 140° C.; δ(ppm)); 7.14-7.24 (m, 4H), 7.25-7.33 (m, 2H), 7.57-7.64 (m, 2H), 7.71-7.79 (m, 2H), 8.99-9.05 (m, 2H)

TOF-HRMS (ASAP+); 678.9822 (M+1); Calcd. 678.9826

The solubility of Compound (RR1) was evaluated, and 0.1 wt % of Compound (RR1) was completely dissolved in all of toluene, and mesitylene at 80° C. The solubility in a solvent is improved also by the substitution of a substituent for the ortho position with respect to the thienylene group on the benzene ring.

Reference Example 2

Synthesis of Compound (RR2) (4,8-bis[5-(2-(trifluoromethyl)phenyl) thiophene-2-yl]benzo[1,2-c:4,5-c']bis[1,2,5]thiadiazole)

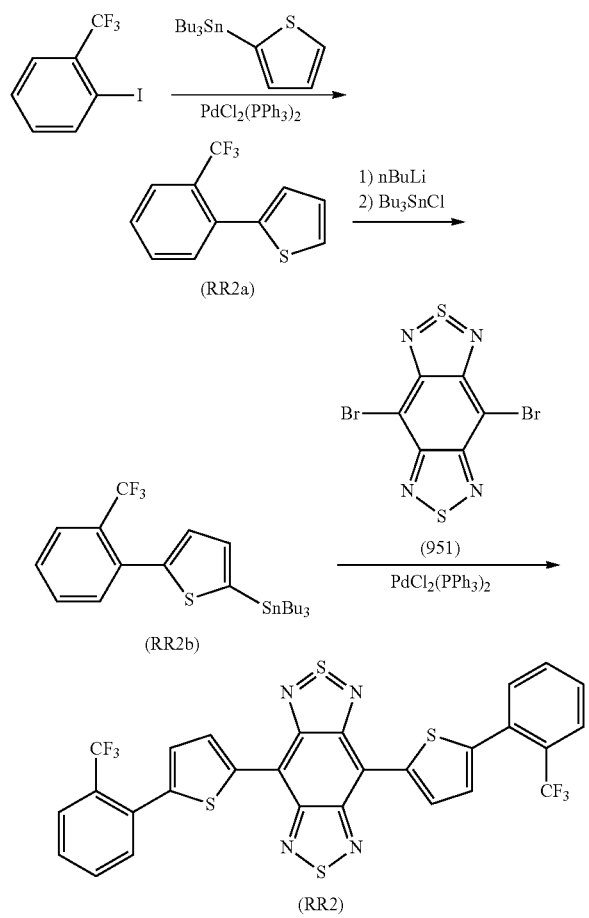

Compound (RR2) was obtained in the same way as in Example 1, except that 1-iodo-2-(trifluoromethyl)benzene was used instead of 1-bromo-3-(trifluoromethoxy)benzene.

The properties of Compound (RR2a) were as follows.
$^1$H-NMR (400MHz; CDCl$_3$; δ(ppm)); 7.04-7.11 (m, 1H), 7.11-7.16 (m, 1H), 7.35-7.42 (m, 1H), 7.42-7.61 (m, 3H), 7.72-7.80 (m, 1H)

The properties of Compound (RR2b) were as follows.
$^1$H-NMR (400MHz; CDCl$_3$; δ(ppm)); 0.83-0.98 (m, 15H), 1.23-1.42 (m, 6H), 1.42-1.68 (m, 6H), 7.11-7.12 (m, 1H), 7.19-7.27 (m, 1H), 7.40-7.54 (m, 3H), 7.74-7.75 (m, 1H)

The properties of Compound (RR2) were as follows.
$^1$H-NMR (400MHz; CDCl$_3$; δ(ppm)); 7.38-7.39 (m, 2H), 7.53-7.55 (m, 2H), 7.63-7.65 (m, 2H), 7.70-7.72 (m, 2H), 7.82-7.84 (m, 2H), 9.07-9.08 (m, 2H)

The solubility of Compound (RR2) at 25° C. was evaluated, and 0.1 wt % of Compound (RR2) was completely dissolved in all of toluene, mesitylene, chlorobenzene, and ortho-dichlorobenzene at 25° C. The solubility in a solvent is improved also by the substitution of a substituent for the ortho position with respect to the thienylene group on the benzene ring.

Reference Example P-3

Synthesis of Compound (C3) (4,8-bis[5-(3,5-bis(trifluoromethyl)phenyl) thiophene-2-yl]benzo[1,2-c:4,5-c']bis[1,2,5]thiadiazole)

(Step 3-1: Synthesis of Compound (C3a))

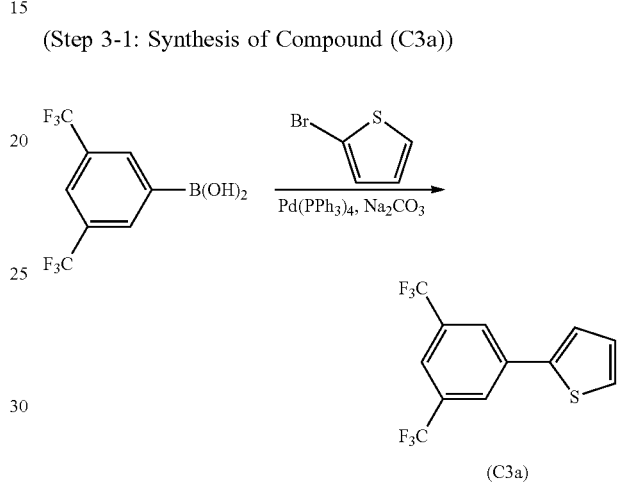

Into a 250-mL glass reaction vessel equipped with a stirring apparatus were placed 2.84 g (11.0 mmol) of 3,5-bis(trifluoromethyl)phenyl boronate, 1.15 g (1.0 mmol) of tetrakistriphenylphosphine palladium (0), 4.24 g (400 mmol) of sodium carbonate, 968 μl (10.0 mmol) of 2-bromothiophene, and 70 mL of anhydrous toluene and 35 mL of anhydrous ethanol. The mixture was reacted at an internal temperature of about 80° C. for 16 hours. After the completion of the reaction, the solvent was concentrated, and then 150 mL of water was added to the residue, and the mixture was subjected to extraction with 300 mL of diethyl ether, and then the extract was dried over magnesium sulfate, and the solvent was distilled off under a reduced pressure. The obtained crude reaction product was purified by silica gel column chromatography, to provide 2.9 g of Compound (C3a) in the form of a white solid.

The properties of Compound (C3a) were as follows.
$^1$H-NMR (400MHz; CDCl$_3$; δ(ppm)); 7.16-7.18 (m, 1H), 7.45-7.46 (m, 1H), 7.48-7.49 (m, 1H), 7.79 (brs, 1H), 8.05 (brs, 2H)

(Step 3-2: Synthesis of Compound (C3))

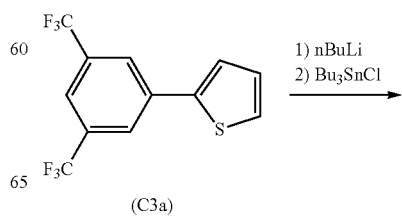

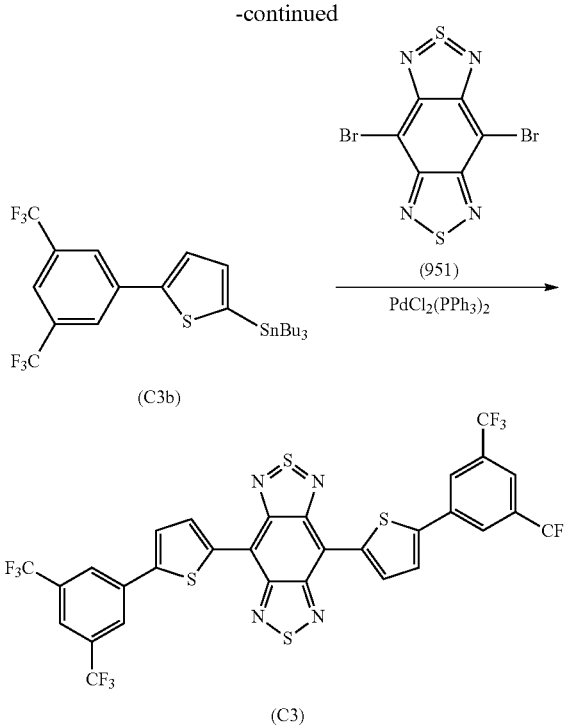

Compound (C3) was obtained in the same way as in Steps 1-2 to 1-3 in Example 1, except that Compound (C3a) was used instead of Compound (C1a).

The properties of Compound (C3b) were as follows.
$^1$H-NMR (400MHz; CDCl$_3$; δ(ppm)); 0.89-0.93 (m, 9H), 1.15-1.19 (m, 6H), 1.33-1.39 (m, 6H), 1.58-1.62 (m, 6H), 7.19-7.25 (m, 1H), 7.57-7.59 (m, 1H), 7.75 (brs, 1H), 8.05 (brs, 2H)

The properties of Compound (C3) were as follows.
$^1$H-NMR (400MHz; 1,2-dichlorobenzene-d$_4$:100° C.); 7.76-7.77 (m, 2H), 7.98 (s, 2H), 8.39 (s, 4H), 9.31-9.32 (m, 2H)

The solubility of Compound (C3) was evaluated, and 0.1 wt % of Compound (C3) was completely dissolved in mesitylene at 130° C. and also completely dissolved in chlorobenzene at 130° C. Also, 0.1 wt % of Compound (C3) was completely dissolved in ortho-dichlorobenzene at 100° C.

Example 4

Synthesis of Compound (C4) (Compound of the Formula (15); 4,8-bis[5-(3-(1,1-difluoroundecyl)phenyl)thiophene-2-yl]benzo[1,2-c:4,5-c']bis[1,2,5]thiadiazole)

(Step 4-1: Synthesis of Compound (C4a))

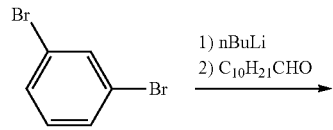

Under nitrogen atmosphere, into a 300-mL glass reaction vessel equipped with a thermometer and a stirring apparatus were placed 5.0 g (21.2 mmol) of 1,3-dibromobenzene, and 50 mL of tetrahydrofuran. And then, the internal temperature was cooled to −78° C. While the mixture was stirred and the internal temperature was kept at −78° C., 14.6 mL (23.3 mmol) of 1.6 mol/L solution of n-butyl lithium in hexane was added to the mixture, and then the mixture was stirred for 1 hour. A solution in which 4.33 g (25.4 mmol) of undecanal was dissolved in 20 mL of tetrahydrofuran was prepared, and the solution was slowly added to the reaction solution at −78° C. While the temperature of the mixture was gradually increased to room temperature, the mixture was stirred overnight. A saturated aqueous solution of ammonium chloride was added to the reaction solution, and then the reaction solution was concentrated, and the concentrate was subjected to extraction with ethyl acetate. The extract was washed with water, and dried over anhydrous magnesium sulfate, and then the solvent was distilled off under a reduced pressure, to provide 7.23 g of Compound (C4a) in the form of a yellow liquid.

The properties of Compound (C4a) were as follows.
$^1$H-NMR (400MHz; CDCl$_3$; δ(ppm)); 0.86-0.89 (m, 3H), 1.25 (br, 18H), 4.62-4.65 (m, 1H), 7.19-7.53 (m, 4H)
CI-MS; 328 (M+1)

(Step 4-2: Synthesis of Compound (C4b))

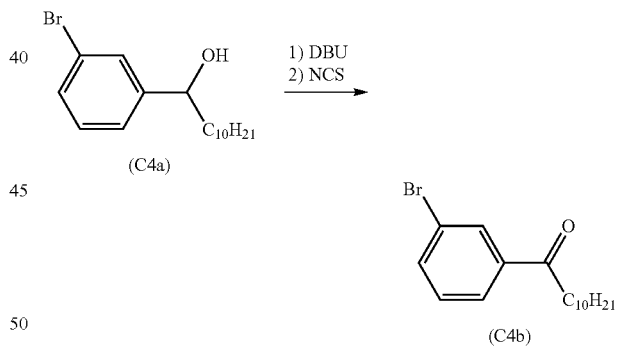

Under nitrogen atmosphere, into a 1000-mL glass reaction vessel equipped with a thermometer and a stirring apparatus were placed 66.53 g (203 mmol) of Compound (C4a), and 400 mL of dichloromethane. And then, the reaction solution was cooled to 0° C. to 10° C. in an ice bath. A solution prepared by diluting 34 g (223.3 mmol) of diazabicycloundecene (DBU) with 34 mL of dichloromethane was added to the reaction solution, and furthermore a solution prepared by diluting 5.52 g (30.45 mmol) of N-t-butylphenyl sulfonamide with 20 mL of dichloromethane was added thereto. A solution prepared by diluting 30 g (224.7 mmol) of N-chlorosuccinimide (NCS) with 300 mL of dichloromethane was added dropwise to the mixture over 30 minutes, and then the mixture was stirred at the same temperature for 1 hour. The reaction solution was mildly poured into a solution of 35.5 g of sodium thiosulfate and 100 mL of water, and then the mixture was stirred for 30 minutes. The reaction mixture was separated into a water layer and an organic layer, and the organic layer was washed with water, and then dried over anhydrous magnesium sulfate, and then the solvent was distilled off under a reduced pressure, to provide 83.94 g of a crude target product in the form of a black liquid. The crude product was purified by normal phase silica gel column chromatography, to provide 14.5 g of Compound (C4b) in the form of a blue-green liquid.

The properties of Compound (C4b) were as follows.

$^1$H-NMR (400MHz; CDCl$_3$; δ(ppm)); 0.86-0.90 (m, 3H), 1.27-1.39 (m, 14H), 1.65-1.76 (m, 2H), 2.90-2.94 (m, 2H), 7.32-7.36 (m, 1H), 7.66-7.72 (m, 1H), 7.86-7.88 (m, 1H), 8.07-8.08 (m, 1H)

EI-MS; 326 (M)

CI-MS; 327 (M+1)

(Step 4-3: Synthesis of Compound (C4c))

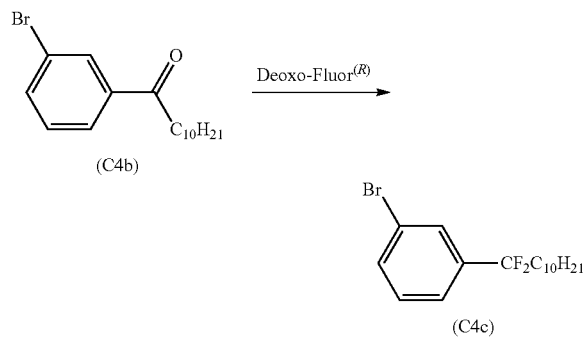

Under argon atmosphere, into a 200-mL reaction vessel made of tetrafluoroethylene-perfluoroalkyl vinyl ether copolymer (PFA) and equipped with a stirring apparatus were placed 14.5 g (44.6 mmol) of Compound (C4b), 39.5 g (179 mmol) of bis(2-methoxyethyl)aminosulfur trifluoride (made by Wako Pure Chemical Industries, Ltd., Trade name: Deoxo-Fluor®), and 145 mL of anhydrous chloroform. A homogeneous solution was prepared therefrom, and then the solution was reacted at an internal temperature of about 50° C. for 35 hours. Subsequently, the reaction solution was cooled to room temperature, and then the reaction solution was added to 500 mL of a saturated aqueous solution of sodium hydrogen carbonate, which was cooled in ice, to stop the reaction, and then the mixture was subjected to extraction with 500 mL of chloroform. The organic layer was dried over anhydrous magnesium sulfate, and then the solvent was distilled off under a reduced pressure, and then the obtained reaction mixture was purified by silica gel column chromatography, to provide 8.43 g of Compound (C4c) in the form of a colorless liquid.

The properties of Compound (C4c) were as follows.

$^1$H-NMR (400MHz; CDCl$_3$; δ(ppm)); 0.86-0.89 (m, 3H), 1.24-1.50 (m, 16H), 2.02-2.14 (m, 2H), 7.27-7.31 (m, 1H), 7.38-7.40 (m, 1H), 7.54-7.56 (m, 1H), 7.61 (s, 1H)

CI-MS; 348 (M+1)

(Step 4-4: Synthesis of Compound (C4))

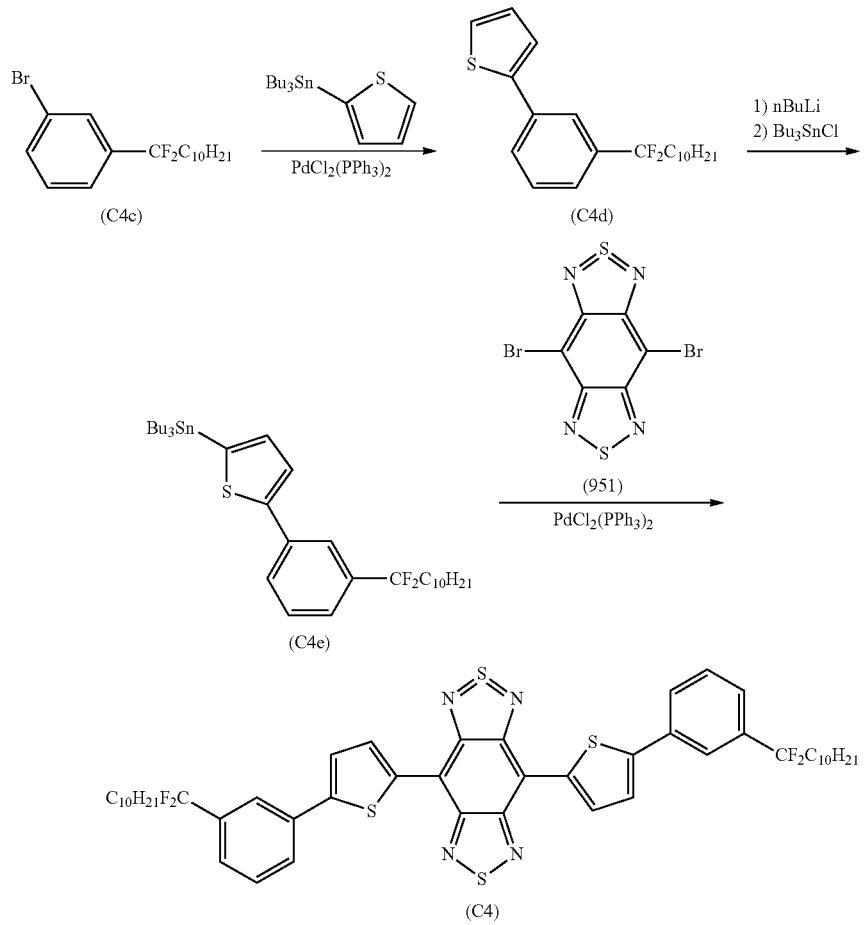

Compound (C4) was obtained in the same way as in Example 1, except that Compound (C4c) was used instead of 1-bromo-3-(trifluoromethoxy)benzene.

The properties of Compound (C4d) were as follows.
$^1$H-NMR (400MHz; CDCl$_3$; δ(ppm)); 0.85-0.89 (m, 3H), 1.24-1.48 (m, 16H), 2.07-2.19 (m, 2H), 7.08-7.11 (m, 1H), 7.30-7.44 (m, 4H), 7.64-7.69 (m, 2H)
EI-MS: 350 (M+)

The properties of Compound (C4e) were as follows.
$^1$H-NMR (400MHz; CDCl$_3$; δ(ppm)); 0.85-0.95 (m, 12H), 1.05-1.49 (m, 30H), 1.51-1.70 (m, 4H), 2.07-2.19 (m, 2H), 7.12-7.18 (m, 1H), 7.32-7.47 (m, 3H), 7.65-7.69 (m, 2H)
CI-MS; 639 (M+)

The properties of Compound (C4) were as follows.
$^1$H-NMR (400MHz; 1,2-dichlorobenzene-d$_4$: 140° C.; δ(ppm)); 0.81-0.82 (m, 3H), 1.23-1.31 (m, 14H), 1.50-1.55 (m, 2H), 2.13-2.24 (m, 2H), 7.34-7.41 (m, 2H), 7.48-7.49 (m, 1H), 7.74-7.76 (m, 1H), 7.97 (s, 1H), 9.00-9.01 (m, 1H)
TOFMS (posi); 891 (M+)

The solubility of Compound (C4) at 25° C. was evaluated, and 0.03 wt % of Compound (C4) was completely dissolved in all of toluene, mesitylene, chlorobenzene, and ortho-dichlorobenzene at 25° C. Also, 0.1 wt % of Compound (C4) was completely dissolved in all of toluene, mesitylene, chlorobenzene, and ortho-dichlorobenzene at 60° C. Also, 0.5 wt % of Compound (C4) was completely dissolved in all of chlorobenzene, and ortho-dichlorobenzene at 60° C. Also, 0.5 wt % of Compound (C4) was completely dissolved in all of toluene, and mesitylene at 100° C.

Comparative Example 3

Synthesis of Compound (RC3) (4,8-bis[5-(4-(1,1-difluoroundecyl)phenyl) thiophene-2-yl]benzo[1,2-c: 4,5-c']bis[1,2,5]thiadiazole)

(Step R3-1: Synthesis of Compound (RC3a))

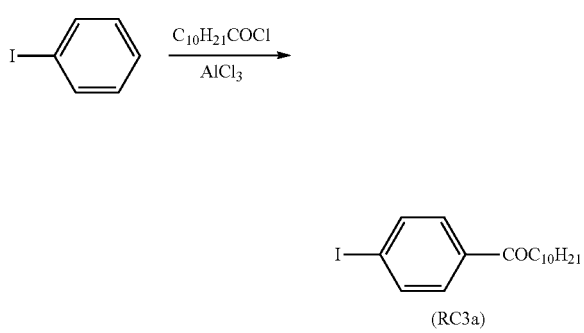

Under nitrogen atmosphere, into a 200-mL glass reaction vessel equipped with a thermometer and a stirring apparatus were placed 40 g (255 mmol) of aluminum chloride, and 90 mL of carbon disulfide. And then, while the mixture was stirred and the internal temperature was kept at −5° C. to 5° C., 45 g (221 mmol) of 4-iodobenzene, and then 59 g (290 mmol) of undecanoyl chloride were slowly added dropwise to the mixture. While the temperature of the mixture was increased to room temperature, the mixture was reacted overnight. After the completion of the reaction, the obtained reaction solution was added to 200 mL of 1 mol/L hydrochloric acid, which was cooled in ice. Subsequently, the mixture was subjected to extraction with ethyl acetate, and the organic layer was washed with water, and then with a solution of salt. The organic layer was dried over anhydrous magnesium sulfate, and then the solvent was distilled off under a reduced pressure. The obtained reaction mixture was purified by reverse phase silica gel column chromatography, to provide 22.4 g of Compound (RC3a) in the form of a white solid.

The properties of Compound (RC3a) were as follows.
$^1$H-NMR (400MHz; CDCl$_3$; δ(ppm)); 0.86-0.90 (m, 3H), 1.26-1.75 (m, 16H), 2.89-2.93 (m, 2H), 7.64-7.68 (m, 2H), 7.80-7.84 (m, 2H)
CI-MS; 373 (M+1)

Step R3-2: Synthesis of Compound (RC3b)

Compound (RC3b) was obtained in the same way as in Step 4-3 in Example 4, except that Compound (RC3a) was used instead of Compound (C4b).

The properties of Compound (RC3b) were as follows.
$^1$H-NMR (400MHz; CDCl$_3$; δ(ppm)); 0.86-0.89 (m, 3H), 1.24-1.46 (m, 16H), 2.01-2.13 (m, 2H), 7.18-7.20 (m, 2H), 7.74-7.77 (m, 2H)
EI-MS; 394 (M+)

(Step R3-3: Synthesis of Compound (RC3))

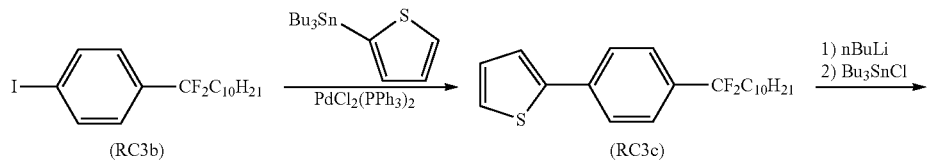

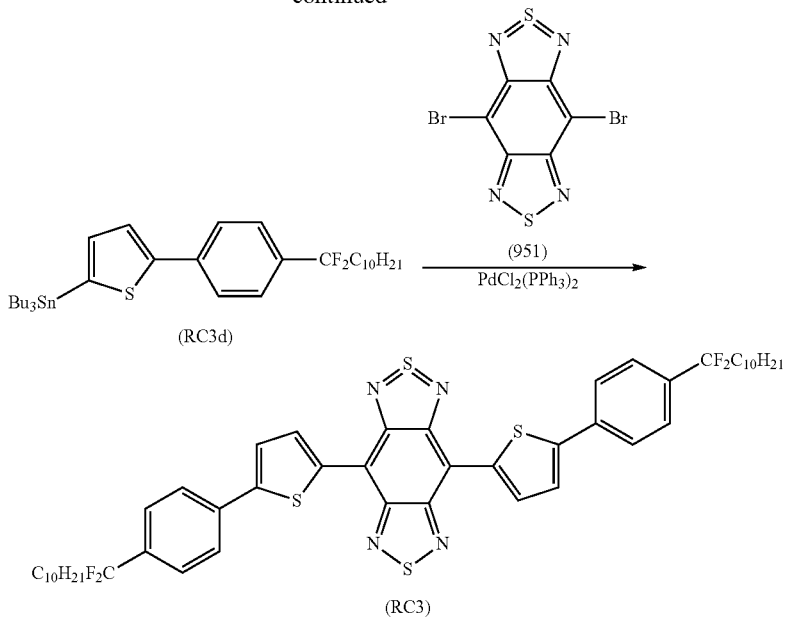

Compound (RC3) was obtained in the same way as in Example 1, except that Compound (RC3b) was used instead of 1-bromo-3-(trifluoromethoxy)benzene.

The properties of Compound (RC3c) were as follows.

$^1$H-NMR (400MHz; CDCl$_3$; δ(ppm)); 0.85-0.91 (m, 3H), 1.24-1.44 (m, 16H), 2.06-2.18 (m, 2H), 7.08-7.10 (m, 1H), 7.30-7.35 (m, 2H), 7.45-7.47 (m, 2H), 7.63-7.65 (m, 2H)

EI-MS; 350 (M+);

The properties of Compound (RC3d) were as follows.

$^1$H-NMR (400MHz; CDCl$_3$; δ(ppm)); 0.84-0.94 (m, 12H), 1.02-1.21 (m, 6H), 1.21-1.72 (m, 28H), 2.02-2.22 (m, 2H), 7.11-7.19 (m, 1H), 7.40-7.50 (m, 3H), 7.62-7.69 (m, 2H)

The properties of Compound (RC3) were as follows.

$^1$H-NMR (400MHz; 1,2-dichlorobenzene-d$_4$: 140° C.; δ(ppm)); 0.78-0.90 (m, 6H), 1.18-1.40 (m, 28H), 1.46-1.60 (m, 4H), 2.05-2.30 (m, 4H), 7.44-7.58 (m, 6H), 7.70-7.84 (m, 4H), 9.00-9.07 (m, 2H)

TOF-HRMS (ASAP+); 891.3223 (M+1); Calcd. 891.3246

The solubility of Compound (RC3) at 60° C. was evaluated, and 0.03 wt % of Compound (RC3) was not completely dissolved in any of toluene, mesitylene, and chlorobenzene.

Example 5

Synthesis of Compound (C5) (Compound of the Formula (9); 4,8-bis[5-(3-cyanophenyl)thiophene-2-yl]benzo[1,2-c:4,5-c']bis[1,2,5]thiadiazole)

(Step 5-1: Synthesis of Compound (C5a))

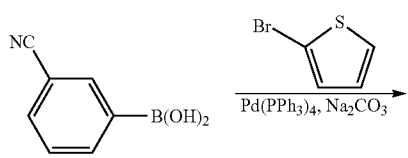

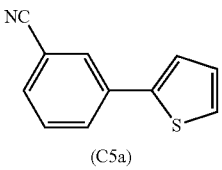

Compound (C5a) was obtained in the same way as in Step 3-1 in Reference Example P-3, except that 3-cyanophenyl boronate was used instead of 3, 5-bis(trifluoromethyl)phenyl boronate.

The properties of Compound (C5a) were as follows.

$^1$H-NMR (400MHz; CDCl$_3$; δ(ppm)); 7.12-7.14 (m, 1H), 7.38-7.40 (m, 2H), 7.47-7.52 (m, 1H), 7.55-7.58 (m, 1H), 7.83-7.85 (m, 1H), 7.89-7.91 (m, 1H)

(Step 5-2: Synthesis of Compound (C5b))

Into a 50-mL glass reaction vessel equipped with a stirring apparatus were placed 926 mg (5.0 mmol) of Compound (C5a), and 15 mL of anhydrous tetrahydrofuran. While the internal temperature was kept at −75° C., 5.0 mL of 1.1 mol/L solution of lithium diisopropylamide (LDA) in hexane-tetrahydrofuran was added to the mixture. The mixture was stirred at the same temperature for 1 hour, and then 1.5 mL (5.5 mmol) of tributyl tin chloride was added to the mixture at the same temperature. The temperature of the mixture was increased to room temperature, and the mixture was stirred for 1 hour. And then, methanol was added to the reaction solution to stop the reaction, and then the solvent was distilled off. Subsequently, hexane was added to the obtained crude reaction product, and the crude reaction product was purified by column chromatography using amino group-modified silica gel, to provide 2.1 g of Compound (C5b) in the form of a colorless liquid.

The properties of Compound (C5b) were as follows.
$^1$H-NMR (400MHz; CDCl$_3$; δ(ppm)); 0.89-0.93 (m, 9H), 1.13-1.17 (m, 6H), 1.31-1.40 (m, 6H), 1.56-1.62 (m, 6H), 7.18-7.19 (m, 1H), 7.46-7.54 (m, 3H), 7.84-7.86 (m, 1H), 7.90-7.91 (m, 1H)

(Step 5-3: Synthesis of Compound (C5))

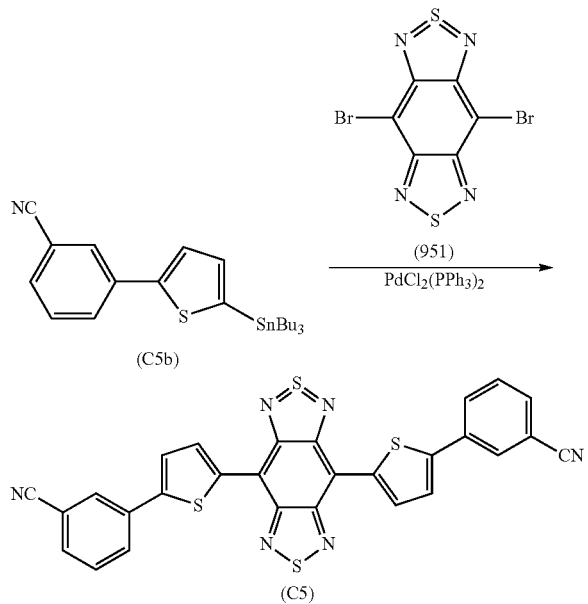

Compound (C5) was obtained in the same way as in Step 1-3 in Example 1, except that Compound (C5b) was used instead of Compound (C1b).

The properties of Compound (C5) were as follows.
FAB-MS (M/Z): 560 (M+H)$^+$

Comparative Example 4

Synthesis of Compound (RC4) (4,8-bis[5-(4-cyanophenyl)thiophene-2-yl]benzo[1,2-c:4,5-c']bis[1,2,5]thiadiazole)

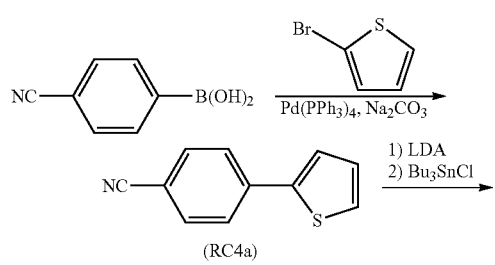

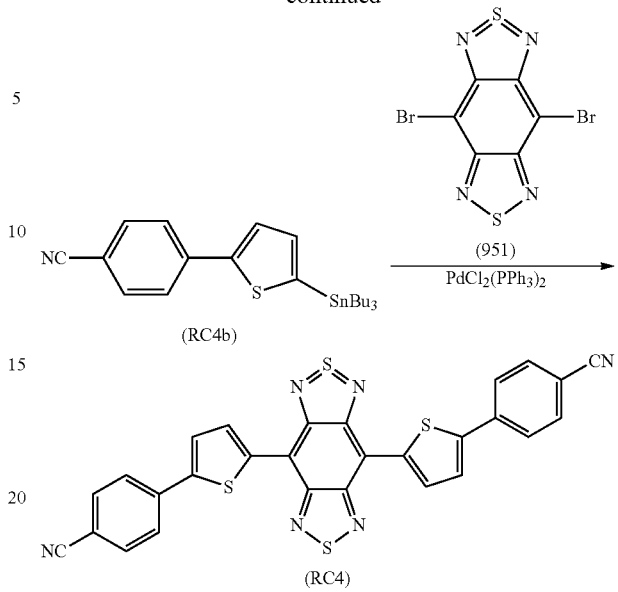

Compound (RC4) was obtained in the same way as in Example 5, except that 4-cyanophenyl boronate was used instead of 3-cyanophenyl boronate.

The properties of Compound (RC4a) were as follows.
$^1$H-NMR (400MHz; CDCl$_3$; δ(ppm)); 7.13-7.15 (m, 1H), 7.42-7.44 (m, 1H), 7.45-7.47 (m, 1H), 7.65-7.74 (m, 4H)

The properties of Compound (RC4b) were as follows.
$^1$H-NMR (400MHz; CDCl$_3$; δ(ppm)); 0.89-0.92 (m, 9H), 1.13-1.18 (m, 6H), 1.31-1.40 (m, 6H), 1.55-1.63 (m, 6H), 7.17-7.23 (m, 1H), 7.55-7.57 (m, 1H), 7.63-7.66 (m, 2H), 7.71-7.74 (m, 2H)

The properties of Compound (RC4) were as follows.
FAB-MS (M/Z): 560 (M+H)$^+$

Reference Example 3

Synthesis of Compound (RR3) (4,8-bis[5-(2-cyanophenyl)thiophene-2-yl]benzo[1,2-c:4,5-c']bis[1,2,5]thiadiazole)

(Step RR3-1: Synthesis of Compound (RR3a))

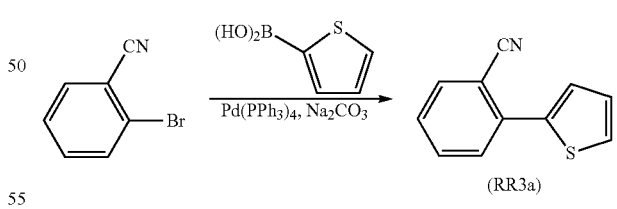

Into a 30-mL glass reaction vessel equipped with a stirring apparatus were placed 385 mg (3.0 mmol) of 2-thiophene boronate, 346 mg (0.3 mmol) of tetrakistriphenylphosphine palladium (0), 848 mg (8.8 mmol) of sodium carbonate, 400 mg (2.2 mmol) of 1-bromo-2-cyanobenzene, and 14 mL of anhydrous toluene and 7 mL of anhydrous ethanol. The mixture was reacted at an internal temperature of about 80° C. for 39 hours. After the completion of the reaction, 20 mL of water was added to the reaction solution, and the mixture was subjected to extraction with 60 mL of diethyl ether, and the organic layer was dried over magnesium sulfate, and then the solvent was distilled off under a reduced pressure. The obtained crude reaction product was purified by silica gel column chromatography, to provide 290 mg of Compound (RR3a) in the form of a white solid.

The properties of Compound (RR3a) were as follows.
$^1$H-NMR (400MHz; CDCl$_3$; δ(ppm)); 7.14-7.20 (m, 1H), 7.35-7.42 (m, 3H), 7.42-7.47 (m, 1H), 7.55-7.67 (m, 1H), 7.70-7.76 (m, 1H)

(Step RR3-2: Synthesis of Compound (RR3))

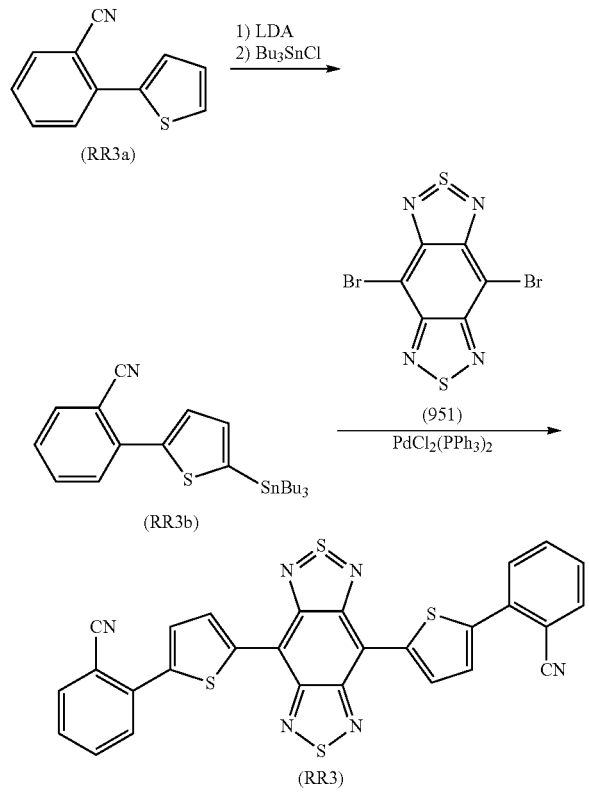

Compound (RR3) was obtained in the same way as in Steps 5-2 to 5-3 in Example 5, except that Compound (RR3a) was used instead of Compound (C5a).

The properties of Compound (RR3b) were as follows.
$^1$H-NMR (400MHz; CDCl$_3$; δ(ppm)); 0.82-0.98 (m, 9H), 1.03-1.26 (m, 6H), 1.26-1.42 (m, 6H), 1.47-1.71 (m, 6H), 7.17-7.25 (m, 1H), 7.30-7.37 (m, 1H), 7.53-7.76 (m, 3H), 7.76-7.82 (m, 1H)

The properties of Compound (RR3) were as follows.
FD-MS (M/Z); 560 (M), 280 (M/2)

Example 6

Synthesis of Compound (C6) (Compound of the Formula (4); 4,8-bis[5-(3-((trifluoromethyl)thio)phenyl)thiophene-2-yl]benzo[1,2-c:4,5-c']bis[1,2,5]thiadiazole)

(Step 6-1: Synthesis of Compound (C6a))

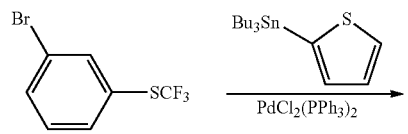

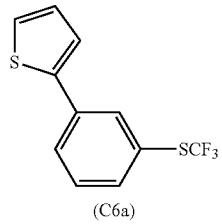

Into a 300-mL glass reaction vessel equipped with a stirring apparatus were placed 10.0 g (39 mmol) of 3-bromotrifluoromethylthiobenzene, 2.7 g (3.9 mmol) of dichlorobis(triphenylphosphine) palladium (II), 18.9 g (51 mmol) of 2-(tributyltin)thiophene, and 100 mL of anhydrous toluene. The mixture was reacted at an internal temperature of about 100° C. for 4 hours. After the completion of the reaction, the solvent was concentrated, and then 300 mL of hexane was added to the concentrate, and the mixture was filtered through [silica gel:potassium carbonate=90:10 (wt %)]. The filtrate was concentrated, and the concentrate was purified by silica gel column chromatography, to provide 8.8 g of Compound (C6a) in the form of a colorless liquid.

The properties of Compound (C6a) were as follows.
$^1$H-NMR (400MHz; CDCl$_3$; δ(ppm)); 7.06-7.14 (m, 1H), 7.30-7.38 (m, 2H), 7.40-7.46 (m, 1H), 7.52-7.58 (m, 1H), 7.68-7.74 (m, 1H), 7.86-7.92 (m, 1H)
DI-MS (EI); 260 (M+)

(Step 6-2: Synthesis of Compound (C6b))

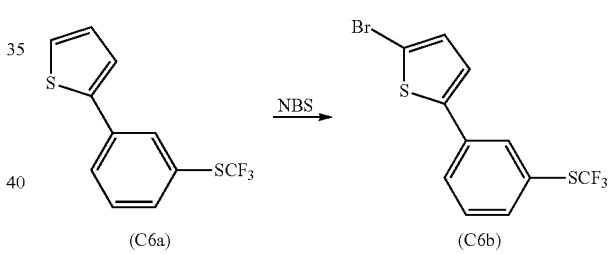

Into a 300-mL glass reaction vessel equipped with a stirring apparatus were placed 8.25 g (31.7 mmol) of Compound (C6a), and 80 mL of anhydrous tetrahydrofuran. While the internal temperature was kept at −25° C. to −10° C., a solution prepared by adding 5.25 g (29.5 mmol) of N-bromosuccinimide (NBS) to 80 mL of tetrahydrofuran was added dropwise to the mixture. And furthermore, a solution prepared by adding 2.26 g (12.7 mmol) of N-bromosuccinimide to 20 mL of tetrahydrofuran was added dropwise thereto. The mixture was reacted for 2 hours, and then 300 mL of hexane and 300 mL of water were added to the reaction mixture, and the mixture was subjected to liquid separation. The water layer was subjected to extraction with hexane, and then the combined hexane layer was washed with water. The concentrate was purified by silica gel column chromatography, to provide 9.3 g of Compound (C6b) in the form of a pale yellow solid.

The properties of Compound (C6b) were as follows.
$^1$H-NMR (400MHz; CDCl$_3$; δ(ppm)); 7.03-7.07 (m, 1H), 7.07-7.11 (m, 1H), 7.39-7.46 (m, 1H), 7.54-7.63 (m, 2H), 7.76-7.82 (m, 1H)
DI-MS (EI); 338 (M+), 340 (M+2)

(Step 6-3: Synthesis of Compound (C6c))

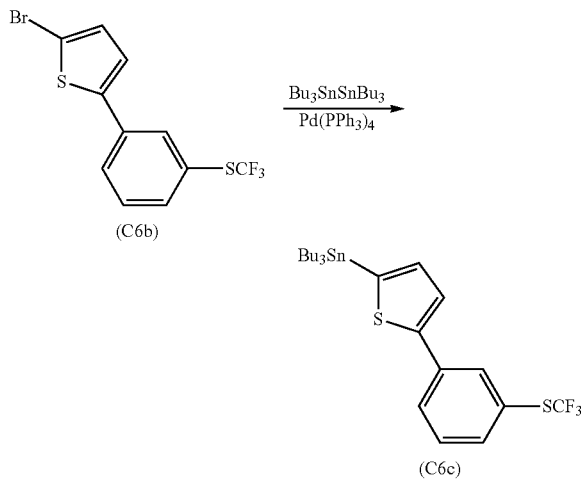

Into a 100-mL glass reaction vessel equipped with a stirring apparatus were placed 7.0 g (26.7 mmol) of Compound (C6b), 62.4 g (107.6 mmol) of bis(tributyltin), 5.44 g (53.8 mmol) of triethylamine, 6.22 g (5.4 mmol) of tetrakis (triphenylphosphine) palladium (0), and 140 mL of anhydrous toluene. The mixture was reacted at 88° C. for 4 hours. The reaction mixture was concentrated under a reduced pressure, and then the concentrate was purified by basic silica gel column chromatography, to provide 3.6 g of Compound (C6c) in the form of a colorless liquid.

The properties of Compound (C6c) were as follows.
$^1$H-NMR (400MHz; CDCl$_3$; δ(ppm)); 0.86-0.96 (m, 9H), 1.04-1.24 (m, 6H), 1.30-1.42 (m, 6H), 1.46-1.72 (m, 6H), 7.10-7.20 (m, 1H), 7.36-7.44 (m, 1H), 7.44-7.49 (m, 1H), 7.49-7.56 (m, 1H), 7.68-7.76 (m, 1H), 7.86-7.94 (m, 1H)

(Step 6-4: Synthesis of Compound (C6))

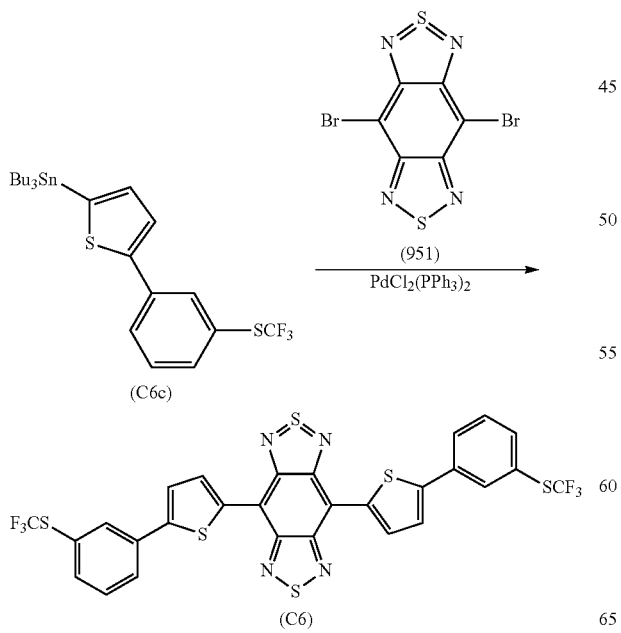

Compound (C6) was obtained in the same way as in Step 1-3 in Example 1, except that Compound (C6c) was used instead of Compound (C1b).

The properties of Compound (C6) were as follows.
$^1$H-NMR (400MHz; 1,2-dichlorobenzene-d$_4$: 140° C.; δ(ppm)); 7.50-7.65 (m, 1H), 7.65-7.85 (m, 2H), 7.95-8.10 (m, 1H), 8.31 (s, 1H), 9.20-9.35 (m, 1H)
TOF-HRMS (ASAP+); 710.9364 (M+1); Calcd. 710.9369

The solubility of Compound (C6) was evaluated, and 0.1 wt % of Compound (C6) was completely dissolved in all of toluene, mesitylene, chlorobenzene, and ortho-dichlorobenzene at 80° C. Also, 0.3 wt % of Compound (C6) was completely dissolved in mesitylene at 130° C. Also, 0.5 wt % of Compound (C6) was completely dissolved in all of chlorobenzene, and ortho-dichlorobenzene at 130° C.

Comparative Example 5

Synthesis of Compound (RC5) (4,8-bis[5-(4-((trifluoromethyl)thio)phenyl) thiophene-2-yl]benzo[1,2-c:4,5-c']bis[1,2,5]thiadiazole)

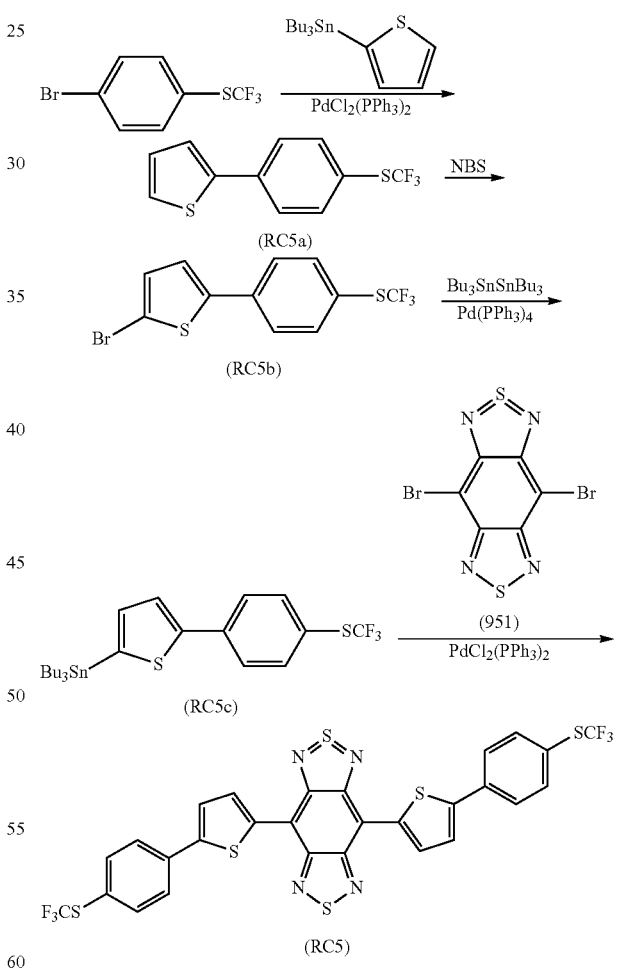

Compound (RC5) was obtained in the same way as in Example 6, except that 4-bromotrifluoromethylthiobenzene was used instead of 3-bromotrifluoromethylthiobenzene.

The properties of Compound (RC5a) were as follows.
$^1$H-NMR (400MHz; CDCl$_3$; δ(ppm)); 7.07-7.12 (m, 1H), 7.31-7.35 (m, 1H), 7.35-7.39 (m, 1H), 7.59-7.68 (br, 4H)
DI-MS (EI); 260 (M+)

The properties of Compound (RC5b) were as follows.

$^1$H-NMR (400MHz; CDCl$_3$; δ(ppm)); 7.03-7.07 (m, 1H), 7.09-7.13 (m, 1H), 7.50-7.57 (m, 2H), 7.61-7.68 (m, 2H)

DI-MS (EI); 338 (M+), 340 (M+2)

The properties of Compound (RC5c) were as follows.

$^1$H-NMR (400MHz; CDCl$_3$; δ(ppm)); 0.87-0.95 (m, 9H), 1.04-1.24 (m, 6H), 1.28-1.44 (m, 6H), 1.45-1.72 (m, 6H), 7.10-7.20 (m, 1H), 7.44-7.52 (m, 1H), 7.58-7.70 (m, 4H)

The properties of Compound (RC5) were as follows.

$^1$H-NMR (400MHz; 1,2-dichlorobenzene-d$_4$: 140° C.; δ(ppm)); 7.72-7.80 (m, 1H), 7.80-7.92 (m, 2H), 7.92-8.04 (m, 2H), 9.20-9.40 (m, 1H)

TOF-HRMS (ASAP+); 710.9359 (M+1); Calcd. 710.9369

The solubility of Compound (RC5) at 100° C. was evaluated, and 0.03 wt % of Compound (RC5) was not completely dissolved in any of toluene, mesitylene, chlorobenzene, and ortho-dichlorobenzene.

Example 7

Synthesis of Compound (C7) (Compound of the Formula (105); 4,8-bis[5-(3-cyano-4-hexylphenyl)thiophene-2-yl]benzo[1,2-c:4,5-c']bis[1,2,5]thiadiazole)

(Step 7-1: Synthesis of Compound (C7a))

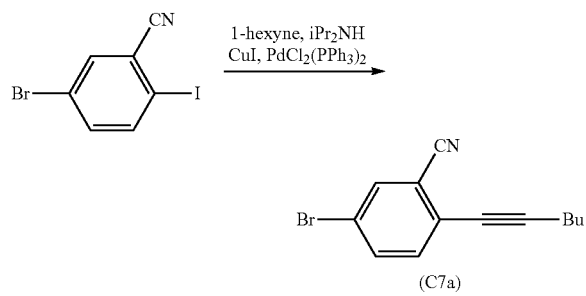

Into a 300-mL glass reaction vessel equipped with a stirring apparatus were placed 7.2 g (23.4 mmol) of 5-bromo-2-iodo-benzonitrile, and 70 mL of anhydrous tetrahydrofuran. A homogeneous solution was prepared therefrom, and then 14 mL of diisopropylamine, 0.45 g (2.34 mmol) of copper (I) iodide, 1.64 g (2.34 mmol) of dichlorobis(triphenylphosphine) palladium (II), and 1.92 g (23.4 mmol) of 1-hexyne were added to the solution, and the mixture was reacted at an internal temperature of 25° C. to 35° C. for 1 hour. And then, 0.19 g (2.3 mmol) of 1-hexyne was added to the reaction solution, and the mixture was further reacted for 1.5 hours. The reaction solution was concentrated under a reduced pressure, and the concentrate was purified by silica gel column chromatography, to provide 5.9 g of Compound (C7a) in the form of a pale yellow liquid.

The properties of Compound (C7a) were as follows.

$^1$H-NMR (400MHz; CDCl$_3$: room temperature; δ(ppm)); 0.94-0.97 (m, 3H), 1.46-1.67 (m, 4H), 2.46-2.50 (m, 2H), 7.33-7.35 (m, 1H), 7.61-7.63 (m, 1H), 7.72-7.73 (m, 1H)

CI-MS: 262 (M+1)

(Step 7-2: Synthesis of Compound (C7b))

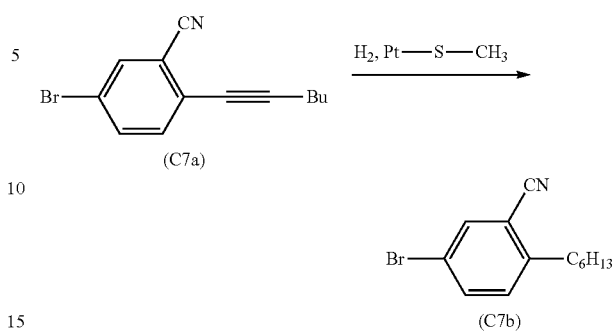

Into a 500-mL glass reaction vessel equipped with a stirring apparatus were placed 4.9 g (18.7 mmol) of Compound (C7a), 2.51 g of 54%-hydrous 3%-platinum-sulfur/carbon, and 150 mL of anhydrous tetrahydrofuran. The mixture was reacted at an internal temperature of 20° C. to 30° C. for 26 hours under hydrogen atmosphere. The reaction solution was filtered, and the filtrate was concentrated, and then the concentrate was purified by silica gel column chromatography, to provide 3.0 g of Compound (C7b) in the form of a pale brown liquid.

The properties of Compound (C7b) were as follows.

$^1$H-NMR (400MHz; CDCl$_3$: room temperature; δ(ppm)); 0.84-0.90 (m, 3H), 1.26-1.43 (m, 6H), 1.60-1.68 (m, 2H), 2.75-2.81 (m, 2H), 7.15-7.20 (m, 1H), 7.59-7.63 (m, 1H), 7.71-7.72 (m, 1H)

CI-MS; 266 (M+1)

(Step 7-3: Synthesis of Compound (C7c))

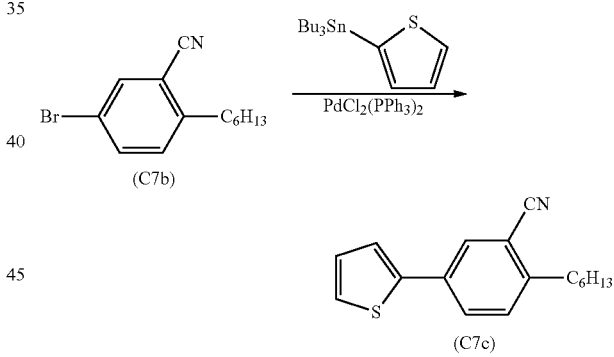

Into a 200-mL glass reaction vessel equipped with a stirring apparatus were placed 3.1 g (11.5 mmol) of Compound (C7b), 0.9 g (1.2 mmol) of dichlorobis(triphenylphosphine) palladium (II), 5.59 g (14.9 mmol) of 2-(tributyltin)thiophene, and 111 mL of toluene. The mixture was reacted at an internal temperature of about 100° C. for 6 hours. After the completion of the reaction, 100 mL of hexane was added to the reaction solution, and the mixture was purified by potassium carbonate-silica gel column chromatography, and then purified by reverse phase column chromatography and then by silica gel column chromatography, to provide 1.46 g of Compound (C7c) in the form of a yellow oil.

The properties of Compound (C7c) were as follows.

$^1$H-NMR (400MHz; CDCl$_3$: room temperature; δ(ppm)); 0.87-0.94 (m, 3H), 1.28-1.41 (m, 6H), 1.61-1.72 (m, 2H), 2.81-2.86 (m, 2H), 7.08-7.11 (m, 1H), 7.30-7.33 (m, 3H), 7.69-7.72 (m, 1H), 7.81-7.82 (m, 1H)

EI-MS: 269 (M+)

(Step 7-4: Synthesis of Compound (C7d))

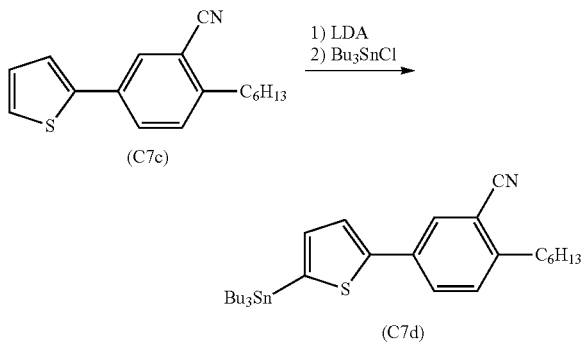

Into a 100-mL glass reaction vessel equipped with a stirring apparatus were placed 0.26 g (1.0 mmol) of Compound (C7c), and 5 mL of anhydrous tetrahydrofuran. While the internal temperature was kept at −55° C. or lower, 11 mL (1.1 mmol) of 0.1 mol/L solution of lithium diisopropylamide (LDA) in hexane, which was cooled to −55° C. or lower, was added to the mixture. The mixture was stirred at the same temperature for 60 minutes, and then 0.36 g (1.1 mmol) of tributyl tin chloride was added to the mixture at the same temperature. The temperature of the mixture was increased to room temperature, and the mixture was stirred overnight. And then, ethanol was added to the reaction solution to stop the reaction, and the solvent was distilled off. The crude product was purified by amine-modified silica gel column chromatography, to provide 0.34 g of Crude product (A) of Compound (C7d) in the form of a pale yellow liquid.

The reaction as described above was carried out in the same way, except that 1.22 g (4.43 mmol) of Compound (C7c) was added and 0.1 mol/L solution of lithium diisopropylamide in hexane at room temperature was added, to provide 1.98 g of Crude product (B) of Compound (C7d) in the form of a pale yellow liquid.

The Crude product (A) of Compound (C7d) and the Crude product (B) of Compound (C7d) were combined, and then the mixture was subjected to reverse phase silica gel chromatography, to provide 1.84 g of Compound (C7d) in the form of a pale yellow liquid.

The properties of Compound (C7d) were as follows.
$^1$H-NMR (400MHz; CDCl$_3$: room temperature; δ(ppm)); 0.87-0.93 (m, 3H), 1.05-1.71 (m, 35H), 2.81-2.85 (m, 2H), 7.11-7.18 (m, 1H), 7.27-7.30 (m, 1H), 7.41-7.43 (m, 1H), 7.71-7.73 (m, 1H), 7.82-7.83 (m, 1H)
EI-MS; 559 (M+1)

(Step 7-5: Synthesis of Compound (C7))

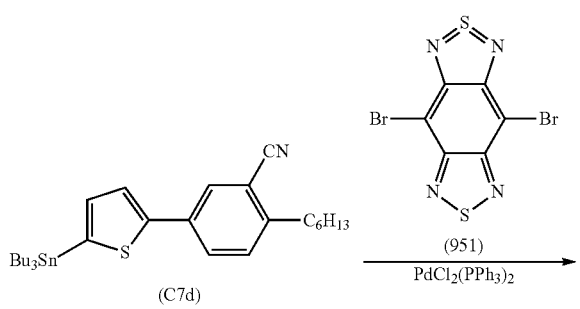

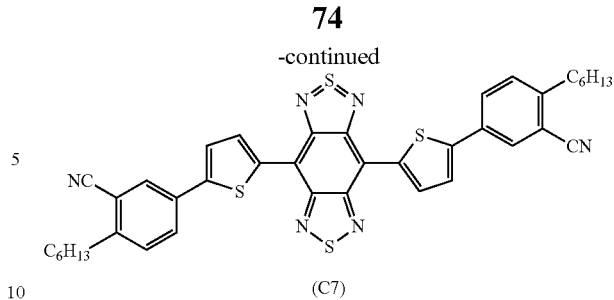

Compound (C7) was obtained in the same way as in Step 1-3 in Example 1, except that Compound (C7d) was used instead of Compound (C1b).

The properties of Compound (C7) were as follows.
$^1$H-NMR (400MHz; CDCl$_3$: room temperature; δ(ppm)); 0.90-0.94 (m, 3H), 1.33-1.45 (m, 6H), 1.64-1.71 (m, 2H), 2.77-2.81 (m, 2H), 7.28-7.31 (m, 2H), 7.72-7.81 (m, 2H), 8.67-8.69 (m, 1H)
TOF-MS (ASAP–posi); 729 (M+)

The solubility of Compound (C7) was evaluated, and 0.1 wt % of Compound (C7) was completely dissolved in chlorobenzene at 25° C. Also, 0.1 wt % of Compound (C7) was completely dissolved in all of toluene, mesitylene, and ortho-dichlorobenzene at 60° C. Also, 0.5 wt % of Compound (C7) was completely dissolved in all of chlorobenzene, and ortho-dichlorobenzene at 60° C. Also, 0.5 wt % of Compound (C7) was completely dissolved in mesitylene at 80° C. Also, 0.5 wt % of Compound (C7) was completely dissolved in toluene at 100° C.

Example 8

Synthesis of Compound (C8) (Compound of the Formula (133); 4,8-bis[5-(4-cyano-3-hexylphenyl)thiophene-2-yl]benzo[1,2-c:4,5-c']bis[1,2,5]thiadiazole)

(Step 8-1: Synthesis of Compound (C8a))

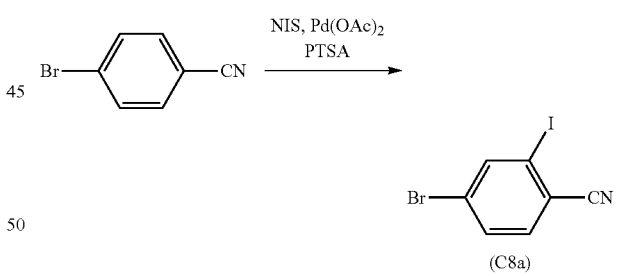

Under nitrogen atmosphere, into a 500-mL glass reaction vessel equipped with a thermometer and a stirring apparatus were placed 14.15 g (77.7 mmol) of 4-bromobenzonitrile, 300 mL of 1,2-dichloroethane, 26.24 g (116.6 mmol) of N-iodosuccinimide (NIS), 1.75 g (7.8 mmol) of palladium acetate, and 7.40 g (38.9 mmol) of para-toluene sulfonic acid monohydrate. The mixture was reacted under stirring at 70° C. for 4 hours. And furthermore, 8.75 g (38.9 mmol) of N-iodosuccinimide, and 0.88 g (3.9 mmol) of palladium acetate were added to the reaction solution, and the mixture was stirred at 70° C. for 2 hours. The reaction solution was cooled to room temperature, and then was filtered with Celite and the filtrate was concentrated. Subsequently, ethyl acetate and water were added to the concentrate, which was subjected to extraction, and the organic layer was washed with water. The organic layer was dried over anhydrous magnesium sulfate, and then the solvent was distilled off under a reduced pressure. The obtained reaction mixture was purified by silica gel column chromatography, to provide 15.29 g of Compound (C8a) in the form of a yellow-white solid.

The properties of Compound (C8a) were as follows.
$^1$H-NMR (400MHz; CDCl$_3$; δ(ppm)); 7.45-7.47 (m, 1H), 7.60-7.62 (m, 1H), 8.10-8.12 (m, 1H)
EI-MS; 307 (M)
CI-MS; 308 (M+1)

(Step 8-2: Synthesis of Compound (C8))

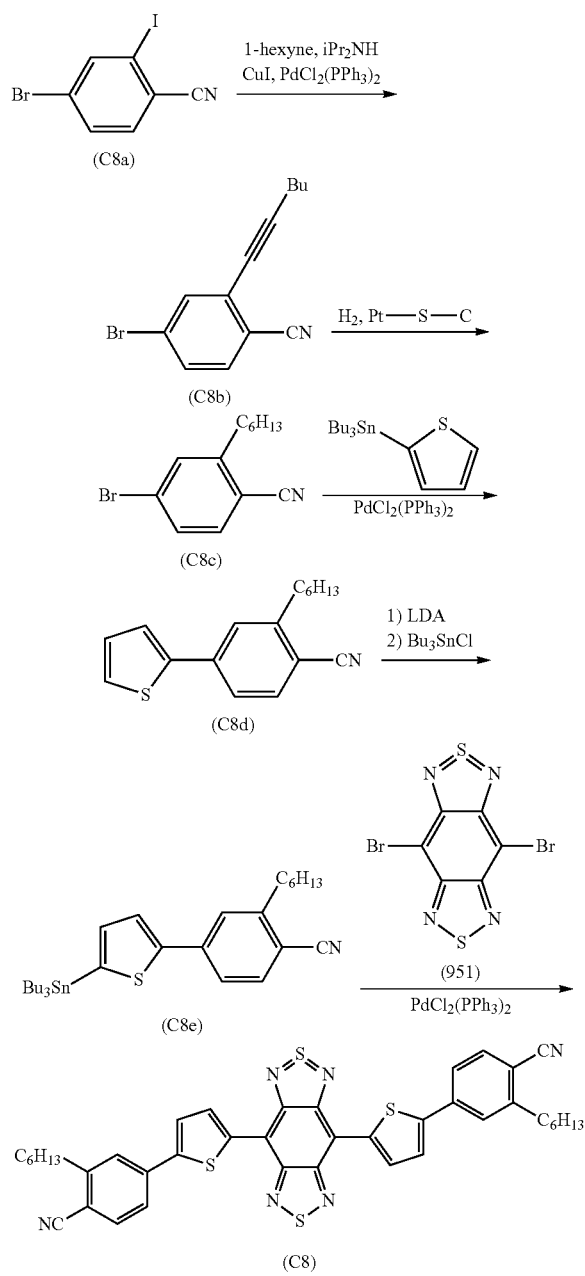

Compound (C8) was obtained in the same way as in Example 7, except that Compound (C8a) was used instead of 4-bromo-1-iodo-2-benzonitrile.

The properties of Compound (C8b) were as follows.
$^1$H-NMR (400MHz; CDCl$_3$; δ(ppm)); 0.94-0.98 (m, 3H), 1.44-1.67 (m, 4H), 2.48-2.51 (m, 2H), 7.44-7.52 (m, 2H), 7.64-7.65 (m, 1H)
EI-MS; 262 (M)
CI-MS; 262 (M)

The properties of Compound (C8c) were as follows.
$^1$H-NMR (400MHz; CDCl$_3$; δ(ppm)); 0.73-0.94 (m, 3H), 1.26-1.42 (m, 6H), 1.58-1.70 (m, 2H), 2.78-2.82 (m, 2H), 7.41-7.51 (m, 3H)
EI-MS; 266 (M)
CI-MS; 266 (M)

The properties of Compound (C8d) were as follows.
$^1$H-NMR (400MHz; CDCl$_3$; δ(ppm)); 0.88-0.91 (m, 3H), 1.27-1.45 (m, 6H), 1.67-1.74 (m, 2H), 2.83-2.87 (m, 2H), 7.11-7.60 (m, 6H)
EI-MS; 269 (M)
CI-MS; 270 (M+1)

The properties of Compound (C8e) were as follows.
$^1$H-NMR (400MHz; CDCl$_3$; δ(ppm)); 0.88-1.74 (m, 38H), 2.83-2.87 (m, 2H), 7.14-7.58 (m, 5H)
EI-MS; 559 (M)
CI-MS; 560 (M+1)

The properties of Compound (C8) were as follows.
$^1$H-NMR (400MHz; CDCl$_3$; δ(ppm)); 0.91-0.94 (m, 3H), 1.36-1.48 (m, 6H), 1.72-1.80 (m, 2H), 2.89-2.92 (m, 2H), 7.58-7.68 (m, 4H), 9.02-9.03 (m, 1H)
TOF-HRMS (ASAP+); 729.1954 (M+1); Calcd. 729.1963

The solubility of Compound (C8) at 25° C. was evaluated, and 0.03 wt % of Compound (C8) was completely dissolved in all of chlorobenzene, and ortho-dichlorobenzene at 25° C. Also, 0.1 wt % of Compound (C8) was completely dissolved in mesitylene at 130° C. Also, 0.1 wt % of Compound (C8) was completely dissolved in all of chlorobenzene, and ortho-dichlorobenzene at 80° C. Also, 0.3 wt % of Compound (C8) was completely dissolved in mesitylene at 130° C. Also, 0.3 wt % of Compound (C8) was completely dissolved in chlorobenzene at 80° C. Also, 0.5 wt % of Compound (C8) was completely dissolved in ortho-dichlorobenzene at 80° C.

Moreover, the solubility of Compound (C8) was evaluated, and 0.05 wt % of Compound (C8) was completely dissolved in chloroform at 60° C. Also, 0.2 wt % of Compound (C8) was completely dissolved in chloroform at 80° C. Also, 0.3 wt % of Compound (C8) was completely dissolved in all of chlorobenzene, and ortho-dichlorobenzene at 80° C. 0.3 wt % of Compound (C8) was completely dissolved in para-chlorotoluene at 100° C.

Example 9

Synthesis of Compound (C9) (Compound of the Formula (87); 4,8-bis[5-(4-hexyl-3-(trifluoromethyl)phenyl)thiophene-2-yl]benzo[1,2-c:4,5-c']bis[1,2,5]thiadiazole)

(Step 9-1: Synthesis of Compound (C9c))

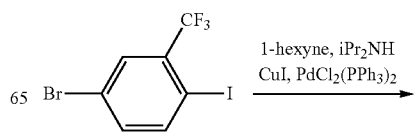

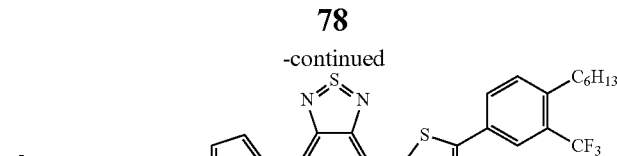

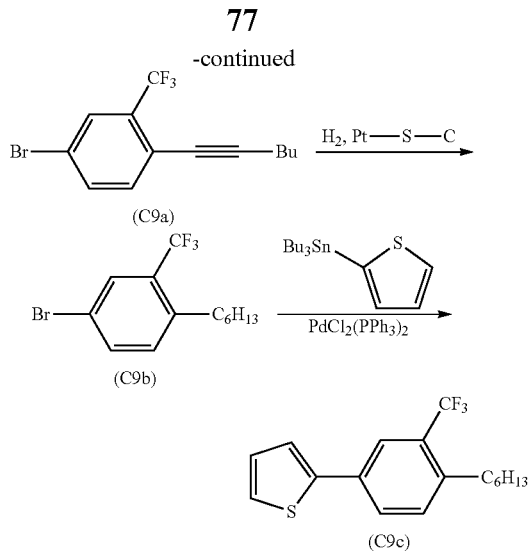

Compound (C9c) was obtained in the same way as in Steps 7-1 to 7-3 in Example 7, except that 4-bromo-1-iodo-2-trifluoromethylbenzene was used instead of 4-bromo-1-iodo-2-benzonitrile.

The properties of Compound (C9a) were as follows.

¹H-NMR (400MHz; CDCl₃; δ(ppm)); 0.93-0.96 (m, 3H), 1.40-1.63 (m, 4H), 2.41-2.44 (m, 2H), 7.36-7.75 (m, 3H)

EI-MS; 304 (M)

CI-MS; 304 (M)

The properties of Compound (C9b) were as follows.

¹H-NMR (400MHz; CDCl₃; δ(ppm)); 0.84-0.93 (m, 3H), 1.26-1.48 (m, 6H), 1.54-1.65 (m, 2H), 2.69-2.73 (m, 2H), 7.19-7.73 (m, 3H)

EI-MS; 310 (M+1)

CI-MS; 310 (M+1)

The properties of Compound (C9c) were as follows.

¹H-NMR (400MHz; CDCl₃; δ(ppm)); 0.87-0.93 (m, 3H), 1.24-1.49 (m, 6H), 1.51-1.68 (m, 2H), 2.75-2.78 (m, 2H), 7.08-7.82 (m, 6H)

EI-MS; 312 (M)

CI-MS; 313 (M+1)

(Step 9-2: Synthesis of Compound (C9))

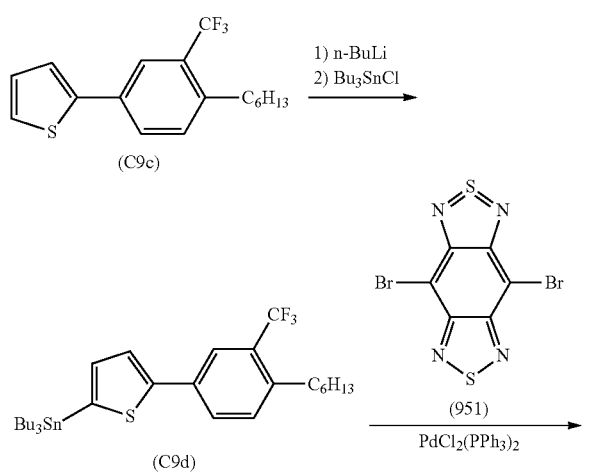

Compound (C9) was obtained in the same way as in Steps 1-2 to 1-3 in Example 1, except that Compound (C9c) was used instead of Compound (C1a).

The properties of Compound (C9d) were as follows.

¹H-NMR (400MHz; CDCl₃; δ(ppm)); 0.80-1.00 (m, 12H), 1.02-1.24 (m, 6H), 1.24-1.45 (m, 12H), 1.45-1.74 (m, 8H), 2.66-2.84 (m, 2H), 7.08-7.19 (m, 1H), 7.22-7.33 (m, 1H), 7.36-7.46 (m, 1H), 7.60-7.71 (m, 1H), 7.80-7.89 (m, 1H)

The properties of Compound (C9) were as follows.

¹H-NMR (400MHz; 1,2-dichlorobenzene-d₄: 140° C.; δ(ppm)); 1.04-1.26 (m, 6H), 1.44-1.80 (m, 12H), 1.84-2.06 (m, 4H), 2.96-3.20 (m, 4H), 7.52-7.64 (m, 2H), 7.66-7.80 (m, 2H), 7.96-8.12 (m, 2H), 8.24-8.38 (s, 2H), 9.19-9.34 (m, 2H)

TOF-HRMS (ASAP+); 815.1798 (M+1); Calcd. 815.1805

The solubility of Compound (C9) at 25° C. was evaluated, and 0.03 wt % of Compound (C9) was completely dissolved in all of toluene, mesitylene, chlorobenzene, and ortho-dichlorobenzene at 25° C. Also, 0.1 wt % of Compound (C9) was completely dissolved in all of toluene, mesitylene, chlorobenzene, and ortho-dichlorobenzene at 60° C. Also, 0.5 wt % of Compound (C9) was completely dissolved in all of toluene, and mesitylene at 80° C. Also, 0.5 wt % of Compound (C9) was completely dissolved in all of chlorobenzene, and ortho-dichlorobenzene at 60° C.

Example 10

Synthesis of Compound (C10) (Compound of the Formula (115); 4,8-bis[5-(3-hexyl-4-(trifluoromethyl)phenyl)thiophene-2-yl]benzo[1,2-c:4,5-c']bis[1,2,5]thiadiazole)

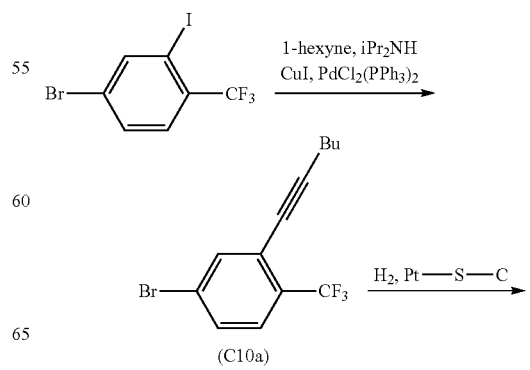

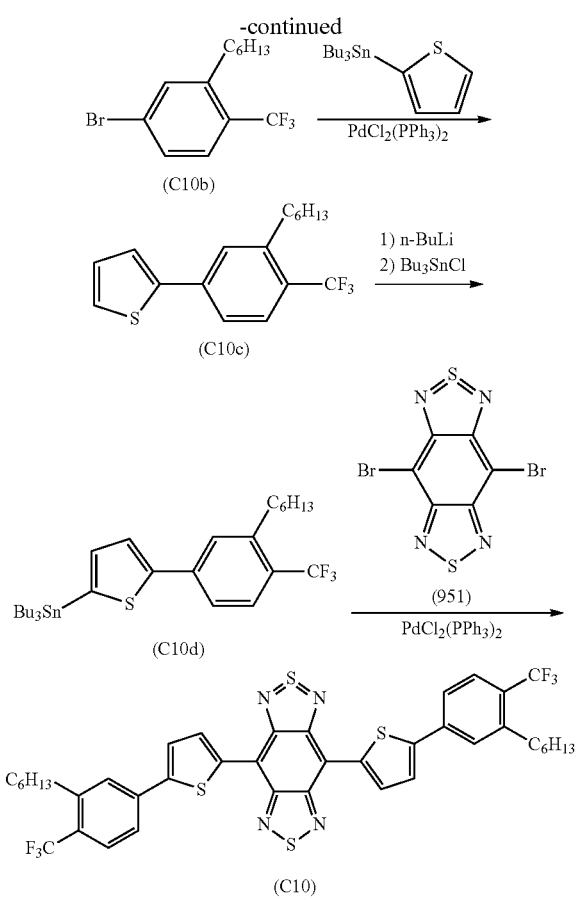

(C10b)

(C10c)

(C10d)

(C10)

Compound (C10) was obtained in the same way as in Example 9, except that 4-bromo-2-iodo-1-trifluoromethylbenzene was used instead of 4-bromo-1-iodo-2-trifluoromethylbenzene.

The properties of Compound (C10a) were as follows.
$^1$H-NMR (400MHz; CDCl$_3$; δ(ppm)); 0.93-0.97 (m, 3H), 1.43-1.53 (m, 2H), 1.55-1.64 (m, 2H), 2.43-2.46 (m, 2H), 7.44-7.49 (m, 2H), 7.67 (s, 1H)
EI-MS; 306 (M+1)

The properties of Compound (C10b) were as follows.
$^1$H-NMR (400MHz; CDCl$_3$; δ(ppm)); 0.85-0.95 (m, 3H), 1.22-1.43 (m, 6H), 1.56-1.62 (m, 2H), 2.71-2.74 (m, 2H), 7.39-7.48 (m, 3H)
EI-MS; 310 (M+1)

The properties of Compound (C10c) were as follows.
$^1$H-NMR (400MHz; CDCl$_3$; δ(ppm)); 0.86-0.95 (m, 3H), 1.27-1.46 (m, 6H), 1.61-1.69 (m, 2H), 2.76-2.80 (m, 2H), 7.09-7.13 (m, 1H), 7.32-7.38 (m, 2H), 7.47-7.60 (m, 3H)
EI-MS; 312 (M+)

The properties of Compound (C10d) were as follows.
$^1$H-NMR (400MHz; CDCl$_3$; δ(ppm)); 0.88-0.93 (m, 12H), 1.05-1.29 (m, 6H), 1.31-1.77 (m, 20H), 2.76-2.80 (m, 2H), 7.13-7.19 (m, 1H), 7.48-7.68 (m, 4H)
CI-MS; 603 (M+2)

The properties of Compound (C10) were as follows.
$^1$H-NMR (400MHz; 1,2-dichlorobenzene-d$_4$; 140° C.; δ(ppm)); 0.87-0.89 (m, 3H), 1.32-1.42 (m, 6H), 1.68-1.76 (m, 2H), 2.84-2.88 (m, 2H), 7.52-7.53 (m, 1H), 7.58 (s, 2H), 7.75 (s, 1H), 9.00-9.01 (m, 1H)
TOFMS (posi); 815 (M+1)

The solubility of Compound (C10) at 25° C. was evaluated, and 0.03 wt % of Compound (C10) was completely dissolved in all of toluene, mesitylene, chlorobenzene, and ortho-dichlorobenzene at 25° C. Also, 0.1 wt % of Compound (C10) was completely dissolved in all of toluene, and mesitylene at 80° C. Also, 0.1 wt % of Compound (C10) was completely dissolved in all of chlorobenzene, and ortho-dichlorobenzene at 60° C. Also, 0.3 wt % of Compound (C10) was completely dissolved in all of toluene, mesitylene, and chlorobenzene at 80° C. Also, 0.5 wt % of Compound (C10) was completely dissolved in all of ortho-dichlorobenzene at 100° C.

Example 11

Synthesis of Compound (C11) (Compound of the Formula (93); 4,8-bis[5-(4-hexyl-3-(trifluoromethoxy)phenyl)thiophene-2-yl]benzo[1,2-c:4,5-c']bis[1,2,5]thiadiazole)

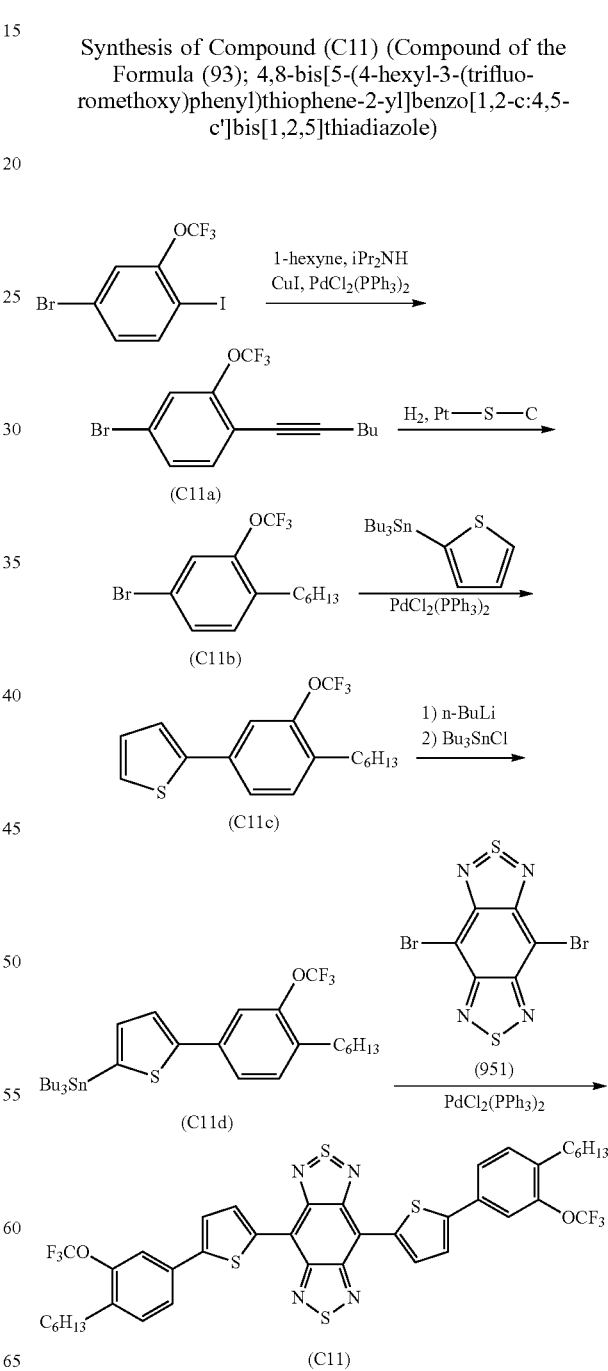

(C11a)

(C11b)

(C11c)

(C11d)

(C11)

Compound (C11) was obtained in the same way as in Example 9, except that 4-bromo-1-iodo-2-trifluoromethoxybenzene was used instead of 4-bromo-1-iodo-2-trifluoromethylbenzene.

The properties of Compound (C11a) were as follows.
$^1$H-NMR (400MHz; CDCl$_3$; δ(ppm)); 0.91-0.98 (m, 3H), 1.41-1.66 (m, 4H), 2.38-2.48 (m, 2H), 7.28-7.33 (m, 1H), 7.33-7.38 (m, 1H), 7.38-7.43 (m, 1H)
DI-MS (EI); 320 (M+), 322 (M+2)

The properties of Compound (C11b) were as follows.
$^1$H-NMR (400MHz; CDCl$_3$; δ(ppm)); 0.80-0.96 (m, 3H), 1.20-1.40 (m, 6H), 1.48-1.64 (m, 2H), 2.53-2.67 (m, 2H), 7.07-7.17 (m, 1H), 7.29-7.41 (m, 2H)
DI-MS (EI); 324 (M+), 326 (M+2)

The properties of Compound (C11c) were as follows.
$^1$H-NMR (400MHz; CDCl$_3$; δ(ppm)); 0.81-0.98 (m, 3H), 1.21-1.44 (m, 6H), 1.52-1.69 (m, 2H), 2.60-2.72 (m, 2H), 7.03-7.11 (m, 1H), 7.21-7.32 (m, 3H), 7.39-7.47 (m, 2H)
DI-MS (EI); 328 (M+)

The properties of Compound (C11d) were as follows.
$^1$H-NMR (400MHz; CDCl$_3$; δ(ppm)); 0.84-0.96 (m, 12H), 1.12-1.24 (m, 6H), 1.24-1.44 (m, 12H), 1.44-1.72 (m, 8H), 2.57-2.73 (m, 2H), 7.08-7.18 (m, 1H), 7.19-7.27 (m, 1H), 7.36-7.42 (m, 1H), 7.42-7.49 (m, 2H)

The properties of Compound (C11) were as follows.
$^1$H-NMR (400MHz; 1,2-dichlorobenzene-d$_4$; 140° C.; δ(ppm)); 1.11-1.24 (m, 6H), 1.44-1.78 (m, 12H), 1.81-2.05 (m, 4H), 2.87-3.08 (m, 4H), 7.43-7.58 (m, 2H), 7.62-7.78 (m, 2H), 7.78-7.90 (m, 2H), 7.90-8.00 (m, 2H), 9.20-9.35 (m, 2H)
TOF-HRMS (ASAP+); 847.1688 (M+1); Calcd. 847.1704

The solubility of Compound (C11) was evaluated, and 0.1 wt % of Compound (C11) was completely dissolved in all of toluene, chlorobenzene, and ortho-dichlorobenzene at 60° C. Also, 0.1 wt % of Compound (C11) was completely dissolved in mesitylene at 80° C. Also, 0.5 wt % of Compound (C11) was completely dissolved in all of toluene, chlorobenzene, and ortho-dichlorobenzene at 80° C. Also, 0.5 wt % of Compound (C11) was completely dissolved in mesitylene at 100° C.

Example 12

Synthesis of Compound (C12) (Compound of the Formula (121); 4,8-bis[5-(3-hexyl-4-(trifluoromethyl)phenyl)thiophene-2-yl]benzo[1,2-c:4,5-c']bis[1,2,5]thiadiazole)

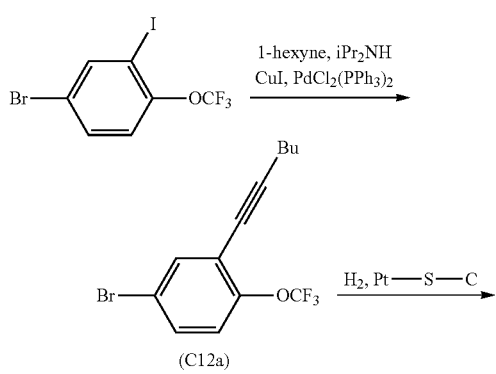

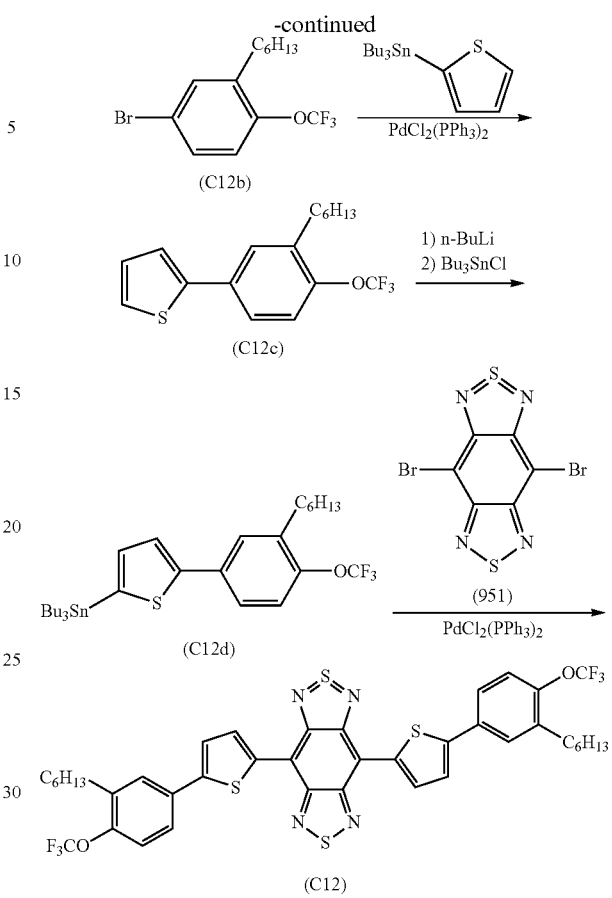

Compound (C12) was obtained in the same way as in Example 9, except that 4-bromo-2-iodo-1-trifluoromethoxybenzene was used instead of 4-bromo-1-iodo-2-trifluoromethylbenzene.

The properties of Compound (C12a) were as follows.
$^1$H-NMR (400MHz; CDCl$_3$; δ(ppm)); 0.90-0.99 (m, 3H), 1.37-1.69 (m, 4H), 2.37-2.50 (m, 2H), 7.04-7.14 (m, 1H), 7.35-7.43 (m, 1H), 7.55-7.61 (m, 1H)
DI-MS (EI); 320 (M+), 322 (M+2)

The properties of Compound (C12b) were as follows.
$^1$H-NMR (400MHz; CDCl$_3$; δ(ppm)); 0.80-0.98 (m, 3H), 1.20-1.45 (m, 6H), 1.48-1.67 (m, 2H), 2.54-2.69 (m, 2H), 7.02-7.13 (m, 1H), 7.28-7.36 (m, 2H), 7.36-7.44 (m, 1H)
DI-MS (EI); 324 (M+), 326 (M+2)

The properties of Compound (C12c) were as follows.
$^1$H-NMR (400MHz; CDCl$_3$; δ(ppm)); 0.82-0.96 (m, 3H), 1.19-1.48 (m, 6H), 1.53-1.72 (m, 2H), 2.59-2.75 (m, 2H), 7.03-7.11 (m, 1H), 7.16-7.24 (m, 1H), 7.24-7.32 (m, 2H), 7.39-7.45 (m, 1H), 7.45-7.50 (m, 1H)
DI-MS (EI); 328 (M+)

The properties of Compound (C12d) were as follows.
$^1$H-NMR (400MHz; CDCl$_3$; δ(ppm)); 0.80-1.00 (m, 12H), 1.02-1.23 (m, 6H), 1.23-1.45 (m, 12H), 1.46-1.74 (m, 8H), 2.59-2.76 (m, 2H), 7.09-7.23 (m, 2H), 7.34-7.41 (m, 1H), 7.41-7.46 (m, 1H), 7.46-7.51 (m, 1H)

The properties of Compound (C12) were as follows.
$^1$H-NMR (400MHz; 1,2-dichlorobenzene-d$_4$; 140° C.; δ(ppm)); 1.03-1.25 (m, 6H), 1.45-1.77 (m, 12H), 1.87-2.05 (m, 4H), 2.91-3.10 (m, 4H), 7.44-7.52 (m, 2H), 7.67-7.77 (m, 2H), 7.77-7.88 (m, 2H), 7.93-8.02 (m, 2H), 9.22-9.35 (m, 2H)

TOF-HRMS (ASAP+); 847.1692 (M+1); Calcd. 847.1704

The solubility of Compound (C12) was evaluated, and 0.1 wt % of Compound (C12) was completely dissolved in all of chlorobenzene, and ortho-dichlorobenzene at 60° C. Also, 0.1 wt % of Compound (C12) was completely dissolved in all of toluene, and mesitylene at 80° C. Also, 0.3 wt % of Compound (C12) was completely dissolved in toluene at 80° C. Also, 0.5 wt % of Compound (C12) was completely dissolved in mesitylene at 130° C. Also, 0.5 wt % of Compound (C12) was completely dissolved in chlorobenzene, and ortho-dichlorobenzene at 80° C.

Example 13

Synthesis of Compound (C13) (Compound of the Formula (133); 4,8-bis[5-(4-cyano-3-heptylphenyl)thiophene-2-yl]benzo[1,2-c:4,5-c']bis[1,2,5]thiadiazole)

(Step 13-1: Synthesis of Compound (C13))

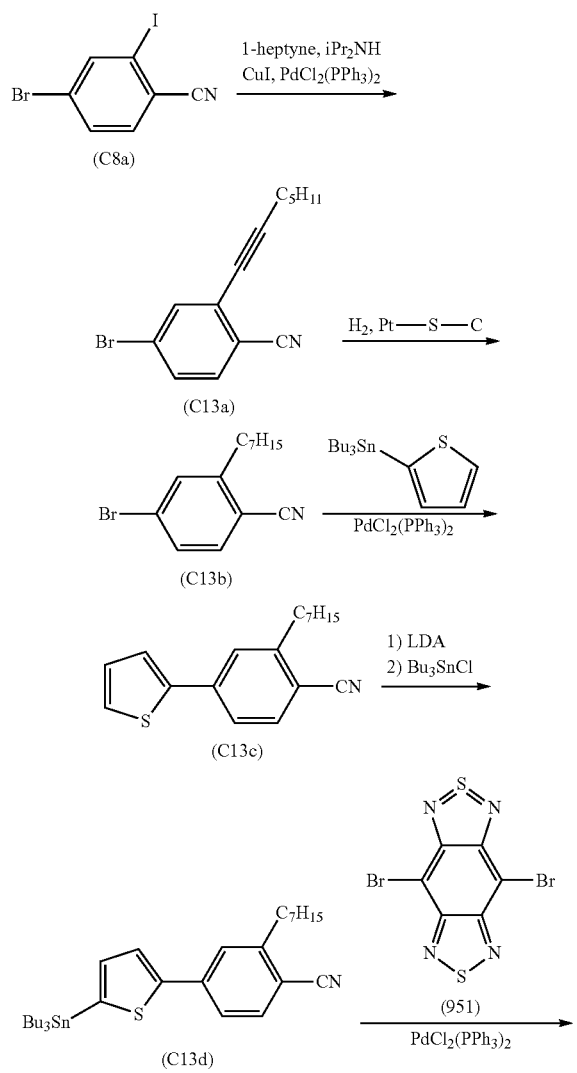

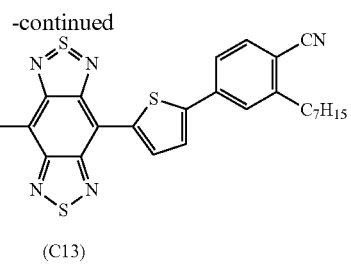

Compound (C13) was obtained in the same way as in Example 8, except that 1-heptyne was used instead of 1-hexyne.

The properties of Compound (C13a) were as follows.
¹H-NMR (400MHz; CDCl₃; δ(ppm)); 0.91-0.95 (m, 3H), 1.30-1.50 (m, 4H), 1.62-1.69 (m, 2H), 2.47-2.50 (m, 2H), 7.44-7.52 (m, 2H), 7.64-7.65 (m, 1H)
CI-MS; 278 (M+3), 276 (M+1)

The properties of Compound (C13b) were as follows.
¹H-NMR (400MHz; CDCl₃; δ(ppm)); 0.87-0.90 (m, 3H), 1.22-1.41 (m, 8H), 1.62-1.70 (m, 2H), 2.78-2.82 (m, 2H), 7.41-7.49 (m, 3H)
CI-MS; 282 (M+3), 280 (M+1)

The properties of Compound (C13c) were as follows.
¹H-NMR (400MHz; CDCl₃; δ(ppm)); 0.87-0.90 (m, 3H), 1.28-1.44 (m, 8H), 1.67-1.74 (m, 2H), 2.83-2.87 (m, 2H), 7.11-7.60 (m, 6H)
CI-MS; 284 (M+1)

The properties of Compound (C13d) were as follows.
¹H-NMR (400MHz; CDCl₃; δ(ppm)); 0.88-1.74 (m, 40H), 2.82-2.86 (m, 2H), 7.14-7.59 (m, 5H)
EI-MS; 572 (M)
CI-MS; 572 (M)

The properties of Compound (C13) were as follows.
¹H-NMR (400MHz; CDCl₃; δ(ppm)); 0.89-0.93 (m, 6H), 1.31-1.53 (m, 16H), 1.72-1.80 (m, 4H), 2.88-2.92 (m, 4H), 7.58-7.68 (m, 8H), 9.02-9.03 (m, 2H)
TOF-HRMS (ASAP+); 757.2261 (M+1); Calcd. 757.2276

The solubility of Compound (C13) was evaluated, and 0.2 wt % of Compound (C13) was completely dissolved in chloroform at 25° C. Also, 0.3 wt % of Compound (C13) was completely dissolved in all of ortho-dichlorobenzene, chlorobenzene, and para-chlorotoluene at 80° C.

Example 14

Synthesis of Compound (C14) (Compound of the Formula (133); 4,8-bis[5-(4-cyano-3-octylphenyl)thiophene-2-yl]benzo[1,2-c:4,5-c']bis[1,2,5]thiadiazole)

(Step 14-1: Synthesis of Compound (C14))

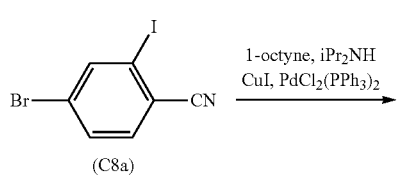

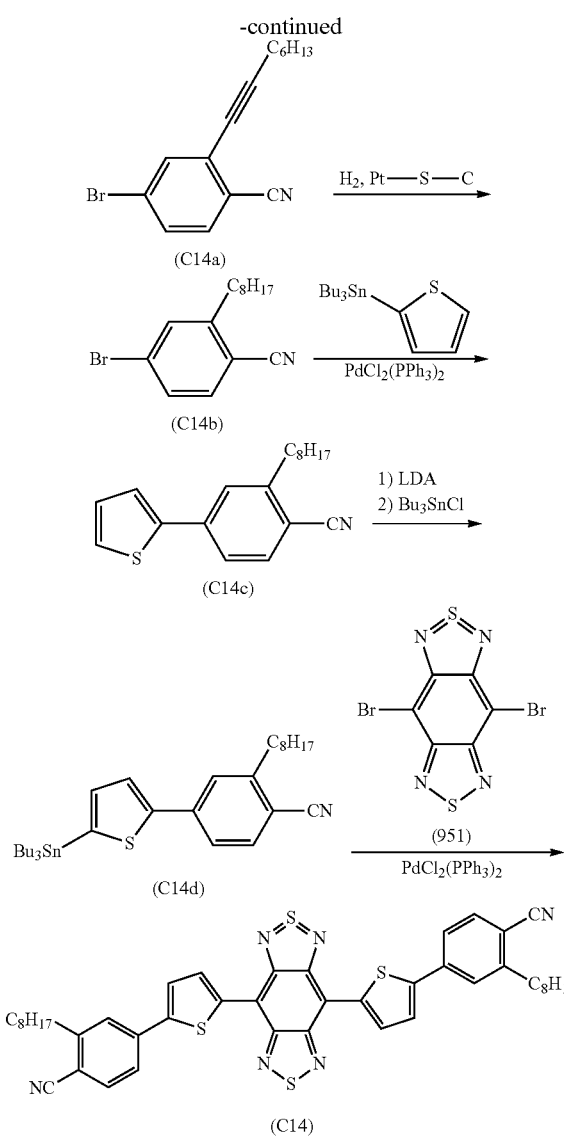

(C14a)

(C14b)

(C14c)

(C14d)

(C14)

Compound (C14) was obtained in the same way as in Example 8, except that 1-octyne was used instead of 1-hexyne.

The properties of Compound (C14a) were as follows.
$^1$H-NMR (400MHz; CDCl$_3$; δ(ppm)); 0.88-0.94 (m, 3H), 1.24-1.68 (m, 8H), 2.47-2.50 (m, 2H), 7.44-7.52 (m, 2H), 7.64-7.65 (m, 1H)
CI-MS; 293 (M+3), 290 (M+1)

The properties of Compound (C14b) were as follows.
$^1$H-NMR (400MHz; CDCl$_3$; δ(ppm)); 0.87-0.90 (m, 3H), 1.27-1.37 (m, 10H), 1.62-1.68 (m, 2H), 2.78-2.82 (m, 2H), 7.43-7.49 (m, 3H)
EI-MS; 294 (M+1), 292 (M−1)

The properties of Compound (C14c) were as follows.
$^1$H-NMR (400MHz; CDCl$_3$; δ(ppm)); 0.86-0.90 (m, 3H), 1.36-1.44 (m, 10H), 1.67-1.74 (m, 2H), 2.83-2.87 (m, 2H), 7.11-7.15 (m, 1H), 7.38-7.61 (m, 5H)
EI-MS; 297 (M)

The properties of Compound (C14d) were as follows.
$^1$H-NMR (400MHz; CDCl$_3$; δ(ppm)); 0.86-0.93 (m, 12H), 1.12-1.72 (m, 30H), 2.82-2.86 (m, 2H), 7.16-7.17 (m, 1H), 7.50-7.56 (m, 4H)
CI-MS; 588 (M+1)

The properties of Compound (C14) were as follows.
$^1$H-NMR (400MHz; 1,2-dichlorobenzene-d$_4$; 140° C.; δ(ppm)); 0.83-0.85 (m, 6H), 1.26-1.41 (m, 20H), 1.73-1.79 (m, 4H), 2.85-2.89 (m, 4H), 7.45-7.56 (m, 6H), 7.66-7.70 (m, 2H), 9.02-9.04 (m, 2H)
TOF-HRMS (ASAP+); 785.2578 (M+1); Calcd. 785.2589

The solubility of Compound (C14) was evaluated, and 0.1 wt % of Compound (C14) was completely dissolved in chloroform at 25° C. Also, 0.2 wt % of Compound (C14) was completely dissolved in chloroform at 60° C. Also, 0.3 wt % of Compound (C14) was completely dissolved in ortho-dichlorobenzene at 60° C. Also, 0.3 wt % of Compound (C14) was completely dissolved in chlorobenzene at 80° C. Also, 0.3 wt % of Compound (C14) was completely dissolved in para-chlorotoluene at 100° C.

Example 15

Synthesis of Compound (C15) (Compound of the Formula (133); 4,8-bis[5-(4-cyano-3-nonylphenyl)thiophene-2-yl]benzo[1,2-c:4,5-c']bis[1,2,5]thiadiazole)

(Step 15-1: Synthesis of Compound (C15))

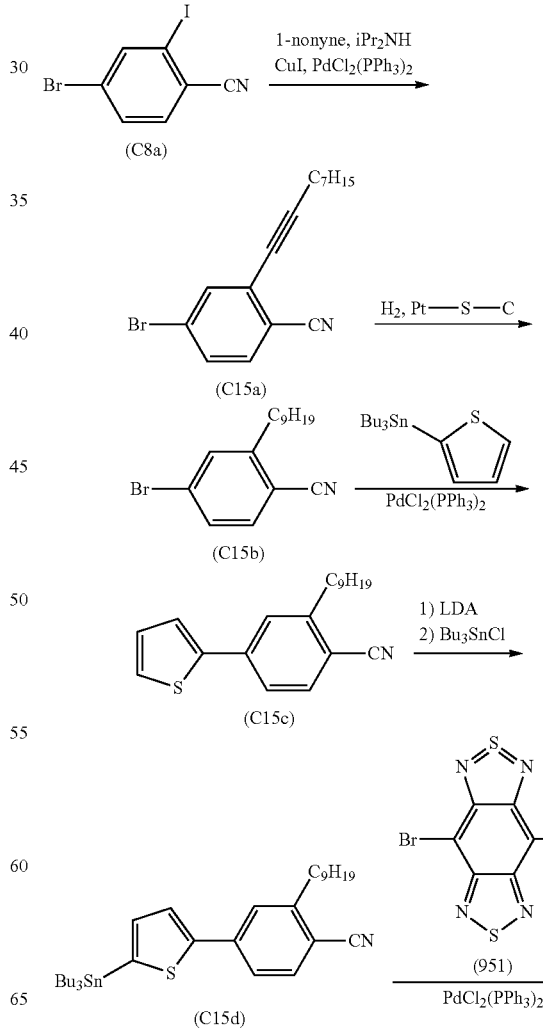

(C8a)

(C15a)

(C15b)

(C15c)

(C15d)

-continued

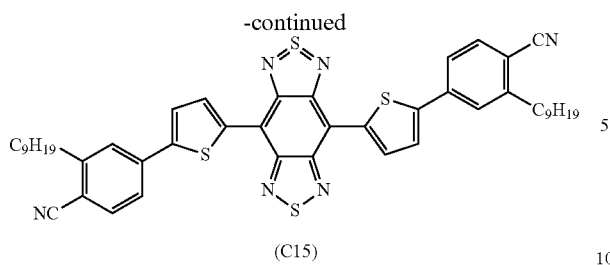

(C15)

Compound (C15) was obtained in the same way as in Example 8, except that 1-nonyne was used instead of 1-hexyne.

The properties of Compound (C15a) were as follows.
$^1$H-NMR (400MHz; CDCl$_3$; δ(ppm)); 0.88-0.91 (m, 3H), 1.43-1.68 (m, 10H), 2.47-2.50 (m, 2H), 7.44-7.52 (m, 2H), 7.64-7.65 (m, 1H)
CI-MS; 306 (M+3), 304 (M+1)

The properties of Compound (C15b) were as follows.
$^1$H-NMR (400MHz; CDCl$_3$; δ(ppm)); 0.86-0.90 (m, 3H), 1.27-1.69 (m, 14H), 2.78-2.82 (m, 2H), 7.41-7.51 (m, 3H)
CI-MS; 310 (M+3), 308 (M+1)

The properties of Compound (C15c) were as follows.
$^1$H-NMR (400MHz; CDCl$_3$; δ(ppm)); 0.85-0.89 (m, 3H), 1.27-1.44 (m, 12H), 1.67-1.74 (m, 2H), 2.83-2.87 (m, 2H), 7.11-7.13 (m, 1H), 7.38-7.61 (m, 5H)
EI-MS; 311 (M)

The properties of Compound (C15d) were as follows.
$^1$H-NMR (400MHz; CDCl$_3$; δ(ppm)); 0.86-0.93 (m, 3H), 1.12-1.72 (m, 41H), 2.82-2.86 (m, 2H), 7.17-7.18 (m, 1H), 7.50-7.58 (m, 4H)
EI-MS; 601 (M)

The properties of Compound (C15) were as follows.
$^1$H-NMR (400MHz; 1,2-dichlorobenzene-d$_4$; 140° C.; δ(ppm)); 0.82-0.84 (m, 6H), 1.25-1.42 (m, 24H), 1.71-1.78 (m, 4H), 2.84-2.88 (m, 4H), 7.44-7.55 (m, 6H), 7.69 (s, 2H), 9.01-9.02 (m, 2H)
TOF-HRMS (ASAP+); 813.2891 (M+1); Calcd. 813.2902

The solubility of Compound (C15) was evaluated, and 0.1 wt % of Compound (C15) was completely dissolved in chloroform at 25° C. Also, 0.2 wt % of Compound (C15) was completely dissolved in chloroform at 60° C. Also, 0.3 wt % of Compound (C15) was completely dissolved in all of chlorobenzene, and ortho-dichlorobenzene at 60° C. Also, 0.3 wt % of Compound (C15) was completely dissolved in para-chlorotoluene at 80° C.

Example 16

Synthesis of Compound (C16) (Compound of the Formula (133); 4,8-bis[5-(4-cyano-3-decylphenyl)thiophene-2-yl]benzo[1,2-c:4,5-c']bis[1,2,5]thiadiazole)

(Step 16-1: Synthesis of Compound (C16))

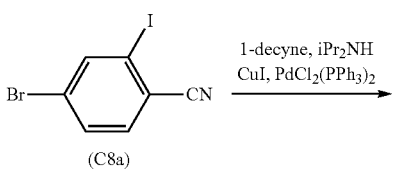

-continued

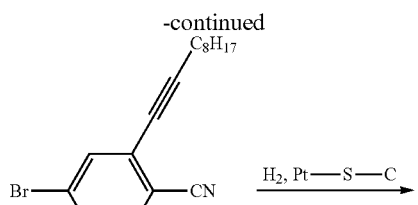

(C16a)

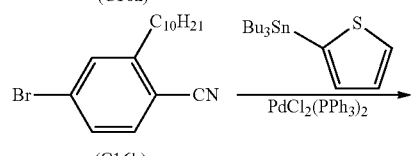

(C16b)

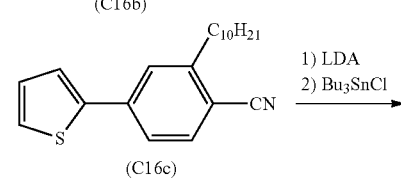

(C16c)

(C16d)

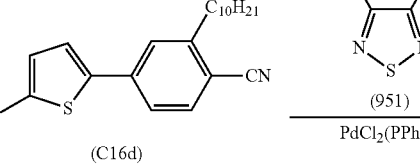

(C16)

Compound (C16) was obtained in the same way as in Example 8, except that 1-decyne was used instead of 1-hexyne.

The properties of Compound (C16a) were as follows.
$^1$H-NMR (400MHz; CDCl$_3$; δ(ppm)); 0.82-0.95 (m, 3H), 1.18-1.39 (m, 8H), 1.39-1.54 (m, 2H), 1.58-1.72 (m, 2H), 2.43-2.54 (m, 2H), 7.41-7.47 (m, 1H), 7.47-7.53 (m, 1H), 7.62-7.68 (m, 1H)
CI-MS; 318 (M+1), 320 (M+3)

The properties of Compound (C16b) were as follows.
$^1$H-NMR (400MHz; CDCl$_3$; δ(ppm)); 0.82-0.94 (m, 3H), 1.15-1.47 (m, 14H), 1.59-1.73 (m, 2H), 2.72-2.87 (m, 2H), 7.40-7.44 (m, 1H), 7.44-7.48 (m, 1H), 7.48-7.51 (m, 1H)
CI-MS; 322 (M+1), 324 (M+3)

The properties of Compound (C16c) were as follows.
$^1$H-NMR (400MHz; CDCl$_3$; δ(ppm)); 0.80-0.96 (m, 3H), 1.14-1.50 (m, 14H), 1.62-1.79 (m, 2H), 2.77-2.94 (m, 2H), 7.06-7.18 (m, 1H), 7.35-7.40 (m, 1H), 7.40-7.44 (m, 1H), 7.46-7.55 (m, 2H), 7.56-7.64 (m, 1H)
EI-MS; 325 (M)
CI-MS; 326 (M+1)

The properties of Compound (C16d) were as follows.

¹H-NMR (400MHz; CDCl₃; δ(ppm)); 0.82-0.98 (m, 12H), 1.02-1.46 (m, 26H), 1.46-1.78 (m, 8H), 2.74-2.94 (m, 2H), 7.12-7.22 (m, 1H), 7.47-7.55 (m, 3H), 7.55-7.60 (m, 1H)

EI-MS; 615 (M)

CI-MS; 616 (M+1)

The properties of Compound (C16) were as follows.

¹H-NMR (400MHz; 1,2-dichlorobenzene-d₄; 140° C.; δ(ppm)); 0.75-0.95 (m, 6H), 1.15-1.55 (m, 28H), 1.68-1.84 (m, 4H), 2.80-2.95 (m, 4H), 7.42-7.50 (m, 2H), 7.50-7.61 (m, 4H), 7.66-7.76 (m, 2H), 8.98-9.09 (m, 2H)

TOF-HRMS (ASAP+); 841.3203 (M+1); Calcd. 841.3215

The solubility of Compound (C16) was evaluated, and 0.2 wt % of Compound (C16) was completely dissolved in chloroform at 60° C. Also, 0.3 wt % of Compound (C16) was completely dissolved in all of ortho-dichlorobenzene, chlorobenzene, and para-chlorotoluene at 80° C.

Example 17

Synthesis of Compound (C17) (Compound of the Formula (133); 4,8-bis[5-(4-cyano-3-dodecylphenyl)thiophene-2-yl]benzo[1,2-c:4,5-c']bis[1,2,5]thiadiazole)

(Step 17-1: Synthesis of Compound (C17))

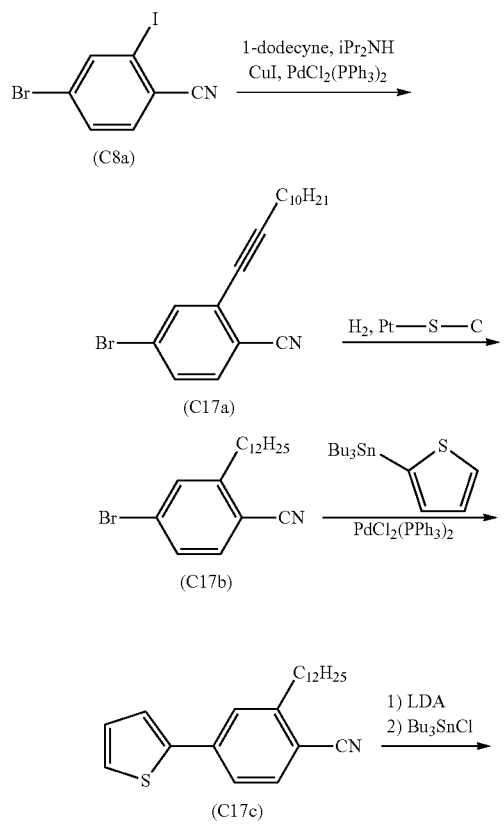

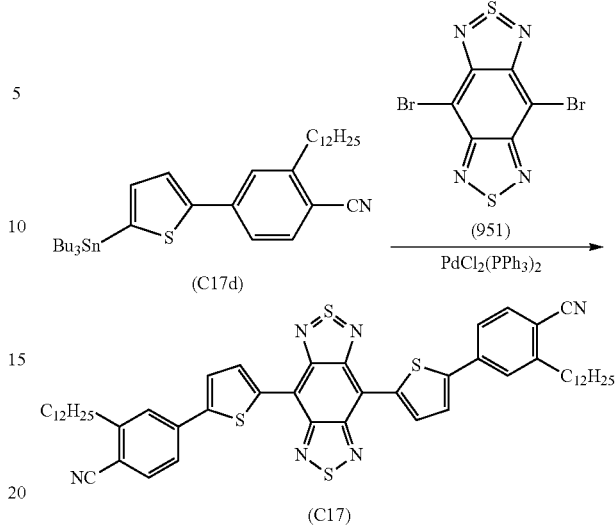

Compound (C17) was obtained in the same way as in Example 8, except that 1-dodecyne was used instead of 1-hexyne.

The properties of Compound (C17a) were as follows.

¹H-NMR (400MHz; CDCl₃; δ(ppm)); 0.86-0.90 (m, 3H), 1.43-1.68 (m, 16H), 2.46-2.50 (m, 2H), 7.44-7.52 (m, 2H), 7.64-7.65 (m, 1H)

CI-MS; 348 (M+3), 346 (M+1)

The properties of Compound (C17b) were as follows.

¹H-NMR (400MHz; CDCl₃; δ(ppm)); 0.86-0.90 (m, 3H), 1.26-1.41 (m, 18H), 1.56-1.69 (m, 2H), 2.78-2.82 (m, 2H), 7.41-7.52 (m, 3H)

CI-MS; 352 (M+3), 350 (M+1)

The properties of Compound (C17c) were as follows.

¹H-NMR (400MHz; CDCl₃; δ(ppm)); 0.86-0.89 (m, 3H), 1.26-1.45 (m, 18H), 1.66-1.74 (m, 2H), 2.83-2.87 (m, 2H), 7.11-7.61 (m, 6H)

EI-MS; 353 (M)

CI-MS; 354 (M+1)

The properties of Compound (C17d) were as follows.

¹H-NMR (400MHz; CDCl₃; δ(ppm)); 0.86-1.74 (m, 50H), 2.82-2.86 (m, 2H), 7.14-7.59 (m, 5H)

EI-MS; 642 (M)

CI-MS; 642 (M)

The properties of Compound (C17) were as follows.

¹H-NMR (400MHz; 1,2-dichlorobenzene-d₄, 140° C.; δ(ppm)); 0.82-0.84 (m, 6H), 1.26-1.42 (m, 36H), 1.73-1.78 (m, 4H), 2.86-2.90 (m, 4H), 7.41-7.71 (m, 8H), 9.04-9.05 (m, 2H)

TOF-HRMS (ASAP+); 897.3823 (M+1); Calcd. 897.3841

The solubility of Compound (C17) was evaluated, and 0.2 wt % of Compound (C17) was completely dissolved in chloroform at 60° C. Also, 0.3 wt % of Compound (C17) was completely dissolved in ortho-dichlorobenzene at 60° C. Also, 0.3 wt % of Compound (C17) was completely dissolved in all of chlorobenzene, and para-chlorotoluene at 80° C. Also, 0.3 wt % of Compound (C17) was completely dissolved in all of xylene at 100° C.

Example 18

Synthesis of Compound (C18) (Compound of the Formula (133); 4,8-bis[5-(4-cyano-3-tetradecylphenyl)thiophene-2-yl]benzo[1,2-c:4,5-c']bis[1,2,5]thiadiazole)

(Step 18-1: Synthesis of Compound (C18))

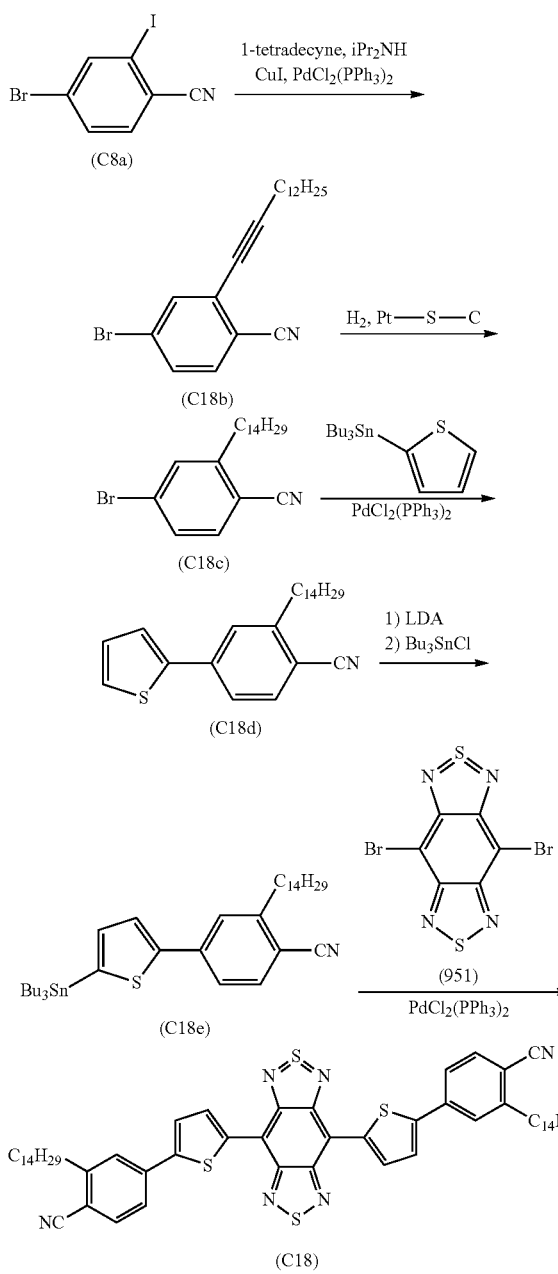

Compound (C18) was obtained in the same way as in Example 8, except that 1-tetradecyne was used instead of 1-hexyne.

The properties of Compound (C18b) were as follows.
$^1$H-NMR (400MHz; CDCl$_3$; δ(ppm)); 0.75-0.99 (m, 3H), 1.10-1.39 (m, 16H), 1.39-1.54 (m, 2H), 1.57-1.72 (m, 2H), 2.36-2.60 (m, 2H), 7.41-7.47 (m, 1H), 7.47-7.53 (m, 1H), 7.61-7.69 (m, 1H)
CI-MS; 374 (M+1)

The properties of Compound (C18c) were as follows.
$^1$H-NMR (400MHz; CDCl$_3$; δ(ppm)); 0.78-0.98 (m, 3H), 1.06-1.50 (m, 22H), 1.58-1.75 (m, 2H), 2.71-2.88 (m, 2H), 7.39-7.44 (m, 1H), 7.44-7.47 (m, 1H), 7.47-7.51 (m, 1H)
EI-MS; 377 (M)
CI-MS; 378 (M+1)

The properties of Compound (C18d) were as follows.
$^1$H-NMR (400MHz; CDCl$_3$; δ(ppm)); 0.75-1.00 (m, 3H), 1.04-1.54 (m, 22H), 1.58-1.82 (m, 2H), 2.72-2.98 (m, 2H), 7.04-7.18 (m, 1H), 7.33-7.45 (m, 2H), 7.45-7.56 (m, 2H), 7.56-7.65 (m, 1H)
EI-MS; 381 (M)
CI-MS; 382 (M+1)

The properties of Compound (C18e) were as follows.
$^1$H-NMR (400MHz; CDCl$_3$; δ(ppm)); 0.81-0.99 (m, 12H), 1.03-1.46 (m, 34H), 1.47-1.78 (m, 8H), 2.75-2.93 (m, 2H), 7.11-7.22 (m, 1H), 7.46-7.55 (m, 3H), 7.55-7.62 (m, 1H)
EI-MS; 671 (M)
CI-MS; 672 (M+1)

The properties of Compound (C18) were as follows.
$^1$H-NMR (400MHz; 1,2-dichlorobenzene-d$_4$, 140° C.; δ(ppm)); 0.70-0.98 (m, 6H), 1.20-1.56 (m, 44H), 1.60-1.90 (m, 4H), 2.72-3.04 (m, 4H), 7.36-7.64 (m, 6H), 7.64-7.80 (br, 2H), 8.85-9.25 (br, 2H)
TOF-HRMS (ASAP+); 953.4460 (M+1); Calcd. 953.4467

The solubility of Compound (C18) was evaluated, and 0.2 wt % of Compound (C18) was completely dissolved in chloroform at 60° C. Also, 0.3 wt % of Compound (C18) was completely dissolved in ortho-dichlorobenzene, and 1-methylnaphthalene at 80° C. Also, 0.3 wt % of Compound (C18) was completely dissolved in chlorobenzene at 100° C.

Example 19

Synthesis of Compound (C19) (Compound of the Formula (133); 4,8-bis[5-(4-cyano-3-hexadecylphenyl)thiophene-2-yl]benzo[1,2-c:4,5-c']bis[1,2,5]thiadiazole))

Step 19-1: Synthesis of Compound (C19))

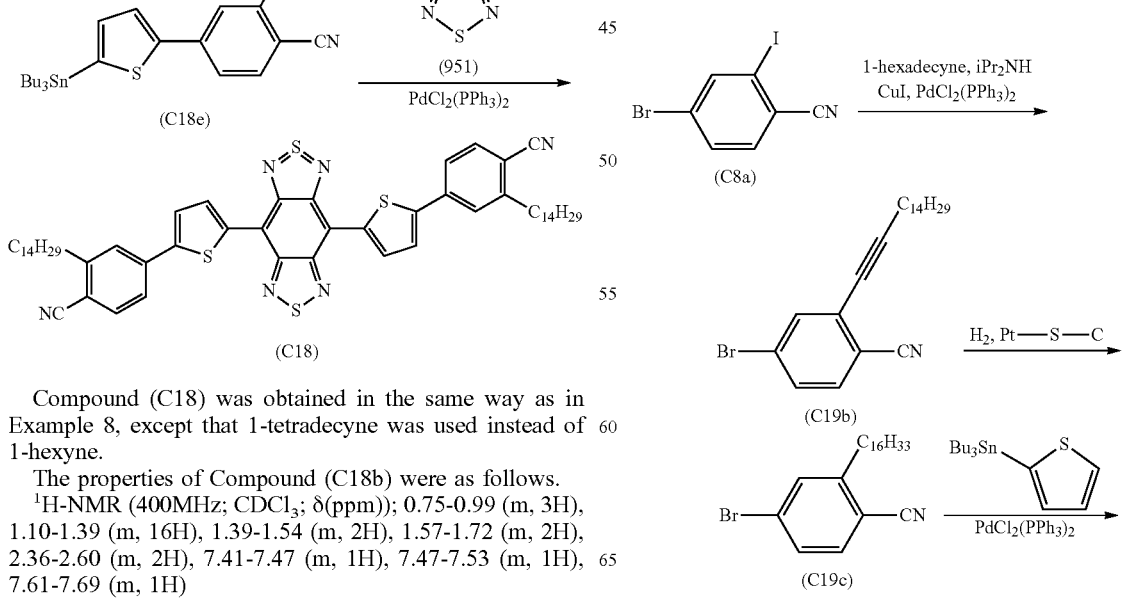

93

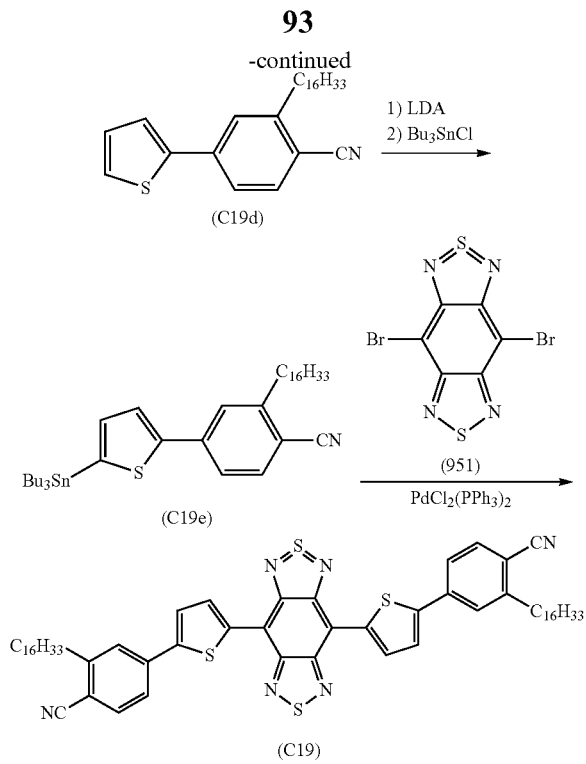

Compound (C19) was obtained in the same way as in Example 8, except that 1-hexadecyne was used instead of 1-hexyne.

The properties of Compound (C19b) were as follows.
¹H-NMR (400MHz; CDCl₃; δ(ppm)); 0.86-0.90 (m, 3H), 1.26-1.30 (m, 20H), 1.45-1.49 (m, 2H), 1.62-1.66 (m, 2H), 2.46-2.50 (m, 2H), 7.44-7.50 (m, 2H), 7.64-7.65 (m, 1H)
CI-MS; 402 (M+1)

The properties of Compound (C19c) were as follows.
¹H-NMR (400MHz; CDCl₃; δ(ppm)); 0.86-0.90 (m, 3H), 1.26-1.39 (m, 26H), 1.64-1.67 (m, 2H), 2.78-2.82 (m, 2H), 7.41-7.50 (m, 3H)
CI-MS; 406 (M+1)

The properties of Compound (C19d) were as follows.
¹H-NMR (400MHz; CDCl₃; δ(ppm)); 0.86-0.89 (m, 3H), 1.25-1.41 (m, 26H), 1.68-1.72 (m, 2H), 2.83-2.87 (m, 2H), 7.11-7.13 (m, 1H), 7.38-7.41 (m, 2H), 7.49-7.52 (m, 2H), 7.58-7.60 (m, 1H)
CI-MS; 410 (M+1)

The properties of Compound (C19e) were as follows.
¹H-NMR (400MHz; CDCl₃; δ(ppm)); 0.86-0.93 (m, 12H), 1.05-1.40 (m, 38H), 1.50-1.70 (m, 8H), 2.82-2.86 (m, 2H), 7.14-7.20 (m, 1H), 7.50-7.58 (m, 4H)
CI-MS; 700 (M+1)

The properties of Compound (C19) were as follows.
¹H-NMR (400MHz; CDCl₃, 55° C.; δ(ppm)); 0.85-0.89 (m, 6H), 1.25-1.49 (m, 52H), 1.73-1.81 (m, 4H), 2.89-2.93 (m, 4H), 7.58-7.69 (m, 8H), 9.04-9.05 (m, 2H)
TOF-HRMS (ASAP+); 1009.5072 (M+1); Calcd. 1009.5093

The solubility of Compound (C19) was evaluated, and 0.3 wt % of Compound (C19) was completely dissolved in 1-methylnaphthalene at 25° C. Also, 0.2 wt % of Compound (C19) was completely dissolved in chloroform at 60° C. Also, 0.3 wt % of Compound (C19) was completely dissolved in all of chlorobenzene, and ortho-dichlorobenzene at 80° C.

94

Example 20

Synthesis of Compound (C20) (Compound of the Formula (133); 4,8-bis[5-(4-cyano-3-octadecylphenyl)thiophene-2-yl]benzo[1,2-c:4,5-c']bis[1,2,5]thiadiazole))

(Step 20-1: Synthesis of Compound (C20))

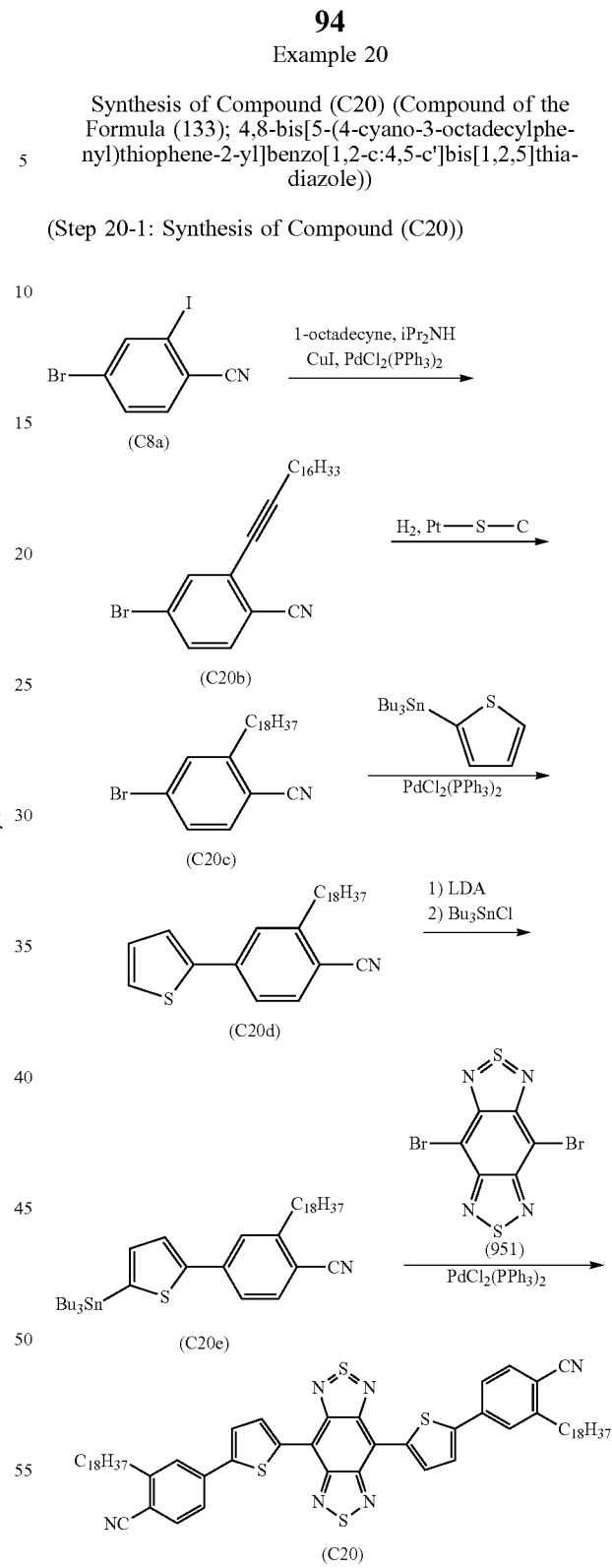

Compound (C20) was obtained in the same way as in Example 8, except that 1-octadecyne was used instead of 1-hexyne.

The properties of Compound (C20b) were as follows.
¹H-NMR (400MHz; CDCl₃; δ(ppm)); 0.86-0.90 (m, 3H), 1.25-1.68 (m, 28H), 2.41-2.50 (m, 2H), 7.44-7.52 (m, 2H), 7.64-7.65 (m, 1H)
CI-MS; 430 (M+1), 432 (M+3)

The properties of Compound (C20c) were as follows.
¹H-NMR (400MHz; CDCl₃; δ(ppm)); 0.86-0.90 (m, 3H), 1.25-1.69 (m, 32H), 2.78-2.86 (m, 2H), 7.41-7.51 (m, 3H)
CI-MS; 434 (M+1), 436 (M+3)

The properties of Compound (C20d) were as follows.
¹H-NMR (400MHz; CDCl₃; δ(ppm)); 0.86-0.92 (m, 3H), 1.25-1.70 (m, 32H), 2.83-2.87 (m, 2H), 7.11-7.61 (m, 6H)
EI-MS; 437 (M)
CI-MS; 438 (M+1)

The properties of Compound (C20e) were as follows.
¹H-NMR (400MHz; CDCl₃; δ(ppm)); 0.88-1.70 (m, 62H), 2.82-2.86 (m, 2H), 7.16-7.59 (m, 5H)
EI-MS; 727 (M)
CI-MS; 727 (M)

The properties of Compound (C20) were as follows.
¹H-NMR (400MHz; 1,2-dichlorobenzene-d4, 140° C.; δ(ppm)); 0.84 (m, 3H), 1.29-1.76 (m, 30H), 1.76 (m, 2H), 2.87 (m, 2H), 7.41-7.72 (m, 4H), 9.07 (m, 1H)
TOF-HRMS (ASAP+); 1065.5709 (M+1); Calcd. 1065.5719

The solubility of Compound (C20) was evaluated, and 0.1 wt % of Compound (C20) was completely dissolved in chloroform at 60° C. Also, 0.3 wt % of Compound (C20) was completely dissolved in ortho-dichlorobenzene at 80° C. Also, 0.3 wt % of Compound (C20) was completely dissolved in all of chlorobenzene, and 1-methylnaphthalene at 100° C.

Example 21

Synthesis of Compound (C21) (Compound of the Formula (133); 4,8-bis[5-(4-cyano-3-(3-methyl-hexyl)phenyl)thiophene-2-yl]benzo[1,2-c:4,5-c']bis[1,2,5]thiadiazole))

(Step 21-1: Synthesis of Compound (C21))

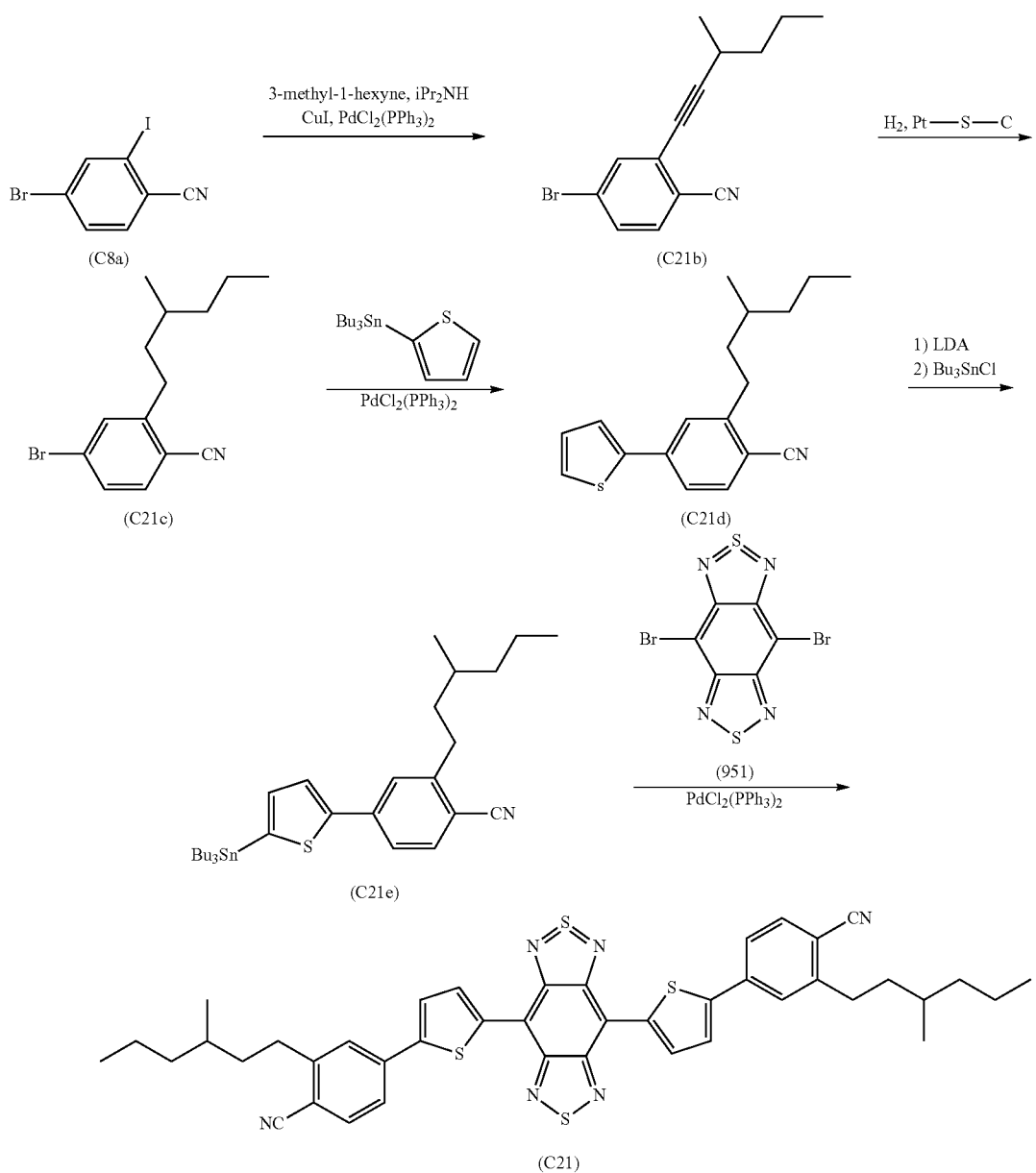

Compound (C21) was obtained in the same way as in Example 8, except that 3-methyl-1-hexyne was used instead of 1-hexyne.

The properties of Compound (C21b) were as follows.
$^1$H-NMR (400MHz; CDCl$_3$; δ(ppm)); 0.93-0.97 (m, 3H), 1.28-1.30 (m, 6H), 1.46-1.63 (m, 4H), 2.71-2.76 (m, 1H), 7.44-7.50 (m, 2H), 7.65-7.66 (m, 1H)
CI-MS; 276 (M+1)

The properties of Compound (C21c) were as follows.
$^1$H-NMR (400MHz; CDCl$_3$; δ(ppm)); 0.89-0.91 (m, 3H), 0.96-0.97 (m, 3H), 1.14-1.68 (m, 7H), 2.74-2.87 (m, 2H), 7.41-7.50 (m, 3H)
CI-MS; 280 (M+1)

The properties of Compound (C21d) were as follows.
$^1$H-NMR (400MHz; CDCl$_3$; δ(ppm)); 0.88-0.92 (m, 3H), 0.98-0.99 (m, 3H), 1.15-1.71 (m, 7H), 2.78-2.93 (m, 2H), 7.11-7.13 (m, 1H), 7.38-7.41 (m, 2H), 7.48-7.52 (m, 2H), 7.58-7.60 (m, 1H)
CI-MS; 284 (M+1)

The properties of Compound (C21e) were as follows.
$^1$H-NMR (400MHz; CDCl$_3$; δ(ppm)); 0.87-0.93 (m, 12H), 0.98-0.99 (m, 3H), 1.05-1.73 (m, 25H), 2.77-2.92 (m, 2H), 7.14-7.20 (m, 1H), 7.49-7.58 (m, 4H)
CI-MS; 574 (M+1)

The properties of Compound (C21) were as follows.
H-NMR (400MHz; 1,2-dichlorobenzene-d$_4$, 140° C.; δ(ppm)); 0.86-0.97 (m, 12H), 1.17-1.79 (m, 14H), 2.85-2.91 (m, 4H), 7.46-7.57 (m, 6H), 7.71 (brs, 2H), 9.03-9.04 (m, 2H)
TOF-HRMS (ASAP+); 757.2261 (M+1); Calcd. 757.2276

The solubility of Compound (C21) was evaluated, and 0.2 wt % of Compound (C21) was completely dissolved in chloroform at 60° C. Also, 0.3 wt % of Compound (C21) was completely dissolved in all of chlorobenzene, ortho-dichlorobenzene, and 1-methylnaphthalene at 80° C.

Reference Example P-22

Synthesis of Compound (C22); 4,8-bis[5-(4-cyano-3,5-dihexylphenyl)thiophene-2-yl]benzo[1,2-c:4,5-c']bis[1,2,5]thiadiazole))

(Step 22-1: Synthesis of Compound (C22))

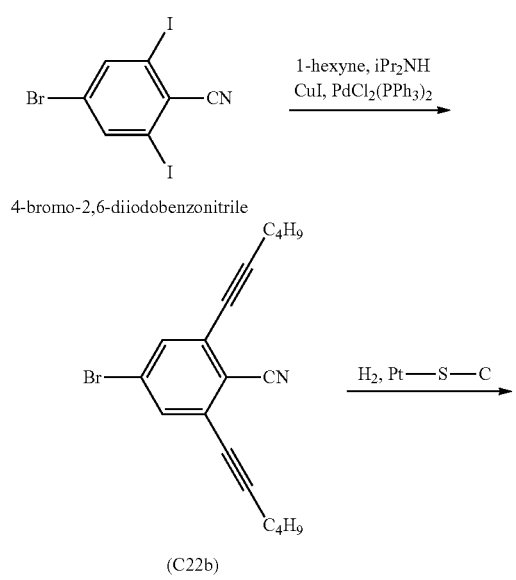

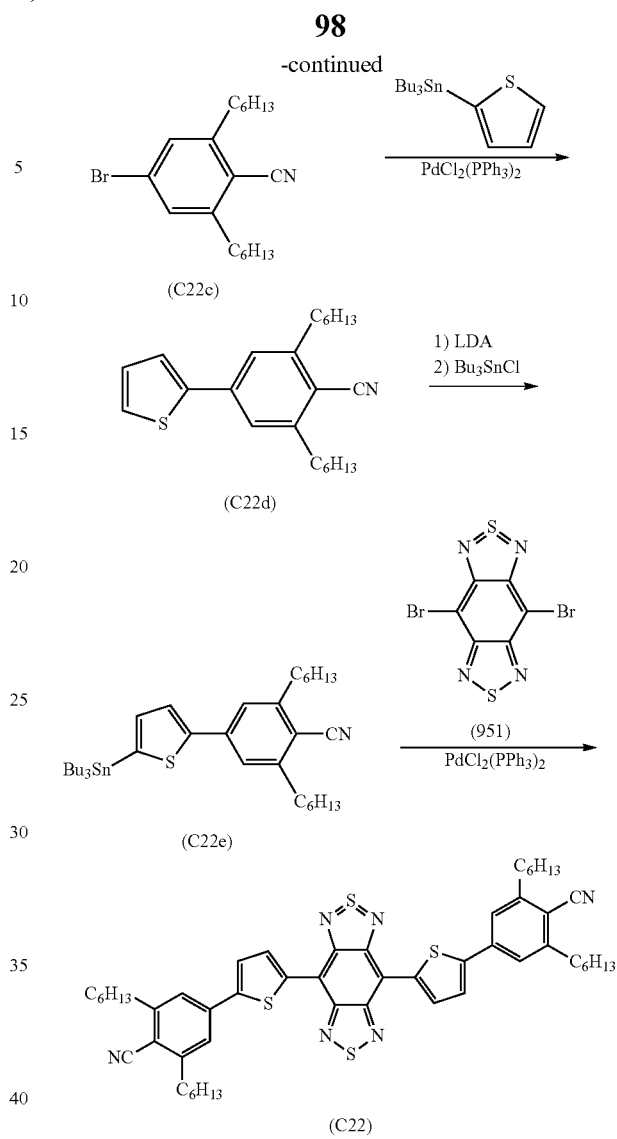

Compound (C22) was obtained in the same way as in Example 8, except that 4-bromo-2,6-diiodobenzonitrile was used instead of 4-bromo-2-iodobenzonitrile.

The properties of Compound (C22b) were as follows.
$^1$H-NMR (400MHz; CDCl$_3$; δ(ppm)); 0.86-0.97 (m, 3H), 1.45-1.66 (m, 4H), 2.48-2.50 (m, 2H), 7.51 (s, 1H)
CI-MS; 342 (M+1), 344 (M+3)

The properties of Compound (C22c) were as follows.
$^1$H-NMR (400MHz; CDCl$_3$; δ(ppm)); 0.87-0.97 (m, 3H), 1.26-1.69 (m, 8H), 2.77-2.82 (m, 2H), 7.29 (s, 1H)
CI-MS; 350 (M+1), 352 (M+3)

The properties of Compound (C22d) were as follows.
$^1$H-NMR (400MHz; CDCl$_3$; δ(ppm)); 0.88-0.91 (m, 6H), 1.26-1.73 (m, 16H), 2.82-2.86 (m, 4H), 7.11-7.40 (m, 5H)
EI-MS; 353 (M)
CI-MS; 354 (M+1)

The properties of Compound (C22e) were as follows.
$^1$H-NMR (400MHz; CDCl$_3$; δ(ppm)); 0.88-1.73 (m, 49H), 2.82-2.86 (m, 4H), 7.16-7.50 (m, 4H)
EI-MS; 643 (M)
CI-MS; 644 (M+1)

The properties of Compound (C22) were as follows.

¹H-NMR (400MHz; CDCl₃; δ(ppm)); 0.94 (m, 3H), 1.35-1.48 (m, 6H), 1.72-1.79 (m, 2H), 2.89-2.92 (m, 2H), 7.58 (s, 2H), 7.63 (m, 1H), 9.10 (m, 1H)

TOF-HRMS (ASAP+); 897.3832 (M+1); Calcd. 897.3841

The solubility of Compound (C22) was evaluated, and 0.3 wt % of Compound (C22) was completely dissolved in toluene at room temperature (25° C.). Also, 0.1 wt % of Compound (C22) was completely dissolved in all of chloroform, ortho-dichlorobenzene, and 1-methylnaphthalene at room temperature (25° C.).

Reference Example 4

Synthesis of Compound (RR4) (4,8-bis[5-(4-cyano-3-octyloxyphenyl) thiophene-2-yl]benzo[1,2-c:4,5-c']bis[1,2,5]thiadiazole))

(Step RR4-1: Synthesis of Compound (RR4))

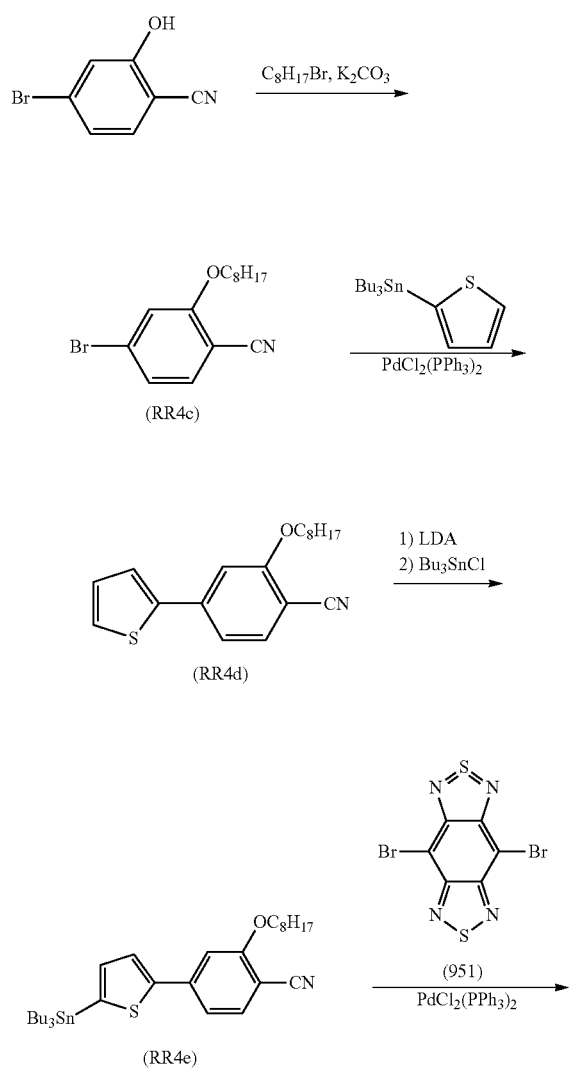

-continued

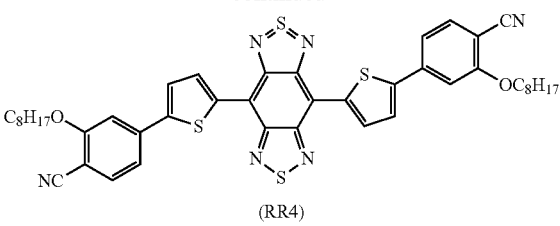

(RR4)

Under nitrogen atmosphere, into a 500-mL glass reaction vessel equipped with a thermometer and a stirring apparatus were placed 10.65 g (53.8 mmol) of 2-cyano-5-bromo-1-benzenephenol, 300 mL of N,N-dimethylformamide, 8.65 g (62.6 mmol) of potassium carbonate, 12.66 g (65.6 mmol) of 1-bromooctane, and 0.84 g (5.1 mmol) of potassium iodide. And then, the internal temperature was heated to 70° C. The mixture was stirred at an internal temperature of 70° C. for 1 hour, under stirring. The reaction solution was cooled to room temperature, and then was filtered and the filtrate was subjected to extraction with ether. The extract was washed with water, and dried over anhydrous magnesium sulfate, and then the solvent was distilled off under a reduced pressure, to provide 14.09 g of Compound (RR4c) in the form of a yellow solid.

The properties of Compound (RR4c) were as follows.

¹H-NMR (400MHz; CDCl₃; δ(ppm)); 0.87-0.91 (m, 3H), 1.29-1.49 (m, 10H), 1.82-1.89 (m, 2H), 4.04-4.07 (m, 2H), 7.11-7.41 (m, 3H)

CI-MS; 310 (M+1), 312 (M+3)

Compound (RR4) was obtained in the same way as in Example 8, except that Compound (RR4c) was used instead of Compound (C8c).

The properties of Compound (RR4d) were as follows.

¹H-NMR (400MHz; CDCl₃; δ(ppm)); 0.87-0.91 (m, 3H), 1.27-1.54 (m, 10H), 1.85-1.90 (m, 2H), 4.11-4.15 (m, 2H), 7.11-7.55 (m, 6H)

EI-MS; 313 (M)

CI-MS; 314 (M+1)

The properties of Compound (RR4e) were as follows.

¹H-NMR (400MHz; CDCl₃; δ(ppm)); 0.87-1.8 (m, 42H), 4.11-4.15 (m, 2H), 7.13-7.52 (m, 5H)

CI-MS; 604 (M+1)

The properties of Compound (RR4) were as follows.

¹H-NMR (400MHz; 1,2-dichlorobenzene-d₄; δ(ppm)); 0.86 (m, 3H), 1.27 (m, 8H), 1.47 (m, 2H), 1.78 (m, 2H), 4.10 (m, 2H), 7.30-7.54 (m, 4H), 9.05 (m, 1H)

TOF-HRMS (ASAP-); 816.2405 (M-1); Calcd. 816.2409

Example 23
Synthesis of Compound (C23) (Compound of the Formula (133); 4,8-bis[5-(4-cyano-3-(2-(4'-pentyl-[1,1'-bi(cyclohexane)]-4-yl)ethyl)phenyl)thiophene-2-yl]benzo[1,2-c:4,5-c']bis[1,2,5]thiadiazole))
(Step 23-1: Synthesis of Compound (C23))
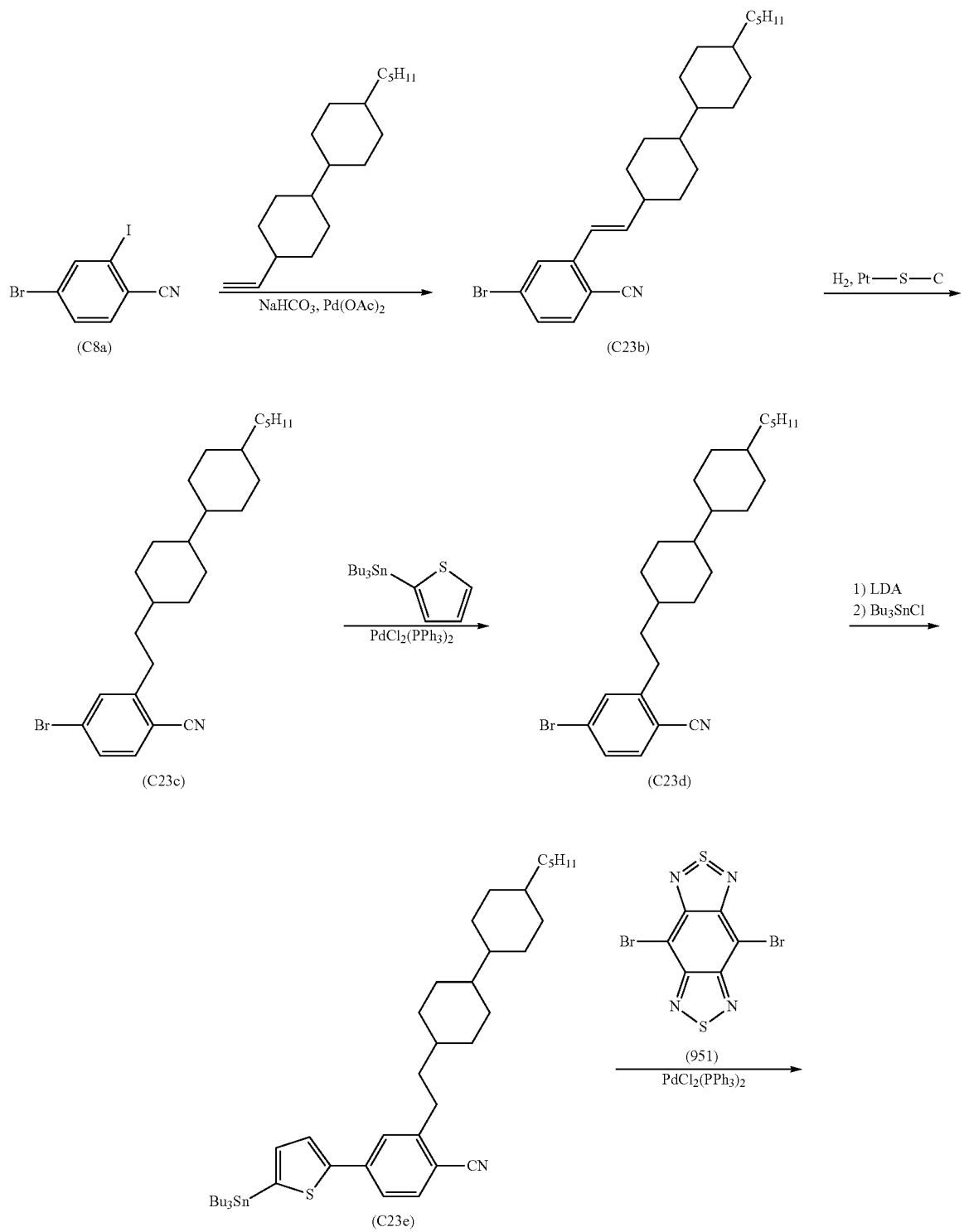

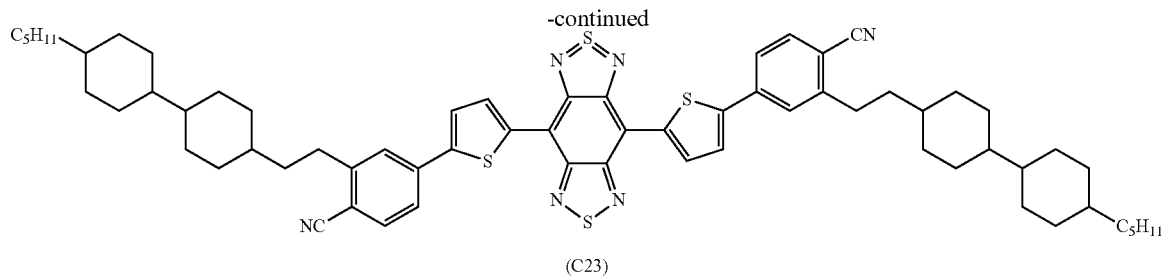

(C23)

Under nitrogen atmosphere, into a 500-mL glass reaction vessel equipped with a thermometer and a stirring apparatus were placed 9.2 g (29.8 mmol) of 2-iodo-4-bromobenzonitrile, 200 mL of N,N-dimethylformamide, 7.9 g (30.0 mmol) of 4-pentyl-4'-vinyl-1,1'-bi(cyclohexane), 0.54 g (2.41 mmol) of palladium acetate, 6.30 g (59.4 mmol) of sodium hydrogen carbonate, and 12.13 g of 4-pentyl-4'-vinyl-1,1'-bicyclohexane. And then, the internal temperature was heated to 80° C. The mixture was stirred at an internal temperature of 80° C. for 8 hours, under stirring. The reaction solution was cooled to room temperature, and then was subjected to extraction with toluene. The extract was washed with water, and dried over anhydrous magnesium sulfate, and then the solvent was distilled off under a reduced pressure, and the residue was purified by column, to provide 4.81 g of Compound (C23b) in the form of a white solid.

The properties of Compound (C23b) were as follows.
$^1$H-NMR (400MHz; CDCl$_3$; δ(ppm)); 0.83-2.15 (m, 31H), 6.34-6.65 (m, 2H), 7.37-7.76 (m, 3H)
CI-MS; 442 (M+1), 444 (M+3)

Compound (C23) was obtained in the same way as in Example 8, except that Compound (C23b) was used instead of Compound (C8b).

The properties of Compound (C23c) were as follows.
$^1$H-NMR (400MHz; CDCl$_3$; δ(ppm)); 0.83-1.85 (m, 33H), 2.78-2.82 (m, 2H), 7.40-7.48 (m, 3H)
CI-MS; 444 (M+1), 446 (M+3)

The properties of Compound (C23d) were as follows.
$^1$H-NMR (400MHz; CDCl$_3$; δ(ppm)); 0.85-1.88 (m, 33H), 2.84-2.88 (m, 2H), 7.11-7.60 (m, 6H)
EI-MS; 447 (M)
CI-MS; 448 (M+1)

The properties of Compound (C23e) were as follows.
$^1$H-NMR (400MHz; CDCl$_3$; δ(ppm)); 0.87-1.76 (m, 60H), 2.83-2.87 (m, 2H), 7.16-7.58 (m, 4H)
EI-MS; 737 (M)
CI-MS; 738 (M+1)

The properties of Compound (C23) were as follows.
FD-MS; 1085 (Calcd. 1085)

Example 24

Synthesis of Compound (C24) (Compound of the Formula (115); 4,8-bis[5-(3-octyl-4-(trifluoromethyl)phenyl)thiophene-2-yl]benzo[1,2-c:4,5-c']bis[1,2,5]thiadiazole))

(Step 24-1: Synthesis of Compound (C24))

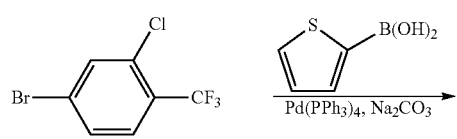

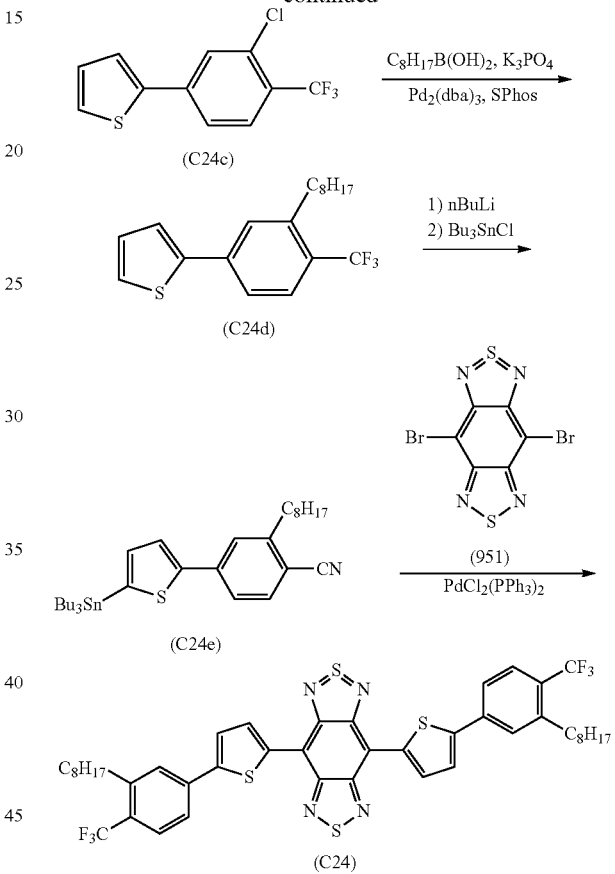

Into a 250 L glass reaction vessel equipped with a stirring apparatus were placed 7.2 g (68.0 mmol) of sodium carbonate, 2.6 g (20.4 mmol) of 2-thiophene boronate, 2.5 mL (17.0 mmol) of 4-bromo-2-chlorobenzotrifluoride, 102 mL of toluene, 51 mL of ethanol, and 2.0 g (1.7 mmol) of tetrakistriphenylphosphine palladium. The mixture was reacted at 80° C. for 16 hours. And then, water was added to the reaction product, and the mixture was subjected to extraction with methylene chloride, and then the extract was dried over magnesium sulfate, and the solvent was distilled off under a reduced pressure, and then the residue was purified by silica gel column chromatography (hexane), to provide 4.4 g of Compound (C24c) in the form of a white solid.

The properties of Compound (C24c) were as follows.
$^1$H-NMR (400MHz; CD$_2$Cl$_2$; δ(ppm)); 7.13-7.17 (m, 1H), 7.43-7.46 (m, 2H), 7.60-7.62 (m, 1H), 7.70 (d, 1H), 7.78 (d, 1H)
EI-MS; 262 (M)

Into a 250 L glass reaction vessel equipped with a stirring apparatus were placed 1.8 g (7.0 mmol) of Compound (C24c), 1.7 g (10.5 mmol) of octyl boronate, 3.7 g (17.5 mmol) of potassium phosphate, 574.7 mg (1.4 mmol) of 2-dicyclohexylphosphino-2',6'-dimethoxybiphenyl, 320.5 mg (0.35 mmol) of tris(dibenzylideneacetone)dipalladium, 21 mL of toluene, and 51 mL of ethanol. The mixture was reacted at 80° C. for 16 hours. And then, water was added to the reaction product, and the mixture was subjected to extraction with diethyl ether, and then the extract was dried over magnesium sulfate, and the solvent was distilled off under a reduced pressure, and then the residue was purified by silica gel column chromatography (hexane), to provide 2.3 g of Compound (C24d) in the form of a colorless liquid.

The properties of Compound (C24d) were as follows.

$^1$H-NMR (400MHz; CD$_2$Cl$_2$; δ(ppm)); 0.88 (t, 3H), 1.28-1.46 (m, 10H), 1.61-1.69 (m, 2H), 2.77-2.81 (m, 2H), 7.11-7.14 (m, 1H), 7.37-7.38 (m, 1H), 7.42-7.43 (m, 1H), 7.51-7.53 (m, 1H), 7.58-7.62 (m, 2H)

EI-MS; 340 (M)

Into a 50-mL glass reaction vessel equipped with a stirring apparatus were placed 1.0 g (3.0 mmol) of Compound (C24d), and 18 mL of anhydrous tetrahydrofuran. While the internal temperature was kept at −73° C., 2.1 mL of 1.6 N solution of n-butyl lithium in hexane was added to the mixture. The mixture was stirred at the same temperature for 1 hour, and then 0.9 mL (3.3 mmol) of tributyl tin chloride was added to the mixture at the same temperature. The temperature of the mixture was increased to room temperature, and the mixture was stirred for 1 hour. And then, methanol was added to the reaction solution for quenching, and the solvent was distilled off. Subsequently, hexane was added to the obtained crude reaction product, and the mixture was purified by silica gel column chromatography (hexane), to provide 1.9 g of Compound (C24e) in the form of a colorless liquid.

The properties of Compound (C24e) were as follows.

$^1$H-NMR (400MHz; CD$_2$Cl$_2$; δ(ppm)); 0.87-0.93 (m, 12H), 1.13-1.17 (m, 4H), 1.29-1.46 (m, 14H), 1.56-1.69 (m, 12H), 2.76-2.80 (m, 2H), 7.18 (d, 1H), 7.51-7.57 (m, 2H), 7.58-7.60 (m, 2H)

FD-MS; 629 (M)

Into a 30-mL glass reaction vessel equipped with a stirring apparatus were placed 1.8 g (2.8 mmol) of Compound (C24e), 246.4 mg (0.7 mmol) of dibromobenzobisthiadiazole, 147.4 mg (0.2 mmol) of dichlorobis(triphenylphosphine) palladium (II), and 10.5 mL of anhydrous toluene. The mixture was reacted at an internal temperature of about 100° C. for 6 hours. The reaction solution was concentrated, and hexane was added to the concentrate, and then the precipitate was separated by filtration, to provide 2.1 g of a crude product. The obtained crude product was subjected to Soxhlet extraction (toluene), and then the extract was cooled to −26° C. and recrystallized, and these operations were repeated, to provide 259.7 mg of Compound (C24) in the form of a dark green powder.

The properties of Compound (C24) were as follows.

$^1$H-NMR (400MHz; C$_6$D$_4$Cl$_2$; δ(ppm)); 1.07-1.10 (m, 6H), 1.48-1.67 (m, 20H), 1.90-1.98 (m, 4H), 3.06-3.10 (m, 4H), 7.80-7.85 (m, 6H), 8.00 (s, 2H), 9.30 (d, 2H)

FD-MS; 871 (M)

The solubility of Compound (C24) was evaluated, and 0.2 wt % of Compound (C24) was completely dissolved in chloroform at 60° C. Also, 0.3 wt % of Compound (C24) was completely dissolved in ortho-dichlorobenzene, toluene, mesitylene, and 1-methylnaphthalene at 60° C.

Example 25

Synthesis of Compound (C25) (Compound of the Formula (87); 4,8-bis[5-(4-octyl-3-(trifluoromethyl)phenyl)thiophene-2-yl]benzo[1,2-c:4,5-c']bis[1,2,5]thiadiazole))

(Step 25-1: Synthesis of Compound (C25))

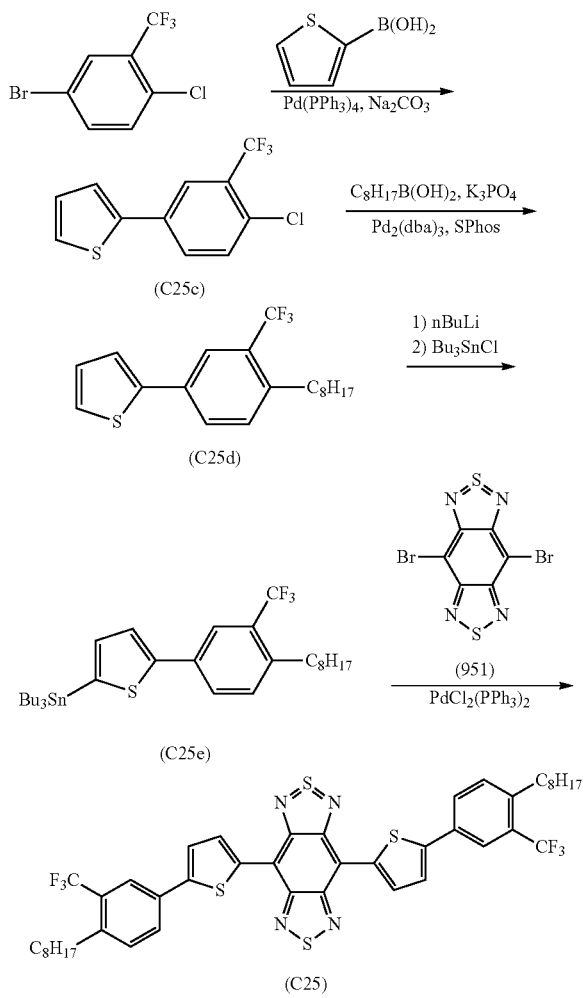

Compound (C25) was obtained in the same way as in Example 24, except that 5-bromo-2-chlorobenzotrifluoride was used instead of 4-bromo-2-chlorobenzotrifluoride.

The properties of Compound (C25c) were as follows.

$^1$H-NMR (400MHz; CD$_2$Cl$_2$; δ(ppm)); 7.11-7.14 (m, 1H), 7.38-7.40 (m, 2H), 7.53 (d, 1H), 7.71-7.74 (m, 1H), 7.92 (d, 1H)

EI-MS; 262 (M)

The properties of Compound (C25d) were as follows.

$^1$H-NMR (400MHz; CD$_2$Cl$_2$; δ(ppm)); 0.89 (t, 3H), 1.27-1.44 (m, 10H), 1.59-1.66 (m, 2H), 2.75-2.79 (m, 2H), 7.08-7.14 (m, 1H), 7.32-7.41 (m, 3H), 7.69-7.72 (m, 1H), 7.83 (d, 1H)

EI-MS; 340 (M)

The properties of Compound (C25e) were as follows.
¹H-NMR (400MHz; CD₂Cl₂; δ(ppm)); 0.91-0.94 (m, 12H), 1.12-1.17 (m, 4H), 1.25-1.40 (m, 18H), 1.56-1.66 (m, 8H), 2.74-2.78 (m, 2H), 7.16 (d, 1H), 7.35 (d, 1H), 7.45-7.46 (m, 1H), 7.70-7.72 (m, 1H), 7.83 (d, 1H)
FD-MS; 629 (M)

The properties of Compound (C25) were as follows.
¹H-NMR (400MHz; C₆D₄Cl₂; δ(ppm)); 1.08-1.11 (m, 6H), 1.49-1.66 (m, 20H), 1.86-1.94 (m, 4H), 3.03-3.07 (m, 4H), 7.54 (d, 2H), 7.72 (d, 2H), 8.01-8.03 (m, 2H), 8.28 (s, 2H), 9.28 (d, 2H)
FD-MS; 871 (M)

The solubility of Compound (C25) was evaluated, and 0.2 wt % of Compound (C25) was completely dissolved in chloroform at 60° C. Also, 0.3 wt % of Compound (C25) was completely dissolved in ortho-dichlorobenzene, toluene, mesitylene, and 1-methylnaphthalene at 60° C.

Example 26

Synthesis of Compound (C26) (Compound of the Formula (106); 4,8-bis[5-(3-cyano-4-octylphenyl)thiophene-2-yl]benzo[1,2-c:4,5-c']bis[1,2,5]thiadiazole))

(Step 26-1: Synthesis of Compound (C26))

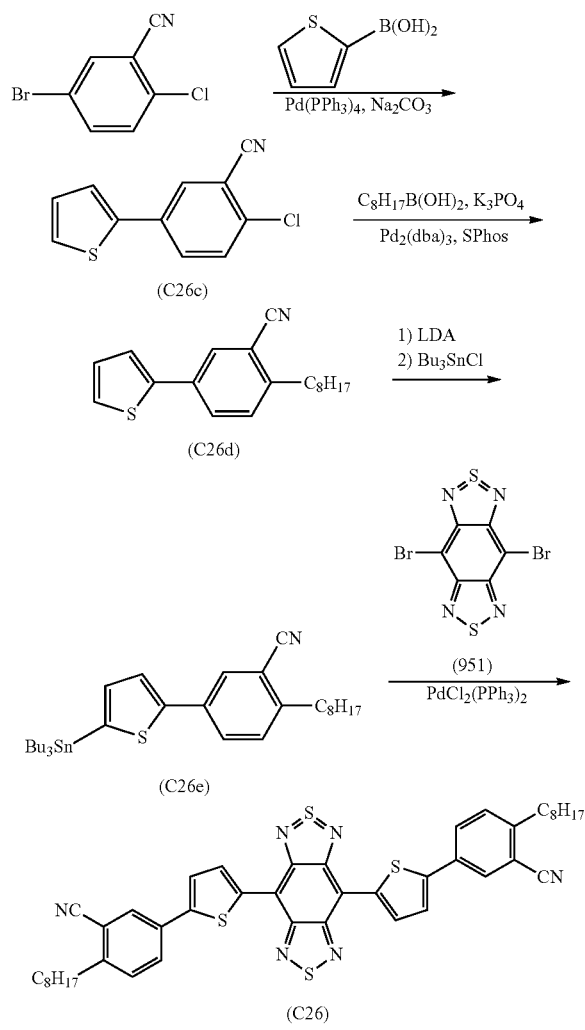

Compound (C26c) and Compound (C26d) were obtained in the same way as in Synthesis of Compound (C24c) and Compound (C24d), respectively, in Example 24, except that 5-bromo-2-chlorobenzonitrile was used instead of 4-bromo-2-chlorobenzotrifluoride.

The properties of Compound (C26c) were as follows.
¹H-NMR (400MHz; CD₂Cl₂; δ(ppm)); 7.12-7.18 (m, 1H), 7.38-7.42 (m, 2H), 7.53 (d, 1H), 7.76-7.79 (m, 1H), 7.92 (d, 1H)
EI-MS; 219 (M)

The properties of Compound (C26d) were as follows.
¹H-NMR (400MHz; CD₂Cl₂; δ(ppm)); 0.89 (t, 3H), 1.28-1.43 (m, 10H), 1.64-1.72 (m, 2H), 2.81-2.85 (m, 2H), 7.10-7.12 (m, 1H), 7.34-7.36 (m, 3H), 7.73-7.75 (m, 1H), 7.84 (d, 1H)
EI-MS; 297 (M)

Into a 30-mL glass reaction vessel equipped with a stirring apparatus were placed 892.4 mg (3.0 mmol) of Compound (C26d), and 9 mL of anhydrous tetrahydrofuran. While the internal temperature was kept at −74° C., 3.0 mL of 1.1 N solution of lithium diisopropylamide in hexane-tetrahydrofuran was added to the mixture. The mixture was stirred at the same temperature for 1 hour, and then 0.9 mL (3.3 mmol) of tributyl tin chloride was added to the mixture at the same temperature. The temperature of the mixture was increased to room temperature, and the mixture was stirred for 1 hour. And then, methanol was added to the reaction solution for quenching, and the solvent was distilled off. Subsequently, hexane was added to the obtained crude reaction product, and the mixture was purified by silica gel column chromatography (hexane:ethyl acetate=50:1, volume ratio), to provide 1.7 g of Compound (C26e) in the form of a colorless liquid.

The properties of Compound (C26e) were as follows.
¹H-NMR (400MHz; CD₂Cl₂; δ(ppm)); 0.86-0.92 (m, 12H), 1.12-1.17 (m, 4H), 1.28-1.40 (m, 18H), 1.55-1.69 (m, 8H), 2.80-2.84 (m, 2H), 7.16 (d, 1H), 7.33 (d, 1H), 7.44-7.46 (m, 1H), 7.73-7.75 (m, 1H), 7.84 (d, 1H)
FD-MS; 586 (M)

Compound (C26) was obtained in the same way as in Synthesis of Compound (C24) in Example 24, except that Compound (C26e) was used instead of Compound (C24e).

The properties of Compound (C26) were as follows.
¹H-NMR (400MHz; C₆D₄Cl₂; δ(ppm)); 1.07-1.10 (m, 6H), 1.47-1.64 (m, 20H), 1.89-1.96 (m, 4H), 3.03-3.07 (m, 4H), 7.47 (d, 2H), 7.67 (d, 2H), 7.99-8.01 (m, 2H), 8.13 (d, 2H), 9.28 (d, 2H)
FD-MS; 784 (M)

The solubility of Compound (C26) was evaluated, and 0.2 wt % of Compound (C26) was completely dissolved in chloroform at room temperature (25° C.). Also, 0.3 wt % of Compound (C26) was completely dissolved in ortho-dichlorobenzene, and 1-methylnaphthalene at 60° C. Also, 0.3 wt % of Compound (C26) was completely dissolved in toluene, and mesitylene at 80° C.

Example 27

Synthesis of Compound (C27) (Compound of the Formula (115); 4,8-bis[5-(3-dodecyl-4-(trifluoromethyl)phenyl)thiophene-2-yl]benzo[1,2-c:4,5-c']bis[1,2,5]thiadiazole))

(Step 27-1: Synthesis of Compound (C27))

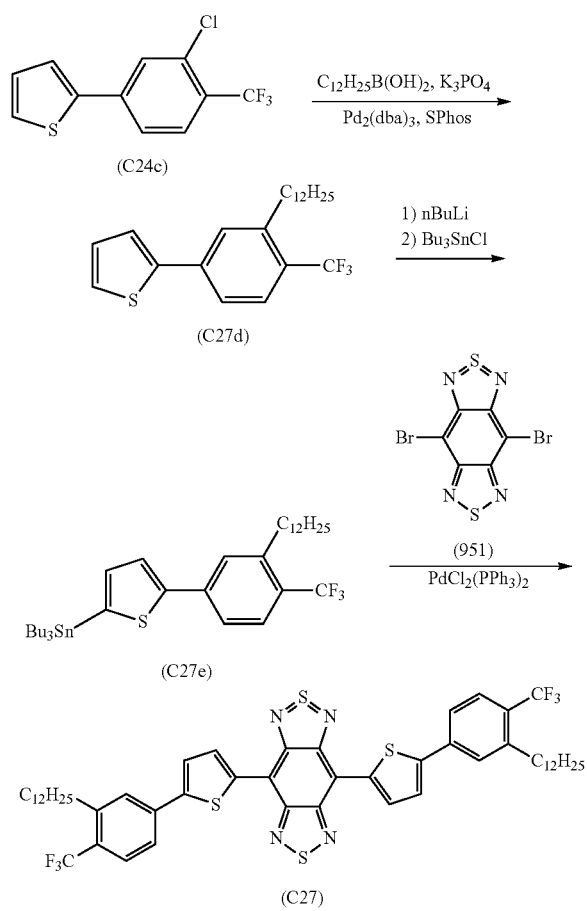

Compound (C27) was obtained in the same way as in Example 24, except that dodecyl boronate was used instead of octyl boronate.

The properties of Compound (C27d) were as follows.

$^1$H-NMR (400MHz; $CD_2Cl_2$; δ(ppm)); 0.88 (t, 3H), 1.27-1.45 (m, 18H), 1.61-1.69 (m, 2H), 2.77-2.81 (m, 2H), 7.11-7.14 (m, 1H), 7.37-7.39 (m, 1H), 7.42-7.43 (m, 1H), 7.51-7.53 (m, 1H), 7.58-7.62 (m, 2H)

EI-MS; 396 (M)

The properties of Compound (C27e) were as follows.

$^1$H-NMR (400MHz; $CD_2Cl_2$; δ(ppm)); 0.86-0.93 (m, 12H), 1.13-1.17 (m, 4H), 1.27-1.42 (m, 26H), 1.56-1.69 (m, 8H), 2.76-2.80 (m, 2H), 7.18 (d, 1H), 7.51-7.53 (m, 2H), 7.58-7.60 (m, 2H)

FD-MS; 685 (M)

The properties of Compound (C27) were as follows.

$^1$H-NMR (400MHz; $C_6D_4Cl_2$; δ(ppm)); 1.06-1.09 (m, 6H), 1.48-1.67 (m, 36H), 1.91-1.99 (m, 4H), 3.07-3.11 (m, 4H), 7.80-7.85 (m, 6H), 8.01 (br, 2H), 9.30 (d, 2H)

FD-MS; 983 (M)

The solubility of Compound (C27) was evaluated, and 0.1 wt % of Compound (C27) was completely dissolved in chloroform at 60° C. Also, 0.3 wt % of Compound (C27) was completely dissolved in ortho-dichlorobenzene, toluene, mesitylene, and 1-methylnaphthalene at 60° C.

Example 28

Synthesis of Compound (C28) (Compound of the Formula (87); 4,8-bis[5-(4-dodecyl-3-(trifluoromethyl)phenyl)thiophene-2-yl]benzo[1,2-c:4,5-c']bis[1,2,5]thiadiazole))

(Step 28-1: Synthesis of Compound (C28))

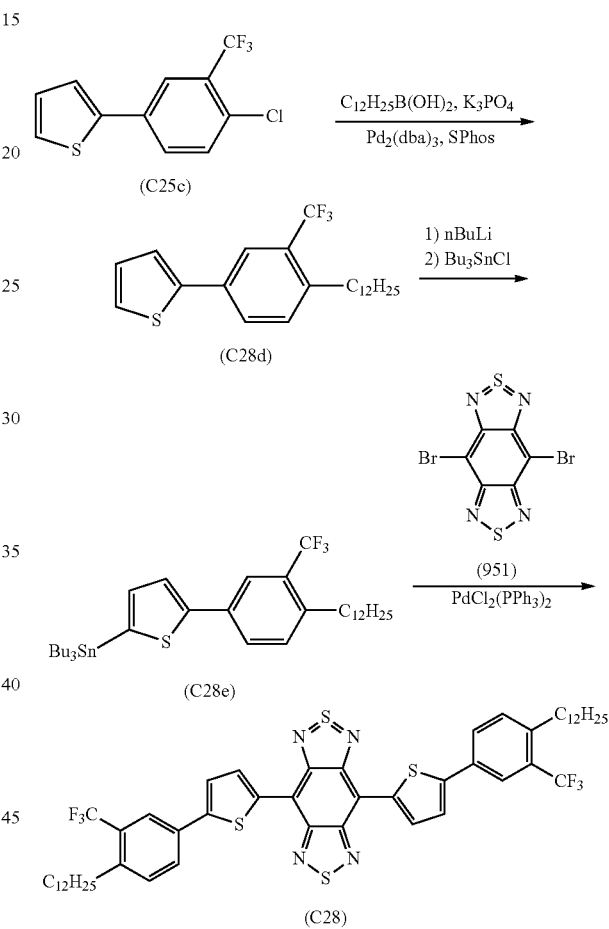

Compound (C28) was obtained in the same way as in Example 25, except that dodecyl boronate was used instead of octyl boronate.

The properties of Compound (C28d) were as follows.

$^1$H-NMR (400MHz; $CD_2Cl_2$; δ(ppm)); 0.88 (t, 3H), 1.27-1.42 (m, 18H), 1.56-1.66 (m, 2H), 2.75-2.79 (m, 2H), 7.09-7.11 (m, 1H), 7.32-7.38 (m, 3H), 7.69-7.72 (m, 1H), 7.83 (d, 1H)

EI-MS; 396 (M)

The properties of Compound (C28e) were as follows.

$^1$H-NMR (400MHz; $CD_2Cl_2$; δ(ppm)); 0.86-0.94 (m, 12H), 1.12-1.16 (m, 4H), 1.27-1.40 (m, 26H), 1.56-1.66 (m, 8H), 2.74-2.78 (m, 2H), 7.16 (d, 1H), 7.35 (d, 1H), 7.45-7.47 (m, 1H), 7.70-7.72 (m, 1H), 7.83 (d, 1H)

FD-MS; 685 (M)

The properties of Compound (C28) were as follows.

$^1$H-NMR (400MHz; $C_6D_4Cl_2$; δ(ppm)); 1.07-1.10 (m, 6H), 1.49-1.67 (m, 36H), 1.88-1.95 (m, 4H), 3.04-3.07 (m, 4H), 7.55 (d, 2H), 7.72 (d, 2H), 8.03 (d, 2H), 8.29 (s, 2H), 9.29 (d, 2H)

FD-MS; 983 (M)

The solubility of Compound (C28) was evaluated, and 0.1 wt % of Compound (C28) was completely dissolved in chloroform at 80° C. Also, 0.3 wt % of Compound (C28) was dissolved in ortho-dichlorobenzene at 80° C. Also, 0.3 wt % of Compound (C28) was completely dissolved in toluene, mesitylene, and 1-methylnaphthalene at 100° C.

Example 29

Synthesis of Compound (C29) (Compound of the Formula (133); 4,8-bis[5-(4-cyano-3-(2-methyl-hexyl)phenyl)thiophene-2-yl]benzo[1,2-c:4,5-c']bis[1,2,5]thiadiazole))

(Step 29-1: Synthesis of Compound (C29))

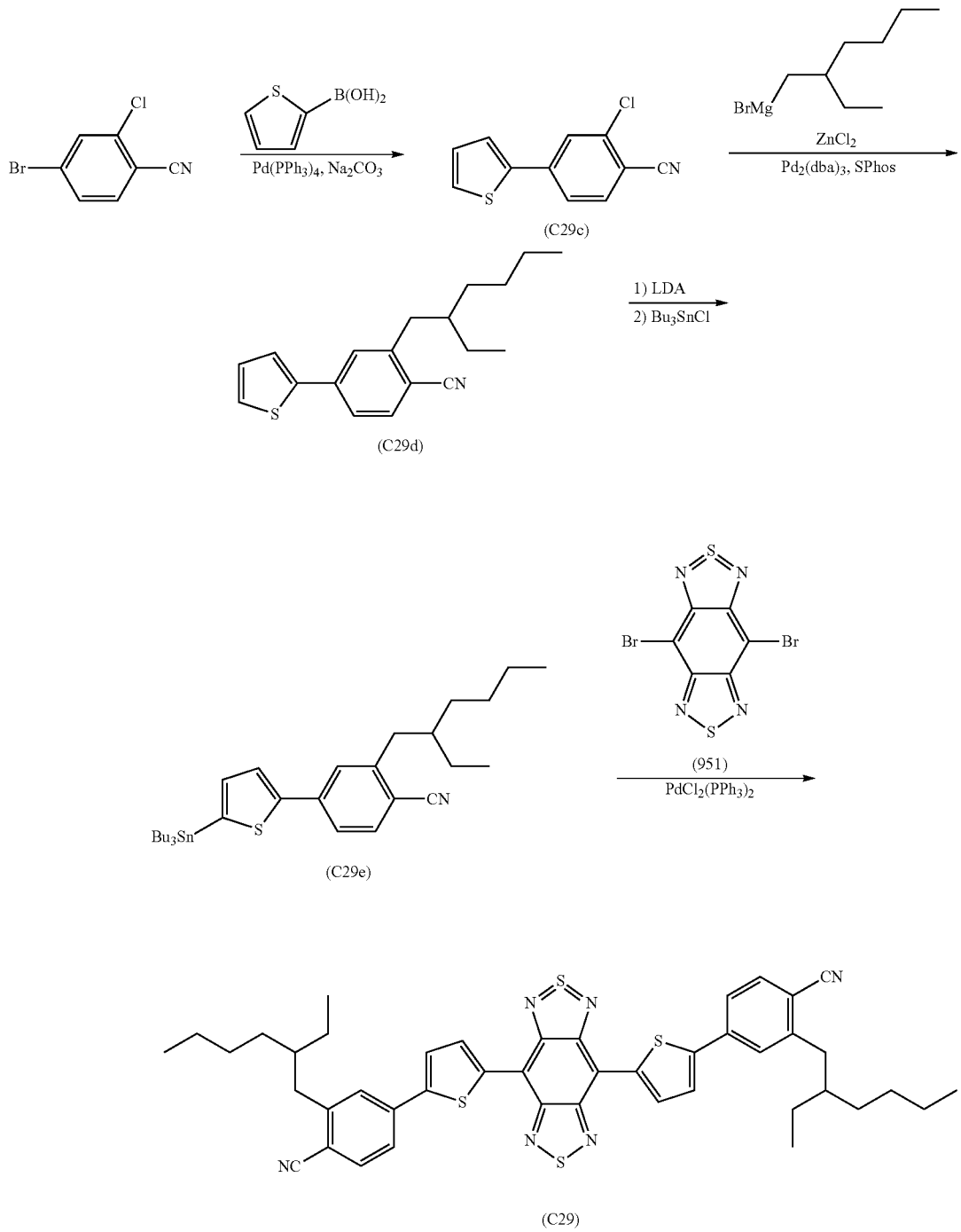

Compound (C29c) was obtained in the same way as in Example 24, except that 4-bromo-2-chlorobenzonitrile was used instead of 4-bromo-2-chlorobenzotrifluoride.

The properties of Compound (C29c) were as follows.

$^1$H-NMR (400MHz; CD$_2$Cl$_2$; δ(ppm)); 7.14-7.17 (m, 1H), 7.46-7.48 (m, 2H), 7.60-7.62 (m, 1H), 7.66-7.69 (m, 1H), 7.77 (d, 1H)

EI-MS; 219 (M)

Into a 50-mL glass reaction vessel equipped with a stirring apparatus was placed 17.4 mL (17.4 mmol: concentration 1.0 M/diethyl ether solution) of 2-ethylhexyl magnesium bromide, which was cooled to 0° C. Subsequently, 15.8 mL (17.4 mmol: concentration 1.1 M/diethyl ether solution) of zinc (II) chloride was added to the solution, and the mixture was stirred at the same temperature for 1 hour. And then, the solvent was distilled off, and 35 mL of tetrahydrofuran was added to the residue, to provide a solution of 2-ethylhexyl zinc chloride. Into a 100-mL glass reaction vessel equipped with a stirring apparatus were placed 531.1 mg (0.58 mmol) of tris(dibenzylideneacetone)dipalladium, 952.4 mg (2.3 mmol) of 2-dicyclohexylphosphino-2',6'-dimethoxybiphenyl, and 23 mL of tetrahydrofuran. The mixture was stirred at room temperature for 15 minutes, and 2.6 g (11.6 mmol) of Compound (C29c) was added to the mixture. Subsequently, the mixture was cooled to 0° C., and the solution of 2-ethylhexyl zinc chloride, which was prepared previously, was added thereto, and then the mixture was reacted at 50° C. for 3 hours. And then, methanol was added to the reaction solution for quenching, and the solvent was distilled off. A saturated aqueous solution of ammonium chloride was added to the residue, and the mixture was subjected to extraction with diethyl ether. The extract was dried over magnesium sulfate, and the solvent was distilled off under a reduced pressure, and then the residue was purified by silica gel column chromatography (hexane:ethyl acetate=95:5), to provide 3.1 g of Compound (C29d) in the form of a white solid.

The properties of Compound (C29d) were as follows.

$^1$H-NMR (400MHz; CD$_2$Cl$_2$; δ(ppm)); 0.86-0.93 (m, 6H), 1.26-1.41 (m, 8H), 1.71-1.77 (m, 1H), 2.78 (d, 2H), 7.13-7.15 (m, 1H), 7.41-7.45 (m, 2H), 7.52-7.54 (m, 2H), 7.60-7.62 (m, 1H)

EI-MS; 297 (M)

Into a 100-mL glass reaction vessel equipped with a stirring apparatus were placed 3.5 g (11.8 mmol) of Compound (C29d), and 35 mL of anhydrous tetrahydrofuran. While the internal temperature was kept at −75° C., 11.9 mL of 1.1 M solution of lithium diisopropylamide in hexane-tetrahydrofuran was added to the mixture. The mixture was stirred at the same temperature for 1 hour, and then 3.5 mL (13.0 mmol) of tributyl tin chloride was added to the mixture at the same temperature. The temperature of the mixture was increased to room temperature, and the mixture was stirred for 1 hour. And then, methanol was added to the reaction solution for quenching, and the solvent was distilled off. Subsequently, hexane was added to the obtained crude reaction product, and the mixture was purified by silica gel column chromatography (hexane:ethyl acetate=50:1, vol %), to provide 4.6 g of Compound (C29e) in the form of a pale yellow liquid.

The properties of Compound (C29e) were as follows.

$^1$H-NMR (400MHz; CD$_2$Cl$_2$; δ(ppm)); 0.86-0.93 (m, 15H), 1.11-1.41 (m, 22H), 1.56-1.65 (m, 5H), 2.78 (d, 2H), 7.19 (d, 1H), 7.52-7.55 (m, 3H), 7.58-7.60 (m, 1H)

FD-MS; 586 (M)

Into a 50-mL glass reaction vessel equipped with a stirring apparatus were placed 4.6 g (7.8 mmol) of Compound (C29e), 683.8 mg (1.9 mmol) of dibromobenzobisthiadiazole, 408.5 mg (0.58 mmol) of dichlorobis(triphenylphosphine) palladium (II), and 30 mL of anhydrous toluene. The mixture was reacted at an internal temperature of about 100° C. for 7 hours. The reaction solution was concentrated, and hexane was added to the concentrate, and then the precipitate was separated by filtration, to provide 1.96 g of a crude product. The obtained crude product was subjected to Soxhlet extraction (chloroform), and then the extract was cooled to −26° C. and recrystallized, and these operations were repeated, to provide 307.1 mg of Compound (C29) in the form of a deep green powder.

The properties of Compound (C29) were as follows.

$^1$H-NMR (400MHz; C$_6$D$_4$Cl$_2$; δ(ppm)); 1.08-1.15 (m, 12H), 1.49-1.64 (m, 16H), 2.03-2.08 (m, 2H), 3.04 (d, 4H), 7.70 (d, 2H), 7.78-7.81 (m, 4H), 7.94 (d, 2H), 9.29 (d, 2H)

FD-MS; 785 (M)

The solubility of Compound (C29) was evaluated, and 0.1 wt % of Compound (C29) was completely dissolved in chloroform at 60° C., and 0.3 wt % of Compound (C29) was completely dissolved in 1-methylnaphthalene at 60° C.

Example 30

Synthesis of Compound (C30) (Compound of the Formula (115); 4,8-bis[5-(3-(2-methylhexyl)-4-(trifluoromethyl)phenyl)thiophene-2-yl]benzo[1,2-c:4,5-c']bis[1,2,5]thiadiazole))

(Step 30-1: Synthesis of Compound (C30))

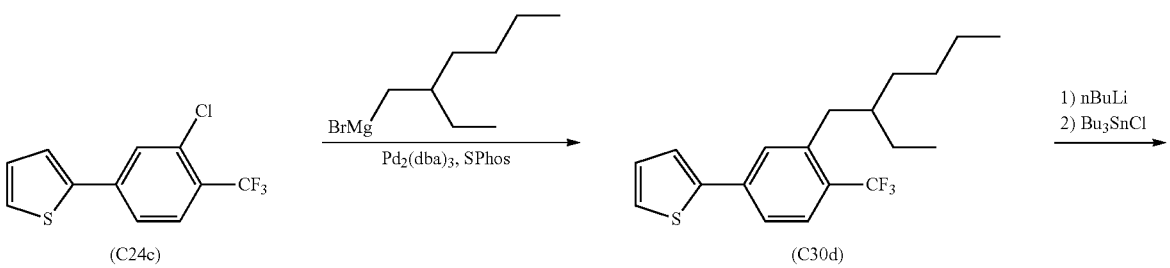

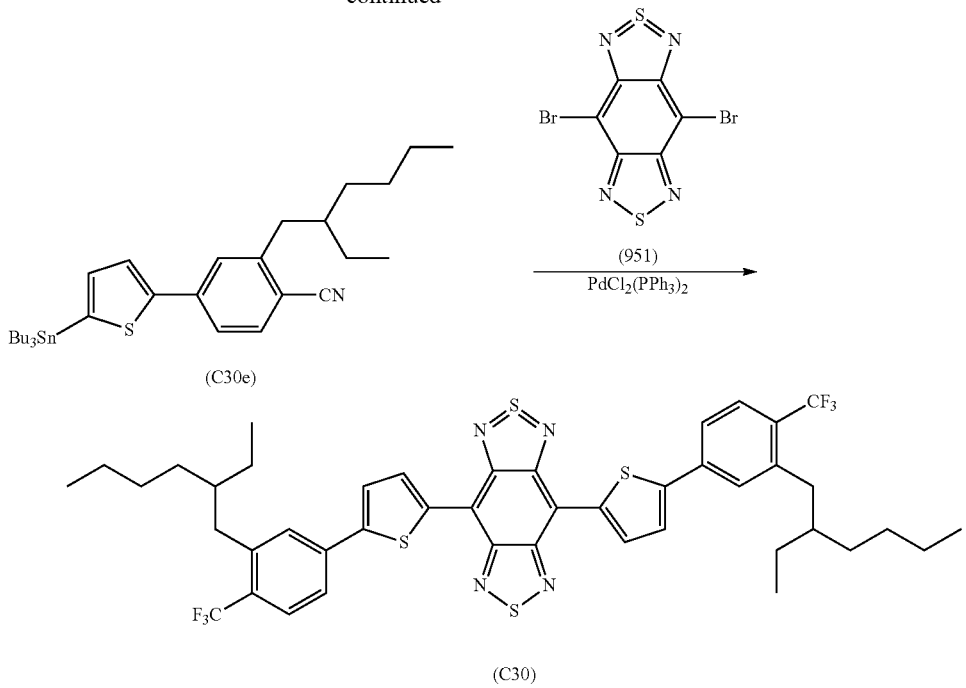

Into a 100-mL glass reaction vessel equipped with a stirring apparatus were placed 457.9 mg (0.5 mmol) of tris(dibenzylideneacetone)dipalladium, 821.1 mg (2.0 mmol) of 2-dicyclohexylphosphino-2',6'-dimethoxybiphenyl, and 20 mL of tetrahydrofuran. The mixture was stirred at room temperature for 15 minutes, and 2.6 g (10.0 mmol) of Compound (C24c) was added to the mixture. Subsequently, the mixture was cooled to 0° C., and 30 mL (15.0 mmol: concentration 0.5 M/tetrahydrofuran solution) of 2-ethylhexyl magnesium bromide was added thereto, and then the mixture was reacted at room temperature for 4 hours. And then, methanol was added to the reaction solution for quenching, and the solvent was distilled off. A saturated aqueous solution of ammonium chloride was added to the residue, and the mixture was subjected to extraction with diethyl ether. The extract was dried over magnesium sulfate, and the solvent was distilled off under a reduced pressure, and then the residue was purified by silica gel column chromatography (hexane), to provide 2.7 g of Compound (C30d) in the form of a pale yellow liquid.

The properties of Compound (C30d) were as follows.

$^1$H-NMR (400MHz; $CD_2Cl_2$; δ(ppm)); 0.85-0.93 (m, 6H), 1.25-1.41 (m, 8H), 1.71-1.74 (m, 1H), 2.74-2.76 (m, 2H), 7.12-7.15 (m, 1H), 7.37-7.46 (m, 2H), 7.52-7.65 (m, 3H)

EI-MS; 340 (M)

Into a 100-mL glass reaction vessel equipped with a stirring apparatus were placed 1.7 g (5.0 mmol) of Compound (C30d), and 30 mL of anhydrous tetrahydrofuran. While the internal temperature was kept at −74° C., 3.4 mL of 1.6 M solution of n-butyl lithium in hexane was added to the mixture. The mixture was stirred at the same temperature for 1 hour, and then 1.5 mL (5.5 mmol) of tributyl tin chloride was added to the mixture at the same temperature. The temperature of the mixture was increased to room temperature, and the mixture was stirred for 1 hour. And then, methanol was added to the reaction solution for quenching, and the solvent was distilled off. Subsequently, hexane was added to the obtained crude reaction product, and the mixture was purified by silica gel column chromatography (hexane), to provide 3.1 g of Compound (C30e) in the form of a pale yellow liquid.

The properties of Compound (C30e) were as follows.

$^1$H-NMR (400MHz; $CD_2Cl_2$; δ(ppm)); 0.80-0.93 (m, 15H), 1.11-1.64 (m, 27H), 2.74 (d, 2H), 7.18 (d, 1H), 7.51-7.54 (m, 2H), 7.57 (s, 1H), 7.60 (d, 1H)

FD-MS; 629 (M)

Into a 50-mL glass reaction vessel equipped with a stirring apparatus were placed 3.0 g (4.8 mmol) of Compound (C30e), 422.4 mg (1.2 mmol) of dibromobenzobisthiadiazole, 252.7 mg (0.36 mmol) of dichlorobis(triphenylphosphine) palladium (II), and 18 mL of anhydrous toluene. The mixture was reacted at an internal temperature of about 100° C. for 7 hours. The reaction solution was concentrated, and hexane was added to the concentrate, and then the precipitate was separated by filtration, to provide 733.8 mg of a crude product. The obtained crude product was subjected to Soxhlet extraction (toluene and chloroform), and then the extract was cooled to −26° C. and recrystallized, and these operations were repeated, to provide 242.3 mg of Compound (C30) in the form of a dark green powder.

The properties of Compound (C30) were as follows.

$^1$H-NMR (400MHz; $C_6D_4Cl_2$; δ(ppm)); 1.08-1.14 (m, 12H), 1.49-1.66 (m, 16H), 2.03-2.08 (m, 2H), 3.01-3.09 (m, 4H), 7.80-7.84 (m, 6H), 8.01 (s, 2H), 9.30 (d, 2H)

FD-MS; 870 (M)

The solubility of Compound (C30) was evaluated, and 0.2 wt % of Compound (C30) was completely dissolved in chloroform at 60° C. Also, 0.3 wt % of Compound (C30) was completely dissolved in 1-methylnaphthalene at 60° C. Also, 0.3 wt % of Compound (C30) was completely dissolved in toluene, mesitylene, and ortho-dichlorobenzene at 80° C.

Example 31

Synthesis of Compound (C31) (Compound of the Formula (87); 4,8-bis[5-(4-(2-methylhexyl)-3-(trifluoromethyl)phenyl)thiophene-2-yl]benzo[1,2-c:4,5-c']bis[1,2,5]thiadiazole))

(Step 31-1: Synthesis of Compound (C31))

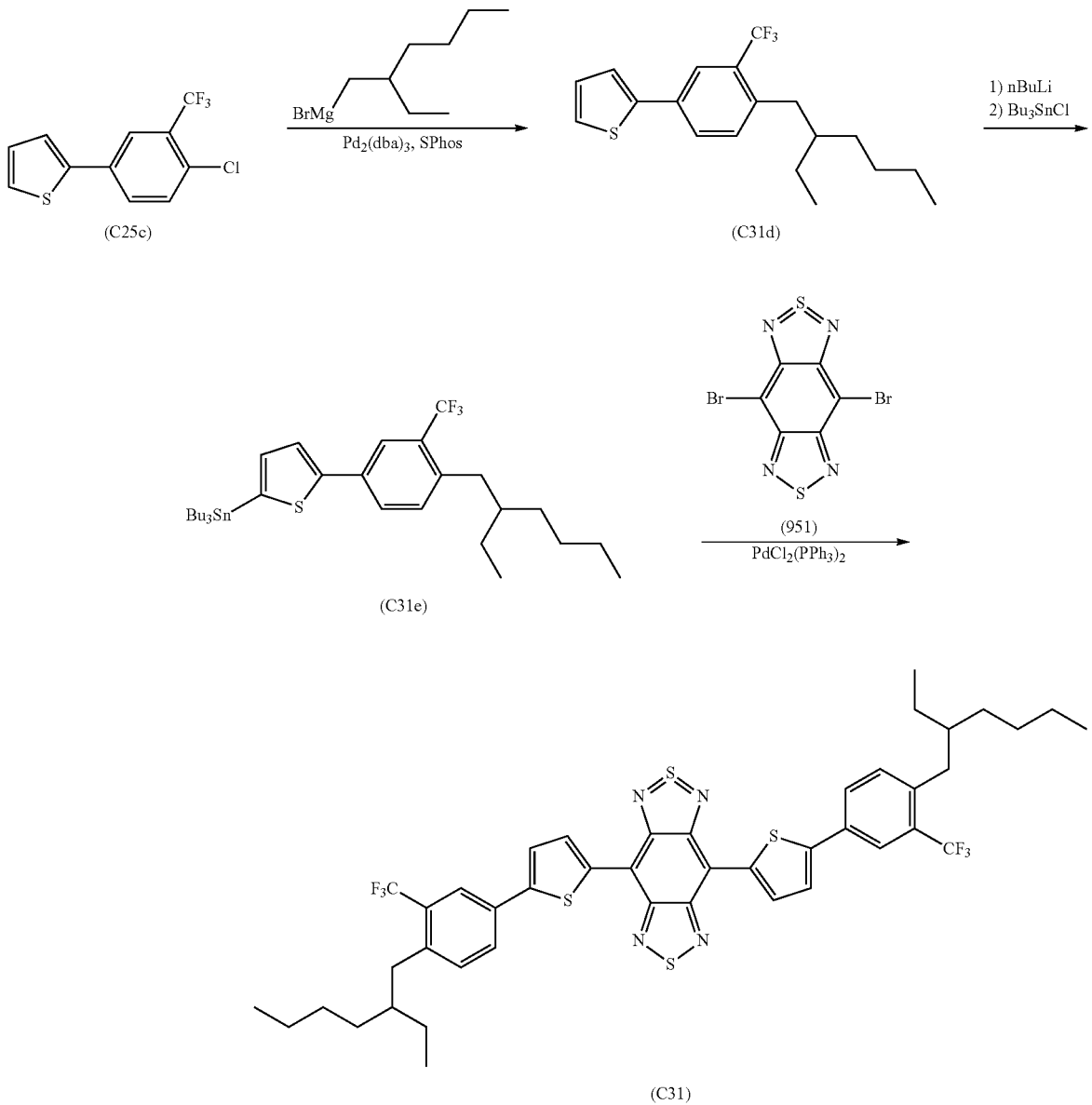

Into a 100-mL glass reaction vessel equipped with a stirring apparatus were placed 320.5 mg (0.35 mmol) of tris(dibenzylideneacetone)dipalladium, 574.7 mg (1.4 mmol) of 2-dicyclohexylphosphino-2',6'-dimethoxybiphenyl, and 15 mL of tetrahydrofuran. The mixture was stirred at room temperature for 15 minutes, and 1.8 g (7.0 mmol) of Compound (C25c) was added to the mixture. Subsequently, the mixture was cooled to 0° C., and 10.5 mL (10.50 mmol: concentration 0.5 M/tetrahydrofuran solution) of 2-ethylhexyl magnesium bromide was added thereto, and then the mixture was reacted at room temperature for 19 hours. And then, methanol was added to the reaction solution for quenching, and the solvent was distilled off. A saturated aqueous solution of ammonium chloride was added to the residue, and the mixture was subjected to extraction with diethyl ether. The extract was dried over magnesium sulfate, and the solvent was distilled off under a reduced pressure, and then the residue was purified by silica gel column chromatography (hexane), to provide 2.1 g of Compound (C31d) in the form of a pale yellow liquid.

The properties of Compound (C31d) were as follows.

$^1$H-NMR (400MHz; $CD_2Cl_2$; δ(ppm)); 0.85-0.93 (m, 6H), 1.25-1.40 (m, 8H), 1.68-1.72 (m, 1H), 2.71-2.74 (m, 2H), 7.09-7.12 (m, 1H), 7.32-7.37 (m, 3H), 7.69-7.71 (m, 1H), 7.85 (d, 1H)

EI-MS; 340 (M)

Into a 100-mL glass reaction vessel equipped with a stirring apparatus were placed 2.1 g (6.2 mmol) of Compound (C31d), and 37 mL of anhydrous tetrahydrofuran.

While the internal temperature was kept at −73° C., 4.2 mL of 1.6 M solution of n-butyl lithium in hexane was added to the mixture. The mixture was stirred at the same temperature for 1 hour, and then 1.8 mL (6.8 mmol) of tributyl tin chloride was added to the mixture at the same temperature. The temperature of the mixture was increased to room temperature, and the mixture was stirred for 1 hour. And then, methanol was added to the reaction solution for quenching, and the solvent was distilled off. Subsequently, hexane was added to the obtained crude reaction product, and the mixture was purified by silica gel column chromatography (hexane), to provide 3.4 g of Compound (C31e) in the form of a pale yellow liquid.

The properties of Compound (C31e) were as follows.

$^1$H-NMR (400MHz; CD$_2$Cl$_2$; δ(ppm)); 0.85-0.92 (m, 15H), 1.13-1.40 (m, 23H), 1.56-1.64 (m, 4H), 2.71 (d, 2H), 7.16 (d, 1H), 7.34 (d, 1H), 7.46-7.47 (m, 1H), 7.69-7.72 (m, 1H), 7.85 (d, 1H)

FD-MS; 630 (M)

Into a 50-mL glass reaction vessel equipped with a stirring apparatus were placed 3.4 g (5.4 mmol) of Compound (C34e), 475.2 mg (1.4 mmol) of dibromobenzobisthiadiazole, 287.8 mg (0.41 mmol) of dichlorobis(triphenylphosphine) palladium (II), and 20 mL of anhydrous toluene. The mixture was reacted at an internal temperature of about 100° C. for 7 hours. The reaction solution was concentrated, and hexane was added to the concentrate, and then the precipitate was separated by filtration, to provide 659.8 mg of a crude product. The obtained crude product was subjected to Soxhlet extraction (chloroform), and then the extract was cooled to −26° C. and recrystallized, and these operations were repeated, to provide 149.9 mg of Compound (C31) in the form of a dark green solid.

The properties of Compound (C31) were as follows.

$^1$H-NMR (400MHz; C$_6$D$_4$Cl$_2$; δ(ppm)); 1.07-1.13 (m, 12H), 1.48-1.63 (m, 16H), 1.97-2.03 (m, 2H), 3.00-3.02 (m, 4H), 7.56 (d, 2H), 7.72 (d, 2H), 8.02-8.04 (m, 2H), 8.31 (d, 2H), 9.28 (d, 2H)

FD-MS; 870 (M)

The solubility of Compound (C31) was evaluated, and 0.2 wt % of Compound (C31) was completely dissolved in chloroform at room temperature. Also, 0.3 wt % of Compound (C31) was completely dissolved in toluene, mesitylene, ortho-dichlorobenzene, and 1-methylnaphthalene at room temperature.

Comparative Example 6

Synthesis of Compound (RC6) (4,8-bis[4-hexyl-5-(3-(2-methylhexyl)-4-(trifluoromethyl)phenyl)thiophene-2-yl]benzo[1,2-c:4,5-c']bis[1,2,5]thiadiazole))

(Step R6-1: Synthesis of Compound (RC6))

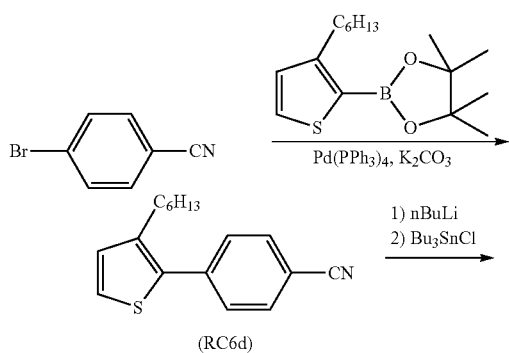

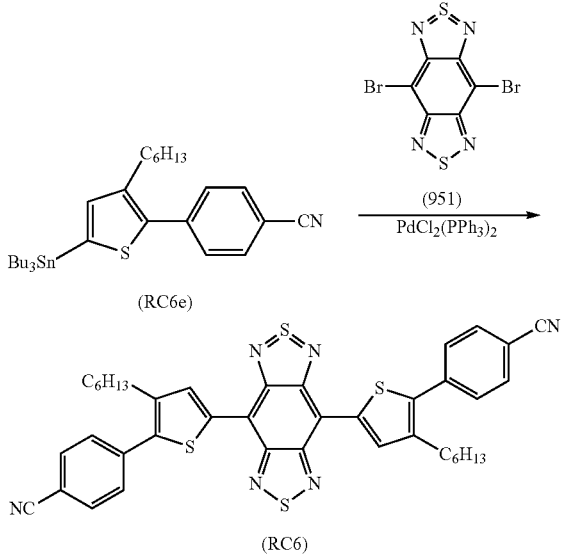

Under an inert gas atmosphere, into a 300-mL glass reaction vessel equipped with a stirring apparatus were placed 6.0 g (33 mmol) of 4-bromo-cyanobenzene, 9.70 g (33 mmol) of 3-hexyl-2-(4,4,5,5-tetramethyl-1,3,2-dioxaborolan-2-yl) thiophene, 5.46 g (39.6 mmol) of potassium carbonate, and 80 mL of anhydrous dimethylformamide. The mixture was subjected to freeze-degassing. Subsequently, 0.57 g (0.5 mmol) of tetrakistriphenylphosphine palladium (0) was added to the mixture, and then the mixture was reacted at an internal temperature of about 90° C. for 4 hours. After the completion of the reaction, 200 mL of hexane and 500 mL of water were added to the reaction solution, and the mixture was subjected to extraction. The combined organic layer was dried over magnesium sulfate, and then was purified by silica gel column chromatography, to provide 7.4 g of Compound (RC6d) in the form of a white solid.

The properties of Compound (RC6d) were as follows.

$^1$H-NMR (400MHz; CDCl$_3$; δ(ppm)); 0.76-0.96 (m, 3H), 1.12-1.42 (m, 6H), 1.48-1.72 (m, 2H), 2.56-2.75 (m, 2H), 6.96-7.06 (m, H), 7.28-7.35 (m, H), 7.48-7.58 (m, H), 7.64-7.74 (m, H)

EI-MS; 269 (M)

CI-MS; 270 (M+1)

Compound (RC6) was obtained in the same way as in Example 8, except that Compound (RC6d) was used instead of Compound (C8d).

The properties of Compound (RC6e) were as follows.

$^1$H-NMR (400MHz; CDCl$_3$; δ(ppm)); 0.78-1.00 (m, 12H), 1.00-1.22 (m, 6H), 1.22-1.44 (m, 12H), 1.44-1.76 (m, 8H), 2.55-2.80 (m, 2H), 6.95-7.10 (m, H), 7.46-7.60 (m, 2H), 7.60-7.74 (m, 2H)

EI-MS; 559 (M)

CI-MS; 560 (M+1)

The properties of Compound (RC6) were as follows.

$^1$H-NMR (400MHz; 1,2-dichlorobenzene-d$_4$, 140° C.; δ(ppm)); 0.72-0.98 (m, 6H), 1.12-1.58 (m, 12H), 1.64-1.96 (m, 4H), 2.66-3.02 (m, 4H), 7.46-7.59 (m, 4H), 7.59-7.74 (m, 4H), 8.95-9.15 (br, 2H)

TOF-HRMS (ASAP+); 729.1954 (M+1); Calcd. 729.1963

Example E-1

With the use of the Compound (C1) obtained in Example 1, a TFT device was produced on a "PS substrate" by spin-coating and evaluated.
(Conditions of Production of Organic Semiconductor Layer)
0.18 mL of a solution (organic semiconductor ink) which was prepared by adding Compound (C1) to mesitylene such that the concentration was 0.3 wt %, and then heating the mixture at 130° C. was dropped onto the "PS substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C1) on the "PS substrate" had a field-effect mobility of $1.3 \times 10^{-1}$ cm$^2$/Vs.

Example E-2

Figure 5:
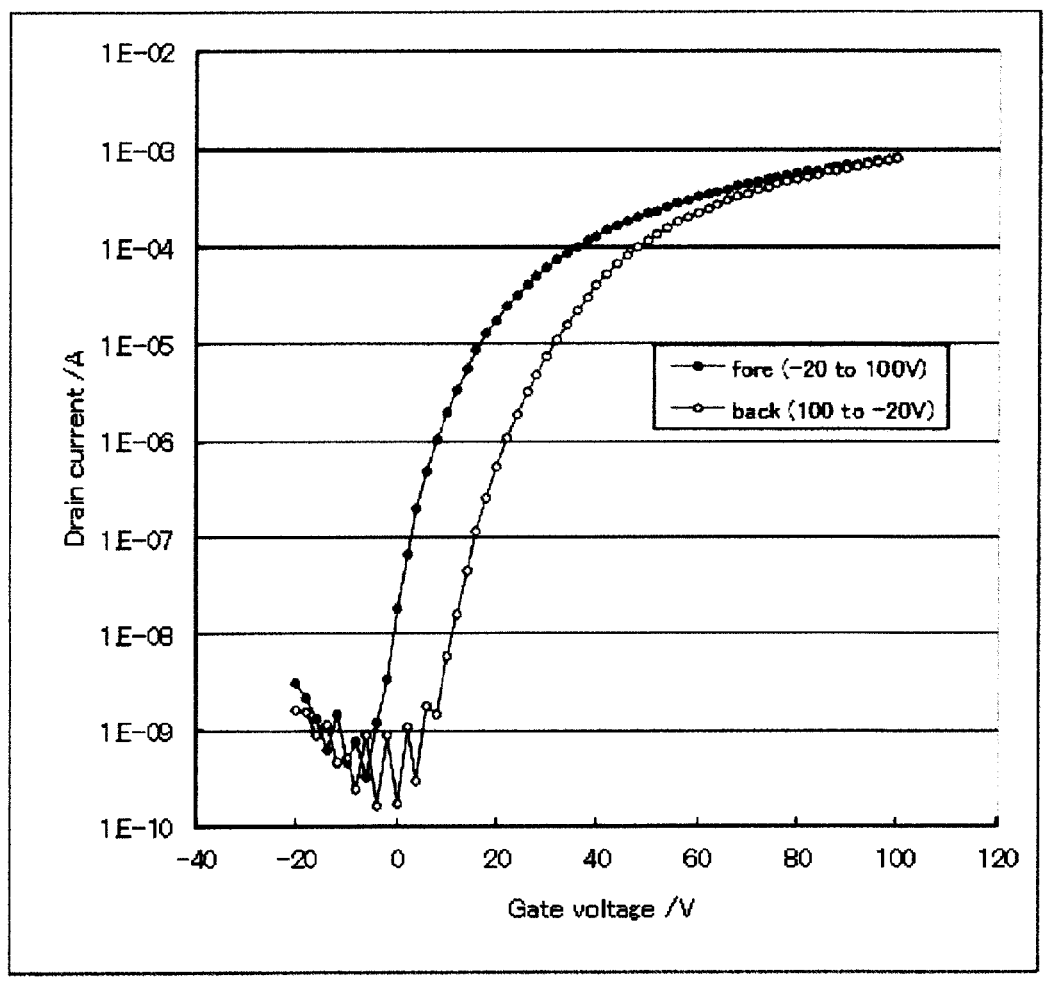
FIG. 5 is a graph showing the electrical properties of the organic TFT of Example E-2.

With the use of the Compound (C1) obtained in Example 1, a TFT device was produced on a "PVP substrate" by spin-coating and evaluated.
(Conditions of Production of Organic Semiconductor Layer)
0.18 mL of a solution (organic semiconductor ink) which was prepared by adding Compound (C1) to mesitylene such that the concentration was 0.3 wt %, and then heating the mixture at 130° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics. The obtained transfer characteristics are shown in FIG. 5. In FIG. 5, the horizontal axis indicates gate voltage (V), and the vertical axis indicates drain current (A).
The field-effect mobility ($\mu$) was calculated using the above-described (Formula A), and as the result thereof, it was found that the organic TFT comprising Compound (C1) on the "PVP substrate" had a field-effect mobility of $6.1 \times 10^{-1}$ cm$^2$/Vs.

Example E-3

With the use of the Compound (C1) obtained in Example 1, a TFT device was produced on a "CYC substrate" by spin-coating and evaluated.
(Conditions of Production of Organic Semiconductor Layer)
0.18 mL of a solution (organic semiconductor ink) which was prepared by adding Compound (C1) to mesitylene such that the concentration was 0.3 wt %, and then heating the mixture at 130° C. was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 210° C. for 1 minute. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C1) on the "CYC substrate" had a field-effect mobility of $1.6 \times 10^{0}$ cm$^2$/Vs.

Example E-4

With the use of the Compound (C1) obtained in Example 1, a TFT device was produced on a "HMDS substrate" by vacuum deposition and evaluated.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C1) on the "HMDS-modified substrate" had a field-effect mobility of $5.6 \times 10^{-1}$ cm$^2$/Vs.
The organic TFT was further left in the atmosphere for 7 days, and then the electrical properties of the organic TFT were evaluated at a drain voltage of 100 V again. As the result thereof, it was found that the organic TFT had a field-effect mobility of $4.8 \times 10^{-1}$ cm$^2$/Vs.
The organic TFT was further left in the atmosphere for 7 days, i.e. 14 days in total, and then the electrical properties of the organic TFT were evaluated at a drain voltage of 100 V. As the result thereof, it was found that the organic TFT had a field-effect mobility of $4.9 \times 10^{-1}$ cm$^2$/Vs.
The organic TFT was further left in the atmosphere for 14 days, i.e. 28 days in total, and then the electrical properties of the organic TFT were evaluated at a drain voltage of 100 V. As the result thereof, it was found that the organic TFT had a field-effect mobility of $4.8 \times 10^{-1}$ cm$^2$/Vs.
The organic TFT was further left in the atmosphere for 32 days, i.e. 60 days in total, and then the electrical properties of the organic TFT were evaluated at a drain voltage of 100 V. As the result thereof, it was found that the organic TFT had a field-effect mobility of $4.8 \times 10^{-1}$ cm$^2$/Vs.
The organic TFT was further left in the atmosphere for 29 days, i.e. 89 days in total, and then the electrical properties of the organic TFT were evaluated at a drain voltage of 100 V. As the result thereof, it was found that the organic TFT had a field-effect mobility of $4.7 \times 10^{-1}$ cm$^2$/Vs.
The organic TFT was further left in the atmosphere for 29 days, i.e. 118 days in total, and then the electrical properties of the organic TFT were evaluated at a drain voltage of 100 V. As the result thereof, it was found that the organic TFT had a field-effect mobility of $6.3 \times 10^{-1}$ cm$^2$/Vs.

Example E-5

With the use of the Compound (C1) obtained in Example 1, a TFT device was produced on a "PS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C1) on the "PS substrate" had a field-effect mobility of $5.3 \times 10^{-1}$ cm$^2$/Vs.

The organic TFT was further left in the atmosphere for 7 days, and then the electrical properties of the organic TFT were evaluated at a drain voltage of 100 V again. As the result thereof, it was found that the organic TFT had a field-effect mobility of $4.1 \times 10^{-1}$ cm$^2$/Vs.

The organic TFT was further left in the atmosphere for 7 days, i.e. 14 days in total, and then the electrical properties of the organic TFT were evaluated at a drain voltage of 100 V. As the result thereof, it was found that the organic TFT had a field-effect mobility of $4.1 \times 10^{-1}$ cm$^2$/Vs.

The organic TFT was further left in the atmosphere for 14 days, i.e. 28 days in total, and then the electrical properties of the organic TFT were evaluated at a drain voltage of 100 V. As the result thereof, it was found that the organic TFT had a field-effect mobility of $4.1 \times 10^{-1}$ cm$^2$/Vs.

The organic TFT was further left in the atmosphere for 32 days, i.e. 60 days in total, and then the electrical properties of the organic TFT were evaluated at a drain voltage of 100 V. As the result thereof, it was found that the organic TFT had a field-effect mobility of $4.1 \times 10^{-1}$ cm$^2$/Vs.

The organic TFT was further left in the atmosphere for 29 days, i.e. 89 days in total, and then the electrical properties of the organic TFT were evaluated at a drain voltage of 100 V. As the result thereof, it was found that the organic TFT had a field-effect mobility of $4.2 \times 10^{-1}$ cm$^2$/Vs.

The organic TFT was further left in the atmosphere for 29 days, i.e. 118 days in total, and then the electrical properties of the organic TFT were evaluated at a drain voltage of 100 V. As the result thereof, it was found that the organic TFT had a field-effect mobility of $4.2 \times 10^{-1}$ cm$^2$/Vs.

Example E-6

With the use of the Compound (C1) obtained in Example 1, a bottom gate-top contact device (organic TFT) was produced on a glass substrate in accordance with the procedure as described below, and evaluated.
(Production of Device)

An aluminum film with a thickness of about 30 nm was formed on a glass substrate by vacuum deposition, using a metal mask, to form a gate electrode. A solution prepared by dissolving polyvinylphenol and melamine, which were commercially available, in propylene glycol monomethyl ether acetate was applied by spin-coating onto the glass substrate on which the gate electrode was formed, and then heated at 150° C. for 1 hour, to form a polyvinylphenol-melamine thin film with a thickness of about 210 nm on the surface of the substrate.

A partition wall pattern to receive a semiconductor ink in the next step was formed on the polyvinylphenol-melamine thin film with the use of a solution prepared by dissolving 1 wt % Teflon® AF1600X in Fluorinert™ FC-43, which was commercially available, and heated at 100° C. for 30 minutes, to form a partition wall.

An organic semiconductor ink, which was prepared by adding Compound (C1) obtained in Example 1 to methyl salicylate such that the concentration was 0.2 wt %, and then heating the mixture at 100° C., was dropped into the partition wall which was formed in the step as described above, and dried at 80° C., to form an organic semiconductor layer. A gold film was formed on the organic semiconductor layer by vacuum deposition, using a metal mask, to form a source electrode and a drain electrode, thereby producing an organic TFT. The channel width and the channel length were 1500 μm and 50 μm, respectively. The thickness of the electrode layer was about 50 nm.
(Evaluation of Organic TFT)

The transfer characteristics of the produced organic TFT were measured under the condition that the drain voltage was 40 V, and the organic TFT had the n-type semiconductor characteristics.

The field-effect mobility ($\mu$) was calculated using the above-described (Formula A), and as the result thereof, it was found that the organic TFT comprising Compound (C1) had a field-effect mobility of $6.3 \times 10^{-1}$ cm$^2$/Vs.

Example E-7

With the use of the Compound (C1) obtained in Example 1, a bottom gate-bottom contact device (organic TFT) was produced on a glass substrate in accordance with the procedure as described below, and evaluated.
(Production of Device)

An aluminum film with a thickness of about 30 nm was formed on a glass substrate by vacuum deposition, using a metal mask, to form a gate electrode. A solution prepared by dissolving polyvinylphenol and melamine, which were commercially available, in propylene glycol monomethyl ether acetate was applied by spin-coating onto the glass substrate on which the gate electrode was formed, and then heated at 150° C. for 1 hour, to form a polyvinylphenol-melamine thin film with a thickness of about 210 nm on the surface of the substrate.

A gold film was formed on the polyvinylphenol-melamine thin film by vacuum deposition, using a metal mask, to form a source electrode and a drain electrode. The channel width and the channel length were 1000 μm and 35 μm, respectively. The thickness of the electrode was about 50 nm. A partition wall pattern to receive a semiconductor ink in the next step was formed on the polyvinylphenol-melamine thin film with the use of a solution prepared by dissolving 1 wt % Teflon® AF1600X in Fluorinert™ FC-43, which was commercially available, and heated at 100° C. for 30 minutes, to form a partition wall.

An organic semiconductor ink, which was prepared by adding Compound (C1) obtained in Example 1 to methyl salicylate such that the concentration was 0.2 wt %, and then heating the mixture at 100° C., was dropped into the partition wall which was formed in the step as described above, and dried at 80° C., to form an organic semiconductor layer, thereby producing an organic TFT.
(Evaluation of Organic TFT)

The transfer characteristics of the produced organic TFT were measured under the condition that the drain voltage was 40 V, and the organic TFT had the n-type semiconductor characteristics.

The field-effect mobility ($\mu$) was calculated using the above-described (Formula A), and as the result thereof, it was found that the organic TFT comprising Compound (C1) had a field-effect mobility of $1.0 \times 10^{-1}$ cm$^2$/Vs.

Comparative Example E-1

With the use of the Compound (RCI) obtained in Comparative Example 1, a TFT device was produced on a "PS substrate" by spin-coating and evaluated.
(Conditions of Production of Organic Semiconductor Layer)
0.18 mL of a solution (organic semiconductor ink) which was prepared by adding Compound (RC1) to mesitylene such that the concentration was 0.3 wt %, and then heating the mixture at 130° C. was dropped onto the "PS substrate", and then spin-coating was performed at 1000 rpm for 30 seconds, to form an organic semiconductor layer with a thickness of about 20 nm.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (RC1) on the "PS substrate" had a field-effect mobility of $7.0 \times 10^{-4}$ cm$^2$/Vs.

Comparative Example E-2

With the use of the Compound (RC1) obtained in Comparative Example 1, a TFT device was produced on a "PVP substrate" by spin-coating and evaluated.
(Conditions of Production of Organic Semiconductor Layer)
0.18 mL of a solution (organic semiconductor ink) which was prepared by adding Compound (RC1) to mesitylene such that the concentration was 0.3 wt %, and then heating the mixture at 130° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes.
(Evaluation of Organic TFT)
The transfer characteristics of the produced organic TFT were measured under the condition that the drain voltage was 100 V, and the organic TFT did not have the transistor characteristics.

Comparative Example E-3

With the use of the Compound (RC1) obtained in Comparative Example 1, a TFT device was produced on a "HMDS substrate" by vacuum deposition and evaluated.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (RC1) on the "HMDS-modified substrate" had a field-effect mobility of $5.8 \times 10^{-1}$ cm$^2$/Vs.

Comparative Example E-4

With the use of the Compound (RC1) obtained in Comparative Example 1, a TFT device was produced on a "PS substrate" by vacuum deposition and evaluated.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (RC1) on the "PS substrate" had a field-effect mobility of $1.2 \times 10^{0}$ cm$^2$/Vs.

Reference Example E-1

With the use of the Compound (RR1) obtained in Reference Example 1, a TFT device was produced on a "PS substrate" by spin-coating and evaluated.
(Conditions of Production of Organic Semiconductor Layer)
0.18 mL of a solution (organic semiconductor ink) which was prepared by adding Compound (RR1) to mesitylene such that the concentration was 0.3 wt %, and then heating the mixture at 130° C. was dropped onto the "PS substrate", and then spin-coating was performed at 1000 rpm for 30 seconds, to form an organic semiconductor layer with a thickness of about 20 nm.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (RR1) on the "PS substrate" had a field-effect mobility of $6.2 \times 10^{-5}$ cm$^2$/Vs.

Reference Example E-2

With the use of the Compound (RR1) obtained in Reference Example 1, a TFT device was produced on a "PVP substrate" by spin-coating and evaluated.
(Conditions of Production of Organic Semiconductor Layer)
0.18 mL of a solution (organic semiconductor ink) which was prepared by adding Compound (RR1) to mesitylene such that the concentration was 0.3 wt %, and then heating the mixture at 130° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes.
(Evaluation of Organic TFT)
The transfer characteristics of the produced organic TFT were measured under the condition that the drain voltage was 100 V, and the organic TFT did not have the transistor characteristics.

Reference Example E-3

With the use of the Compound (RR1) obtained in Reference Example 1, a TFT device was produced on a "HMDS substrate" by vacuum deposition and evaluated.
(Evaluation of Organic TFT)
The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (RR1) on the "HMDS-modified substrate" had a field-effect mobility of $6.4 \times 10^{-2}$ cm$^2$/Vs.

Reference Example E-4

With the use of the Compound (RR1) obtained in Reference Example 1, a TFT device was produced on a "PS substrate" by vacuum deposition and evaluated.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (RR1) on the "PS substrate" had a field-effect mobility of $1.7 \times 10^{-1}$ cm$^2$/Vs.

Example E-8

With the use of the Compound (C2) obtained in Example 2, a TFT device was produced on a "PS substrate" by spin-coating and evaluated.
(Conditions of Production of Organic Semiconductor Layer)
0.18 mL of a solution (organic semiconductor ink) which was prepared by adding Compound (C2) to chlorobenzene such that the concentration was 0.3 wt %, and then heating the mixture at 130° C. was dropped onto the "PS substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C2) on the "PS substrate" had a field-effect mobility of $2.9 \times 10^{-2}$ cm$^2$/Vs.

Example E-9

Figure 6:
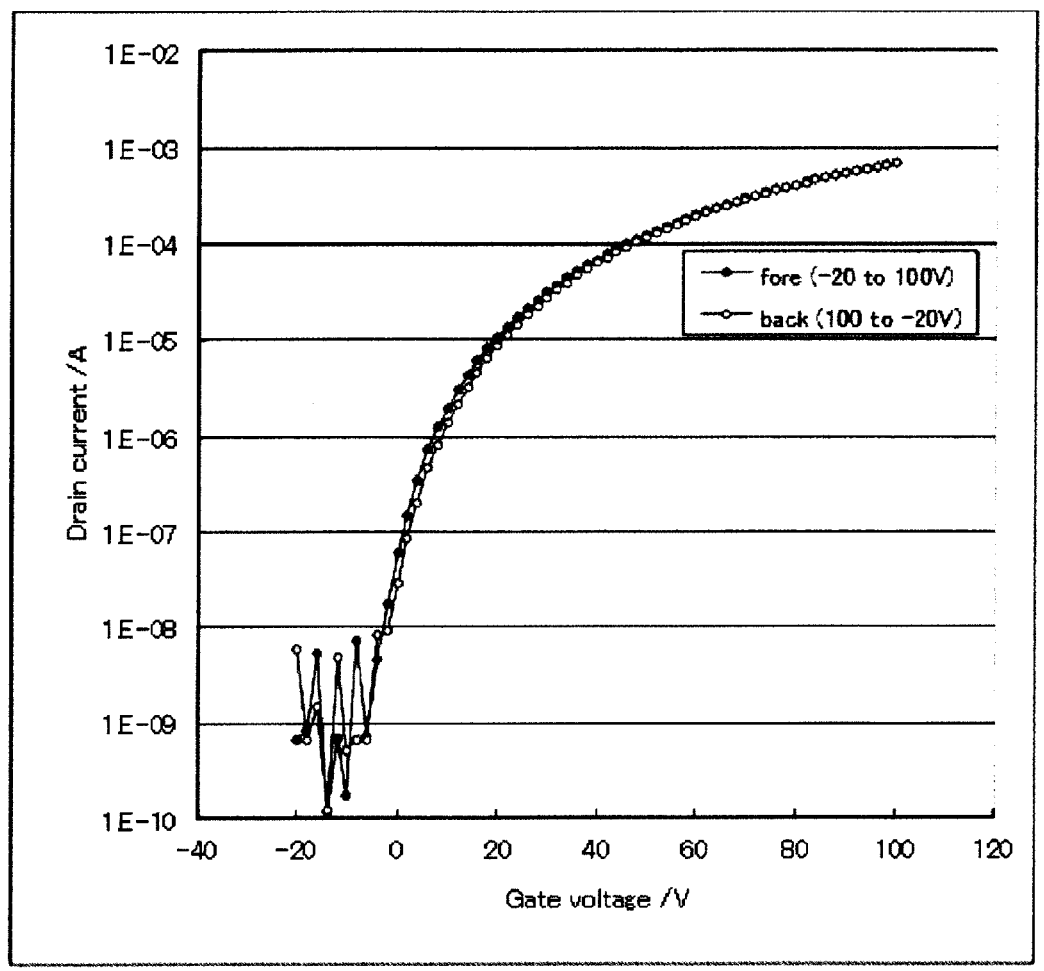
FIG. 6 is a graph showing the electrical properties of the organic TFT of Example E-9.

With the use of the Compound (C2) obtained in Example 2, a TFT device was produced on a "PVP substrate" by spin-coating and evaluated.
(Conditions of Production of Organic Semiconductor Layer)
0.18 mL of a solution (organic semiconductor ink) which was prepared by adding Compound (C2) to chlorobenzene such that the concentration was 0.3 wt %, and then heating the mixture at 130° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 120° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics. The obtained transfer characteristics are shown in FIG. 6. In FIG. 6, the horizontal axis indicates gate voltage (V), and the vertical axis indicates drain current (A).
The field-effect mobility (μ) was calculated using the above-described (Formula A), and as the result thereof, it was found that the organic TFT comprising Compound (C2) on the "PVP substrate" had a field-effect mobility of $3.4 \times 10^{-1}$ cm$^2$/Vs.

Example E-10

With the use of the Compound (C2) obtained in Example 2, a TFT device was produced on a "CYC substrate" by spin-coating and evaluated.
(Conditions of Production of Organic Semiconductor Layer)
0.18 mL of a solution (organic semiconductor ink) which was prepared by adding Compound (C2) to chlorobenzene such that the concentration was 0.3 wt %, and then heating the mixture at 130° C. was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C2) on the "CYC substrate" had a field-effect mobility of $4.5 \times 10^{-1}$ cm$^2$/Vs.

Example E-11

With the use of the Compound (C2) obtained in Example 2, a TFT device was produced on a "HMDS substrate" by vacuum deposition and evaluated.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C2) on the "HMDS-modified substrate" had a field-effect mobility of $3.9 \times 10^{-1}$ cm$^2$/Vs.

Example E-12

With the use of the Compound (C2) obtained in Example 2, a TFT device was produced on a "PS substrate" by vacuum deposition and evaluated.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C2) on the "PS substrate" had a field-effect mobility of $1.4\times10^{-2}$ cm$^2$/Vs.

Reference Example P-E-13

With the use of the Compound (C3) obtained in Reference Example P-3, a TFT device was produced on a "HMDS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C3) on the "HMDS-modified substrate" had a field-effect mobility of $1.8\times10^{-4}$ cm$^2$/Vs.

Reference Example P-E-14

With the use of the Compound (C3) obtained in Reference Example P-3, a TFT device was produced on a "PS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C3) on the "PS substrate" had a field-effect mobility of $5.2\times10^{-4}$ cm$^2$/Vs.

Comparative Example E-5

In an attempt to produce a TFT device by spin-coating with the use of the Compound (RC2) obtained in Comparative Example 2, Compound (RC2) was added to mesitylene such that the concentration was 0.3 wt %, and then the mixture was heated at 130° C. However, all of the compound was not dissolved in mesitylene, and a homogeneous solution was not prepared.

Comparative Example E-6

With the use of the Compound (RC2) obtained in Comparative Example 2, a TFT device was produced on a "HMDS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (RC2) on the "HMDS-modified substrate" had a field-effect mobility of $3.9\times10^{-1}$ cm$^2$/Vs.

Comparative Example E-7

With the use of the Compound (RC2) obtained in Comparative Example 2, a TFT device was produced on a "PS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (RC2) on the "PS substrate" had a field-effect mobility of $4.1\times10^{-1}$ cm$^2$/Vs.

Reference Example E-5

With the use of the Compound (RR2) obtained in Reference Example 2, a TFT device was produced on a "PS substrate" by spin-coating and evaluated.
(Conditions of Production of Organic Semiconductor Layer)

0.18 mL of a solution (organic semiconductor ink) which was prepared by adding Compound (RR2) to mesitylene such that the concentration was 0.3 wt %, and then heating the mixture at 60° C. was dropped onto the "PS substrate", and then spin-coating was performed at 1000 rpm for 30 seconds, to form an organic semiconductor layer with a thickness of about 20 nm.

The transfer characteristics of the produced organic TFT were measured under the condition that the drain voltage was 100 V, and the organic TFT did not have the transistor characteristics.

Reference Example E-6

With the use of the Compound (RR2) obtained in Reference Example 2, a TFT device was produced on a "PVP substrate" by spin-coating and evaluated.
(Conditions of Production of Organic Semiconductor Layer)

0.18 mL of a solution (organic semiconductor ink) which was prepared by adding Compound (RR2) to mesitylene such that the concentration was 0.3 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 120° C. for 35 minutes.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (RR2) on the "PVP substrate" had a field-effect mobility of $5.1\times10^{-2}$ cm$^2$/Vs.

Reference Example E-7

With the use of the Compound (RR2) obtained in Reference Example 2, a TFT device was produced on a "HMDS substrate" by vacuum deposition and evaluated.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (RR2) on the "HMDS-modified substrate" had a field-effect mobility of $3.8 \times 10^{-1}$ cm$^2$/Vs.

Reference Example E-8

With the use of the Compound (RR2) obtained in Reference Example 2, a TFT device was produced on a "PS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (RR2) on the "PS substrate" had a field-effect mobility of $3.1 \times 10^{-2}$ cm$^2$/Vs.

Example E-15

With the use of the Compound (C6) obtained in Example 6, a TFT device was produced on a "PS substrate" by spin-coating and evaluated.
(Conditions of Production of Organic Semiconductor Layer)

0.18 mL of a solution (organic semiconductor ink) which was prepared by adding Compound (C6) to mesitylene such that the concentration was 0.3 wt %, and then heating the mixture at 130° C. was dropped onto the "PS substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C6) on the "PS substrate" had a field-effect mobility of $2.1 \times 10^{-2}$ cm$^2$/Vs.

Example E-16

With the use of the Compound (C6) obtained in Example 6, a TFT device was produced on a "PVP substrate" by spin-coating and evaluated.
(Conditions of Production of Organic Semiconductor Layer)

0.18 mL of a solution (organic semiconductor ink) which was prepared by adding Compound (C6) to mesitylene such that the concentration was 0.3 wt %, and then heating the mixture at 130° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 120° C. for 35 minutes. The appearance of the film was visually observed, and it was confirmed that a homogeneous film was formed, that is, a good film was formed successfully.
(Evaluation of Organic TFT)

Figure 7:
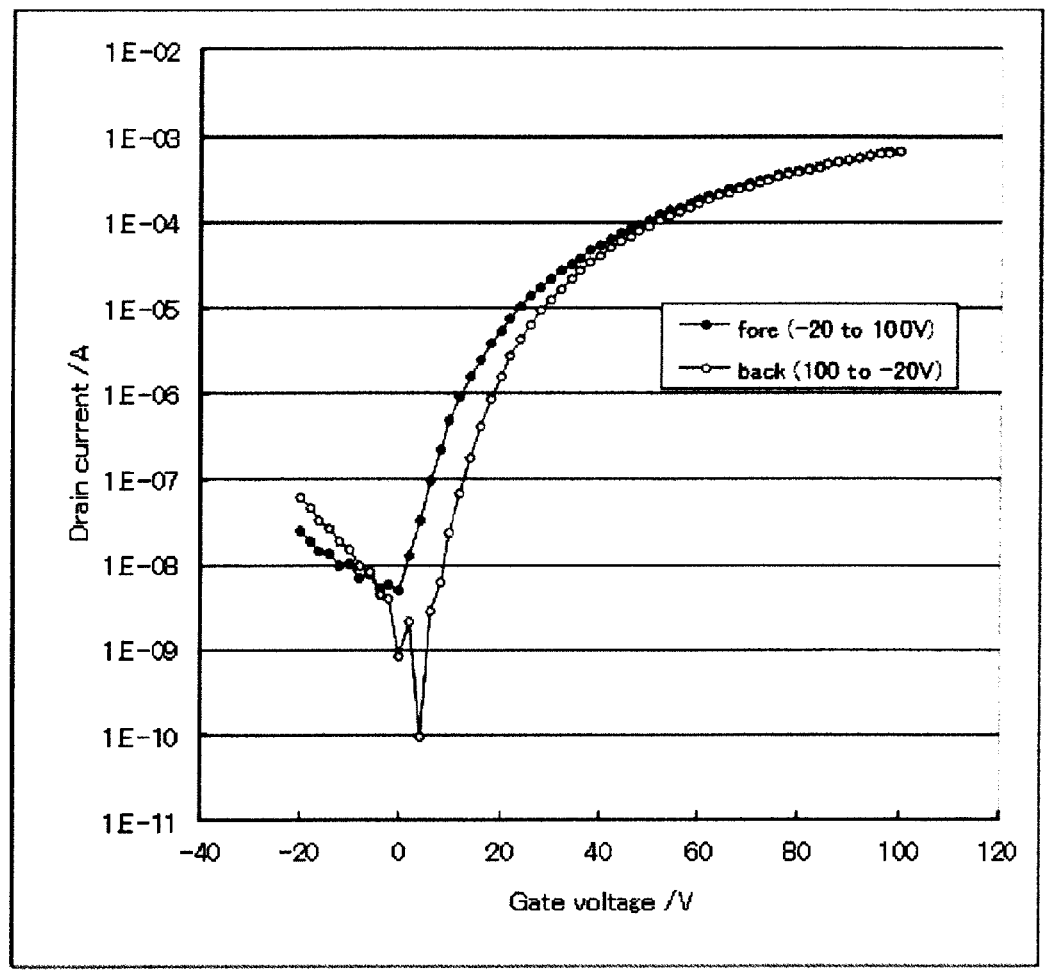
FIG. 7 is a graph showing the electrical properties of the organic TFT of Example E-16.

The transfer characteristics of the produced organic TFT were measured under the condition that the drain voltage was 100 V, and the organic TFT had the n-type semiconductor characteristics. The obtained transfer characteristics are shown in FIG. 7. In FIG. 7, the horizontal axis indicates gate voltage (V), and the vertical axis indicates drain current (A).

The field-effect mobility ($\mu$) was calculated using the above-described (Formula A), and as the result thereof, it was found that the organic TFT comprising Compound (C6) on the "PVP substrate" had a field-effect mobility of $3.9 \times 10^{-1}$ cm$^2$/Vs.

Example E-17

With the use of the Compound (C6) obtained in Example 6, a TFT device was produced on a "CYC substrate" by spin-coating and evaluated.
(Conditions of Production of Organic Semiconductor Layer)

0.18 mL of a solution (organic semiconductor ink) which was prepared by adding Compound (C6) to mesitylene such that the concentration was 0.3 wt %, and then heating the mixture at 130° C. was dropped onto the "CYC substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C6) on the "CYC substrate" had a field-effect mobility of $4.2 \times 10^{-2}$ cm$^2$/Vs.

Example E-18

With the use of the Compound (C6) obtained in Example 6, a TFT device was produced on a "HMDS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C6) on the "HMDS-modified substrate" had a field-effect mobility of $4.0 \times 10^{-1}$ cm$^2$/Vs.

Example E-19

With the use of the Compound (C6) obtained in Example 6, a TFT device was produced on a "PS substrate" by vacuum deposition and evaluated.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C6) on the "PS substrate" had a field-effect mobility of $9.3 \times 10^{-2}$ cm$^2$/Vs.

Comparative Example E-8

In an attempt to produce a TFT device by spin-coating with the use of the Compound (RC5) obtained in Comparative Example 5, Compound (RC5) was added to mesitylene such that the concentration was 0.3 wt %, and then the mixture was heated at 130° C. However, all of the compound was not dissolved in mesitylene, and a homogeneous solution was not prepared.

Comparative Example E-9

With the use of the Compound (RC5) obtained in Comparative Example 5, a TFT device was produced on a "HMDS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (RC5) on the "HMDS-modified substrate" had a field-effect mobility of $3.9 \times 10^{-1}$ cm$^2$/Vs.

Comparative Example E-10

With the use of the Compound (RC5) obtained in Comparative Example 5, a TFT device was produced on a "PS substrate" by vacuum deposition and evaluated.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (RC5) on the "PS substrate" had a field-effect mobility of $7.1 \times 10^{-1}$ cm$^2$/Vs.

Example E-20

With the use of the Compound (C4) obtained in Example 4, a TFT device was produced on a "PS substrate" by spin-coating and evaluated.
(Conditions of Production of Organic Semiconductor Layer)

0.18 mL of a solution (organic semiconductor ink) which was prepared by adding Compound (C4) to 1,2-dichlorobenzene such that the concentration was 0.3 wt %, and then heating the mixture at 130° C. was dropped onto the "PS substrate", and then spin-coating was performed at 1000 rpm for 30 seconds, to form an organic semiconductor layer with a thickness of about 20 nm. And then, the "PS substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C4) on the "PS substrate" had a field-effect mobility of $3.8 \times 10^{-1}$ cm$^2$/Vs.

Example E-21

With the use of the Compound (C4) obtained in Example 4, a TFT device was produced on a "PVP substrate" by spin-coating and evaluated.
(Conditions of Production of Organic Semiconductor Layer)

0.18 mL of a solution (organic semiconductor ink) which was prepared by adding Compound (C4) to mesitylene such that the concentration was 0.5 wt %, and then heating the mixture at 130° C. was dropped onto the "PVP substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C4) on the "PVP substrate" had a field-effect mobility of $2.7 \times 10^{-1}$ cm$^2$/Vs.

Example E-22

With the use of the Compound (C4) obtained in Example 4, a TFT device was produced on a "CYC substrate" by spin-coating and evaluated.
(Conditions of Production of Organic Semiconductor Layer)

0.18 mL of a solution (organic semiconductor ink) which was prepared by adding Compound (C4) to mesitylene such that the concentration was 0.5 wt %, and then heating the mixture at 130° C. was dropped onto the "CYC substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C4) on the "CYC substrate" had a field-effect mobility of $2.7 \times 10^{-1}$ cm$^2$/Vs.

Comparative Example E-11

With the use of the Compound (RC3) obtained in Comparative Example 3, a TFT device was produced on a "PS substrate" by spin-coating and evaluated.
(Conditions of Production of Organic Semiconductor Layer)
0.18 mL of a solution (organic semiconductor ink) which was prepared by adding Compound (RC3) to 1,2-dichlorobenzene such that the concentration was 0.3 wt %, and then heating the mixture at 130° C. was dropped onto the "PS substrate", and then spin-coating was performed at 1000 rpm for 30 seconds, to form an organic semiconductor layer with a thickness of about 20 nm. And then, the "PS substrate" on which the organic semiconductor layer was formed was heated at 180° C. for 35 minutes.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (RC3) on the "PS substrate" had a field-effect mobility of $1.0 \times 10^{-1}$ cm$^2$/Vs.

Comparative Example E-12

With the use of the Compound (RC3) obtained in Comparative Example 3, a TFT device was produced on a "PVP substrate" by spin-coating and evaluated.
(Conditions of Production of Organic Semiconductor Layer)
0.18 mL of a solution (organic semiconductor ink) which was prepared by adding Compound (RC3) to 1,2-dichlorobenzene such that the concentration was 0.3 wt %, and then heating the mixture at 130° C. was dropped onto the "PVP substrate", and then spin-coating was performed at 1000 rpm for 30 seconds, to form an organic semiconductor layer with a thickness of about 20 nm.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (RC3) on the "PVP substrate" had a field-effect mobility of $6.0 \times 10^{-2}$ cm$^2$/Vs.

Example E-23

With the use of the Compound (C7) obtained in Example 7, a TFT device was produced on a "PS substrate" by spin-coating and evaluated.
(Conditions of Production of Organic Semiconductor Layer)
0.18 mL of a solution (organic semiconductor ink) which was prepared by adding Compound (C7) to chloroform such that the concentration was 0.3 wt %, and then heating the mixture at 60° C. was dropped onto the "PS substrate", and then spin-coating was performed at 1000 rpm for 30 seconds, to form an organic semiconductor layer with a thickness of about 20 nm. And then, the "PS substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C7) on the "PS substrate" had a field-effect mobility of $1.0 \times 10^{-3}$ cm$^2$/Vs.

Example E-24

With the use of the Compound (C7) obtained in Example 7, a TFT device was produced on a "PVP substrate" by spin-coating and evaluated.
(Conditions of Production of Organic Semiconductor Layer)
0.18 mL of a solution (organic semiconductor ink) which was prepared by adding Compound (C7) to chloroform such that the concentration was 0.3 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C7) on the "PVP substrate" had a field-effect mobility of $2.5 \times 10^{-3}$ cm$^2$/Vs.

Example E-25

With the use of the Compound (C7) obtained in Example 7, a TFT device was produced on a "CYC substrate" by spin-coating and evaluated.
(Conditions of Production of Organic Semiconductor Layer)
0.18 mL of a solution (organic semiconductor ink) which was prepared by adding Compound (C7) to chloroform such that the concentration was 0.3 wt %, and then heating the mixture at 60° C. was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C7) on the "CYC substrate" had a field-effect mobility of 9.0× $10^{-4}$ cm²/Vs.

Example E-26

With the use of the Compound (C7) obtained in Example 7, a TFT device was produced on a "PVP substrate" by spin-coating and evaluated.
(Conditions of Production of Organic Semiconductor Layer)
0.18 mL of a solution (organic semiconductor ink) which was prepared by adding Compound (C7) to chloroform such that the concentration was 0.3 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C7) on the "PVP substrate" had a field-effect mobility of 7.3× $10^{-3}$ cm²/Vs.

Example E-27

With the use of the Compound (C8) obtained in Example 8, a TFT device was produced on a "PS substrate" by spin-coating and evaluated.
(Conditions of Production of Organic Semiconductor Layer)
0.18 mL of a solution (organic semiconductor ink) which was prepared by adding Compound (C8) to chloroform such that the concentration was 0.1 wt %, and then heating the mixture at 60° C. was dropped onto the "PS substrate", and then spin-coating was performed at 1000 rpm for 30 seconds, to form an organic semiconductor layer with a thickness of about 20 nm. And then, the "PS substrate" on which the organic semiconductor layer was formed was heated at 120° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C8) on the "PS substrate" had a field-effect mobility of 2.7×$10^{-1}$ cm²/Vs.

Example E-28

Figure 8:
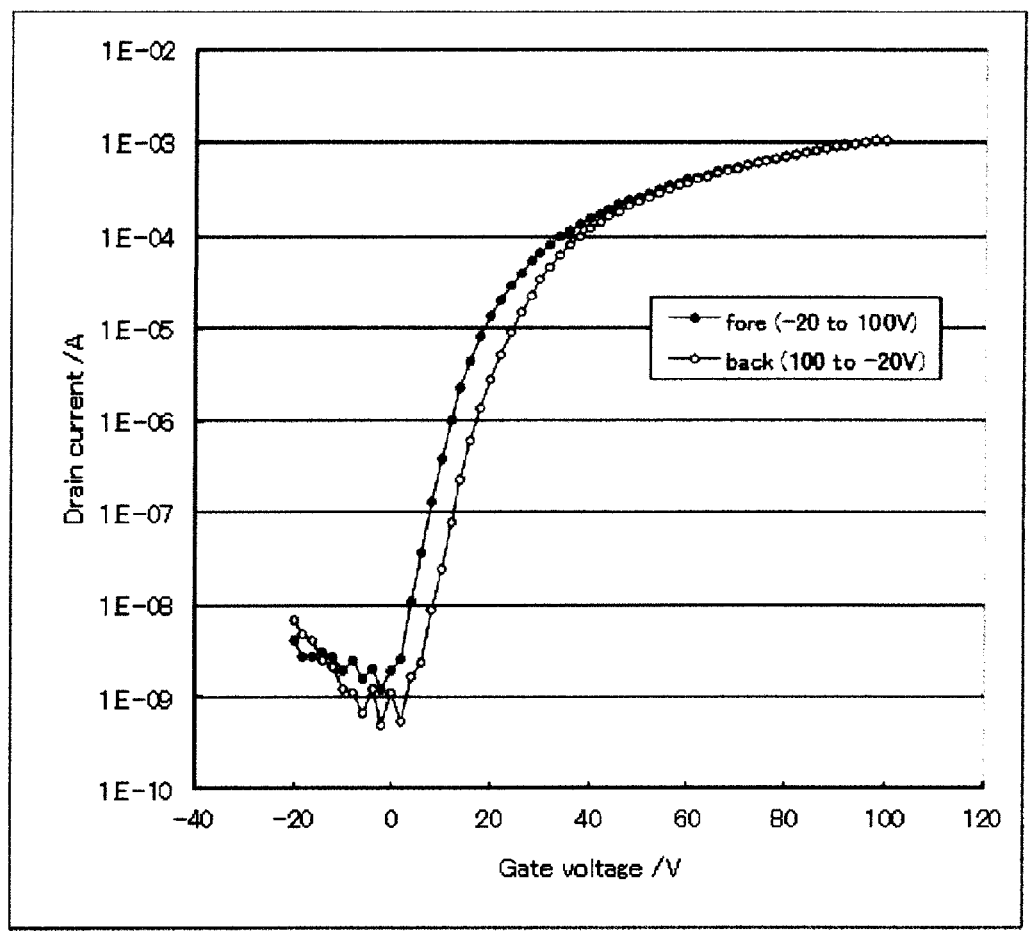
FIG. 8 is a graph showing the electrical properties of the organic TFT of Example E-28.

With the use of the Compound (C8) obtained in Example 8, a TFT device was produced on a "PVP substrate" by spin-coating and evaluated.
(Conditions of Production of Organic Semiconductor Layer)
0.18 mL of a solution (organic semiconductor ink) which was prepared by adding Compound (C8) to chloroform such that the concentration was 0.1 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics. The obtained transfer characteristics are shown in FIG. 8. In FIG. 8, the horizontal axis indicates gate voltage (V), and the vertical axis indicates drain current (A).
The field-effect mobility (μ) was calculated using the above-described (Formula A), and as the result thereof, it was found that the organic TFT comprising Compound (C8) on the "PVP substrate" had a field-effect mobility of 7.3× $10^{-1}$ cm²/Vs.

Example E-29

With the use of the Compound (C8) obtained in Example 8, a TFT device was produced on a "CYC substrate" by spin-coating and evaluated.
(Conditions of Production of Organic Semiconductor Layer)
0.18 mL of a solution (organic semiconductor ink) which was prepared by adding Compound (C8) to chloroform such that the concentration was 0.1 wt %, and then heating the mixture at 60° C. was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C8) on the "CYC substrate" had a field-effect mobility of 4.3× $10^{-1}$ cm²/Vs.

Example E-30

With the use of the Compound (C8) obtained in Example 8, a TFT device was produced on a "CYC substrate" by spin-coating and evaluated.
(Conditions of Production of Organic Semiconductor Layer)
0.18 mL of an organic semiconductor ink which was prepared by adding Compound (C8) to chloroform such that the concentration was 0.1 wt %, and then heating the mixture at 60° C. was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 240° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C8) on the "CYC substrate" had a field-effect mobility of $2.0 \times 10^0$ cm$^2$/Vs.
(Evaluation of Organic TFT)

The transfer characteristics of the produced organic TFT were measured under the condition that the drain voltage was 20 V, and the organic TFT had the n-type semiconductor characteristics.

The field-effect mobility (μ) was calculated using the above-described (Formula A), and as the result thereof, it was found that the organic TFT comprising Compound (C8) on the "CYC substrate" had a field-effect mobility of $4.6 \times 10^{-1}$ cm$^2$/Vs.

Example E-31

With the use of the Compound (C8) obtained in Example 8, a TFT device was produced on a "bare substrate" by spin-coating and evaluated.
(Conditions of Production of Organic Semiconductor Layer)

0.18 mL of an organic semiconductor ink which was prepared by adding Compound (C8) to chloroform such that the concentration was 0.1 wt %, and then heating the mixture at 60° C. was dropped onto the "bare substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C8) on the "bare substrate" had a field-effect mobility of $4.9 \times 10^{-1}$ cm$^2$/Vs.

Example E-32

With the use of the Compound (C8) obtained in Example 8, a TFT device was produced on a "bare substrate" by spin-coating and evaluated.
(Conditions of Production of Organic Semiconductor Layer)

0.18 mL of an organic semiconductor ink which was prepared by adding Compound (C8) to chloroform such that the concentration was 0.1 wt %, and then heating the mixture at 60° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 240° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C8) on the "bare substrate" had a field-effect mobility of $7.1 \times 10^{-1}$ cm$^2$/Vs.

Example E-33

With the use of the Compound (C9) obtained in Example 9, a TFT device was produced on a "PS substrate" by spin-coating and evaluated.
(Conditions of Production of Organic Semiconductor Layer)

0.18 mL of a solution (organic semiconductor ink) which was prepared by adding Compound (C9) to xylene such that the concentration was 0.3 wt %, and then heating the mixture at 70° C. was dropped onto the "PS substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C9) on the "PS substrate" had a field-effect mobility of $5.1 \times 10^{-3}$ cm$^2$/Vs.

Example E-34

With the use of the Compound (C9) obtained in Example 9, a TFT device was produced on a "PVP substrate" by spin-coating and evaluated.
(Conditions of Production of Organic Semiconductor Layer)

0.18 mL of a solution (organic semiconductor ink) which was prepared by adding Compound (C9) to xylene such that the concentration was 0.3 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C9) on the "PVP substrate" had a field-effect mobility of $4.8 \times 10^{-1}$ cm$^2$/Vs.

Example E-35

With the use of the Compound (C9) obtained in Example 9, a TFT device was produced on a "CYC substrate" by spin-coating and evaluated.
(Conditions of Production of Organic Semiconductor Layer)

0.18 mL of a solution (organic semiconductor ink) which was prepared by adding Compound (C9) to xylene such that the concentration was 0.3 wt %, and then heating the mixture at 70° C. was dropped onto the "CYC substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C9) on the "CYC substrate" had a field-effect mobility of $3.1 \times 10^{-1}$ cm$^2$/Vs.

Example E-36

With the use of the Compound (C9) obtained in Example 9, a TFT device was produced on a "bare substrate" by spin-coating and evaluated.
(Conditions of Production of Organic Semiconductor Layer)

0.18 mL of a solution (organic semiconductor ink) which was prepared by adding Compound (C9) to chloroform such that the concentration was 0.1 wt %, and then heating the mixture at 70° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C9) on the "bare substrate" had a field-effect mobility of $5.7 \times 10^{-1}$ cm$^2$/Vs.

Example E-37

With the use of the Compound (C9) obtained in Example 9, a TFT device was produced on a "PVP substrate" by spin-coating and evaluated.
(Conditions of Production of Organic Semiconductor Layer)

0.18 mL of a solution (organic semiconductor ink) which was prepared by adding Compound (C9) to chloroform such that the concentration was 0.1 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C9) on the "PVP substrate" had a field-effect mobility of $8.9 \times 10^{-1}$ cm$^2$/Vs.

Example E-38

With the use of the Compound (C10) obtained in Example 10, a TFT device was produced on a "PS substrate" by spin-coating and evaluated.
(Conditions of Production of Organic Semiconductor Layer)

0.18 mL of a solution (organic semiconductor ink) which was prepared by adding Compound (C10) to xylene such that the concentration was 0.3 wt %, and then heating the mixture at 90° C. was dropped onto the "PS substrate", and then spin-coating was performed at 1000 rpm for 30 seconds, to form an organic semiconductor layer with a thickness of about 20 nm. And then, the "PS substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C10) on the "PS substrate" had a field-effect mobility of $1.9 \times 10^{-2}$ cm$^2$/Vs.

Example E-39

With the use of the Compound (C10) obtained in Example 10, a TFT device was produced on a "PVP substrate" by spin-coating and evaluated.
(Conditions of Production of Organic Semiconductor Layer)

0.18 mL of a solution (organic semiconductor ink) which was prepared by adding Compound (C10) to xylene such that the concentration was 0.3 wt %, and then heating the mixture at 90° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 120° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C10) on the "PVP substrate" had a field-effect mobility of $3.4 \times 10^{-1}$ cm$^2$/Vs.

Example E-40

With the use of the Compound (C10) obtained in Example 10, a TFT device was produced on a "CYC substrate" by spin-coating and evaluated.
(Conditions of Production of Organic Semiconductor Layer)

0.18 mL of a solution (organic semiconductor ink) which was prepared by adding Compound (C10) to xylene such that the concentration was 0.3 wt %, and then heating the mixture at 90° C. was dropped onto the "CYC substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C10) on the "CYC substrate" had a field-effect mobility of $6.0 \times 10^{-2}$ cm$^2$/Vs.

Example E-41

With the use of the Compound (C10) obtained in Example 10, a TFT device was produced on a "bare substrate" by spin-coating and evaluated.
(Conditions of Production of Organic Semiconductor Layer)

0.18 mL of a solution (organic semiconductor ink) which was prepared by adding Compound (C10) to chloroform such that the concentration was 0.1 wt %, and then heating the mixture at 70° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C10) on the "bare substrate" had a field-effect mobility of $1.4 \times 10^{0}$ cm$^2$/Vs.

Example E-42

With the use of the Compound (C10) obtained in Example 10, a TFT device was produced on a "PVP substrate" by spin-coating and evaluated.
(Conditions of Production of Organic Semiconductor Layer)

0.18 mL of a solution (organic semiconductor ink) which was prepared by adding Compound (C10) to chloroform such that the concentration was 0.1 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C10) on the "PVP substrate" had a field-effect mobility of $4.4 \times 10^{0}$ cm$^2$/Vs.

Example E-43

With the use of the Compound (C11) obtained in Example 11, a TFT device was produced on a "PS substrate" by spin-coating and evaluated.
(Conditions of Production of Organic Semiconductor Layer)

0.18 mL of a solution (organic semiconductor ink) which was prepared by adding Compound (C11) to toluene such that the concentration was 0.3 wt %, and then heating the mixture at 100° C. was dropped onto the "PS substrate", and then spin-coating was performed at 1000 rpm for 30 seconds, to form an organic semiconductor layer with a thickness of about 20 nm. And then, the "PS substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C11) on the "PS substrate" had a field-effect mobility of $8.5 \times 10^{-3}$ cm$^2$/Vs.

Example E-44

With the use of the Compound (C11) obtained in Example 11, a TFT device was produced on a "PVP substrate" by spin-coating and evaluated.
(Conditions of Production of Organic Semiconductor Layer)

0.18 mL of a solution (organic semiconductor ink) which was prepared by adding Compound (C11) to toluene such that the concentration was 0.3 wt %, and then heating the mixture at 100° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C11) on the "PVP substrate" had a field-effect mobility of $8.1 \times 10^{-1}$ cm$^2$/Vs.

Example E-45

With the use of the Compound (C11) obtained in Example 11, a TFT device was produced on a "CYC substrate" by spin-coating and evaluated.

(Conditions of Production of Organic Semiconductor Layer)

0.18 mL of a solution (organic semiconductor ink) which was prepared by adding Compound (C11) to toluene such that the concentration was 0.3 wt %, and then heating the mixture at 100° C. was dropped onto the "CYC substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C11) on the "CYC substrate" had a field-effect mobility of $4.0 \times 10^{-1}$ cm$^2$/Vs.

Example E-46

With the use of the Compound (C12) obtained in Example 12, a TFT device was produced on a "PS substrate" by spin-coating and evaluated.

(Conditions of Production of Organic Semiconductor Layer)

0.18 mL of a solution (organic semiconductor ink) which was prepared by adding Compound (C12) to toluene such that the concentration was 0.3 wt %, and then heating the mixture at 100° C. was dropped onto the "PS substrate", and then spin-coating was performed at 1000 rpm for 30 seconds, to form an organic semiconductor layer with a thickness of about 20 nm. And then, the "PS substrate" on which the organic semiconductor layer was formed was heated at 150° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C12) on the "PS substrate" had a field-effect mobility of $3.5 \times 10^{-1}$ cm$^2$/Vs.

Example E-47

With the use of the Compound (C12) obtained in Example 12, a TFT device was produced on a "PVP substrate" by spin-coating and evaluated.

(Conditions of Production of Organic Semiconductor Layer)

0.18 mL of a solution (organic semiconductor ink) which was prepared by adding Compound (C12) to toluene such that the concentration was 0.3 wt %, and then heating the mixture at 100° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C12) on the "PVP substrate" had a field-effect mobility of $2.5 \times 10^{0}$ cm$^2$/Vs.

Example E-48

With the use of the Compound (C12) obtained in Example 12, a TFT device was produced on a "CYC substrate" by spin-coating and evaluated.

(Conditions of Production of Organic Semiconductor Layer)

0.18 mL of a solution (organic semiconductor ink) which was prepared by adding Compound (C12) to toluene such that the concentration was 0.3 wt %, and then heating the mixture at 100° C. was dropped onto the "CYC substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C12) on the "CYC substrate" had a field-effect mobility of $6.9 \times 10^{-2}$ cm$^2$/Vs.

Example E-49

With the use of the Compound (C13) obtained in Example 13, a TFT device was produced on a "bare substrate" by spin-coating and evaluated.
(Conditions of Production of Organic Semiconductor Layer)

0.18 mL of an organic semiconductor ink which was prepared at room temperature by adding Compound (C13) to chloroform such that the concentration was 0.1 wt % was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 240° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C13) on the "bare substrate" had a field-effect mobility of $7.9 \times 10^{-1}$ cm$^2$/Vs.

Example E-50

With the use of the Compound (C13) obtained in Example 13, a TFT device was produced on a "PVP substrate" by spin-coating and evaluated.
(Conditions of Production of Organic Semiconductor Layer)

0.18 mL of an organic semiconductor ink which was prepared at room temperature by adding Compound (C13) to chloroform such that the concentration was 0.1 wt % was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 90 V, and the organic TFT had the n-type semiconductor characteristics.

The field-effect mobility ($\mu$) was calculated using the above-described (Formula A), and as the result thereof, it was found that the organic TFT comprising Compound (C13) on the "PVP substrate" had a field-effect mobility of $6.8 \times 10^{-1}$ cm$^2$/Vs.

Example E-51

With the use of the Compound (C13) obtained in Example 13, a TFT device was produced on a "CYC substrate" by spin-coating and evaluated.
(Conditions of Production of Organic Semiconductor Layer)

0.18 mL of an organic semiconductor ink which was prepared at room temperature by adding Compound (C13) to chloroform such that the concentration was 0.1 wt % was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 240° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C13) on the "CYC substrate" had a field-effect mobility of $1.4 \times 10^{0}$ cm$^2$/Vs.

Example E-52

With the use of the Compound (C14) obtained in Example 14, a TFT device was produced on a "bare substrate" by spin-coating and evaluated.
(Conditions of Production of Organic Semiconductor Layer)

0.18 mL of an organic semiconductor ink which was prepared at room temperature by adding Compound (C14) to chloroform such that the concentration was 0.1 wt % was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C14) on the "bare substrate" had a field-effect mobility of $8.5 \times 10^{-1}$ cm$^2$/Vs.

Example E-53

With the use of the Compound (C14) obtained in Example 14, a TFT device was produced on a "PVP substrate" by spin-coating and evaluated.
(Conditions of Production of Organic Semiconductor Layer)

0.18 mL of an organic semiconductor ink which was prepared at room temperature by adding Compound (C14) to chloroform such that the concentration was 0.1 wt % was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 80 V, and the organic TFT had the n-type semiconductor characteristics.

Example E-54

With the use of the Compound (C14) obtained in Example 14, a TFT device was produced on a "CYC substrate" by spin-coating and evaluated.
(Conditions of Production of Organic Semiconductor Layer)
0.18 mL of an organic semiconductor ink which was prepared at room temperature by adding Compound (C14) to chloroform such that the concentration was 0.1 wt % was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 240° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C14) on the "CYC substrate" had a field-effect mobility of $2.0\times10^0$ cm$^2$/Vs.

Example E-55

With the use of the Compound (C14) obtained in Example 14, a TFT device was produced on a "bare substrate" by spin-coating in the atmosphere and evaluated.
(Conditions of Production of Organic Semiconductor Layer)
In the atmosphere, 0.18 mL of an organic semiconductor ink which was prepared at room temperature by adding Compound (C14) to chloroform such that the concentration was 0.1 wt % was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes in the atmosphere. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C14) on the "bare substrate" had a field-effect mobility of $6.5\times10^{-1}$ cm$^2$/Vs.

Example E-56

With the use of the Compound (C14) obtained in Example 14, a TFT device was produced on a "PVP substrate" by spin-coating in the atmosphere and evaluated.
(Conditions of Production of Organic Semiconductor Layer)
In the atmosphere, 0.18 mL of an organic semiconductor ink which was prepared at room temperature by adding Compound (C14) to chloroform such that the concentration was 0.1 wt % was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes in the atmosphere. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C14) on the "PVP substrate" had a field-effect mobility of $6.9\times10^{-1}$ cm$^2$/Vs.

Example E-57

With the use of the Compound (C15) obtained in Example 15, a TFT device was produced on a "bare substrate" by spin-coating and evaluated.
(Conditions of Production of Organic Semiconductor Layer)
0.18 mL of an organic semiconductor ink which was prepared at room temperature by adding Compound (C15) to chloroform such that the concentration was 0.1 wt % was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C15) on the "bare substrate" had a field-effect mobility of $1.5\times10^0$ cm$^2$/Vs.

Example E-58

With the use of the Compound (C15) obtained in Example 15, a TFT device was produced on a "PVP substrate" by spin-coating and evaluated.
(Conditions of Production of Organic Semiconductor Layer)
0.18 mL of an organic semiconductor ink which was prepared at room temperature by adding Compound (C15) to chloroform such that the concentration was 0.1 wt % was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C15) on the "PVP substrate" had a field-effect mobility of $1.3 \times 10^0$ cm$^2$/Vs.

Example E-59

With the use of the Compound (C15) obtained in Example 15, a TFT device was produced on a "CYC substrate" by spin-coating and evaluated.
(Conditions of Production of Organic Semiconductor Layer)

0.18 mL of an organic semiconductor ink which was prepared at room temperature by adding Compound (C15) to chloroform such that the concentration was 0.1 wt % was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 240° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C15) on the "CYC substrate" had a field-effect mobility of $1.1 \times 10^0$ cm$^2$/Vs.

Example E-60

With the use of the Compound (C16) obtained in Example 16, a TFT device was produced on a "bare substrate" by spin-coating and evaluated.
(Conditions of Production of Organic Semiconductor Layer)

0.18 mL of an organic semiconductor ink which was prepared by adding Compound (C16) to chloroform such that the concentration was 0.1 wt %, and then heating the mixture at 60° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C16) on the "bare substrate" had a field-effect mobility of $1.4 \times 10^0$ cm$^2$/Vs.

Example E-61

With the use of the Compound (C16) obtained in Example 16, a TFT device was produced on a "PVP substrate" by spin-coating and evaluated.
(Conditions of Production of Organic Semiconductor Layer)

0.18 mL of an organic semiconductor ink which was prepared by adding Compound (C16) to chloroform such that the concentration was 0.1 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C16) on the "PVP substrate" had a field-effect mobility of $1.3 \times 10^0$ cm$^2$/Vs.

Example E-62

With the use of the Compound (C16) obtained in Example 16, a TFT device was produced on a "CYC substrate" by spin-coating and evaluated.
(Conditions of Production of Organic Semiconductor Layer)

0.18 mL of an organic semiconductor ink which was prepared by adding Compound (C16) to chloroform such that the concentration was 0.1 wt %, and then heating the mixture at 60° C. was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 240° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C16) on the "CYC substrate" had a field-effect mobility of $2.4 \times 10^0$ cm$^2$/Vs.

Example E-63

With the use of the Compound (C17) obtained in Example 17, a TFT device was produced on a "bare substrate" by spin-coating and evaluated.

(Conditions of Production of Organic Semiconductor Layer)

0.18 mL of an organic semiconductor ink which was prepared by adding Compound (C17) to chloroform such that the concentration was 0.1 wt %, and then heating the mixture at 60° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C17) on the "bare substrate" had a field-effect mobility of $2.3 \times 10^0$ cm$^2$/Vs.

Example E-64

With the use of the Compound (C17) obtained in Example 17, a TFT device was produced on a "PVP substrate" by spin-coating and evaluated.

(Conditions of Production of Organic Semiconductor Layer)

0.18 mL of an organic semiconductor ink which was prepared by adding Compound (C17) to chloroform such that the concentration was 0.1 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

Figure 9:
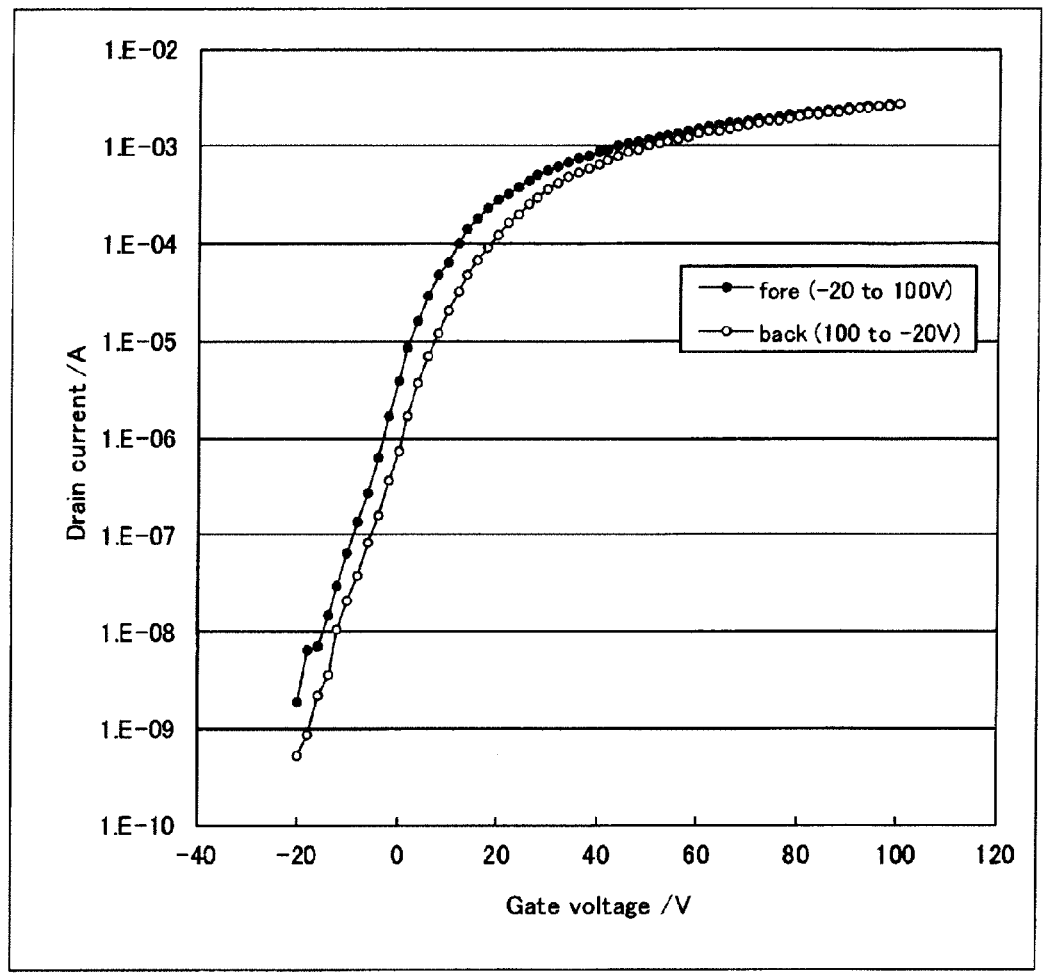
FIG. 9 is a graph showing the electrical properties of the organic TFT of Example E-64, which was measured at 100 V.

The transfer characteristics of the produced organic TFT were measured under the condition that the drain voltage was 100 V, and the organic TFT had the n-type semiconductor characteristics. The obtained transfer characteristics are shown in FIG. 9. In FIG. 9, the horizontal axis indicates gate voltage (V), and the vertical axis indicates drain current (A).

The field-effect mobility ($\mu$) was calculated using the above-described (Formula A), and as the result thereof, it was found that the organic TFT comprising Compound (C17) on the "PVP substrate" had a field-effect mobility of $3.1 \times 10^0$ cm$^2$/Vs.

(Evaluation of Organic TFT)

Figure 10:
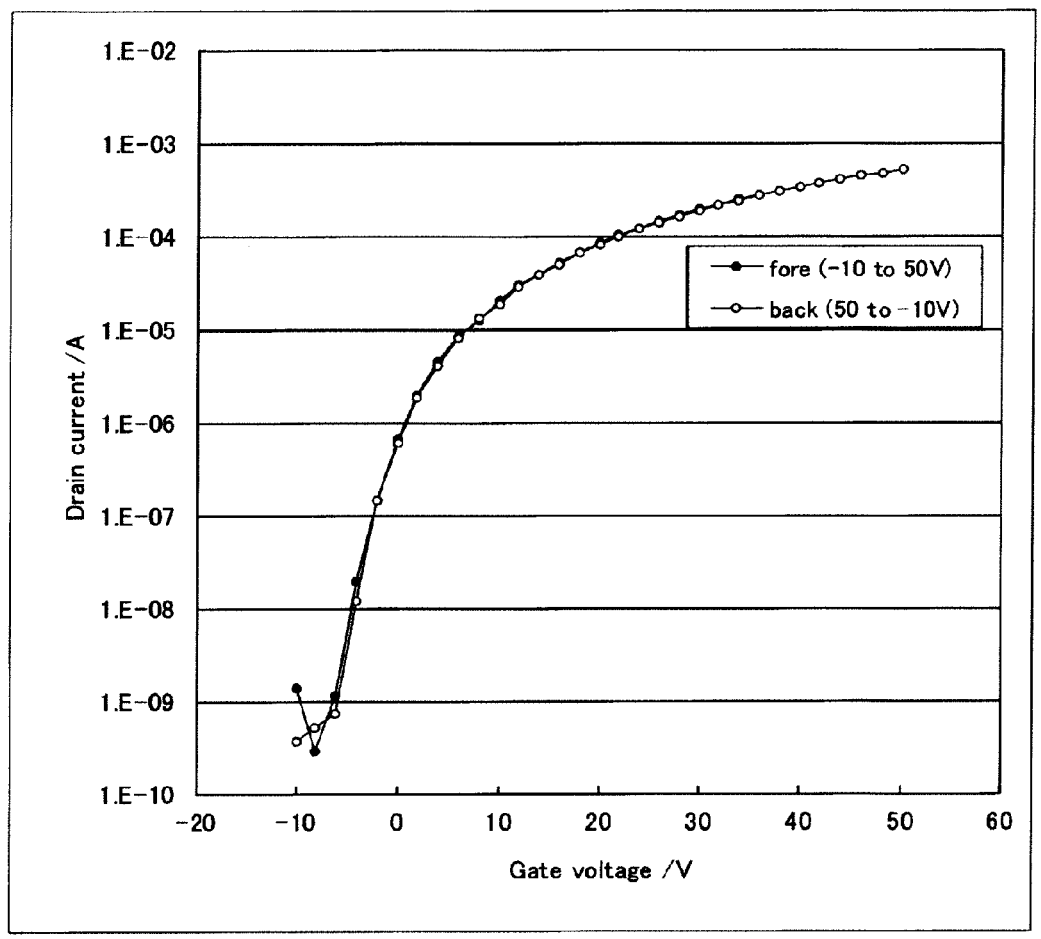
FIG. 10 is a graph showing the electrical properties of the organic TFT of Example E-64, which was measured at 50 V.

The transfer characteristics of the produced organic TFT were measured under the condition that the drain voltage was 50 V, and the organic TFT had the n-type semiconductor characteristics. The obtained transfer characteristics are shown in FIG. 10. In FIG. 10, the horizontal axis indicates gate voltage (V), and the vertical axis indicates drain current (A).

The field-effect mobility ($\mu$) was calculated using the above-described (Formula A), and as the result thereof, it was found that the organic TFT comprising Compound (C17) on the "PVP substrate" had a field-effect mobility of $1.1 \times 10^0$ cm$^2$/Vs.

(Evaluation of Organic TFT)

The transfer characteristics of the produced organic TFT were measured under the condition that the drain voltage was 20 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $8.8 \times 10^{-1}$ cm$^2$/Vs.

Example E-65

With the use of the Compound (C17) obtained in Example 17, a TFT device was produced on a "CYC substrate" by spin-coating and evaluated.

(Conditions of Production of Organic Semiconductor Layer)

0.18 mL of an organic semiconductor ink which was prepared by adding Compound (C17) to chloroform such that the concentration was 0.1 wt %, and then heating the mixture at 60° C. was dropped onto the "CYC substrate", and then spin-coating was performed at 1000 rpm for 30 seconds, to form an organic semiconductor layer with a thickness of about 20 nm. And then, the "CYC substrate" on which the organic semiconductor layer was formed was heated at 240° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C17) on the "CYC substrate" had a field-effect mobility of $3.1 \times 10^0$ cm$^2$/Vs.

(Evaluation of Organic TFT)

The transfer characteristics of the produced organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "CYC substrate" had a field-effect mobility of $2.2 \times 10^0$ cm$^2$/Vs.

(Evaluation of Organic TFT)

The transfer characteristics of the produced organic TFT were measured under the condition that the drain voltage was 20 V, and the organic TFT had the n-type semiconductor characteristics.

The field-effect mobility ($\mu$) was calculated using the above-described (Formula A), and as the result thereof, it was found that the organic TFT comprising Compound (C17) on the "CYC substrate" had a field-effect mobility of $1.1 \times 10^0$ cm$^2$/Vs.

Example E-66

With the use of the Compound (C18) obtained in Example 18, a TFT device was produced on a "bare substrate" by spin-coating and evaluated.

(Conditions of Production of Organic Semiconductor Layer)

0.18 mL of a solution (organic semiconductor ink) which was prepared by adding Compound (C18) to chloroform such that the concentration was 0.1 wt %, and then heating the mixture at 70° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 120° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 50 V, and the organic TFT had the n-type semiconductor characteristics.

The field-effect mobility (μ) was calculated using the above-described (Formula A), and as the result thereof, it was found that the organic TFT comprising Compound (C18) on the "bare substrate" had a field-effect mobility of $1.5 \times 10^0$ cm$^2$/Vs.

Example E-67

With the use of the Compound (C18) obtained in Example 18, a TFT device was produced on a "PVP substrate" by spin-coating and evaluated.

(Conditions of Production of Organic Semiconductor Layer)

0.18 mL of a solution (organic semiconductor ink) which was prepared by adding Compound (C18) to chloroform such that the concentration was 0.1 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 30 V, and the organic TFT had the n-type semiconductor characteristics.

The field-effect mobility (μ) was calculated using the above-described (Formula A), and as the result thereof, it was found that the organic TFT comprising Compound (C18) on the "PVP substrate" had a field-effect mobility of $2.1 \times 10^0$ cm$^2$/Vs.

Example E-68

With the use of the Compound (C19) obtained in Example 19, a TFT device was produced on a "bare substrate" by spin-coating and evaluated.

(Conditions of Production of Organic Semiconductor Layer)

0.18 mL of a solution (organic semiconductor ink) which was prepared by adding Compound (C19) to chloroform such that the concentration was 0.1 wt %, and then heating the mixture at 70° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 60 V, and the organic TFT had the n-type semiconductor characteristics.

The field-effect mobility (μ) was calculated using the above-described (Formula A), and as the result thereof, it was found that the organic TFT comprising Compound (C19) on the "bare substrate" had a field-effect mobility of $2.2 \times 10^0$ cm$^2$/Vs.

Example E-69

With the use of the Compound (C19) obtained in Example 19, a TFT device was produced on a "PVP substrate" by spin-coating and evaluated.

(Conditions of Production of Organic Semiconductor Layer)

0.18 mL of a solution (organic semiconductor ink) which was prepared by adding Compound (C19) to chloroform such that the concentration was 0.1 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 120° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 60 V, and the organic TFT had the n-type semiconductor characteristics.

The field-effect mobility (μ) was calculated using the above-described (Formula A), and as the result thereof, it was found that the organic TFT comprising Compound (C19) on the "PVP substrate" had a field-effect mobility of $2.9 \times 10^0$ cm$^2$/Vs.

Example E-70

With the use of the Compound (C20) obtained in Example 20, a TFT device was produced on a "bare substrate" by spin-coating and evaluated.

(Conditions of Production of Organic Semiconductor Layer)

0.18 mL of a solution (organic semiconductor ink) which was prepared by adding Compound (C20) to chloroform such that the concentration was 0.1 wt %, and then heating the mixture at 70° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 120° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 80 V, and the organic TFT had the n-type semiconductor characteristics.

The field-effect mobility (μ) was calculated using the above-described (Formula A), and as the result thereof, it was found that the organic TFT comprising Compound (C20) on the "bare substrate" had a field-effect mobility of $2.3 \times 10^0$ cm$^2$/Vs.

Example E-71

With the use of the Compound (C20) obtained in Example 20, a TFT device was produced on a "PVP substrate" by spin-coating and evaluated.
(Conditions of Production of Organic Semiconductor Layer)
0.18 mL of a solution (organic semiconductor ink) which was prepared by adding Compound (C20) to chloroform such that the concentration was 0.1 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 40 V, and the organic TFT had the n-type semiconductor characteristics.
The field-effect mobility (μ) was calculated using the above-described (Formula A), and as the result thereof, it was found that the organic TFT comprising Compound (C20) on the "PVP substrate" had a field-effect mobility of $3.0 \times 10^0$ cm$^2$/Vs.

Example E-72

With the use of the Compound (C21) obtained in Example 21, a TFT device was produced on a "bare substrate" by spin-coating and evaluated.
(Conditions of Production of Organic Semiconductor Layer)
0.18 mL of a solution (organic semiconductor ink) which was prepared at room temperature by adding Compound (C21) to chloroform such that the concentration was 0.1 wt % was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 120° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C21) on the "bare substrate" had a field-effect mobility of $6.1 \times 10^{-1}$ cm$^2$/Vs.

Example E-73

With the use of the Compound (C21) obtained in Example 21, a TFT device was produced on a "PVP substrate" by spin-coating and evaluated.
(Conditions of Production of Organic Semiconductor Layer)
0.18 mL of a solution (organic semiconductor ink) which was prepared at room temperature by adding Compound (C21) to chloroform such that the concentration was 0.1 wt % was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 120° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C21) on the "PVP substrate" had a field-effect mobility of $8.0 \times 10^{-1}$ cm$^2$/Vs.

Reference Example P-E-74

With the use of the Compound (C22) obtained in Reference Example P-22, a TFT device was produced on a "bare substrate" by spin-coating and evaluated.
(Conditions of Production of Organic Semiconductor Layer)
0.18 mL of a solution (organic semiconductor ink) which was prepared at room temperature by adding Compound (C22) to chloroform such that the concentration was 0.1 wt % was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 120° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT did not have the transistor characteristics.

Reference Example P-E-75

With the use of the Compound (C22) obtained in Reference Example P-22, a TFT device was produced on a "PVP substrate" by spin-coating and evaluated.
(Conditions of Production of Organic Semiconductor Layer)
0.18 mL of a solution (organic semiconductor ink) which was prepared at room temperature by adding Compound (C22) to chloroform such that the concentration was 0.1 wt % was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 120° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT did not have the transistor characteristics.

Example E-76

With the use of the Compound (C24) obtained in Example 24, a TFT device was produced on a "bare substrate" by spin-coating and evaluated.
(Conditions of Production of Organic Semiconductor Layer)
0.18 mL of a solution (organic semiconductor ink) which was prepared by adding Compound (C24) to chloroform such that the concentration was 0.1 wt %, and then heating the mixture at 70° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C24) on the "bare substrate" had a field-effect mobility of $7.3 \times 10^{-1}$ cm$^2$/Vs.

Example E-77

With the use of the Compound (C24) obtained in Example 24, a TFT device was produced on a "PVP substrate" by spin-coating and evaluated.
(Conditions of Production of Organic Semiconductor Layer)
0.18 mL of a solution (organic semiconductor ink) which was prepared by adding Compound (C24) to chloroform such that the concentration was 0.1 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C24) on the "PVP substrate" had a field-effect mobility of $8.5 \times 10^{-1}$ cm$^2$/Vs.

Example E-78

With the use of the Compound (C25) obtained in Example 25, a TFT device was produced on a "bare substrate" by spin-coating and evaluated.
(Conditions of Production of Organic Semiconductor Layer)
0.18 mL of a solution (organic semiconductor ink) which was prepared by adding Compound (C25) to chloroform such that the concentration was 0.1 wt %, and then heating the mixture at 70° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C25) on the "bare substrate" had a field-effect mobility of $4.4 \times 10^{-1}$ cm$^2$/Vs.

Example E-79

With the use of the Compound (C25) obtained in Example 25, a TFT device was produced on a "PVP substrate" by spin-coating and evaluated.
(Conditions of Production of Organic Semiconductor Layer)
0.18 mL of a solution (organic semiconductor ink) which was prepared by adding Compound (C25) to chloroform such that the concentration was 0.1 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility ($\mu$) was calculated using the above-described (Formula A), and as the result thereof, it was found that the organic TFT comprising Compound (C25) on the "PVP substrate" had a field-effect mobility of $1.1 \times 10^{0}$ cm$^2$/Vs.

Example E-80

With the use of the Compound (C26) obtained in Example 26, a TFT device was produced on a "bare substrate" by spin-coating and evaluated.
(Conditions of Production of Organic Semiconductor Layer)
0.18 mL of a solution (organic semiconductor ink) which was prepared at room temperature by adding Compound (C26) to chloroform such that the concentration was 0.1 wt % was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C26) on the "bare substrate" had a field-effect mobility of $2.5 \times 10^{-3}$ cm$^2$/Vs.

Example E-81

With the use of the Compound (C26) obtained in Example 26, a TFT device was produced on a "PVP substrate" by spin-coating and evaluated.
(Conditions of Production of Organic Semiconductor Layer)

0.18 mL of a solution (organic semiconductor ink) which was prepared at room temperature by adding Compound (C26) to chloroform such that the concentration was 0.1 wt % was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C26) on the "PVP substrate" had a field-effect mobility of $5.1 \times 10^{-3}$ cm$^2$/Vs.

Example E-82

With the use of the Compound (C27) obtained in Example 27, a TFT device was produced on a "bare substrate" by spin-coating and evaluated.
(Conditions of Production of Organic Semiconductor Layer)

0.18 mL of a solution (organic semiconductor ink) which was prepared by adding Compound (C27) to chloroform such that the concentration was 0.1 wt %, and then heating the mixture at 60° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C27) on the "bare substrate" had a field-effect mobility of $1.1 \times 10^0$ cm$^2$/Vs.

Example E-83

With the use of the Compound (C27) obtained in Example 27, a TFT device was produced on a "PVP substrate" by spin-coating and evaluated.
(Conditions of Production of Organic Semiconductor Layer)

0.18 mL of a solution (organic semiconductor ink) which was prepared by adding Compound (C27) to chloroform such that the concentration was 0.1 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C27) on the "PVP substrate" had a field-effect mobility of $1.9 \times 10^0$ cm$^2$/Vs.

Example E-84

With the use of the Compound (C28) obtained in Example 28, a TFT device was produced on a "bare substrate" by spin-coating and evaluated.
(Conditions of Production of Organic Semiconductor Layer)

0.18 mL of a solution (organic semiconductor ink) which was prepared by adding Compound (C28) to chloroform such that the concentration was 0.1 wt %, and then heating the mixture at 70° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.
(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C28) on the "bare substrate" had a field-effect mobility of $8.0 \times 10^{-1}$ cm$^2$/Vs.

Example E-85

With the use of the Compound (C28) obtained in Example 28, a TFT device was produced on a "PVP substrate" by spin-coating and evaluated.

(Conditions of Production of Organic Semiconductor Layer)

0.18 mL of a solution (organic semiconductor ink) which was prepared by adding Compound (C28) to chloroform such that the concentration was 0.1 wt %, and then heating the mixture at 70° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C28) on the "PVP substrate" had a field-effect mobility of $1.7 \times 10^0$ cm$^2$/Vs.

Example E-86

With the use of the Compound (C29) obtained in Example 29, a TFT device was produced on a "bare substrate" by spin-coating and evaluated.

(Conditions of Production of Organic Semiconductor Layer)

0.18 mL of a solution (organic semiconductor ink) which was prepared by adding Compound (C29) to chloroform such that the concentration was 0.1 wt %, and then heating the mixture at 60° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C29) on the "bare substrate" had a field-effect mobility of $2.0 \times 10^0$ cm$^2$/Vs.

Example E-87

With the use of the Compound (C29) obtained in Example 29, a TFT device was produced on a "PVP substrate" by spin-coating and evaluated.

(Conditions of Production of Organic Semiconductor Layer)

0.18 mL of a solution (organic semiconductor ink) which was prepared by adding Compound (C29) to chloroform such that the concentration was 0.1 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C29) on the "PVP substrate" had a field-effect mobility of $1.8 \times 10^0$ cm$^2$/Vs.

Example E-88

With the use of the Compound (C30) obtained in Example 30, a TFT device was produced on a "bare substrate" by spin-coating and evaluated.

(Conditions of Production of Organic Semiconductor Layer)

0.18 mL of a solution (organic semiconductor ink) which was prepared by adding Compound (C30) to chloroform such that the concentration was 0.1 wt %, and then heating the mixture at 60° C. was dropped onto the "bare substrate", and then spin-coating was performed at 1000 rpm for 30 seconds, to form an organic semiconductor layer with a thickness of about 20 nm. And then, the "bare substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C30) on the "bare substrate" had a field-effect mobility of $8.9 \times 10^{-1}$ cm$^2$/Vs.

Example E-89

With the use of the Compound (C30) obtained in Example 30, a TFT device was produced on a "PVP substrate" by spin-coating and evaluated.

(Conditions of Production of Organic Semiconductor Layer)

0.18 mL of a solution (organic semiconductor ink) which was prepared by adding Compound (C30) to chloroform such that the concentration was 0.1 wt %, and then heating the mixture at 60° C. was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 180° C. for 35 minutes. The appearance of the film was visually observed, and it was confirmed that a homogeneous film was formed, that is, a good film was formed successfully.

(Evaluation of Organic TFT)

The transfer characteristics of the produced organic TFT were measured under the condition that the drain voltage was 100 V, and the organic TFT had the n-type semiconductor characteristics.

The field-effect mobility (μ) was calculated using the above-described (Formula A), and as the result thereof, it was found that the organic TFT comprising Compound (C30) on the "PVP substrate" had a field-effect mobility of $1.7 \times 10^0$ cm²/Vs.

Example E-90

With the use of the Compound (C31) obtained in Example 31, a TFT device was produced on a "bare substrate" by spin-coating and evaluated.
(Conditions of Production of Organic Semiconductor Layer)
0.18 mL of a solution (organic semiconductor ink) which was prepared at room temperature by adding Compound (C31) to chloroform such that the concentration was 0.1 wt % was dropped onto the "bare substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C31) on the "bare substrate" had a field-effect mobility of $5.1 \times 10^{-1}$ cm²/Vs.

Example E-91

With the use of the Compound (C31) obtained in Example 31, a TFT device was produced on a "PVP substrate" by spin-coating and evaluated.
(Conditions of Production of Organic Semiconductor Layer)
0.18 mL of a solution (organic semiconductor ink) which was prepared at room temperature by adding Compound (C31) to chloroform such that the concentration was 0.1 wt % was dropped onto the "PVP substrate", and then spin-coating was performed at 1000 rpm for 30 seconds, to form an organic semiconductor layer with a thickness of about 20 nm. And then, the "PVP substrate" on which the organic semiconductor layer was formed was heated at 150° C. for 35 minutes. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C31) on the "PVP substrate" had a field-effect mobility of $4.7 \times 10^{-1}$ cm²/Vs.

Comparative Example E-13

With the use of the Compound (RC6) obtained in Comparative Example 6, a TFT device was produced on a "bare substrate" by spin-coating and evaluated.
(Conditions of Production of Organic Semiconductor Layer)
0.18 mL of a solution (organic semiconductor ink) which was prepared at room temperature by adding Compound (RC6) to chloroform such that the concentration was 0.1 wt % was dropped onto the "bare substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT did not have the transistor characteristics.

Comparative Example E-14

With the use of the Compound (RC6) obtained in Comparative Example 6, a TFT device was produced on a "PVP substrate" by spin-coating and evaluated.
(Conditions of Production of Organic Semiconductor Layer)
0.18 mL of a solution (organic semiconductor ink) which was prepared at room temperature by adding Compound (RC6) to chloroform such that the concentration was 0.1 wt % was dropped onto the "PVP substrate", and then spin-coating was performed at 1000 rpm for 30 seconds, to form an organic semiconductor layer with a thickness of about 20 nm. The appearance of the film was visually observed, and it was confirmed that a homogeneous film was formed, that is, a good film was formed successfully.
(Evaluation of Organic TFT)
The transfer characteristics of the produced organic TFT were measured under the condition that the drain voltage was 100 V, and the organic TFT did not have the transistor characteristics.

Example E-92

(Conditions of Production of Organic Semiconductor Layer)
An organic semiconductor ink was prepared by adding Compound (C1) to 1,2-dichlorobenzene such that the concentration was 0.1 wt %, and then heating the mixture at 130° C. Under nitrogen atmosphere, the organic semiconductor ink was drop-casted at 130° C. into the partition wall which was formed on the "PVP substrate", and then dried at 80° C., to form an organic semiconductor layer.
(Evaluation of Organic TFT)
The transfer characteristics of the produced organic TFT were measured under the condition that the drain voltage was 100 V, and the organic TFT had the n-type semiconductor characteristics.
The field-effect mobility (μ) was calculated using the above-described (Formula A), and as the result thereof, it was found that the organic TFT comprising Compound (C1) on the "PVP substrate" had a field-effect mobility of $2.0 \times 10^{-1}$ cm²/Vs.

Example E-93

(Conditions of Production of Organic Semiconductor Layer)
An organic semiconductor ink was prepared by adding Compound (C8) to 1,2-dichlorobenzene such that the concentration was 0.03 wt %, and then heating the mixture at 130° C. Under nitrogen atmosphere, the organic semiconductor ink was drop-casted at 100° C. into the partition wall which was formed on the "PVP substrate", to form an organic semiconductor layer.

(Evaluation of Organic TFT)

The transfer characteristics of the produced organic TFT were measured under the condition that the drain voltage was 100 V, and the organic TFT had the n-type semiconductor characteristics.

The field-effect mobility ($\mu$) was calculated using the above-described (Formula A), and as the result thereof, it was found that the organic TFT comprising Compound (C8) on the "PVP substrate" had a field-effect mobility of $7.3 \times 10^{-1}$ cm$^2$/Vs.

Example E-94

(Conditions of Production of Organic Semiconductor Layer)

An organic semiconductor ink was prepared by adding Compound (C17) to tetralin such that the concentration was 0.03 wt %, and then heating the mixture at 100° C. The organic semiconductor ink was drop-casted into the partition wall which was formed on the "PVP substrate", to form an organic semiconductor layer. And then, the "PVP substrate" on which the organic semiconductor layer was formed was heated at 100° C. for 35 minutes.

(Evaluation of Organic TFT)

The transfer characteristics of the produced organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $2.7 \times 10^{-1}$ cm$^2$/Vs.

Example E-95

(Conditions of Production of Organic Semiconductor Layer)

An organic semiconductor ink was prepared by adding Compound (C17) to cyclohexylbenzene such that the concentration was 0.01 wt %, and then heating the mixture at 100° C. The organic semiconductor ink was drop-casted into the partition wall which was formed on the "PVP substrate", to form an organic semiconductor layer. And then, the "PVP substrate" on which the organic semiconductor layer was formed was heated at 100° C. for 35 minutes.

(Evaluation of Organic TFT)

The transfer characteristics of the produced organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $1.6 \times 10^{-1}$ cm$^2$/Vs.

Example E-96

(Conditions of Production of Organic Semiconductor Layer)

An organic semiconductor ink was prepared by adding Compound (C17) to 1-methylnaphthalene such that the concentration was 0.03 wt %, and then heating the mixture at 100° C. The organic semiconductor ink was drop-casted into the partition wall which was formed on the "PVP substrate", to form an organic semiconductor layer. And then, the "PVP substrate" on which the organic semiconductor layer was formed was heated at 100° C. for 35 minutes.

(Evaluation of Organic TFT)

The transfer characteristics of the produced organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $6.0 \times 10^{-2}$ cm$^2$/Vs.

Example E-97

(Conditions of Production of Organic Semiconductor Layer)

An organic semiconductor ink was prepared by adding Compound (C17) to chlorobenzene such that the concentration was 0.03 wt %, and then heating the mixture at 100° C. The organic semiconductor ink was drop-casted into the partition wall which was formed on the "PVP substrate", to form an organic semiconductor layer. And then, the "PVP substrate" on which the organic semiconductor layer was formed was heated at 100° C. for 35 minutes.

(Evaluation of Organic TFT)

The transfer characteristics of the produced organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $3.1 \times 10^{-1}$ cm$^2$/Vs.

Example E-98

(Conditions of Production of Organic Semiconductor Layer)

An organic semiconductor ink was prepared by adding Compound (C17) to methyl benzoate such that the concentration was 0.03 wt %, and then heating the mixture at 100° C. The organic semiconductor ink was drop-casted into the partition wall which was formed on the "PVP substrate", to form an organic semiconductor layer. And then, the "PVP substrate" on which the organic semiconductor layer was formed was heated at 100° C. for 35 minutes.

(Evaluation of Organic TFT)

The transfer characteristics of the produced organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $3.8 \times 10^{-1}$ cm$^2$/Vs.

Example E-99

(Conditions of Production of Organic Semiconductor Layer)

An organic semiconductor ink was prepared by adding Compound (C17) to a mixed solvent of [cyclohexylbenzene:1-methylnaphthalene=1:0.3] such that the concentration was 0.01 wt %, and then heating the mixture at 100° C. The organic semiconductor ink was drop-casted into the partition wall which was formed on the "PVP substrate", to form an organic semiconductor layer. And then, the "PVP substrate" on which the organic semiconductor layer was formed was heated at 100° C. for 35 minutes.

(Evaluation of Organic TFT)

The transfer characteristics of the produced organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $1.8 \times 10^{-1}$ cm$^2$/Vs.

Example E-100

(Conditions of Production of Organic Semiconductor Layer)

An organic semiconductor ink was prepared by adding Compound (C17) to 1-methylnaphthalene such that the concentration was 0.1 wt %, and then heating the mixture at 120° C. In order to produce a bottom gate-bottom contact type organic TFT, the organic semiconductor ink was drop-casted into the partition wall which was formed on the "PVP substrate" having a source electrode and a drain electrode thereon, to form an organic semiconductor layer. And then, the "PVP substrate" on which the organic semiconductor layer was formed was heated at 150° C. for 35 minutes.

(Evaluation of Organic TFT)

The transfer characteristics of the produced bottom gate-bottom contact type organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $1.6 \times 10^{-2}$ cm$^2$/Vs.

Example E-101

(Conditions of Production of Organic Semiconductor Layer)

An organic semiconductor ink was prepared by adding Compound (C17) to a mixed solvent of [1-methylnaphthalene:methyl salicylate=1:1] such that the concentration was 0.1 wt %, and then heating the mixture at 120° C. In order to produce a bottom gate-bottom contact type organic TFT, the organic semiconductor ink was drop-casted into the partition wall which was formed on the "PVP substrate" having a source electrode and a drain electrode thereon, to form an organic semiconductor layer. And then, the "PVP substrate" on which the organic semiconductor layer was formed was heated at 150° C. for 35 minutes.

(Evaluation of Organic TFT)

The transfer characteristics of the produced bottom gate-bottom contact type organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $2.6 \times 10^{-2}$ cm$^2$/Vs.

Example E-102

(Conditions of Production of Organic Semiconductor Layer)

An organic semiconductor ink was prepared by mixing a Compound (C17) solution (1), which was prepared by adding Compound (C17) to 1-methylnaphthalene such that the concentration was 0.2 wt %, and then heating the mixture at 120° C., and an octadecanethiol solution (2), which was prepared by adding octadecanethiol to 1-methylnaphthalene such that the concentration was 200 μmol/L, in a ratio of (1):(2)=1:1. In order to produce a bottom gate-bottom contact type organic TFT, the organic semiconductor ink was drop-casted into the partition wall which was formed on the "PVP substrate" having a source electrode and a drain electrode thereon, to form an organic semiconductor layer. And then, the "PVP substrate" on which the organic semiconductor layer was formed was heated at 150° C. for 35 minutes.

(Evaluation of Organic TFT)

The transfer characteristics of the produced bottom gate-bottom contact type organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $2.8 \times 10^{-2}$ cm$^2$/Vs.

Example E-103

(Conditions of Production of Organic Semiconductor Layer)

An organic semiconductor ink was prepared by mixing a Compound (C17) solution (1), which was prepared by adding Compound (C17) to 1-methylnaphthalene such that the concentration was 0.2 wt %, and then heating the mixture at 120° C., and a hexanethiol solution (2), which was prepared by adding hexanethiol to 1-methylnaphthalene such that the concentration was 200 μmol/L, in a ratio of (1):(2)=1:1. In order to produce a bottom gate-bottom contact type organic TFT, the organic semiconductor ink was drop-casted into the partition wall which was formed on the "PVP substrate" having a source electrode and a drain electrode thereon, to form an organic semiconductor layer. And then, the "PVP substrate" on which the organic semiconductor layer was formed was heated at 150° C. for 35 minutes.

(Evaluation of Organic TFT)

The transfer characteristics of the produced bottom gate-bottom contact type organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $3.3 \times 10^{-2}$ cm$^2$/Vs.

Example E-104

(Conditions of Production of Organic Semiconductor Layer)

An organic semiconductor ink was prepared by mixing a Compound (C17) solution (1), which was prepared by adding Compound (C17) to 1-methylnaphthalene such that the concentration was 0.2 wt %, and then heating the mixture at 120° C., and a 4-methylbenzenethiol solution (2), which was prepared by adding 4-methylbenzenethiol to 1-methylnaphthalene such that the concentration was 20 μmol/L, in a ratio of (1):(2)=1:1. In order to produce a bottom gate-bottom contact type organic TFT, the organic semiconductor ink was drop-casted into the partition wall which was formed on the "PVP substrate" having a source electrode and a drain electrode thereon, to form an organic semiconductor layer. And then, the "PVP substrate" on which the organic semiconductor layer was formed was heated at 150° C. for 35 minutes.
(Evaluation of Organic TFT)

The transfer characteristics of the produced bottom gate-bottom contact type organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $3.2 \times 10^{-2}$ cm$^2$/Vs.

Example E-105

(Conditions of Production of Organic Semiconductor Layer)

An organic semiconductor ink was prepared by adding Compound (C17) to 1-methylnaphthalene such that the concentration was 0.06 wt %, and then heating the mixture at 120° C. In order to produce a bottom gate-bottom contact type organic TFT, the organic semiconductor ink was drop-casted into the partition wall which was formed on the "PVP substrate" having a source electrode and a drain electrode thereon, to form an organic semiconductor layer. And then, the "PVP substrate" on which the organic semiconductor layer was formed was heated at 150° C. for 35 minutes.
(Evaluation of Organic TFT)

The transfer characteristics of the produced bottom gate-bottom contact type organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $5.1 \times 10^{-3}$ cm$^2$/Vs.

Example E-106

(Conditions of Production of Organic Semiconductor Layer)

An organic semiconductor ink was prepared by mixing a Compound (C17) solution (1), which was prepared by adding Compound (C17) to 1-methylnaphthalene such that the concentration was 0.12 wt %, and then heating the mixture at 120° C., and a dodecanol solution (2), which was prepared by adding dodecanol to 1-methylnaphthalene such that the concentration was 200 $\mu$mol/L, in a ratio of (1):(2)=1:1. In order to produce a bottom gate-bottom contact type organic TFT, the organic semiconductor ink was drop-casted into the partition wall which was formed on the "PVP substrate" having a source electrode and a drain electrode thereon, to form an organic semiconductor layer. And then, the "PVP substrate" on which the organic semiconductor layer was formed was heated at 150° C. for 35 minutes.
(Evaluation of Organic TFT)

The transfer characteristics of the produced bottom gate-bottom contact type organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $2.8 \times 10^{-2}$ cm$^2$/Vs.

Example E-107

(Conditions of Production of Organic Semiconductor Layer)

An organic semiconductor ink was prepared by mixing a Compound (C17) solution (1), which was prepared by adding Compound (C17) to 1-methylnaphthalene such that the concentration was 0.12 wt %, and then heating the mixture at 120° C., and a dodecylamine solution (2), which was prepared by adding dodecylamine to 1-methylnaphthalene such that the concentration was 20 $\mu$mol/L, in a ratio of (1):(2)=1:1. In order to produce a bottom gate-bottom contact type organic TFT, the organic semiconductor ink was drop-casted into the partition wall which was formed on the "PVP substrate" having a source electrode and a drain electrode thereon, to form an organic semiconductor layer. And then, the "PVP substrate" on which the organic semiconductor layer was formed was heated at 150° C. for 35 minutes.
(Evaluation of Organic TFT)

The transfer characteristics of the produced bottom gate-bottom contact type organic TFT were measured under the condition that the drain voltage was 50 V, and the organic TFT had the n-type semiconductor characteristics.

The field-effect mobility ($\mu$) was calculated using the above-described (Formula A), and as the result thereof, it was found that the organic TFT comprising Compound (C17) on the "PVP substrate" had a field-effect mobility of $3.0 \times 10^{-2}$ cm$^2$/Vs.

Example I-1

(Production of Inverter Circuit)
(Planarizing Layer)

A mixture solution of polyvinylphenol and melamine in propylene glycol monomethyl ether acetate as the solvent was applied onto a blue flat glass (soda-lime glass) with a size of 20 mm×25 mm by spin-coating, and then heated at 150° C. for 1 hour, to form a polyvinylphenol-melamine thin film with a thickness of about 240 nm as a planarizing layer on the surface of the substrate.

(Gate Electrode)

Subsequently, the formed polyvinylphenol-melamine thin film was subjected to oxygen plasma treatment at 100 W and at the oxygen flow rate of 30 sccm for 60 seconds, and then silver nanoparticles were printed thereon using an ink-jet device, and calcined at 140° C. for 30 minutes, to form a gate electrode.

(Gate Insulating Film)

A mixture solution of polyvinylphenol and melamine in propylene glycol monomethyl ether acetate as the solvent was applied onto the gate electrode by spin-coating, and then heated at 150° C. for 1 hour, to form a polyvinylphenol-melamine thin film with a thickness of about 800 nm as a gate insulating film.

(Source Electrode and Drain Electrode)

Silver nanoparticles were printed on the formed polyvinylphenol-melamine thin film using an ink-jet device, and calcined at 120° C. for 30 minutes, to form a source electrode and a drain electrode. The channel widths and the channel lengths of both the p-type device and the n-type device were 1040 $\mu$m and 50 $\mu$m, respectively.

(Partition Wall)

A partition wall pattern to receive a semiconductor ink in the next step was formed thereon with the use of a solution prepared by dissolving 1 wt % Teflon® AF1600X in Fluorinert™ FC-43, which was commercially available, and heated at 100° C. for 30 minutes, to form a partition wall.

(PFBT Treatment)

The substrate in which the partition wall was formed was immersed in a solution prepared by dissolving 2,3,4,5,6- pentafluorothiophenol, which was commercially available, in 2-propanol at a concentration of 30 mmol/L for 5 minutes, and then the substrate was dried under nitrogen stream, to treat the surfaces of the source electrode and the drain electrode.

(Application of p-Type Semiconductor)

A p-type semiconductor ink, which was prepared by adding 2,8-difluoro-5,11-bis(triethylsilylethynyl)anthradithiophene to mesitylene such that the concentration was 0.5 wt %, was dropped into the partition wall which was formed in the step as described above, and then dried at room temperature, to form a p-type semiconductor layer.

(Application of n-Type Semiconductor)

An n-type semiconductor ink, which was prepared by adding Compound (C17) to 1-methylnaphthalene such that the concentration was 0.1 wt %, and then heating the mixture at 120° C. for 30 minutes, was dropped into the partition wall which was formed in the step as described above, and then dried at room temperature, to form an n-type semiconductor layer.

(Thermal Annealing)

Figure 11:
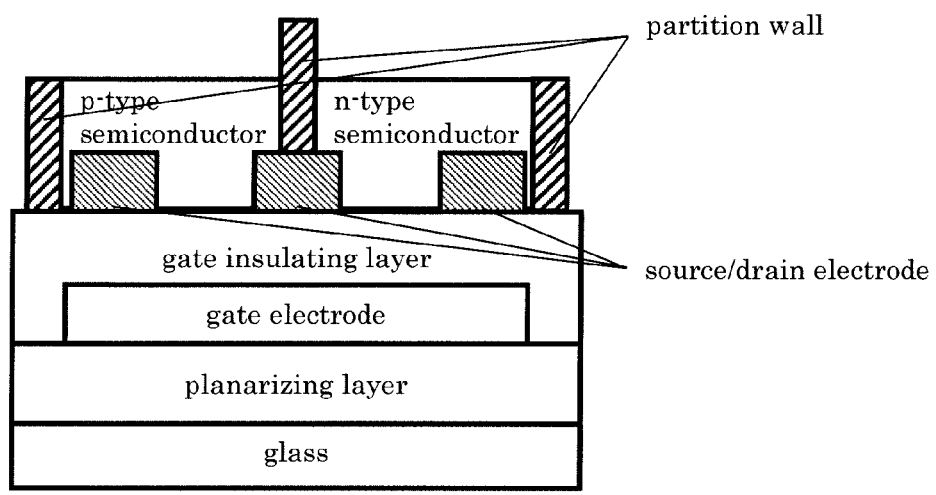
FIG. 11 is a drawing illustrating the configuration of the inverter circuit produced in Example I-1.

The substrate in which the p-type semiconductor layer and the n-type semiconductor layer were formed was heated at 120° C. for 30 minutes under nitrogen atmosphere, to produce an inverter circuit as shown in FIG. 11.

(Evaluation of Inverter Circuit)

The output characteristics were measured under the condition that the drive voltage was 40 V, and as the result thereof, the circuit had the inverter characteristics. The gain (defined as ΔVout/ΔVin) of the inverter circuit was calculated on the assumption of ΔVin=0.2 V, and the maximum gain of 7.9 was achieved. Thus, it was found that Compound (C17) functioned well as an n-type semiconductor portion of an inverter circuit.

As can be seen from the above-described results, the benzobis(thiadiazole) derivative of the present invention has high field-effect mobility at the initial stage and even after being left for 118 days. That is to say, it was demonstrated that the benzobis(thiadiazole) derivative of the present invention combines high field-effect mobility with the property of being stable in the atmosphere.

INDUSTRIAL APPLICABILITY

According to the present invention, there may be provided a benzobis(thiadiazole) derivative, which is soluble in an organic solvent and allows the formation of a thin film by a coating method, and has an excellent mobility of hole and/or electron (field-effect mobility) and an excellent stability in the atmosphere.

Because the benzobis(thiadiazole) derivative of the present invention is thermally stable and has high field-effect mobility, high field-effect mobility may be achieved when the compound is used for a semiconductor layer of an organic TFT. In addition, high luminous efficiency may be achieved when the compound is used for a hole transport layer and/or an electron transport layer of an organic EL device. Additionally, high photoelectric conversion efficiency may be achieved when the compound is used for a charge separation layer and/or a hole transport layer and/or an electron transport layer of a photovoltaic cell.

In addition, the organic EL display comprising arranged pixels, in which the organic TFT of the present invention, and the organic EL device of the present invention or other type of organic EL device are combined, has the advantages of having an excellent luminous efficiency; and having excellent response properties. Additionally, the organic TFT of the present invention may be suitably used as an organic TFT by which a RFID tag or a sensor is activated.

DESCRIPTION OF THE MAIN SYMBOLS 11, 21, 31, 111 Substrate
12, 106 Gate electrode
13, 107 Gate insulating film
14, 110 Drain electrode
15, 109 Source electrode
16, 108 Organic semiconductor layer
22, 105 Anode
23, 104 Hole transport layer
24, 103 Luminescent layer
25, 102 Electron transport layer
26, 101 Cathode
112 Barrier layer
113 Protective layer
120 Organic EL device
121 Organic TFT
32 Anode
33 Charge separation layer
34 Cathode

The invention claimed is:
1. A benzobis(thiadiazole) derivative represented by the following general formula (1):

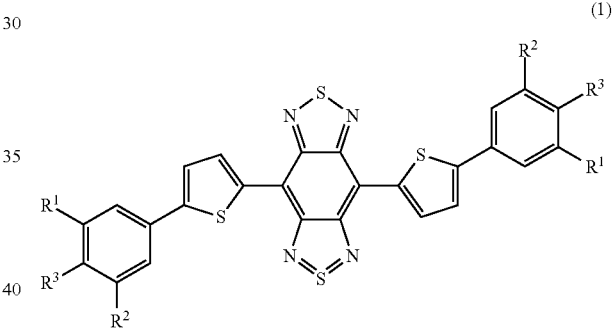

wherein
  $R^1$ represents a linear or branched alkyl group, or any one of the groups of the following formula (2):

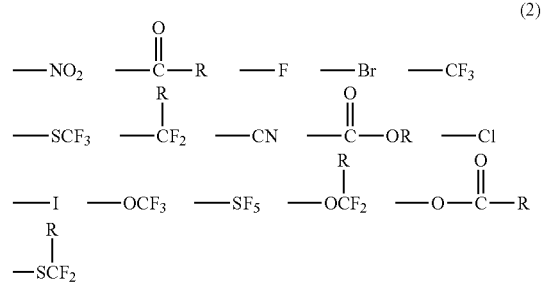

wherein R represents a linear or branched alkyl group;
  $R^2$ represents a hydrogen atom; and
  $R^3$ represents a hydrogen atom, a linear or branched alkyl group, or any one of the groups of the formula (2);
with the proviso that
  at least one of $R^1$ and $R^3$ represents any one of the groups of the formula (2); and two R¹ groups, two R² groups, and two R³ groups may be the same as, or different from each other.

2. The benzobis(thiadiazole) derivative according to claim 1, wherein
R¹ is any one of the groups of the formula (2);
R² is a hydrogen atom; and
R³ is a hydrogen atom, or a linear or branched alkyl group.

3. The benzobis(thiadiazole) derivative according to claim 1, wherein
R¹ is a linear or branched alkyl group;
R² is a hydrogen atom; and
R³ is any one of the groups of the formula (2).

4. The benzobis(thiadiazole) derivative according to claim 1, wherein the group of the formula (2) is any one of the groups of the following formula (3):

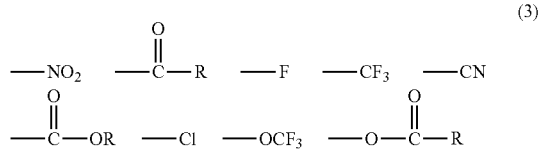

wherein R represents a linear or branched alkyl group.

5. The benzobis(thiadiazole) derivative according to claim 1, wherein
R¹ is a linear or branched alkyl group;
R² is a hydrogen atom; and
R³ is any one of trifluoromethyl group, trifluoromethoxy group, or cyano group.

6. The benzobis(thiadiazole) derivative according claim 1, wherein the benzobis(thiadiazole) derivative is soluble in an organic solvent.

7. An organic semiconductor ink comprising the benzobis(thiadiazole) derivative according to claim 1.

8. An organic semiconductor ink comprising two or more of organic semiconductors, wherein one or more of the organic semiconductors is the benzobis(thiadiazole) derivative according to claim 1.

9. An organic electronic device comprising an organic layer, which comprises the benzobis(thiadiazole) derivative according to claim 1.

10. An organic thin film transistor, comprising a gate electrode, a gate insulating layer, an organic semiconductor layer, a source electrode, and a drain electrode on a substrate, wherein
the organic semiconductor layer comprises the benzobis(thiadiazole) derivative according to claim 1.

11. An organic electroluminescence device, comprising an anode, a luminescent layer, a hole transport layer and/or an electron transport layer, and a cathode on a substrate, wherein
the hole transport layer and/or the electron transport layer comprise the benzobis(thiadiazole) derivative according to claim 1.

12. A display device, in which an organic electroluminescence device is driven/lighted by the use of an organic thin film transistor, wherein
the organic thin film transistor is the organic thin film transistor according to claim 10.

13. An active-matrix display device, wherein
pixels are arranged in a matrix form, the pixel comprising the organic thin film transistor according to claim 10 and an organic electroluminescence device.

14. A display device, in which an organic electroluminescence device is driven/lighted by the use of an organic thin film transistor, wherein
the organic electroluminescence device is the organic electroluminescence device according to claim 11.

15. An organic thin film photovoltaic cell, comprising an anode, a charge separation layer comprising a hole transport material and an electron transport material, and a cathode on a substrate, wherein
the charge separation layer comprises the benzobis(thiadiazole) derivative according to claim 1.

16. An organic thin film photovoltaic cell, comprising an anode, a charge separation layer comprising a hole transport material and an electron transport material, a hole transport layer and/or an electron transport layer, and a cathode on a substrate, wherein
the hole transport layer and/or the electron transport layer comprise the benzobis(thiadiazole) derivative according to claim 1.

17. The organic electronic device according to claim 9, further comprising a flexible substrate.

18. A display device, in which an organic electroluminescence device is driven/lighted by the use of an organic thin film transistor, wherein
the organic thin film transistor comprises a gate electrode, a gate insulating layer, an organic semiconductor layer, a source electrode, and a drain electrode, wherein the organic semiconductor layer comprises the benzobis(thiadiazole) derivative according to claim 1, and
the organic electroluminescence device comprises an anode, a luminescent layer, a hole transport layer and/or an electron transport layer, and a cathode, wherein the hole transport layer and/or the electron transport layer comprise the benzobis(thiadiazole) derivative according to claim 1.

19. An active-matrix display device, wherein
pixels are arranged in a matrix form, the pixel comprising an organic thin film transistor and an organic electroluminescence device, and
the organic thin film transistor comprises a gate electrode, a gate insulating layer, an organic semiconductor layer, a source electrode, and a drain electrode, wherein the organic semiconductor layer comprises the benzobis(thiadiazole) derivative according to claim 1, and
the organic electroluminescence device comprises an anode, a luminescent layer, a hole transport layer and/or an electron transport layer, and a cathode, wherein the hole transport layer and/or the electron transport layer comprise the benzobis(thiadiazole) derivative according to claim 1.

* * * * *